(12) United States Patent
Pike et al.

(10) Patent No.: US 10,718,785 B2
(45) Date of Patent: Jul. 21, 2020

(54) MATERIALS AND METHODS FOR DIAGNOSIS AND TREATMENT OF ALZHEIMER'S DISEASE

(71) Applicant: ELECTROPHORETICS LIMITED, London (GB)

(72) Inventors: Ian Hugo Pike, London (GB); Claire Louise Russell, London (GB); Malcolm Ward, London (GB)

(73) Assignee: ELECTROPHORETICS LIMITED, London (GB)

( * ) Notice: Subject to any disclaimer, the term of this patent is extended or adjusted under 35 U.S.C. 154(b) by 0 days.

(21) Appl. No.: 15/559,371

(22) PCT Filed: Mar. 17, 2016

(86) PCT No.: PCT/EP2016/055883
§ 371 (c)(1),
(2) Date: Sep. 18, 2017

(87) PCT Pub. No.: WO2016/146783
PCT Pub. Date: Sep. 22, 2016

(65) Prior Publication Data
US 2018/0067133 A1  Mar. 8, 2018

(30) Foreign Application Priority Data
Mar. 17, 2015 (GB) .................................. 1504432.4

(51) Int. Cl.
| | | |
|---|---|---|
| *G01N 33/68* | (2006.01) | |
| *A61K 31/13* | (2006.01) | |
| *C07K 14/575* | (2006.01) | |
| *C12N 9/90* | (2006.01) | |
| *C07C 49/757* | (2006.01) | |

(52) U.S. Cl.
CPC ......... *G01N 33/6896* (2013.01); *A61K 31/13* (2013.01); *C07C 49/757* (2013.01); *C07K 14/57581* (2013.01); *C12N 9/90* (2013.01); *C12Y 504/02002* (2013.01); *G01N 33/68* (2013.01); *G01N 2800/2821* (2013.01)

(58) Field of Classification Search
CPC .............. G01N 33/68; G01N 33/6896; G01N 2800/2821
See application file for complete search history.

(56) References Cited

U.S. PATENT DOCUMENTS

| | | |
|---|---|---|
| 4,376,110 A | 3/1983 | David et al. |
| 4,946,778 A | 8/1990 | Ladner et al. |
| 2007/0105105 A1 | 5/2007 | Clelland et al. |
| 2013/0029362 A1 | 1/2013 | Jeromin et al. |

FOREIGN PATENT DOCUMENTS

| | | | |
|---|---|---|---|
| JP | 2007502971 A | 2/2007 | |
| JP | 2013524220 A | 6/2013 | |
| WO | WO 2004/01865 A2 | 3/2004 | |
| WO | WO-2005047484 A2 * | 5/2005 | ......... G01N 33/6842 |
| WO | WO-2006110621 A2 * | 10/2006 | ......... G01N 33/6896 |
| WO | WO-2010084327 A2 * | 7/2010 | ......... G01N 33/6896 |
| WO | WO 2010/111587 A1 | 9/2010 | |
| WO | WO 2011/005893 A2 | 1/2011 | |
| WO | WO 2013/086429 A2 | 6/2013 | |
| WO | 2014135546 A1 | 9/2014 | |
| WO | WO 2014/195715 A1 | 12/2014 | |
| WO | WO 2015/087087 A1 | 6/2015 | |

OTHER PUBLICATIONS

Ding B et al. Gene expression profiles of entorhinal cortex in Alzheimer's disease. Am J Alz Dis Other Dementias, 29(6):526-532. Epub Feb. 20, 2014. (Year: 2014).*
Liu Y et al. Biomarkers in Alzheimer's disease analysis by mass spectrometry-based proteomics. Int J Mol Sci. 15:7865-7882. (Year: 2014).*
Schneider LS. Alzheimer disease pharmacologic treatment and treatment research. Continuum (Minneap Minn) 19(2):339-357. (Year: 2013).*
Sultana R et al. Proteomics analysis of the Alzheimer's disease hippocampal proteome. J Alz Dis. 11:153-164. (Year: 2007).*
Begcevic, I. et al.; "Semiquantitative proteomic analysis of human hippocampal tissues from Alzheimer's disease and age-matched control brains"; Clinical Proteomics; vol. 10; 2013; 8 pages.
Bingqian, D. M. et al.; "Gene Expression Profiles of Entorhinal Cortex in Alzheimer's Disease"; American Journal of Alzheimer's Disease and Other Dementias; vol. 29; No. 6; 2014; pp. 526-532.
Bird, R. E. et al; "Single-Chain Antigen-Binding Proteins"; Science; vol. 242; Oct. 21, 1988; pp. 423-426.
Bishnoi, R. J. et al.; "Vitamin D Binding Protein as a Serum Biomarker of Alzheimer's Disease"; Journal of Alzheimer's Disease; vol. 43; 2015; pp. 37-45.
Blasi, E. et al.; "Immortalization of murine microglial cells by a v-raf/v-myc carrying retrovirus"; Journal of Neuroimmunology; vol. 27; 1990; pp. 229-237.
Blennow, K. et al.; "Cerebrospinal fluid and plasma biomarkers in Alzeimers disease"; Nature Reviews, Neurology; vol. 6; Mar. 2010; pp. 131-144.
Boche, D. et al.; "Review: Activation patters of microglia and their identificationi in the human brain"; Neuropathology and Applied Neurobiology; vol. 39; 2013; pp. 3-18.

(Continued)

*Primary Examiner* — Kimberly Ballard
(74) *Attorney, Agent, or Firm* — Arent Fox LLP

(57) ABSTRACT

Alzheimer's disease (AD) is the most common type of dementia in aging adults with the number of people living with AD projected to increase, making the search for treatments and tools to diagnose and measure disease progression increasingly urgent. In particular, ideal biomarkers for diagnosis of AD should not only have high specificity for disease versus non-disease and high sensitivity for distinguishing between disease types but also should be able to detect changes at a very early stage of the disease. Using microglia activation as an early event of AD's onset, the present inventors have identified a panel of biomarkers in CSF which has the potential to diagnose, stage and determine the likelihood of developing AD.

21 Claims, 8 Drawing Sheets
Specification includes a Sequence Listing.

(56) References Cited

OTHER PUBLICATIONS

Cole, S.P.C. et al.; "The EBV-Hybridoma Technique and Its Application to Human Lung Cancer"; Monoclonal Antibodies and Cancer Therapy; Alan R. Liss, Inc.; 1985; pp. 77-96.
Cote, R. J. et al.; "Generation of human monoclonal antibodies reactive with cellular antigens"; Proc. Natl. Acad. Sci., USA Immunology; vol. 80; Apr. 1983; pp. 2026-2030.
Crehan, H. et al.; "Microglia, Alzheimer's Disease, and Complement"; International Journal of Alzheimer's Disease; vol. 2012, Article ID 983640; 10 pages.
Dale, D. C. et al.; "The phagocytes: neutriphils and monocytes"; Blood; vol. 112; No. 4; Aug. 15, 2008; pp. 935-945.
De Livera, A. M. et al.; "Normalizing and Integrating Metabolomics Data"; Analytical Chemistry; vol. 84; 2012; pp. 10768-10776.
GB Search Report issued for Application No. GB1504432.4, dated Dec. 8, 2015.
Gordon, S. et al.; "Monocyte and Macrophage Heterogeneity"; Nature Reviews Immunology; vol. 5; Dec. 2005; pp. 953-964.
Hansson, O. et al.; "Association between CSF biomarkers and incipient Alzheimer's disease in patients with mild cognitive impairment: a follow-up study"; Lancet Neurol; vol. 5; 2006; pp. 228-234.
Henkel, J. S. et al.; "Microglia in ALS: The Good, The Bad, and The Resting"; J. Neuroimmune Pharmacol; vol. 4; 2009; pp. 389-398.
Henn, A. et al.; "The Suitability of BV2 Cells as Alternative Model System for Primary Microglia Cultures or for Animal Experiments Examining Brain Inflammation"; Altex; vol. 26; Feb. 20, 2009; pp. 83-94.
Huemer, A. F. et al.; "Protein analysis in human cerebrospinal fluid: Physiological aspects, current progress and future challenges"; Disease Markers 22; 2006; pp. 3-26.
Huse, W. D. et al.; "Generation of a Large Combinatorial Library of the Immunoglobulin Repertoire in Phage Lambda"; Science; vol. 246; Dec. 8, 1989; pp. 1275-1281.
Huston, J. S. et al.; "Protein engineering of antibody binding sites: Recovery of specific activity in an anti-digoxin single-chain Fv analogue produced in *Escherichia coli*"; Proc. Natl. Acad. Sci. USA; vol. 85; Aug. 1988; pp. 5879-5883.
International Search Report issued for PCT/EP2016/055883, dated Jun. 28, 2016.
Kim, S. H. et al.; "Protein levels of human peroxiredoxin subtypes in brains of patients with Alzheimer's disease and Down Syndrome"; Protein Expression in Down Syndrome Brain; vol. 61; 2001; pp. 223-235.
Koehler, G. et al.; "Continuous cultures of fused cells secreting antibody of predefined specificity"; Nature; vol. 256; Aug. 7, 1975; pp. 495-497.
Kozbor, D. et al.; "The production of monoclonal antibodies from human lymphocites"; Immunology Today; vol. 4; No. 3; 1983; pp. 72-79.
Li, M. D. et al.; "Integrated multi-cohort transcriptional meta-analysis of neurodegenerative disease"; Acta Neuropathologica Communications; vol. 2; 2014; 23 pages.
Mandrekar, S. et al.; "Microglia and Inflammation in Alzheimer's Disease"; CNS Neurol Disord Drug Targets; vol. 9; No. 2; 2010; pp. 156-167.
Merched, A. et al.; "Apolipoprotein E, transthyretin and actin in the CSF of Alzheimer's patients: relation with the senile plaques and cytoskeleton biochemisty"; FEBS Letters 425; 1998; pp. 225-228.
Milner, J. D. MD et al.; "Impaired Glycosylation Due to Autosomal Recessive PGM3 Mutations Results in Atopy, Immune Deficiency, Autoimmunity, and Neurocognitive Impairment"; J Allergy Clin Immunol; vol. 133; No. 2; AB161; 2014; 1 page.
Morrison, S. L. et al.; "Chimeric human antibody molecules: Mouse antigen-binding domains with human constant region domains"; Proc. Natl. Acad. Sci. USA; vol. 81; Nov. 1984; pp. 6851-6855.
Murphy, A. et al.; "Induction of protein kinase C Substrates, Myristoylated alanine-rich C kinase substrate (MARCKS) and MARCKS-related protein (MRP), by amyloid β-protein in mouse BV-2 microglial cells"; Neuroscience Letters 347; 2003; pp. 9-12.
Musunuri, S. et al.; "Quantification of the Brain Proteome in Alzheimer's Disease Using Multiplexed Mass Spectrometry"; Journal of Proteome Research; vol. 13; Mar. 10, 2014; pp. 2056-2068.
Neuberger, M. S. et al.; "Recombinant antibodies possessing novel effector functions"; Nature; vol. 312; Dec. 13, 1984; pp. 604-608.
Poynton, R. A. et al.; "Peroxiredoxins as biomarkers of oxidative stress"; Biochimica et Biophysica Acta; vol. 1840; 2013; pp. 906-912.
Robinson, M. D. et al.; "edgeR: a Bioconductor package for differential expression analysis of digital gene expression data"; Bioinformatics; vol. 26; No. 1; 2010; pp. 139-140.
Rossier, J. S. et al.; "Microchannel networks for electrophoretic separations"; Electrophoresis; vol. 20; 1999; pp. 727-731.
Schlachetzki, J. C. M. et al.; "Studying neurodegenerative diseases in culture models"; Revista Brasileira de Psiquiatria; vol. 35; Jan. 1, 2013; pp. S92-S100.
Selkoe, D. J.; "Alzheimer's Disease: Genes, Proteins, and Therapy"; Physiological Reviews; vol. 81; No. 2; Apr. 2001; pp. 741-766.
Stansley, B. et al.; "A comparative review of cell culture systems for the study of microglial biology in Alzheimer's disease"; Journal of Neuroinflammation; vol. 9; No. 115; 2012; 8 pages.
Sunohara, J. R. et al.; "Regulation of MARCKS and MARCKS-related protein expression in BV-2 microglial cells in response to lipopolysaccharide"; Journal of Neurochemistry; vol. 78; 2001; pp. 664-672.
Takeda, S. et al.; "Construction of chimaeric processed immunoglobulin genes containing mouse variable and human constant region sequences"; Nature; vol. 314; Apr. 4, 1985; pp. 452-454.
Ward, E. S. et al.; "Binding activities of a repertoire of single immunoglobulin variable domains secreted from *Escherichia coli*"; Letters to Nature; vol. 341; Oct. 12, 1989; pp. 544-546.
Wisniewski, H. M. et al.; "Ultrastructural studies of the cells forming amyloid in the cortical vessel wall in Alzheimer's disease"; Acta Neuropathol; vol. 84; 1992; pp. 117-127.
Zhang, M. et al.; "Overexpression of ubiquitin carboxyl-terminal hydrolase L1 (UCHL1) delays Alzheimer's progression in vivo"; Scientific Reports; vol. 4; No. 7298; Dec. 3, 2014; 6 pages.
Zhang, Y. PhD et al.; "Autosomal recessive phosphoglucomutase 3 (PGM3) mutations link glycosylation defects to atopy, immune deficiency, autoimmunity, and neurocognitive impairment"; J. Allergy Clin Immunol; vol. 133; No. 5; May 2014; pp. 1400-1409.e5.
Japanese Office Action issued for JP2017-549301 dated Jan. 14, 2020 (4 pages) and (english translation of Japanese OA attached (6 pages)).

* cited by examiner

Fig. 1

```
         10         20         30         40         50
MVKIVTVKTQ AYQDQKPGTS GLRKRVKVFQ SSANYAENFI QSIISTVEPA
*                *
         60         70         80         90        100
QRQEATLVVG GDGRFYMKEA IQLIARIAAA NGIGRLVIGQ NGILSTPAVS 110        120        130        140        150
CIIRKIKAIG GIILTASHNP GGPNGDFGIK FNISNGGPAP EAITDKIFQI
                  *
        160        170        180        190        200
SKTIEEYAVC PDLKVDLGVL GKQQFDLENK FKPFTVEIVD SVEAYATMLR 210        220        230        240        250
SIFDFSALKE LLSGPNRLKI RIDAMHGVVG PYVKKILCEE LGAPANSAVN 260        270        280        290        300
CVPLEDFGGH HPDPNLTYAA DLVETMKSGE HDFGAAFDGD GDRNMILGKH 310        320        330        340        350
GFFVNPSDSV AVIAANIFSI PYFQQTGVRG FARSMPTSGA LDRVASATKI
                                                      *
        360        370        380        390        400
ALYETPTGWK FFGNLMDASK LSLCGEESFG TGSDHIREKD GLWAVLAWLS
  *
        410        420        430        440        450
ILATRKQSVE DILKDHWQKY GRNFFTRYDY EEVEAEGANK MMKDLEALMF
                  *
        460        470        480        490        500
DRSFVGKQFS ANDKVYTVEK ADNFEYSDPV DGSISRNQGL RLIFTDGSRI
                *
        510        520        530        540        550
VFRLSGTGSA GATIRLYIDS YEKDVAKINQ DPQVMLAPLI SIALKVSQLQ
   *
        560
ERTGRTAPTV IT
```

Fig. 2

```
        10         20         30         40
MSDKPDMAEI EKFDKSKLKK TETQEKNPLP SKETIEQEKQ AGES
*                     *                *
```

Fig. 3
A
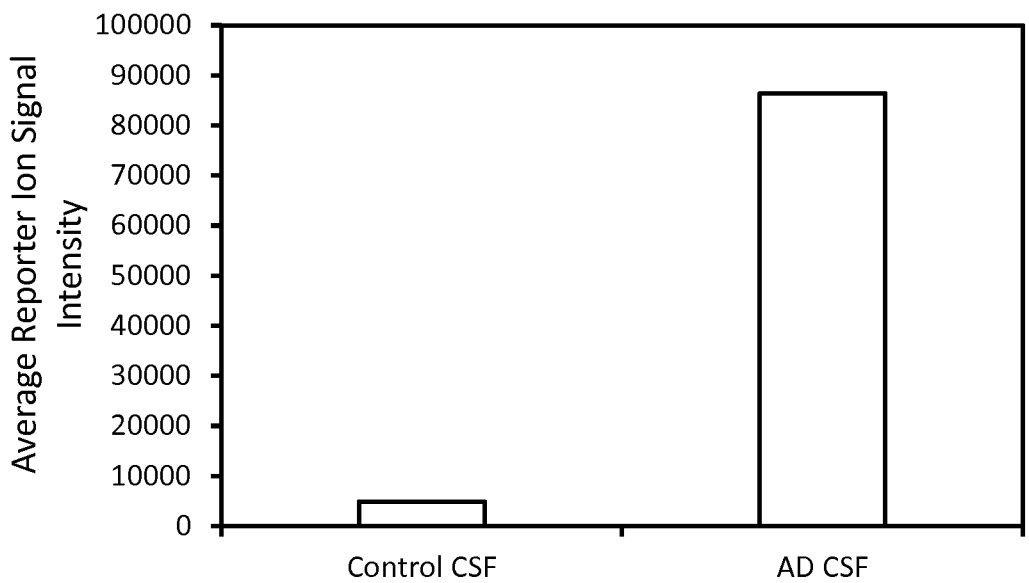
B
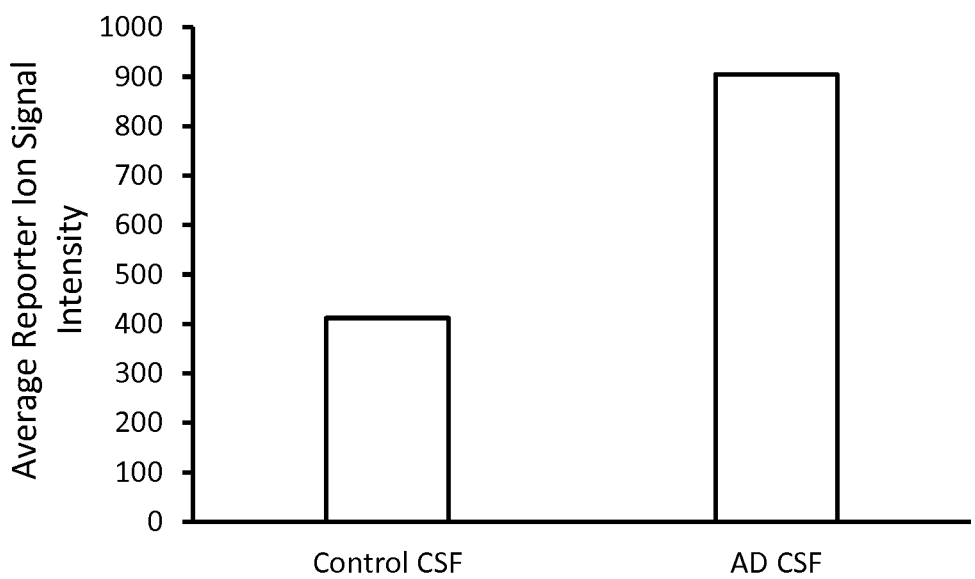

MATERIALS AND METHODS FOR DIAGNOSIS AND TREATMENT OF ALZHEIMER'S DISEASE

CROSS-REFERENCE TO RELATED APPLICATIONS

This application is the U.S. National Stage Application of International Patent Application No. PCT/EP2016/055883 filed on Mar. 17, 2016, which claims priority to GB Application No. 1504432.4, filed on Mar. 17, 2015, the contents of each of which is incorporated herein by reference in its entirety.

FIELD OF THE INVENTION

The invention relates to biomarker panels and methods for diagnosing, staging and assessing the likelihood of developing a neurocognitive disorder. In particular, the invention concerns biomarker panels useful in methods for the diagnosis and treatment of Alzheimer's disease.

BACKGROUND OF THE INVENTION

Alzheimer's disease (AD) is the most common type of dementia in aging adults with the number of people living with AD projected to increase dramatically over the next few decades, making the search for treatments and tools to diagnose and measure disease progression increasingly urgent.

Approved treatments are few and of limited efficacy, serving mostly to slow or delay progression. Currently there is no cure.

AD gives rise to an irreversible progressive loss of cognitive functions and of functional autonomy. While the time it takes for AD to develop will vary from person to person, advanced signs include severe memory impairment, confusion, language disturbances, impaired judgment, personality and behaviour changes. Patients with AD may become non-communicative and hostile. As the disease ends its course in profound dementia, patients are unable to care for themselves and often require institutionalization or professional care in the home setting. While some patients may live for many years after being diagnosed with AD, the average life expectancy after diagnosis is eight years.

Although AD can only be definitively diagnosed by brain biopsy or upon autopsy after a patient died, in clinical settings brain biopsy is rarely performed and diagnosis is still primarily made based on the history of the symptoms and depends on a battery of neurological, psychometric and biochemical tests, which include the measurement of biomarkers.

Nevertheless, these present methods are still not satisfactory in the diagnosing of AD and other neurocognitive disorders at the early stage of the disease when potential therapies are more likely to prevent or slow down neurodegeneration.

As the brain is in direct contact with the cerebrospinal fluid (CSF), and pathological changes in the brain often result in altered biochemical composition of the CSF, this makes it an ideal source for biomarkers of neurocognitive disorders. In AD, currently three "core" CSF biomarkers (amyloid $\beta$1-42, total tau and phosphorylated tau) are routinely used to diagnose AD. All three of these CSF biomarkers demonstrate high levels of sensitivity (falling within the 80-90% criteria specified by the National Institute of Neurological and Disorders and Stroke and the Alzheimer Disease and Related Disorders Work Group) but struggle to differentiate AD from other forms of dementia and neurological disorders. For example, CSF amyloid $\beta$1-42 levels are decreased in AD but are also reportedly lower in Lewy body dementia (LBD), fronto-temporal dementia (FTD), vascular dementia (VaD), amyotrophic lateral sclerosis (ALS) and Creutzfeldt-Jakob disease (CJD) (Blennow K et al., Nat Rev Neurol. 2010, 6:131-44). Similarly, total tau levels are raised in AD but are also found elevated following stroke, traumatic brain injury, FTD, VaD and CJD1.

Two key features of an ideal biomarker are high specificity for disease versus non-disease and high sensitivity to distinguish between disease types. In addition, biomarkers that reflect the pathological process of AD and that are able to detect changes at a very early stage of the disease, before degeneration is observed by brain imaging and neuropathological tests, are very sought after.

The ideal biomarker or biomarker panel would be the first indicator for starting treatment as early as possible, when degeneration is still limited, it would prove immensely valuable in screening the effectiveness of new therapies in clinical trial settings, particularly those trials that are focused on preventing the development of neuropathological changes. Such biomarker or biomarker panel would also be useful in the follow-up of the development of the disease.

Hence, there remains a need for biomarkers that may perform with superior sensitivity and/or specificity in the early diagnosis, staging and prognostic monitoring of patients with Alzheimer's disease and other neurocognitive disorders.

SUMMARY OF THE INVENTION

The present invention, therefore, provides novel biomarker panels for use in methods for diagnosing, staging and assessing the likelihood of developing a neurocognitive disorder, in particular Alzheimer's disease.

In a first aspect, the present invention provides for a biomarker panel comprising:
  i) phosphoglucomutase 1 comprising or having the amino acid sequence of SEQ ID NO:1 or an isoform or a variant or a fragment thereof; and/or
  ii) thymosin beta-4 comprising or having the amino acid sequence of SEQ ID NO:2 or a variant or a fragment thereof.

In one embodiment of this first aspect, the panel further comprises ubiquitin carboxy-terminal hydrolase L1 which comprises or has an amino acid sequence of SEQ ID NO:4 or an isoform or a variant or a fragment thereof; and/or vitamin D binding protein which comprises or has an amino acid sequence of SEQ ID NO: 5 or an isoform or a variant or a fragment thereof.

In another embodiment of this first aspect, the panel further comprises one or more biomarkers selected from a protein involved in a KEGG pathway wherein KEGG pathway is selected from the group of complement and coagulation cascade, or glycolysis/glycogenesis, or prion disease, or amino and nucleotide sugar metabolism, or antigen processing and presentation, or extracellular matrix-receptor interaction, or focal adhesion, or regulation of actin cytoskeleton or alanine/aspartate/glutamate metabolism.

In another embodiment of this aspect the panel further comprises at least one, optionally two or more, biomarkers selected from any one of Tables 1, 2, 3, 4, 5, 6, 7, or 8 or fragments thereof.

In another embodiment of this aspect, the panel further comprises at least two or more, optionally at least three or more biomarkers selected from the group of Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

In a second aspect, there is provided a method for diagnosing a neurocognitive disorder in a subject, the method comprising:
a) assaying a sample obtained from said subject for the biomarkers of the biomarker panel according to the first aspect and its embodiments;
b) measuring in said sample the concentration or the amount of each of the biomarkers of said biomarker panel;
c) determining whether that subject has a neurocognitive disorder by comparing said concentration or amount of each of the biomarker of the biomarker panel in said sample with reference concentrations or amounts of said biomarkers.

In a third aspect, there is provided a method for staging a neurocognitive disorder in a subject, the method comprising:
a) assaying a sample obtained from said subject for the biomarkers of the biomarker panel according to the first aspect and its embodiments;
b) measuring in said sample the concentration or the amount of each of the biomarkers of said biomarker panel;
c) determining the stage of the neurocognitive disorder in said subject by comparing said concentration or amount of each of the biomarkers of the biomarker panel in said sample with reference concentrations or amounts of said biomarkers.

In a fourth aspect the present invention provides for a method for assessing in a subject the likelihood of developing a neurocognitive disorder, the method comprising:
a) assaying a sample obtained from said subject for the biomarkers of the biomarker panel according to the first aspect and its embodiments;
b) measuring in said sample the concentration or the amount of each of the biomarkers of said biomarker panel;
c) determining whether that subject is likely to develop a neurocognitive disorder by comparing said concentration or amount of each of the biomarkers of the biomarker panel in said sample with reference concentrations or amounts of said biomarkers.

In embodiments of these second, third and fourth aspects, the neurocognitive disorder is characterised by microglia activation and/or is selected from the group of mild cognitive impairment, Alzheimer's disease, vascular dementia, dementia with lewy bodies, fronto-temporal dementia or combinations thereof.

In particular, the neurocognitive disorder is Alzheimer's disease.

In a fifth aspect of the present invention there is provided a method for treating Alzheimer's disease in a subject, the method comprising:
a) assaying a sample obtained from said subject for the biomarkers of the biomarker panel according to the first aspect and its embodiments;
b) measuring in said sample the concentration or the amount of each of the biomarkers of said biomarker panel;
c) determining whether that subject has Alzheimer's disease by comparing said concentration or amount of each of the biomarkers in said sample with reference concentrations or amounts of said biomarkers;
d) administering to said subject an Alzheimer's disease treatment selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

In a sixth aspect of the present invention there is provided a method for aiding the prognosis of a treatment for Alzheimer's disease in a subject, the method comprising:
a) assaying a sample obtained from said subject for the biomarkers of the biomarker panel according to the first aspect and its embodiments;
b) measuring in said sample the concentration or the amount of each of the biomarkers of said biomarker panel;
c) determining whether said treatment for Alzheimer's disease is successful by comparing said concentration or amount of each of the biomarker in said sample with reference concentrations or amounts of said biomarkers.

In embodiments of this sixth aspects the treatment for Alzheimer's disease may be selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

In other embodiments of the second to sixth aspects the sample is selected from the group of cerebrospinal fluid (CSF), blood, plasma, serum, saliva, urine, tissue (e.g. brain tissue) or combinations thereof. Preferably, the sample is CSF and/or the subject is a human subject, optionally a human subject previously diagnosed with mild cognitive impairment or a human subject undergoing further clinical assessment of dementia.

In other embodiments of the second to sixth aspects the assaying in step a) and/or the measuring in step b) comprise:
i) contacting said sample with one or more binding agents to each of said biomarkers of the biomarker panel; or
ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or
iv) detecting in said sample by 2D gel electrophoresis each of said biomarkers of the biomarker panel; or
v) any combinations of i), ii), iii) and/or iv).

Preferably, the assaying step a) and/or the measuring step b) comprise detecting one or more fragments of said biomarker in the biomarker panel.

Optionally, the sample is immobilised on a solid support.

In a seventh aspect the present invention provides for a method for identifying biomarkers in a sample obtained from a subject, wherein the biomarkers are suitable for diagnosing or staging Alzheimer's disease, wherein the method comprises using activate microglia cells (e.g. BV2 cells) and/or their culture media in mass spectrometry and/or wherein the biomarkers are identified in said sample by using activated microglia cells as a reference.

Preferably, the biomarker panel comprises the biomarkers as defined in the first aspect and its embodiments.

In embodiments of this seventh aspect, the sample is selected from the group of CSF, blood, serum or plasma.

In an eighth aspect the present invention provides for a kit comprising reagents for assaying and/or measuring in a sample biomarkers of a biomarker panel according to the first aspect and its embodiments.

In one embodiment of this eighth aspect, the reagents comprise one or more binding agents which specifically bind to the biomarkers of the biomarker panels. Preferably, the one or more binding agents are primary antibodies, wherein each primary antibody specifically binds to a different biomarkers of the biomarker panel.

In another embodiment, the reagents further comprise one or more secondary antibodies which specifically bind to said primary antibodies. Optionally, the secondary antibodies are labelled.

In other embodiments the sample is selected from the group of cerebrospinal fluid (CSF), blood, plasma, serum, saliva, urine, tissue (e.g. brain tissue) or combinations thereof.

BRIEF DESCRIPTION OF THE DRAWINGS

FIG. 1. Sequence of human phosphoglucomutase 1. Amino acids flagged by symbol □ or a * indicate amino acids which are replaced by a different or a modified amino acid in an isoform or a variant of human phosphoglucomutase 1, respectively.

FIG. 2. Sequence of human thymosin beta-4. Amino acids outlined by a * indicates amino acids which are replaced by a different amino acid in a variant of human thymosin beta-4.

DEFINITIONS

Figure 3:
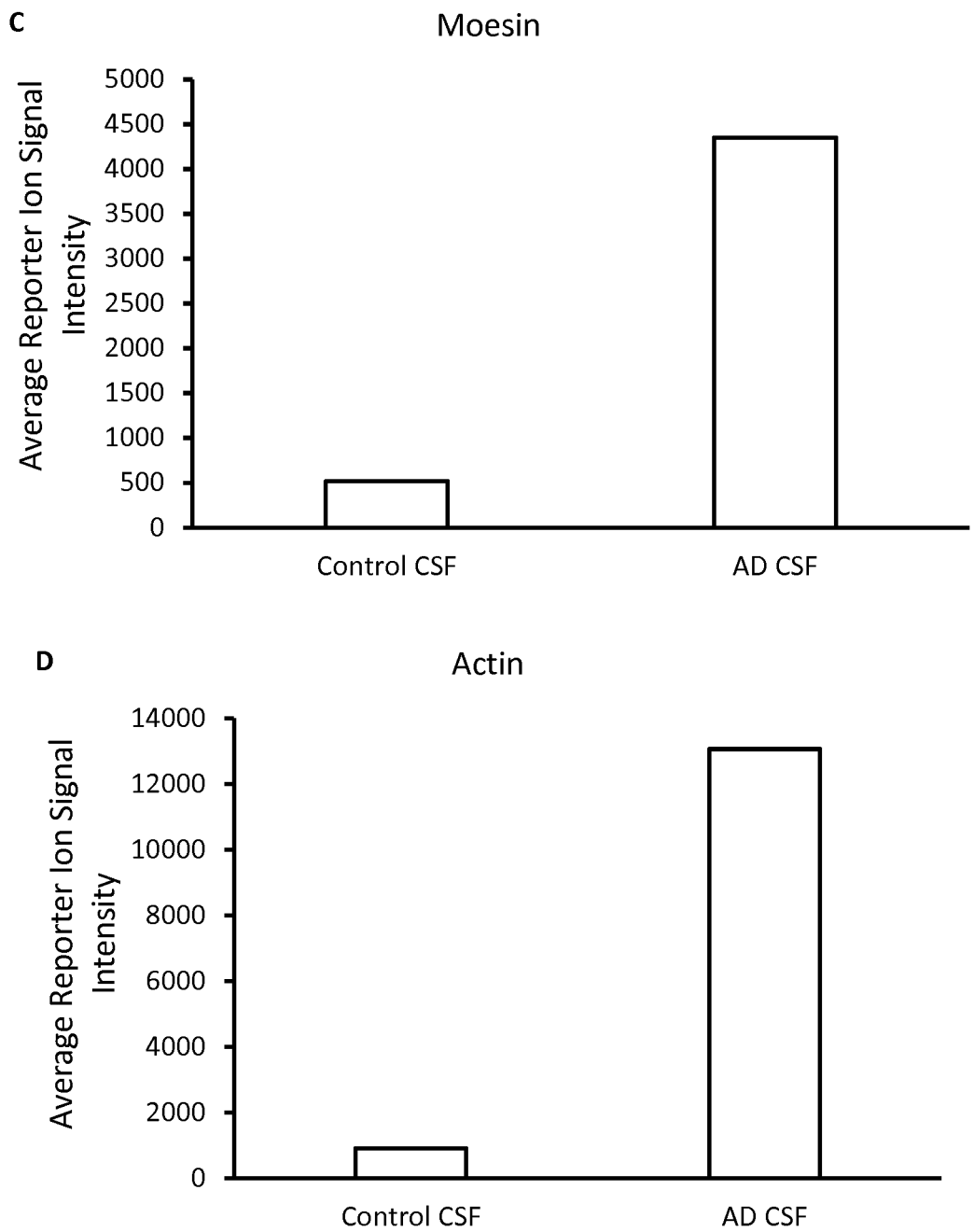
FIG. 3. Up-regulation of peroxideroxin-1 (A), MARCKS-related protein (B), Meosin (C) and Actin (D) in AD CSF versus control CSF shown as function of the average signal intensity.
Figure 4:
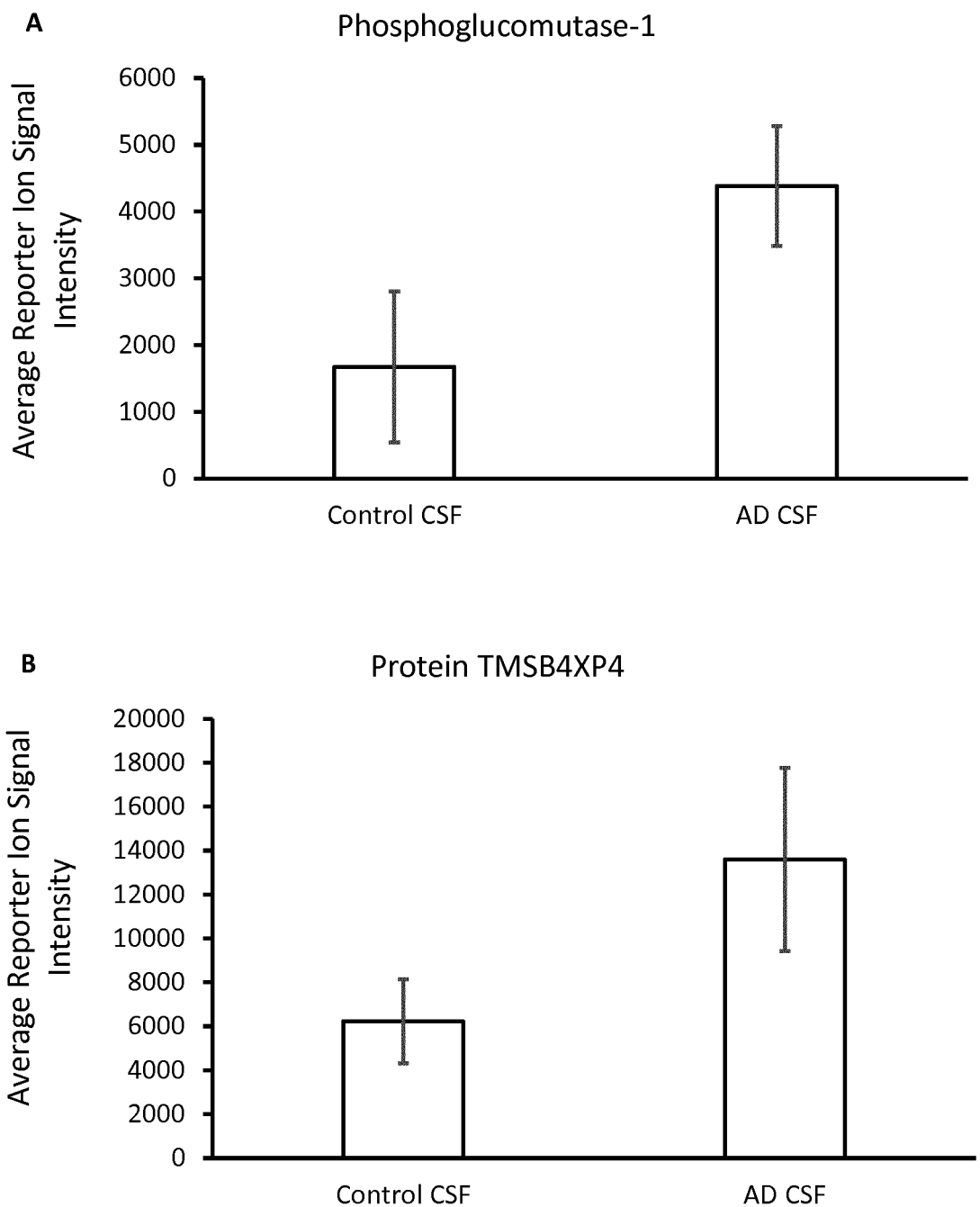
FIG. 4. Up-regulation of Phosphoglucomutase-1 (A), Protein TMSB4XP4 (B), Ubiquitin carboxyl-terminal hydrolase isozyme L1 (C) and Vitamin-D binding protein (D) in AD CSF versus control CSF shown as function of the average signal intensity.
Figure 4:
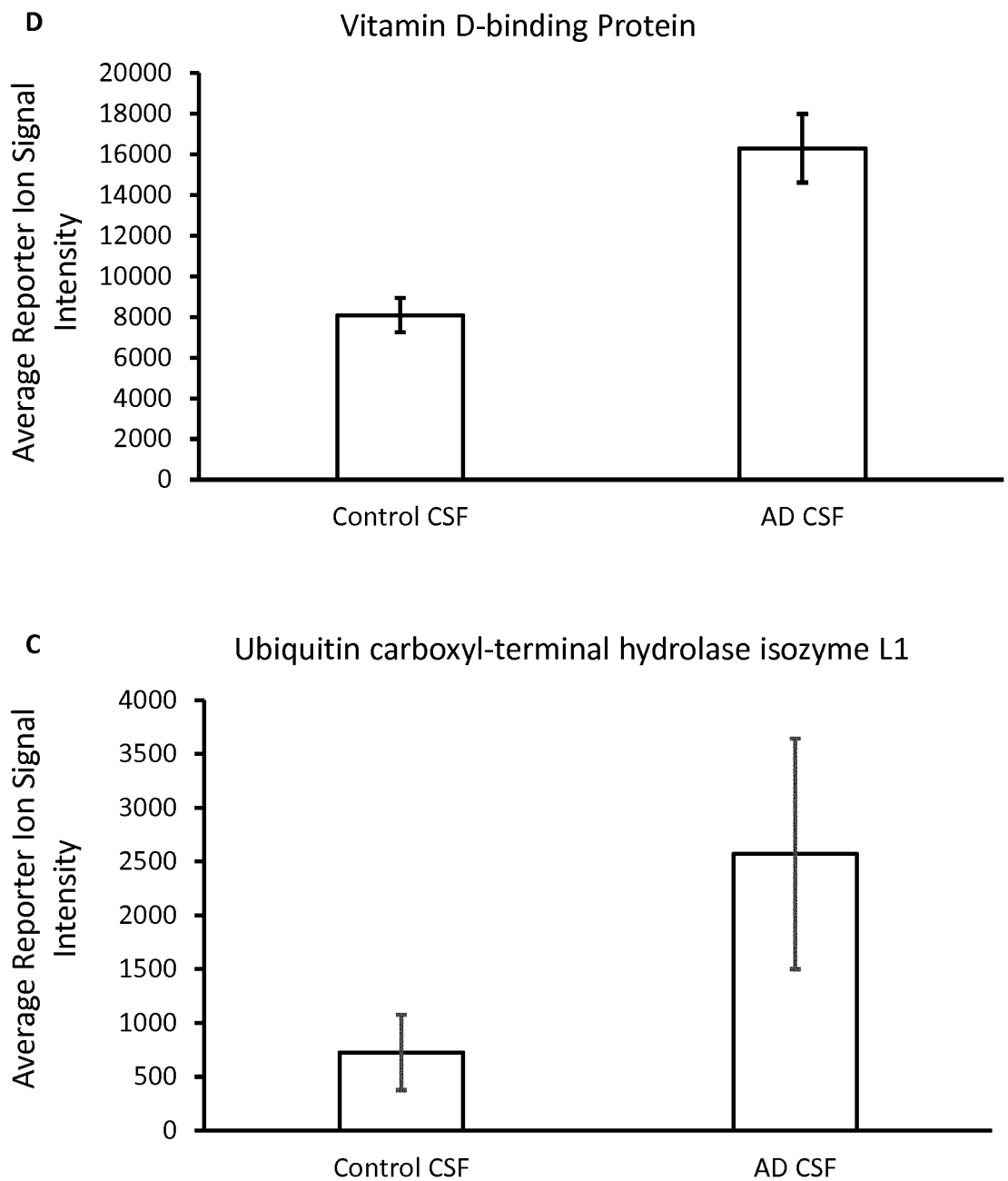

The term "biomarker(s)" includes all biologically relevant forms of the protein identified, including post-translational modifications. For example, the biomarker can be present in a glycosylated, phosphorylated, multimeric, fragmented or precursor form. A biomarker fragment may be naturally occurring or, for example, enzymatically generated and still retaining the biologically active function of the full protein. Fragments will typically be at least about 10 amino acids, usually at least about 50 amino acids in length, and can be as long as 300 amino acids in length or longer.

The term "canonical sequence" is used herein as to refer to the most prevalent sequence and/or the most similar sequence among orthologous species. In particular, unless otherwise specified, the canonical sequence refers herein to the human sequence.

The term "KEGG pathway" refers to a collection of manually drawn pathway maps representing molecular interactions and reaction networks for metabolism, genetic information processing, environmental information processing, cellular processes, organismal systems, human diseases and drug development. "KEGG pathways mapping" is the process to map molecular datasets, especially large-scale datasets in genomics, transcriptomics, proteomics, and metabolomics, to the KEGG pathway maps for biological interpretation of higher-level systemic functions; (genome.jp/kegg/pathway.html).

The term "concentration or amount" refers to the relative concentration or amount of biomarker in the sample, for example as determined by LC-MS/MS label free quantification approaches such as area under the curve and spectral counting.

The term "comparing" or "compare" or grammatical equivalents thereof, means measuring the relative concentration or amount of a biomarker in a sample relative to other samples (for example protein concentrations or amounts stored in proprietary or public database).

The term "reference concentration or amount" or "reference value" refers to, but it is not limited to, protein concentrations or amounts stored in proprietary or public databases. The "reference concentration or amount" may have been obtained from a large screening of patients, or by reference to a known or previously determined correlation between such a determination and clinical information in control patients. For example, the reference values may be determined by comparison to the concentration or amount of the biomarkers in a control subject, for example a healthy person (i.e. without dementia) of similar age and gender as the subject. Alternatively, the reference values are values which can be found in literature such as the ApoE ε4 allele presence whereby the presence or absence of the mutations at position 112 and 158 represent the reference to be compared to, or like the levels of total tau (T-tau)>350 ng/L, phospho-tau (P-tau)>80 ng/L and Aβ42<530 ng/L in the CSF (Hansson O, et al., Lancet Neurol. 2006, 5:228-34). In addition, the reference values may have been obtained from the same subject at one or more time points which precede in time the test time point. Such earlier sample may be taken one week or more, one month or more, three months or more, most preferably six months or more before the date of the test time point. In some embodiments, multiple earlier samples may be compared in a longitudinal manner and the slope of change in biomarker expression may be calculated as a correlate of cognitive decline. The reference value or reference level can be an absolute value; a relative value; a value that has an upper or a lower limit; a range of values; an average value; a median value, a mean value, or a value as compared to a particular control or baseline value.

According to the present invention, the level of a biomarker is increased when the level of said biomarker in a sample is higher than a reference value. The levels of a biomarker are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more higher than the reference value.

Likewise, in the context of the present invention, the level of a biomarker is decreased when the level of said biomarker in a sample is lower than a reference value. The levels of a biomarker are considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more lower than the reference value.

The term "control" or as used herein "non AD control" or "non AD subject" refers to a tissue sample or a bodily fluid sample taken from a human or non-human subject diagnosed or presenting symptoms of a cognitive abnormality but defined, with respect to the existing biochemical tests, as non AD subjects.

The term "antibody" includes polyclonal antiserum, monoclonal antibodies, fragments of antibodies such as single chain and Fab fragments, and genetically engineered antibodies. The antibodies may be chimeric or of a single species.

The terms "selected reaction monitoring", "SRM" and "MRM" means a mass spectrometry assay whereby precursor ions of known mass-to-charge ratio representing known biomarkers are preferentially targeted for analysis by tandem mass spectrometry in an ion trap or triple quadrupole mass spectrometer. During the analysis the parent ion is fragmented and the number of daughter ions of a second predefined mass-to-charge ratio is counted. Typically, an equivalent precursor ion bearing a predefined number of stable isotope substitutions but otherwise chemically identical to the target ion is included in the method to act as a quantitative internal standard.

The term "isolated", or grammatical equivalents thereof, means throughout this specification, that the protein, antibody, polynucleotide or chemical molecule as the case may be, exists in a physical milieu distinct from that in which it may occur in nature.

As used herein, the term "subject" includes any human or non-human animal. The term "non-human animal" includes all vertebrates, e.g., mammals and non-mammals, such as non-human primates, rodents, sheep, dogs, cats, horses, cows, chickens, amphibians, reptiles, etc.

The term "treat", "treating", "treatment", "prevent", "preventing" or "prevention", or grammatical equivalents thereof, includes therapeutic treatments, prophylactic treatments and applications in which one reduces the risk that a subject will develop a disorder or other risk factor. Treatment does not require the complete curing of a disorder and encompasses the reduction of the symptoms or underlying risk factors.

The term "diagnosis", or grammatical equivalents thereof, as used herein, includes the provision of any information concerning the existence or presence, non-existence or absence or probability of the disorder in a patient. It further includes the provision of information concerning the type or classification of the disorder or of symptoms which are or may be experienced in connection with it. This may include, for example, diagnosis of the severity of the disorder. It encompasses prognosis of the medical course of the disorder, for example its duration, severity and the course of progression from mild cognitive impairment (MCI) to AD or other dementias.

The term "staging", or grammatical equivalents thereof, as used herein, means identifying in a subject the stage of a neurocognitive disorder, in particular AD. For example, AD is characterised by 3 stage or 7 stages, depending on the diagnostic framework used. The Global Dementia Scale is one such measure of global function. It is measured by assessment of severity including cognition and function against a standardised set of severity criteria.

The term "efficacy" indicates the capacity for beneficial change of a given intervention (e.g. a drug, medical device, surgical procedure, etc.). If efficacy is established, that intervention is likely to be at least as good as other available interventions, to which it will have been compared. The term "efficacy" and "effectiveness" are used herein interchangeably.

The term "comprising" indicates that the subject includes all the elements listed, but may, optionally, also include additional, unnamed elements (i.e. open).

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless the context dictates otherwise, the definitions of the features/terms set out above are not limited to any particular aspect or embodiment of the invention and apply equally to all aspects and embodiments which are described herein.

Abbreviations

CSF (cerebrospinal fluid); LBD (Lewy body dementia); FTD (fronto-temporal dementia); VaD (vascular dementia); ALS (amyotrophic lateral sclerosis); CJD (Creutzfeldt-Jakob disease); CNS (central nervous system); LPS (lipopolysaccharide); INFγ (interferon-gamma); TMT® (Tandem Mass Tag®); TEAB (Tetra-ethylamonium Bicarbonate), SDS (Sodium dodecyl sulfate); TCEP (Tris(2-carboxyethyl) phosphine); ACN (Acetonitril); PGM1 (phosphoglucomutase 1); TMS4 (Thymosin beta-4).

DETAILED DESCRIPTION

The brains of patients with AD are characterized by amyloid plaques and neurofibrillary "tangles". Numerous lines of genetic, epidemiologic, and pathologic evidence point to the amyloid precursor protein and its proteolytic product, amyloid β-peptide (Aβ), as central players in AD etiology (Selkoe D J, Physiol. Rev. 2001, 81:741-66). While plaques and tangles are most often associated with the disease, a third pathological feature "gliosis" or inflammation of the brain is also much more integral to AD pathoetiology than once appreciated.

Early events in neurodegenerative pathology, including those typical of AD, involves activation of microglial cells (Mandrekar S et al., CNS Neurol Disord Drug Targets. 2010, 9:156-67). Much interest has been focused on the role of microglia in neurodegenerative diseases in recent times due to an increasing number of genetic and biomarker discovery programs and growing evidence suggesting that inflammation has a role in disease pathogenesis (Wisniewski H M, et al., Acta Neuropathol. 1992, 84:117-27).

Microglia are a type of glial cell and are the resident macrophage-like cells of the central nervous system (CNS) (Mandrekar S et al., CNS Neurol Disord Drug Targets. 2010, 9:156-67). Within the CNS, microglial cells perform a variety of different functions related to the immune response and the maintenance of cellular homeostasis. Microglia sense the environment around them, can be activated by various factors and referee neuroinflammatory and neuroprotective responses in the brain, responding to the formation of amyloid plaques in brains of AD patients. This activation can take different forms, and the so called M1 activation state causes the release of pro-inflammatory cytokines such as TNF-α, IL-1β and reactive oxygen/nitrogen species ROS/NOS (Henkel J, Neuroimmune Pharmacol. 2009, 4:389-98). This ultimately may cause or increase neuronal damage.

There appears to be different mechanisms of microglial activation, including in vivo intrinsic regulation, Aβ phagocytosis, and microglial Aβ receptor complex (Mandrekar S et al., CNS Neurol Disord Drug Targets. 2010, 9:156-67).

The present inventors hypothesize that, during the early stage of AD pathology, activated microglia will secrete distinct proteins into the brain. Such proteins would then transfer into the cerebrospinal fluid (CSF) and other biological fluids and could be identified and validated as biomarkers for early AD pathology.

1. Biomarker Panels and Methods of Using Thereof

The present invention relates to such novel biomarkers and their use in methods for diagnosing, staging and assessing the likelihood of developing a neurocognitive disorder, in particular Alzheimer's disease (AD).

The biomarker panels disclosed herein represent a peripheral signal that reflects events and pathways modulation in brain tissue that could not be tested by biopsy or other invasive tests. Because the biomarker panels reflect the neuroinflammation resulting from microglia activation in AD subject, they represent ideal measurable indicators of the disease at an early stage.

The biomarker panel comprises phosphoglucomutase 1 comprising or having the amino acid sequence of SEQ ID NO:1 or thymosin beta-4 comprising or having the amino acid sequence of SEQ ID NO:2.

Human phosphoglucomutase 1 (PMG1; P36871) is an isozyme of phosphoglucomutase (PGM) and belongs to the phosphohexose mutase family. There are several PGM isozymes, which are encoded by different genes and catalyse the transfer of phosphate between the 1 and 6 positions of glucose. Mutations in this gene cause glycogen storage disease type 14. Alternatively spliced transcript variants encoding different isoforms have been identified.

Human thymosin beta-4 (TMSB4X; P62328) plays an important role in the organization of the cytoskeleton. It binds to and sequesters actin monomers (G-actin) and therefore inhibits actin polymerization.

The biomarker panel may also comprises phosphoglucomutase 1 comprising or having the amino acid sequence of SEQ ID NO:1 and thymosin beta-4 comprising or having the amino acid sequence of SEQ ID NO:2.

The biomarker panel may also comprise an isoform or a variant or a fragment of phosphoglucomutase 1 comprising or having the amino acid sequence of SEQ ID NO:1; and/or a variant or a fragment of thymosin beta-4 comprising or having the amino acid sequence of SEQ ID NO:2.

An isoform is described herein as an alternative protein sequence with respect to the canonical sequence. Isoforms can be generated from the same gene by a single or by the combination of alternative promoter usage, alternative splicing, alternative initiation and ribosomal frameshifting.

A variant is described herein as to include natural variants such as (naturally occurring) polymorphisms, variations between strains, isolates or cultivars, disease-associated mutations and RNA editing events. A variant is generally reported as the amino acid change with respect to the canonical sequence. Most naturally occurring polymorphisms (also called single amino acid polymorphisms or SAPs) are due to a single nucleotide change at the codon level. RNA editing events include conversion, insertion and deletion of nucleotides.

A fragment is described herein as the result of proteolytic (enzymatic or else) cleavage of a protein. Fragments may be the results of natural proteolytic cleavage for example fragments generated during the activation of complement, the clotting cascade, or from enzymatic cleavage of matrix proteins. Alternatively, fragments may be generated in-vivo and/or in-vitro for example with proteases.

In one embodiment, the variant of phosphoglucomutase 1 comprises or has the amino acid sequence of SEQ ID NO: 1 and wherein
   a) threonine at position 19 is replaced by alanine; or
   b) asparagine at position 38 is replaced by tyrosine; or
   c) glutamine at position 41 is replaced by arginine; or
   d) aspartic acid at position 62 is replaced by histamine; or
   e) lysine at position 68 is replaced by methionine; or
   f) isoleucine at position 88 is replaced by valine; or
   g) threonine at position 115 is replaced by alanine; or
   h) glycine at position 121 is replaced by arginine; or
   i) arginine at position 221 is replaced by cysteine; or
   j) aspartic acid at position 263 is replaced by glycine or tyrosine; or
   k) glycine at position 291 is replaced by arginine; or
   l) glycine at position 330 is replaced by arginine; or
   m) glutamic acid at position 377 is replaced by lysine; or
   n) glutamic acid at position 388 is replaced by lysine; or
   o) tyrosine at position 420 is replaced by histidine; or
   p) valine at position 501 is replaced by isoleucine; or
   q) leucine at position 516 is replaced by proline; or
   r) methionine at position 1 is N-acetylmethionine; or
   s) lysine at position 16 is N6-acetyllysine; or
   t) serine at position 117 is phosphoserine; or
   u) lysine at position 349 is N6-acetyllysine; or
   v) tyrosine at position 353 is phosphotyrosine; or
   w) lysine at position 419 is N6-succinyllysine; or
   x) threonine at position 467 is phosphothreonine; or
   y) threonine at position 507 is phosphothreonine.

FIG. 1 shows the human sequence of human phosphoglucomutase 1 (SEQ ID NO:1); flagged by symbol □ are those amino acids that are replaced with a different amino acid in isoforms of human phosphoglucomutase 1 as indicated above in a) to q). Amino acids flagged by a * are those amino acids which are replaced by modified amino acids in isoforms of human phosphoglucomutase 1 as indicated above in r) to y).

In another embodiment the isoform of phosphoglucomutase 1 comprises or has the amino acid sequence of
a) SEQ ID NO:3 (isoform 2) and wherein methionine 1 is N-acetylmethionine; or
b) SEQ ID NO:1 from amino acids 198 to 562 (isoform 3).

In another embodiment the fragment of phosphoglucomutase 1 comprises or has the amino acid sequence of any one of SEQ ID NO: 6, SEQ ID NO: 7, SEQ ID NO: 8, SEQ ID NO: 9, or SEQ ID NO: 10; or SEQ ID NO: 11; or SEQ ID NO: 12; or SEQ ID NO: 13.

In another embodiment the variant of thymosin beta-4 comprises or has the amino acid sequence of SEQ ID NO: 2 and
   a) lysine at position 12 is replaced by proline; or
   b) serine at position 16 replaced by alanine; or
   c) leucine at position 18 is replaced by alanine or proline; or
   d) serine at position 2 is N-acetylserine; or
   e) lysine at position 26 is N6-acetyllysine; or
   f) lysine at position 9 is N6-acetyllysine.

FIG. 2 shows the sequence human of thymosin beta-4 (SEQ ID NO:2); flagged by symbol □ are those amino acids that are replaced with a different amino acid in isoforms of human thymosin beta-4 as indicated in a) to c) in the previous paragraph. Amino acids flagged by a * are those amino acids which are replaced by modified amino acids in isoforms of human thymosin beta-4 as indicated above in d) to f) in the previous paragraph.

In another embodiment the fragment of thymosin beta-4 comprises or has the amino acid sequence of any one of SEQ ID NO: 14, SEQ ID NO: 15, or SEQ ID NO: 16.

As shown later herein in the experimental section, the biomarker panels disclosed herein have been identified as a set of upregulated proteins found in the CSF of AD patients with respect to individual who present mild cognitive impairment but are not diagnosed with AD. In general clinical practice, biomarkers are measured as a set of at least 2, preferably at least 3 or 4.

Therefore, the biomarker panel according to the invention may further comprise ubiquitin carboxy-terminal hydrolase L1 (UCH-L1; D6R956) which comprises or has an amino acid sequence of SEQ ID NO:4 or an isoform or a variant or a fragment thereof; and/or vitamin D binding protein (VBPD; D6RBJ7) which comprises or has an amino acid sequence of SEQ ID NO: 5 or an isoform or a variant or a fragment thereof.

Examples of isoforms, variants or fragments of ubiquitin carboxy-terminal hydrolase L1 or vitamin D binding protein can be found in publically accessible databases such as Uniprot.

In one embodiment, the fragment of ubiquitin carboxy-terminal hydrolase L1 has or comprises the sequence as shown in SEQ ID NO:17. In another embodiment, the fragment of vitamin D binding protein has or comprises the sequence as shown in SEQ ID NO:18.

Hence, in one embodiment the biomarker panel comprises phosphoglucomutase 1 comprising or having the amino acid sequence of SEQ ID NO:1 or an isoform or a variant or a fragment thereof; and thymosin beta-4 comprising or having the amino acid sequence of SEQ ID NO:2 or a variant or a fragment thereof; and ubiquitin carboxy-terminal hydrolase L1 comprising or having the amino acid sequence of SEQ ID NO:4 or an isoform or a variant or a fragment thereof and/or vitamin D binding protein comprising or having the amino acid sequence of SEQ ID NO: 5 or an isoform or variant or a fragment thereof.

The biomarker panel may further comprise one or more biomarkers selected from proteins involved in a KEGG pathway wherein the KEGG pathway is selected from the group of complement and coagulation cascade, or glycolysis/glycogenesis, or prion disease, or amino and nucleotide sugar metabolism, or antigen processing and presentation, or extracellular matrix-receptor interaction, or focal adhesion, or regulation of actin cytoskeleton or alanine/aspartate/glutamate metabolism.

The biomarker panel may further comprise at least one, optionally two or more, biomarkers selected from any one of Tables 1, 2, 3, 4, 5, 6, 7, or 8 or fragments thereof.

In one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, optionally two or more biomarkers selected from Table 1 or fragments thereof.

TABLE 1

| Uniprot ID | Protein Name | All Uniprot matches |
|---|---|---|
| K7EJ74 | 116 kDa U5 small nuclear ribonucleoprotein component | K7EJ74; Q15029-3; K7EP67; Q15029; Q15029-2 |
| B4DJF2 | 14-3-3 protein epsilon (cDNA FLJ51975, moderately similar to 14-3-3 protein epsilon (14-3-3E)) | B4DJF2; I3L3T1; P62258 |
| E5RH77 | 40S ribosomal protein S14 | E5RH77; H0YB22; P62263 |
| M0R210 | 40S ribosomal protein S16 (Ribosomal protein S16, isoform CRA_a) | M0R210; P62249 |
| P63220 | 40S ribosomal protein S21 | P63220; Q8WVC2 |
| D6R9B6 | 40S ribosomal protein S3a (Ribosomal protein S3A, isoform CRA_e) | D6R9B6; D6RAT0; D6RG13; E9PFI5; F5H4F9; H0Y9Y4; P61247; D6RB09 |
| B5MCP9 | 40S ribosomal protein S7 | B5MCP9; P62081 |
| P10809 | 60 kDa heat shock protein, mitochondrial (60 kDa chaperonin) (Chaperonin 60) (CPN60) (Heat shock protein 60) (HSP-60) (Hsp60) (HuCHA60) (Mitochondrial matrix protein P1) (P60 lymphocyte protein) | E7ESH4; E7EXB4; P10809 |
| P30050 | 60S ribosomal protein L12 | P30050; P30050-2 |
| H0YKD8 | 60S ribosomal protein L28 | H0YKD8; H0YLP6; H0YMF4; P46779; P46779-2; P46779-3; P46779-4; P46779-5 |
| C9K025 | 60S ribosomal protein L35a | C9K025; F8WB72; F8WBS5; P18077 |
| P11021 | 78 kDa glucose-regulated protein (GRP-78) (Endoplasmic reticulum lumenal Ca(2+)-binding protein grp78) (Heat shock 70 kDa protein 5) (Immunoglobulin heavy chain-binding protein) (BiP) | P11021 |
| A6NL76 | Actin, alpha skeletal muscle | A6NL76; B8ZZJ2; C9JTX5; C9JUM1; F6QUT6; F8WB63; G5E9R0; I3L1U9; I3L3R2; J3KT65; K7EM38; P60709; P62736; P63261; P63267; P68032; P68133; Q562R1; Q5T8M7; Q5T8M8; C9JFL5; C9JZR7; E7EVS6 |
| P01009 | Alpha-1-antitrypsin (Alpha-1 protease inhibitor) (Alpha-1-antiproteinase) (Serpin A1) [Cleaved into: Short peptide from AAT (SPAAT)] | P01009; P01009-2 |
| P02765 | Alpha-2-HS-glycoprotein (Alpha-2-Z-globulin) (Ba-alpha-2-glycoprotein) (Fetuin-A) [Cleaved into: Alpha-2-HS-glycoprotein chain A; Alpha-2-HS-glycoprotein chain B] | P02765 |

TABLE 1-continued

| Uniprot ID | Protein Name | All Uniprot matches |
|---|---|---|
| F5GXS2 | Alpha-actinin-4 | F5GXS2; H0YJ11; H0YJW3; H7C144; H7C5W8; H9KV75; O43707; O43707-2; O43707-3; P12814; P12814-2; P12814-3; P12814-4 |
| P06733 | Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein) | P06733; P06733-2 |
| J3KMX3 | Alpha-fetoprotein | J3KMX3; P02771 |
| E9PEV0 | Amyloid beta A4 protein* | E9PEV0; P05067; P05067-11; P05067-2; P05067-3; P05067-4; P05067-5; P05067-6; P05067-7; P05067-8; P05067-9 |
| E9PK76 | Amyloid-like protein 2 | E9PK76; E9PQS3; Q06481; Q06481-2; Q06481-3; Q06481-4; Q06481-5; Q06481-6; E9PSC7 |
| D6RBE9 | Annexin | D6RBE9; D6RBL5; P08758 |
| A8MUN2 | Apolipoprotein B-100 | A8MUN2; P04114 |
| P00505 | Aspartate aminotransferase, mitochondrial (mAspAT) (EC 2.6.1.1) (EC 2.6.1.7) (Fatty acid-binding protein) (FABP-1) (Glutamate oxaloacetate transaminase 2) (Kynurenine aminotransferase 4) (Kynurenine aminotransferase IV) (Kynurenine--oxoglutarate transaminase 4) (Kynurenine--oxoglutarate transaminase IV) (Plasma membrane-associated fatty acid-binding protein) (FABPpm) (Transaminase A) | P00505-2; P00505 |
| Q9NVP1 | ATP-dependent RNA helicase DDX18 (EC 3.6.4.13) (DEAD box protein 18) (Myc-regulated DEAD box protein) (MrDb) | Q9NVP1 |
| O75531 | Barrier-to-autointegration factor (Breakpoint cluster region protein 1) [Cleaved into: Barrier-to-autointegration factor, N-terminally processed] | O75531 |
| F5H6I0 | Beta-2-microglobulin form pI 5.3 | F5H6I0; H0YLF3; P61769 |
| P80723 | Brain acid soluble protein 1 (22 kDa neuronal tissue-enriched acidic protein) (Neuronal axonal membrane protein NAP-22) | P80723; P80723-2; U3KQP0 |
| P04003 | C4b-binding protein alpha chain (C4bp) (Proline-rich protein) (PRP) | P04003 |
| F8VPD4 | CAD protein | F8VPD4; H7C2E4; P27708 |
| E7EMB3 | Calmodulin | E7EMB3; E7ETZ0; H0Y7A7; P62158; G3V361; Q96HY3 |
| P04040 | Catalase (EC 1.11.1.6) | P04040 |
| B4DRT0 | cDNA FLJ50184, highly similar to Histone-binding protein RBBP4 | B4DRT0; E9PC52; H0YCT5; H0YDK2; H0YEU5; H0YF10; Q09028; Q09028-2; Q09028-3; Q09028-4; Q16576; Q16576-2; Q5JP02 |
| B4DY72 | cDNA FLJ52360, highly similar to Heat-shock protein 105 kDa | B4DY72; Q92598-4; Q92598; Q92598-2; Q92598-3 |
| B4E3Q1 | cDNA FLJ61580, highly similar to Calsyntenin-1 | B4E3Q1; O94985; O94985-2; Q5SR54 |
| P62633 | Cellular nucleic acid-binding protein (CNBP) (Zinc finger protein 9) | P62633-7; P62633; P62633-2; P62633-3; P62633-4; P62633-5; P62633-6; P62633-8 |
| Q9Y696 | Chloride intracellular channel protein 4 (Intracellular chloride ion channel protein p64H1) | Q9Y696 |
| P12259 | Coagulation factor V (Activated protein C cofactor) (Proaccelerin, labile factor) [Cleaved into: Coagulation factor V heavy chain; Coagulation factor V light chain] | P12259 |
| E9PGP2 | Coagulation factor XI | E9PGP2; P03951; P03951-2; X6R3B1 |
| J3KR35 | Coiled-coil domain containing 12, isoform CRA_a (Coiled-coil domain-containing protein 12) | J3KR35; Q8WUD4 |
| P01031 | Complement C5 (C3 and PZP-like alpha-2-macroglobulin domain-containing protein 4) [Cleaved into: Complement C5 beta chain; Complement C5 alpha chain; C5a anaphylatoxin; Complement C5 alpha' chain] | P01031 |
| P10643 | Complement component C7 | P10643 |
| F5GX68 | Cytosine-specific methyltransferase (EC 2.1.1.37) | F5GX68; P26358; P26358-2; P26358-3 |
| E5RIA2 | Ectonucleotide pyrophosphatase/phosphodiesterase family member 2 | E5RIA2; E7EUF1; Q13822; Q13822-2; Q13822-3 |

TABLE 1-continued

| Uniprot ID | Protein Name | All Uniprot matches |
|---|---|---|
| Q9H4M9 | EH domain-containing protein 1 (PAST homolog 1) (hPAST1) (Testilin) | Q9H4M9; Q9NZN3 |
| A6PW80 | Elongation factor 1-alpha 1 | P68104; Q05639; Q5JR01; Q5VTE0; A6PW80 |
| K7EM90 | Enolase (EC 4.2.1.11) | K7EM90; P06733; P06733-2 |
| P47813 | Eukaryotic translation initiation factor 1A, X-chromosomal (eIF-1A X isoform) (Eukaryotic translation initiation factor 4C) (eIF-4C) | P47813; X6RAC9 |
| C9JQN7 | Eukaryotic translation initiation factor 3 subunit B | C9JQN7; P55884; P55884-2 |
| O60841 | Eukaryotic translation initiation factor 5B (eIF-5B) (Translation initiation factor IF-2) | O60841 |
| Q15024 | Exosome complex component RRP42 (Exosome component 7) (Ribosomal RNA-processing protein 42) (p8) | Q15024 |
| O14980 | Exportin-1 (Exp1) (Chromosome region maintenance 1 protein homolog) | O14980 |
| B1AK85 | F-actin-capping protein subunit beta (cDNA FLJ43095 fis, clone CORDB2000541, highly similar to F-actin capping protein subunit beta) | B1AK85; B1AK87; B1AK88; F6Q0E3; F6USW4; P47756; P47756-2 |
| P02671 | Fibrinogen alpha chain [Cleaved into: Fibrinopeptide A; Fibrinogen alpha chain] | P02671; P02671-2 |
| C9JC84 | Fibrinogen gamma chain | C9JC84; C9JEU5; P02679; P02679-2 |
| E9PHF0 | Filamin-A | E9PHF0; P21333; P21333-2; Q5HY54 |
| F8WE98 | Filamin-A | F8WE98; O75369; O75369-2; O75369-3; O75369-4; O75369-5; O75369-6; O75369-8; O75369-9; P21333; P21333-2; Q14315; Q14315-2; Q5HY54 |
| E7EN95 | Filamin-B | E7EN95; O75369; O75369-2; O75369-3; O75369-4; O75369-5; O75369-6; O75369-7; O75369-8; O75369-9 |
| H3BPS8 | Fructose-bisphosphate aldolase A | H3BPS8; H3BQN4; H3BR04; H3BU78; J3KPS3; P04075; P04075-2 |
| H3BMQ8 | Fructose-bisphosphate aldolase A | H3BMQ8; H3BQN4; H3BR04; H3BUH7; J3KPS3; P04075 |
| P17931 | Galectin-3 (Gal-3) (35 kDa lectin) (Carbohydrate-binding protein 35) (CBP 35) (Galactose-specific lectin 3) (Galactoside-binding protein) (GALBP) (IgE-binding protein) (L-31) (Laminin-binding protein) (Lectin L-29) (Mac-2 antigen) | P17931 |
| P06396 | Gelsolin (AGEL) (Actin-depolymerizing factor) (ADF) (Brevin) | P06396 |
| E7EUT5 | Glyceraldehyde-3-phosphate dehydrogenase (EC 1.2.1.12) | E7EUT5; P04406; P04406-2 |
| B5MDF5 | GTP-binding nuclear protein Ran (RAN, member RAS oncogene family, isoform CRA_c) | B5MDF5; H0YFC6; J3KQE5; P62826 |
| H0Y300 | Haptoglobin | H0Y300; H3BS21; J3QLC9; J3QR68; P00738; P00739; P00739-2; P00738-2 |
| G3V1N2 | HCG1745306, isoform CRA_a (Hemoglobin subunit alpha) | G3V1N2; P69905 |
| A8K7Q2 | Heat shock cognate 71 kDa protein (cDNA FLJ77848) | A8K7Q2; E7EP94; E9PKE3; E9PNE6; E9PS65; P08107; P08107-2; P11142; P17066; P34931; P54652; V9GZ37; E9PM13 |
| P08238 | Heat shock protein HSP 90-beta (HSP 90) (Heat shock 84 kDa) (HSP 84) (HSP84) | P08238 |
| E9PEW8 | Hemoglobin subunit delta | E9PEW8; E9PFT6; F8W6P5; P02042; P68871 |
| F8VTQ5 | Heterogeneous nuclear ribonucleoprotein A1 | F8VTQ5; F8VYN5; F8VZ49; F8W6I7; P09651; P09651-2; P09651-3; Q32P51 |
| Q00839 | Heterogeneous nuclear ribonucleoprotein U (hnRNP U) (Scaffold attachment factor A) (SAF-A) (p120) (pp120) | Q00839; Q00839-2; Q5RI18 |
| P22626 | Heterogeneous nuclear ribonucleoproteins A2/B1 (hnRNP A2/61) | P22626; P22626-2 |
| C9J0D1 | Histone H2A | C9J0D1; C9J386; P0C0S5; Q71UI9; Q71UI9-2; Q71UI9-3; Q71UI9-4 |
| Q8N257 | Histone H2B type 3-B (H2B type 12) | Q8N257; Q96A08; Q99880 |
| P01871 | Ig mu chain C region | P01871; P01871-2; P04220 |
| Q9Y6R7 | IgGFc-binding protein (Fcgamma-binding protein antigen) (FcgammaBP) | Q9Y6R7 |
| Q15181 | Inorganic pyrophosphatase (EC 3.6.1.1) (Pyrophosphate phospho-hydrolase) (PPase) | Q15181; Q5SQT6 |

TABLE 1-continued

| Uniprot ID | Protein Name | All Uniprot matches |
|---|---|---|
| Q16270 | Insulin-like growth factor-binding protein 7 (IBP-7) (IGF-binding protein 7) (IGFBP-7) (IGFBP-rP1) (MAC25 protein) (PGI2-stimulating factor) (Prostacyclin-stimulating factor) (Tumor-derived adhesion factor) (TAF) | Q16270; Q16270-2 |
| F5H7E1 | Inter-alpha-trypsin inhibitor heavy chain H1* | F5H7E1; F8WAS2; P19827 |
| E7ET33 | Inter-alpha-trypsin inhibitor heavy chain H3 | E7ET33; Q06033; Q06033-2 |
| O75874 | Isocitrate dehydrogenase [NADP] cytoplasmic (IDH) (EC 1.1.1.42) (Cytosolic NADP-isocitrate dehydrogenase) (IDP) (NADP(+)-specific ICDH) (Oxalosuccinate decarboxylase) | O75874 |
| Q9BR39 | Junctophilin-2 (JP-2) (Junctophilin type 2) | Q9BR39; Q9BR39-2 |
| P13645 | Keratin, type I cytoskeletal 10 (Cytokeratin-10) (CK-10) (Keratin-10) (K10) | P13645; Q7Z3Y7 |
| K7EMD9 | Keratin, type I cytoskeletal 13 | K7EMD9; K7ERE3; P13645; P13646; P13646-2; P13646-3; Q2M2I5 |
| P02533 | Keratin, type I cytoskeletal 14 (Cytokeratin-14) (CK-14) (Keratin-14) (K14) | P02533; P08779; P13645; Q7Z3Y7; Q7Z3Y8; Q7Z3Y9; Q7Z3Z0 |
| A8MT21 | Keratin, type I cytoskeletal 15 | A8MT21; B3KRA2; C9JM50; C9JTG5; F5GWP8; K7EMS3; K7EPJ9; P02533; P08727; P08779; P19012; Q04695 |
| K7EQQ3 | Keratin, type I cytoskeletal 9 | K7EQQ3; P35527 |
| P04264 | Keratin, type II cytoskeletal 1 (67 kDa cytokeratin) (Cytokeratin-1) (CK-1) (Hair alpha protein) (Keratin-1) (K1) (Type-II keratin Kb1) | P04264 |
| F5GY66 | Keratin, type II cytoskeletal 1b* | F5GY66; Q7Z794 |
| P35908 | Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2) | P35908 |
| P04259 | Keratin, type II cytoskeletal 6B (Cytokeratin-6B) (CK-6B) (Keratin-6B) (K6B) (Type-II keratin Kb10) | P04259; P04264 |
| P01042 | Kininogen-1 (Alpha-2-thiol proteinase inhibitor) (Fitzgerald factor) (High molecular weight kininogen) (HMWK) (Williams-Fitzgerald-Flaujeac factor) [Cleaved into: Kininogen-1 heavy chain; T-kinin (Ile-Ser-Bradykinin); Bradykinin (Kallidin I); Lysyl-bradykinin (Kallidin II); Kininogen-1 light chain; Low molecular weight growth-promoting factor] | P01042; P01042-2; P01042-3 |
| E7EQB2 | Lactotransferrin | E7EQB2; E7ER44; P02788; P02788-2 |
| P49006 | MARCKS-related protein (MARCKS-like protein 1) (Macrophage myristoylated alanine-rich C kinase substrate) (Mac-MARCKS) (MacMARCKS) | P49006 |
| Q9NU22 | Midasin (MIDAS-containing protein) | Q9NU22 |
| P26038 | Moesin (Membrane-organizing extension spike protein) | P26038 |
| C9JH43 | Neuronal cell adhesion molecule | C9JH43; C9JYY6; F8W775; Q92823; Q92823-2; Q92823-3; Q92823-4; Q92823-5; Q92823-6 |
| O15240 | Neurosecretory protein VGF [Cleaved into: Neuroendocrine regulatory peptide-1 (NERP-1); Neuroendocrine regulatory peptide-2 (NERP-2); Antimicrobial peptide VGF[554-577]] | O15240 |
| C9IZL7 | Non-POU domain-containing octamer-binding protein | C9IZL7; C9J4X2; Q15233; Q15233-2; Q8WXF1; Q8WXF1-2; C9JYS8; X6RDA4 |
| P23515 | Oligodendrocyte-myelin glycoprotein | P23515 |
| C9J5S7 | Peptidyl-prolyl cis-trans isomerase (EC 5.2.1.8) | C9J5S7; F8WE65; P62937 |
| P62937 | Peptidyl-prolyl cis-trans isomerase A (PPIase A) (EC 5.2.1.8) (Cyclophilin A) (Cyclosporin A-binding protein) (Rotamase A) [Cleaved into: Peptidyl-prolyl cis-trans isomerase A, N-terminally processed] | P62937; Q567Q0 |
| P23284 | Peptidyl-prolyl cis-trans isomerase B (PPIase B) (EC 5.2.1.8) (CYP-S1) (Cyclophilin B) (Rotamase B) (S-cyclophilin) (SCYLP) | P23284 |
| Q9Y3C6 | Peptidyl-prolyl cis-trans isomerase-like 1 (PPIase) (EC 5.2.1.8) (Rotamase PPIL1) | Q9Y3C6 |

TABLE 1-continued

| Uniprot ID | Protein Name | All Uniprot matches |
|---|---|---|
| Q06830 | Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2) | Q06830 |
| H7C3T4 | Peroxiredoxin-4 | H7C3T4; Q13162 |
| B7Z7A9 | Phosphoglycerate kinase 1 (EC: 2.7.2.3) (Cell migration-inducing gene 10 protein) (Primer recognition protein 2) (prp 2) | B7Z7A9; E7ERH5; P00558; P07205 |
| P18669 | Phosphoglycerate mutase 1 (EC 3.1.3.13) (EC 5.4.2.11) (EC 5.4.2.4) (BPG-dependent PGAM 1) (Phosphoglycerate mutase isozyme B) (PGAM-B) | P18669; P36871; P36871-2; P36871-3 |
| H0YGH6 | Pregnancy zone protein* | H0YGH6; P01023; P20742; P20742-2 |
| P12004 | Proliferating cell nuclear antigen (PCNA) (Cyclin) | P12004 |
| H0YKK6 | Proteasome activator complex subunit 1 | H0YKK6; Q06323-3; Q06323; Q06323-2 |
| F5H246 | Protein NAMPTL | F5H246; P43490; Q5SYT8 |
| Q15437 | Protein transport protein Sec23B (SEC23-related protein B) | Q15437; Q5QPE1 |
| A6NEC2 | Puromycin-sensitive aminopeptidase-like protein (EC 3.4.11.—) | A6NEC2; A6NEC2-2; B7Z463; E5RJ24; I3L083; E9PLK3; F5GZY4; H0YAQ6; P55786; E7EWZ2 |
| H0Y825 | Putative homeodomain transcription factor 1 | H0Y825; Q5TCQ3; Q5TCQ5; Q9UMS5; Q9UMS5-2 |
| A6NM43 | Putative T-complex protein 1 subunit theta-like 1 | A6NM43; Q96SF2 |
| H3BQ34 | Pyruvate kinase PKM (EC 2.7.1.40) (Cytosolic thyroid hormone-binding protein) (CTHBP) (Opa-interacting protein 3) (OIP-3) (Pyruvate kinase 2/3) (Pyruvate kinase muscle isozyme) (Thyroid hormone-binding protein 1) (THBP1) (Tumor M2-PK) (p58) | H3BQ34; H3BT25; H3BTJ2; H3BTN5; H3BUW1; P14618; P14618-2; P14618-3 |
| A8MSP2 | RAB37, member RAS oncogene family, isoform CRA_e (Ras-related protein Rab-37) (cDNA FLJ45130 fis, clone BRAWH3037428, highly similar to Homo sapiens RAB37, member RAS oncogene family (RAB37), transcript variant 3, mRNA) | Q9H082; G3V196; G3V562; J3QSF4; P59190; P59190-2; Q6MZX6; Q9NRW1-2; C9JB90; C9JU14; H0YGL6; H7BYW1; J3KR73; P20340; P20340-2; P20340-4; Q14964; Q9NRW1; A8MSP2; A8MTC6; A8MZI4; B4DEK7; B7Z3L0; C9JFM7; Q86YS6-2; E9PI18; E9PJQ5; E9PMJ1; E9PNB9; E9PRF7; E9PS06; F5GY21; F5H157; H0YDK7; H0YMN7; H0YNE9; M0R0X1; M0R1E0; M0R257; O95716; P20336; P20337; P20338; P61006; P61018; P61018-2; P61026; P61106; P62820; Q15286; Q15286-2; Q15771; Q6IQ22; Q15771-2; Q6PIK3; Q86YS6; Q92928; Q92930; Q96AX2; Q96AX2-2; Q96AX2-3; Q96AX2-4; Q96DA2; Q96E17; Q9H0U4; X6RFL8 |
| P60602 | Reactive oxygen species modulator 1 (ROS modulator 1) (Epididymis tissue protein Li 175) (Glyrichin) (Mitochondrial targeting GxxxG motif protein) (MTGM) (Protein MGR2 homolog) | P60602 |
| A8M172 | Reticulon | B7Z4M1; F5H617; O95197; O95197-2; O95197-3; O95197-4; O95197-5; O95197-6; O95197-7; A8MT72; Q16799; Q16799-2; Q16799-3 |
| P02753 | Retinol-binding protein 4 (Plasma retinol-binding protein) (PRBP) (RBP) [Cleaved into: Plasma retinol-binding protein(1-182); Plasma retinol-binding protein(1-181); Plasma retinol-binding protein(1-179); Plasma retinol-binding protein(1-176)] | P02753; Q5VY30 |
| G3V357 | Ribonuclease pancreatic | G3V357; P07998 |
| B3KQV6 | Serine/threonine-protein phosphatase 2A 65 kDa regulatory subunit A alpha isoform (cDNA FLJ33169 fis, clone ADRGL2000384, highly similar to Serine/threonine-protein phosphatase 2A 65 kDa regulatory subunit A alpha isoform) | B3KQV6; E9PH38; F5H3X9; P30153 |
| P35542 | Serum amyloid A-4 protein (Constitutively expressed serum amyloid A protein) (C-SAA) | P35542 |
| J3KPM9 | Signal transducer and activator of transcription | J3KPM9; P42224; P42224-2 |
| H3BQ21 | Signal-regulatory protein beta-1 isoform 3 | H3BQ21; H3BSK5; H3BU43; P78324; P78324-2; P78324-4; Q5TFQ8 |
| Q9H2G2 | STE20-like serine/threonine-protein kinase (STE20-like kinase) (hSLK) (EC 2.7.11.1) (CTCL tumor antigen se20-9) | Q9H2G2; Q9H2G2-2 |

TABLE 1-continued

| Uniprot ID | Protein Name | All Uniprot matches |
|---|---|---|
| | (STE20-related serine/threonine-protein kinase) (STE20-related kinase) (Serine/threonine-protein kinase 2) | |
| P04179 | Superoxide dismutase [Mn], mitochondrial (EC 1.15.1.1) | P04179; P04179-2; P04179-4 |
| P07996 | Thrombospondin-1 | P07996; P07996-2 |
| P62328 | Thymosin beta-4 (T beta-4) (Fx) [Cleaved into: Hematopoietic system regulatory peptide (Seraspenide)] | P62328; Q5T4B6 |
| Q13263 | Transcription intermediary factor 1-beta (TIF1-beta) (E3 SUMO-protein ligase TRIM28) (EC 6.3.2.—) (KRAB-associated protein 1) (KAP-1) (KRAB-interacting protein 1) (KRIP-1) (Nuclear corepressor KAP-1) (RING finger protein 96) (Tripartite motif-containing protein 28) | Q13263; Q13263-2 |
| P02766 | Transthyretin (ATTR) (Prealbumin) (TBPA) | P02766 |
| P60174 | Triosephosphate isomerase (TIM) (EC 5.3.1.1) (Triose-phosphate isomerase) | P60174; P60174-1 |
| Q08J23 | tRNA (cytosine(34)-C(5))-methyltransferase (EC 2.1.1.203) (Myc-induced SUN domain-containing protein) (Misu) (NOL1/NOP2/Sun domain family member 2) (Substrate of AIM1/Aurora kinase B) (tRNA (cytosine-5-)-methyltransferase) (tRNA methyltransferase 4 homolog) (hTrm4) | Q08J23; Q5SWD1 |
| G5EA42 | Tropomodulin 2 (Neuronal), isoform CRA_a (Tropomodulin-2) | G5EA42; H0YMA2; Q9NZR1; Q9NZR1-2 |
| F8W696 | Truncated apolipoprotein A-I | F8W696; P02647 |
| C9J2C0 | Tubulin alpha-8 chain | F5H5D3; F8VQQ4; P68363; Q13748; Q13748-2; Q6PEY2; Q71U36; Q71U36-2; Q9BQE3; F8VVB9; P68366-2; C9J2C0; C9JDS9; P68366; Q9NY65; Q9NY65-2 |
| P43403 | Tyrosine-protein kinase ZAP-70 (EC 2.7.10.2) (70 kDa zeta-chain associated protein) (Syk-related tyrosine kinase) | P43403; P43403-2; P43403-3; P43405; P43405-2; Q8NFD2 |
| F5GY79 | Tyrosine-protein phosphatase non-receptor type 6 | F5GY79; F5H0N8; F5H5H9; P29350; P29350-2; P29350-3; P29350-4; F5H1Z8 |
| D6R956 | Ubiquitin carboxyl-terminal hydrolase isozyme L1 | D6R956; D6R974; D6RE83; P09936 |
| P62979 | Ubiquitin-40S ribosomal protein S27a (Ubiquitin carboxyl extension protein 80) [Cleaved into: Ubiquitin; 40S ribosomal protein S27a] | P62979 |
| F5H4L7 | Vacuolar protein sorting-associated protein 26A* | F5H4L7; G3V1N8; O75436; O75436-2; S4R3Q6 |
| B0YJC4 | Vimentin (Vimentin variant 3) | B0YJC4; P08670; P17661 |
| D6RBJ7 | Vitamin D-binding protein | D6RBJ7; D6RF20; D6RF35; P02774; P02774-3 |
| B5MCX6 | V-set and transmembrane domain-containing protein 2A | B5MCX6; F8W8J5; Q8TAG5; Q8TAG5-2; X6RBS5 |
| H0YC04 | V-type proton ATPase subunit B, brain isoform | H0YC04; P21281 |

Table 1 discloses proteins whose peptides were found to be regulated by at least 60% in the activated microglia cell line compared to resting cells and also at least 60% in the CSF of AD patients compared to CSF of non-AD subjects. Uniprot ID=annotated ID during data search; Protein names=protein name/s given to matched sequence; All Uniprot matches=All Uniprot IDs that match to the peptide sequence detected at the time of invention. Asterisk (*) indicates those proteins which were annotated as deleted as the entry has been removed from Uniprot (due to redundancy).

In one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, or at least two or more, optionally at least three or all biomarkers selected from the group of Peroxiredoxin-1, MARCKS-related protein, Moesin and Actin or fragments thereof.

In another embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, or at least two or more, optionally at least three or all biomarkers selected from the group of Peroxiredoxin-1, MARCKS-related protein, Moesin, Actin, Protein TMSB4XP4, ApoE, Gelsolin, Secretogranin, Albumin and complement proteins or fragments thereof.

In one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, optionally two or more biomarkers selected from Table 1 and/or Table 2 or fragments thereof.

TABLE 2

| Uniprot ID | Protein Name | All Uniprot matches |
| --- | --- | --- |
| G3V1C1 | 1,5-anhydro-D-fructose reductase (Aldo-keto reductase family 1, member C-like 2, isoform CRA_c) | G3V1C1; Q96JD6; Q96JD6-4; P14550 |
| B8ZZ54 | 10 kDa heat shock protein, mitochondrial (Heat shock 10 kDa protein 1 (Chaperonin 10), isoform CRA_h) | B8ZZ54; B8ZZL8; P61604 |
| P31946 | 14-3-3 protein beta/alpha (Protein 1054) (Protein kinase C inhibitor protein 1) (KCIP-1) [Cleaved into: 14-3-3 protein beta/alpha, N-terminally processed] | P31946; P31946-2; P61981; Q4VY19; Q4VY20 |
| A2IDB1 | 14-3-3 protein eta | A2IDB1; B4DJF2; E5RIR4; E7ESK7; E7EVZ2; E7EX29; E9PD24; E9PG15; F8WEB6; I3L0W5; I3L3T1; P27348; P31946; P31946-2; P31947; P31947-2; P61981; P62258; P63104; Q04917; Q4VY19; Q4VY20; E5RGE1 |
| P61981 | 14-3-3 protein gamma (Protein kinase C inhibitor protein 1) (KCIP-1) [Cleaved into: 14-3-3 protein gamma, N-terminally processed] | P61981 |
| E9PG15 | 14-3-3 protein theta | E9PG15; P27348 |
| B0AZS6 | 14-3-3 protein zeta/delta (cDNA, FLJ79516, highly similar to 14-3-3 protein zeta/delta) | B0AZS6; B7Z2E6; E7EX29; H0YB80; P63104; P63104-2 |
| P16885 | 1-phosphatidylinositol 4,5-bisphosphate phosphodiesterase gamma-2 (EC 3.1.4.11) (Phosphoinositide phospholipase C-gamma-2) (Phospholipase C-IV) (PLC-IV) (Phospholipase C-gamma-2) (PLC-gamma-2) | P16885 |
| P62333 | 26S protease regulatory subunit 10B (26S proteasome AAA-ATPase subunit RPT4) (Proteasome 26S subunit ATPase 6) (Proteasome subunit p42) | H0YJC0; H0YJS8; P62332 |
| P62191 | 26S protease regulatory subunit 4 (P26s4) (26S proteasome AAA-ATPase subunit RPT2) (Proteasome 26S subunit ATPase 1) | P62191-2; P62191 |
| E9PKD5 | 26S protease regulatory subunit 6A | E9PKD5; E9PM69; P17980; R4GNH3; E9PMD8; E9PN50 |
| P43686 | 26S protease regulatory subunit 6B (26S proteasome AAA-ATPase subunit RPT3) (MB67-interacting protein) (MIP224) (Proteasome 26S subunit ATPase 4) (Tat-binding protein 7) (TBP-7) | P43686 |
| B7Z5E2 | 26S protease regulatory subunit 7# | B7Z5E2; P35998 |
| J3KRP2 | 26S protease regulatory subunit 8 | J3KRP2; J3QLH6; J3QQM1; J3QRR3; J3QSA9; P62195; P62195-2 |
| C9J9M4 | 26S proteasome non-ATPase regulatory subunit 1 | C9J9M4; H7BZR6; Q99460; Q99460-2 |
| E9PL38 | 26S proteasome non-ATPase regulatory subunit 13 | E9PL38; Q9UNM6; Q9UNM6-2 |
| O00487 | 26S proteasome non-ATPase regulatory subunit 14 (EC 3.4.19.—) (26S proteasome regulatory subunit RPN11) (26S proteasome-associated PAD1 homolog 1) | O00487 |
| H7C1H2 | 26S proteasome non-ATPase regulatory subunit 2 | Q13200-3; Q13200-2; H7C1H2; Q13200 |
| B4DT72 | 26S proteasome non-ATPase regulatory subunit 3 (CD FLJ54148, highly similar to 26S proteasome non-ATPase regulatory subunit 3) | B4DT72; H0YGV8; O43242 |
| Q16401 | 26S proteasome non-ATPase regulatory subunit 5 (26S protease subunit S5 basic) (26S proteasome subunit S5B) | Q16401; Q16401-2; Q4VXG9 |
| Q13442 | 28 kDa heat- and acid-stable phosphoprotein (PDGF-associated protein) (PAP) (PDGFA-associated protein 1) (PAP1) | Q13442 |
| O75600 | 2-amino-3-ketobutyrate coenzyme A ligase, mitochondrial (AKB ligase) (EC 2.3.1.29) (Aminoacetone synthase) (Glycine acetyltransferase) | O75600; O75600-2 |
| A6NF51 | 3'(2'),5'-bisphosphate nucleotidase 1 | A6NF51; O95861-3; O95861-4; O95861; O95861-2 |
| E5RHF4 | 39S ribosomal protein L15, mitochondrial | E5RHF4; Q9P015 |
| E7ESL0 | 39S ribosomal protein L22, mitochondrial | E7ESL0; J3KQY1; Q9NWU5; Q9NWU5-2; Q9NWU5-3 |
| B5MD38 | 3-ketoacyl-CoA thiolase | P55084-2; B5MD38; F5GZQ3; P55084; C9JE81; C9JEY0 |
| C9JDE9 | 3-ketoacyl-CoA thiolase, peroxisomal | C9JDE9; H7C131; P09110 |
| F6U211 | 40S ribosomal protein S10 | F6U211; P46783; S4R435 |
| M0QZC5 | 40S ribosomal protein S11 | M0QZC5; M0R1H6; P62280 |
| P25398 | 40S ribosomal protein S12 | P25398 |
| P62277 | 40S ribosomal protein S13 | P62277 |
| K7EJ78 | 40S ribosomal protein S15 | K7EJ78; K7ELC2; K7EM56; K7EQJ5; P62841; S4R456 |

TABLE 2-continued

| Uniprot ID | Protein Name | All Uniprot matches |
|---|---|---|
| I3L3P7 | 40S ribosomal protein S15a | I3L3P7; P62244 |
| P62269 | 40S ribosomal protein S18 (Ke-3) (Ke3) | P62269 |
| P39019 | 40S ribosomal protein S19 | M0QXK4; M0QYF7; M0R140; M0R2L9; P39018 |
| E9PQD7 | 40S ribosomal protein S2 | E9PQD7; H0YEN5; P15880 |
| G3XAN0 | 40S ribosomal protein S20 (Ribosomal protein S20, isoform CRA_a) | G3XAN0; P60866; P60866-2 |
| D6R9I7 | 40S ribosomal protein S23 | D6R9I7; D6RD47; D6RDJ2; D6RIX0; P62266 |
| E7ETK0 | 40S ribosomal protein S24 | E7ETK0; P62847; P62847-2; P62847-3; P62847-4 |
| P62851 | 40S ribosomal protein S25 | P62851 |
| P62854 | 40S ribosomal protein S26 | P62854; Q5JNZ5 |
| C9J1C5 | 40S ribosomal protein S27 | C9J1C5; H0YMV8; P42677; Q71UM5 |
| P62273 | 40S ribosomal protein S29 | P62273; P62273-2 |
| E9PL09 | 40S ribosomal protein S3 | E9PL09; E9PPU1; E9PSF4; H0YEU2; P23396; P23396-2 |
| A6NH36 | 40S ribosomal protein S4, X isoform | A6NH36; C9JEH7; P22090; P62701; Q8TD47 |
| M0QZN2 | 40S ribosomal protein S5 | M0QZN2; M0R0F0; M0R0R2; P46782 |
| A2A3R5 | 40S ribosomal protein S6 | A2A3R5; P62753 |
| P46781 | 40S ribosomal protein S9 (Ribosomal protein S9, isoform CRA_c) | B5MCT8; C9JM19; P46780 |
| A6NE09 | 40S ribosomal protein SA (37 kDa laminin receptor precursor) (37/67 kDa laminin receptor) (67 kDa laminin receptor 1) (Laminin receptor 1) (Laminin-binding protein precursor p40) | A6NE09; P08865; C9J9K3 |
| F5GZI0 | 4F2 cell-surface antigen heavy chain | F5GZI0; F5GZS6; J3KPF3; P08195; P08195-2; P08195-3; P08195-4 |
| P49189 | 4-trimethylaminobutyraldehyde dehydrogenase (TMABADH) (EC 1.2.1.47) (Aldehyde dehydrogenase E3 isozyme) (Aldehyde dehydrogenase family 9 member A1) (EC 1.2.1.3) (Gamma-aminobutyraldehyde dehydrogenase) (EC 1.2.1.19) (R-aminobutyraldehyde dehydrogenase) | P49189 |
| B7Z712 | 60 kDa heat shock protein, mitochondrial# | B7Z712; C9JCQ4; C9JL19; C9JL25; E7ESH4; E7EXB4; P10809 |
| F8VQY6 | 60S acidic ribosomal protein P0 | F8VQY6; F8VRK7; F8VS58; F8VU65; F8VWS0; F8VZS0; G3V210; P05388; P05388-2; Q8NHW5 |
| F8W7C6 | 60S ribosomal protein L10 | A6QRI9; F8W7C6; H7C123; H7C2C5; P27635; Q96L21; X1WI27 |
| P62906 | 60S ribosomal protein L10a (CSA-19) (Neural precursor cell expressed developmentally down-regulated protein 6) (NEDD-6) | P62906 |
| P62913 | 60S ribosomal protein L11 (CLL-associated antigen KW-12) | P62913; P62913-2; Q5VVC8; Q5VVC9 |
| P26373 | 60S ribosomal protein L13 (Breast basic conserved protein 1) | J3KS98; P26373; P26373-1 |
| M0QYS1 | 60S ribosomal protein L13a | M0QYS1; P40429 |
| J3KRB3 | 60S ribosomal protein L17 | J3KRX5; J3QLC8; J3QQT2; J3QS96; P18621; P18621-2; P18621-3; J3KRB3 |
| F8VYV2 | 60S ribosomal protein L18 | Q07020-2; F8VYV2; G3V203; H0YHA7; J3QQ67; Q07020 |
| M0R0P7 | 60S ribosomal protein L18a | M0R0P7; M0R117; M0R1A7; M0R3D6; Q02543 |
| G3V1B3 | 60S ribosomal protein L21 (Ribosomal protein L21, isoform CRA_f) | G3V1B3; M0R181; P46778 |
| K7EJT5 | 60S ribosomal protein L22 | K7EJT5; K7EKS7; K7ELC4; K7EMH1; K7EP65; K7ERI7; P35268 |
| C9JYQ9 | 60S ribosomal protein L22-like 1 | C9JYQ9; H0Y8C2; Q6P5R6 |
| B9ZVP7 | 60S ribosomal protein L23 | B9ZVP7; C9JD32; J3KT29; P62829 |
| A8MUS3 | 60S ribosomal protein L23a (Ribosomal protein L23a, isoform CRA_a) | A8MUS3; H7BY10; K7EJV9; K7EMA7; K7ERT8; P62750 |
| E5RIT6 | 60S ribosomal protein L26-like 1 | E5RIT6; J3QQQ9; J3QQV1; J3QRC4; J3QR17; P61254; Q9UNX3; J3KTJ8 |
| F8WCR1 | 60S ribosomal protein L3 | F8WCR1; H7C3M2; H7C422; P39023; B5MCW2; G5E9G0 |
| G5E9G0 | 60S ribosomal protein L3 (Ribosomal protein L3, isoform CRA_e) (Uncharacterized protein) | G5E9G0; P39023; Q92901 |
| B7Z4C8 | 60S ribosomal protein L31 (cDNA FLJ57527, highly similar to 60S ribosomal protein L31) | B7Z4C8; B7Z4E3; B8ZZK4; C9JU56; H7C2W9; P62899; P62899-2; P62899-3 |
| D3YTB1 | 60S ribosomal protein L32 | D3YTB1; F8W727; P62910 |
| P49207 | 60S ribosomal protein L34 | P49207 |
| Q9Y3U8 | 60S ribosomal protein L36 | Q9Y3U8 |
| P61927 | 60S ribosomal protein L37 (G1.16) | P61927 |
| P63173 | 60S ribosomal protein L38 | P63173 |
| H3BM89 | 60S ribosomal protein L4 (Ribosomal protein L4, isoform CRA_a) | H3BM89; P36578 |

TABLE 2-continued

| Uniprot ID | Protein Name | All Uniprot matches |
|---|---|---|
| P46777 | 60S ribosomal protein L5 | P46777 |
| Q02878 | 60S ribosomal protein L6 (Neoplasm-related protein C140) (Tax-responsive enhancer element-binding protein 107) (TaxREB107) | Q02878 |
| P62424 | 60S ribosomal protein L7a (PLA-X polypeptide) (Surfeit locus protein 3) | P62424; Q5T8U2; Q5T8U3 |
| E9PKU4 | 60S ribosomal protein L8 | E9PKZ0; G3V1A1; P62917; E9PKU4 |
| D6RAN4 | 60S ribosomal protein L9 | H0Y9R4; H0Y9V9; P32969; D6RAN4 |
| M0R261 | 6-phosphogluconolactonase | M0R261; O95336 |
| P11021 | 78 kDa glucose-regulated protein (GRP-78) (Endoplasmic reticulum lumel Ca(2+)-binding protein grp78) (Heat shock 70 kDa protein 5) (Immunoglobulin heavy chain-binding protein) (BiP) | P11021 |
| H0YEL7 | Acetyl-CoA acetyltransferase, mitochondrial | H0YEL7; P24752 |
| Q5T0Y8 | Acid sphingomyelinase-like phosphodiesterase 3b | Q5T0Y8; Q92485; Q92485-2 |
| P60709 | Actin, cytoplasmic 1 (Beta-actin) [Cleaved into: Actin, cytoplasmic 1, N-terminally processed] | G5E9R0; I3L1U9; I3L3R2; J3KT65; K7EM38; P60709; P63261; E7EVS6; I3L4N7 |
| I3L4N8 | Actin, cytoplasmic 2 | P60709; P63261; Q6S8J3; I3L4N8 |
| I3L1U9 | Actin, cytoplasmic 2, N-terminally processed | I3L1U9; P60709; P63261; I3L4N8 |
| O94805 | Actin-like protein 6B (53 kDa BRG1-associated factor B) (Actin-related protein Baf53b) (ArpNalpha) (BRG1-associated factor 53B) (BAF53B) | O94805; O96019; O96019-2 |
| F5H6T1 | Actin-related protein 2 | F5H6T1; P61160; P61160-2 |
| P61160 | Actin-related protein 2 (Actin-like protein 2) | P61160; P61160-2 |
| O15143 | Actin-related protein 2/3 complex subunit 1B (Arp2/3 complex 41 kDa subunit) (p41-ARC) | C9J4Z7; C9J6C8; C9JBJ7; C9JEY1; C9JTT6; C9K057; O15142 |
| B1ALC0 | Actin-related protein 2/3 complex subunit 5 | B1ALC0; O15511; O15511-2; Q9BPX5 |
| B4DXW1 | Actin-related protein 3 (cDNA FLJ51148, highly similar to Actin-like protein 3) (cDNA FLJ52434, highly similar to Actin-like protein 3) (cDNA, FLJ79112, highly similar to Actin-like protein 3) (cDNA, FLJ79295, highly similar to Actin-like protein 3) | B4DXW1; F5H3P5; P61158 |
| G3V3W9 | Activator of 90 kDa heat shock protein ATPase homolog 1 | O95433-2; G3V3W9; O95433 |
| B7Z683 | Active breakpoint cluster region-related protein (cDNA FLJ54747, highly similar to Active breakpoint cluster region-related protein) | B7Z683; Q12979; Q12979-2; Q12979-4; I3L434; I3NI05; Q12979-3 |
| G3V2U7 | Acylphosphatase (EC 3.6.1.7) | G3V2U7; P07311 |
| O95372 | Acyl-protein thioesterase 2 (APT-2) (EC 3.1.2.—) (Lysophospholipase II) (LPL-II) (LysoPLA II) | O95372; Q5QPQ0 |
| B5MDS5 | Adenomatous polyposis coli protein 2 | B5MDS5; O95996; O95996-2; O95996-3 |
| P23526 | Adenosylhomocysteinase (AdoHcyase) (EC 3.3.1.1) (S-adenosyl-L-homocysteine hydrolase) | P23526; P23526-2 |
| E7ERF4 | Adenylosuccite lyase | E7ERF4; P30566; P30566-2 |
| G3V232 | Adenylosuccite synthetase isozyme 1 | G3V232; G3V5D8; Q8N142; Q8N142-2 |
| Q01518 | Adenylyl cyclase-associated protein 1 (CAP 1) | Q01518; Q01518-2 |
| H0Y512 | Adipocyte plasma membrane-associated protein | H0Y512; Q9HDC9; Q9HDC9-2 |
| P05141 | ADP/ATP translocase 2 (ADP, ATP carrier protein 2) (ADP, ATP carrier protein, fibroblast isoform) (Adenine nucleotide translocator 2) (ANT 2) (Solute carrier family 25 member 5) [Cleaved into: ADP/ATP translocase 2, N-terminally processed] | P05141 |
| I7HJJ0 | ADP/ATP translocase 3 | I7HJJ0; P05141; P12235; P12236; Q9H0C2; V9GYG0 |
| B7ZB63 | ADP-ribosylation factor 3 (cDNA, FLJ79427, highly similar to ADP-ribosylation factor 3) | B7ZB63; C9J1Z8; C9JPM4; F5H0C7; F5H1V1; F5H423; F5H6T5; F8WDB3; P18085; P61204; P84077; P84085 |
| B0QYR5 | ADP-ribosylation factor-binding protein GGA1 | B0QYR5; B0QYR6; B0QYR9; B0QYS0; B0QYS1; B0QYS3; B0QYS5; B7Z1E9; H3BMM6; H3BPI3; J3KSS7; J3QRP3; J3QRS8; Q6IC75; Q9NZ52; Q9NZ52-4; Q9UJY4; Q9UJY5; Q9UJY5-3; Q9UJY5-4; B0QYS2 |
| Q96BM9 | ADP-ribosylation factor-like protein 8A (ADP-ribosylation factor-like protein 10B) (Novel small G protein indispensable for equal chromosome segregation 2) | Q96BM9; Q9NVJ2 |
| B4DI85 | ADP-ribosylation factor-like protein 8B# | B4DI85; Q9NVJ2; Q96BM9 |
| F8VUB6 | Aladin | F8VUB6; F8VZ44; H3BU82; Q9NRG9; Q9NRG9-2 |
| H3BPK7 | Alanine--tRNA ligase, cytoplasmic | H3BPK7; P49588 |
| P14550 | Alcohol dehydrogenase [NADP(+)] (EC 1.1.1.2) (Aldehyde reductase) (Aldo-keto reductase family 1 member A1) | P14550; Q5T621; V9GYG2; V9GYP9 |

TABLE 2-continued

| Uniprot ID | Protein Name | All Uniprot matches |
|---|---|---|
| H0YAG8 | Alcohol dehydrogese class-3 | H0YAG8; P11766 |
| H0Y2X5 | Aldehyde dehydrogenase 1 family, member A3, isoform CRA_b (Aldehyde dehydrogenase family 1 member A3) | H0Y2X5; H0YMG7; O94788; O94788-2; O94788-3; O94788-4; P00352; P05091; P05091-2; P30837; P47895 |
| P05091 | Aldehyde dehydrogenase, mitochondrial (EC 1.2.1.3) (ALDH class 2) (ALDH-E2) (ALDHI) | P05091; P05091-2; S4R3S4 |
| B8ZZ75 | Aldose 1-epimerase | B8ZZ75; H7C1B5; Q96C23 |
| E9PCX2 | Aldose reductase | E9PCX2; E9PEF9; P15121 |
| P15121 | Aldose reductase (AR) (EC 1.1.1.21) (Aldehyde reductase) (Aldo-keto reductase family 1 member B1) | P15121 |
| P02763 | Alpha-1-acid glycoprotein 1 (AGP 1) (Orosomucoid-1) (OMD 1) | P02763 |
| P19652 | Alpha-1-acid glycoprotein 2 (AGP 2) (Orosomucoid-2) (OMD 2) | P19652 |
| P30533 | Alpha-2-macroglobulin receptor-associated protein (Alpha-2-MRAP) (Low density lipoprotein receptor-related protein-associated protein 1) (RAP) | P30533 |
| G3V2E8 | Alpha-actinin-1 | P35609-2; G3V2E8; G3V2W4; G3V2X9; G3V5M4; H9KV75; P12814; P12814-2; P12814-3; P12814-4; P35609; G3V2N5 |
| C9J196 | Alpha-dystroglycan | Q14118; C9J196; C9JQL4 |
| M0R0I4 | Alpha-soluble NSF attachment protein | M0R0I4; M0R2M1; P54920 |
| A6NKB8 | Aminopeptidase B | A6NKB8; C9JMZ3; Q9H4A4 |
| B7Z4G8 | Amyloid-like protein 1 (cDNA FLJ56046, highly similar to Amyloid-like protein 1 (APLP)(APLP-1)) | B7Z4G8; F5GZ08; K7ELK0; K7EQJ4; P51693; P51693-2 |
| P04083 | Annexin A1 (Annexin I) (Annexin-1) (Calpactin II) (Calpactin-2) (Chromobindin-9) (Lipocortin I) (Phospholipase A2 inhibitory protein) (p35) | P04083 |
| B4DDF9 | Annexin A4# | B4DDF9; P09525; Q6P452 |
| P01008 | Antithrombin-III (ATIII) (Serpin C1) | P01008 |
| C9J1E7 | AP-1 complex subunit beta-1 | C9J1E7; Q10567; Q10567-2; Q10567-3; Q10567-4 |
| O94973 | AP-2 complex subunit alpha-2 (100 kDa coated vesicle protein C) (Adaptor protein complex AP-2 subunit alpha-2) (Adaptor-related protein complex 2 subunit alpha-2) (Alpha-adaptin C) (Alpha2-adaptin) (Clathrin assembly protein complex 2 alpha-C large chain) (Huntingtin yeast partner J) (Huntingtin-interacting protein 9) (HIP-9) (Huntingtin-interacting protein J) (Plasma membrane adaptor HA2/AP2 adaptin alpha C subunit) | O94973; O94973-2; O94973-3; O95782; O95782-2 |
| K7EJT8 | AP-2 complex subunit beta | K7EJT8; P63010; P63010-2; P63010-3 |
| P02649 | Apolipoprotein E (Apo-E) | E7ERP7; E9PEV4; H0Y7L5; P02648 |
| E9PMA0 | Apoptosis-inducing factor 1, mitochondrial | E9PMA0; O95831; O95831-2; O95831-3; O95831-5 |
| C9JLV4 | Apoptotic protease-activating factor 1 | C9JLV4; O14727; O14727-2; O14727-3; O14727-4; O14727-5; Q53F19; Q53F19-2 |
| P20292 | Arachidote 5-lipoxygese-activating protein (FLAP) (MK-886-binding protein) | P20292 |
| B0YIW6 | Archain 1, isoform CRA_a (Coatomer subunit delta) (Coatomer subunit delta variant 2) | B0YIW6; P48444; P48444-2 |
| O43150 | Arf-GAP with SH3 domain, ANK repeat and PH domain-containing protein 2 (Development and differentiation-enhancing factor 2) (Paxillin-associated protein with ARF GAP activity 3) (PAG3) (Pyk2 C-terminus-associated protein) (PAP) | O43150; O43150-2 |
| F5H3T8 | Arginine--tR ligase, cytoplasmic | F5H3T8; P54136; P54136-2 |
| P05089 | Argise-1 (EC 3.5.3.1) (Liver-type argise) (Type I argise) | P05089; P05089-2; P05089-3 |
| P08243 | Asparagine synthetase [glutamine-hydrolyzing] (EC 6.3.5.4) (Cell cycle control protein TS11) (Glutamine-dependent asparagine synthetase) | P08243; P08243-2; P08243-3 |
| O43776 | Asparagine--tRNA ligase, cytoplasmic (EC 6.1.1.22) (Asparaginyl-tRNA synthetase) (AsnRS) | O43776 |
| H7BZ35 | Aspartate--tRNA ligase, cytoplasmic | P14868; Q68CR9; H7BZ35 |
| B1AKZ3 | Astrocytic phosphoprotein PEA-15 (Phosphoprotein enriched in astrocytes 15, isoform CRA_b) (cD FLJ38560 fis, clone HCHON2003642, highly similar to Astrocytic phosphoprotein PEA-15) | B1AKZ3; B1AKZ5; Q15121 |
| D6R9H7 | ATP synthase F(0) complex subunit C1, mitochondrial | D6R9H7; E7EPU7; E7EQ97; I3L0Y5; P05496; P48201; Q06055; Q06055-2; Q06055-3 |

TABLE 2-continued

| Uniprot ID | Protein Name | All Uniprot matches |
|---|---|---|
| P25705 | ATP synthase subunit alpha, mitochondrial | K7EK77; K7ENJ4; P25705-3; K7ERX7; P25705; P25705-2; K7EJP0 |
| B4DL14 | ATP synthase subunit gamma | B4DL14; P36542; P36542-2 |
| H0Y2W2 | ATPase family AAA domain-containing protein 3A | H0Y2W2; J3QSF3; Q5T2N8; Q5T9A4; Q5T9A4-2; Q5T9A4-3; Q9NVI7; Q9NVI7-2; Q9NVI7-3 |
| G3V126 | ATPase, H+ transporting, lysosomal 50/57 kDa, V1 subunit H, isoform CRA_c (V-type proton ATPase subunit H) | G3V126; Q9UI12; Q9UI12-2 |
| B4E3P0 | ATP-citrate synthase (cDNA FLJ55447, highly similar to ATP-citrate synthase (EC 2.3.3.8)) | B4E3P0; P53396; P53396-2 |
| B1APP6 | ATP-dependent 6-phosphofructokinase, platelet type | B1APP6; Q01813; Q01813-2 |
| Q08211 | ATP-dependent RNA helicase A (RHA) (EC 3.6.4.13) (DEAH box protein 9) (Leukophysin) (LKP) (Nuclear DNA helicase II) (NDH II) | Q08211 |
| B1Q2N1 | ATP-dependent RNA helicase DDX39A (DEAD (Asp-Glu-Ala-Asp) box polypeptide 39 transcript variant) | B1Q2N1; B4DIJ6; B4DP52; F6S4E6; F6TRA5; F6UJC5; F6WLT2; F8VQ10; K7EPJ3; K7EQN7; O00148; O00148-2; Q13838; Q13838-2; Q5STU3 |
| B4DLA0 | ATP-dependent RNA helicase DDX3X (cDNA FLJ55031, highly similar to ATP-dependent RNA helicase DDX3X (EC 3.6.1.—)) | B4DLA0; B4E3C4; O00571 |
| B5MCE7 | Basic leucine zipper and W2 domain-containing protein 2 (Basic leucine zipper and W2 domains 2, isoform CRA_b) | B5MCE7; B5MCH7; E7ETZ4; Q75MG1; Q9Y6E2 |
| P51572 | B-cell receptor-associated protein 31 (BCR-associated protein 31) (Bap31) (6C6-AG tumor-associated antigen) (Protein CDM) (p28) | P51572; P51572-2 |
| J3KRP0 | Beta-Ala-His dipeptidase | J3KRP0; Q96KN2 |
| P32121 | Beta-arrestin-2 (Arrestin beta-2) | P32121; P32121-2; P32121-3; P32121-4; P32121-5; Q68DZ5 |
| A2A2P1 | Beta-catenin-like protein 1 | A2A2P1; Q8WYA6-4; Q8WYA6 |
| P42025 | Beta-centractin (Actin-related protein 1B) (ARP1B) | P42025; P61163; R4GMT0 |
| P13929 | Beta-enolase (EC 4.2.1.11) (2-phospho-D-glycerate hydro-lyase) (Enolase 3) (Muscle-specific enolase) (MSE) (Skeletal muscle enolase) | P13929; P13929-2; P13929-3 |
| B4DKE7 | Beta-hexosaminidase subunit alpha# | B4DKE7; E9PGL4; H3BP20; H3BS10; H3BTD4; H3BU85; P06865 |
| P07686 | Beta-hexosaminidase subunit beta (EC 3.2.1.52) (Beta-N-acetylhexosaminidase subunit beta) (Hexosaminidase subunit B) (Cervical cancer proto-oncogene 7 protein) (HCC-7) (N-acetyl-beta-glucosaminidase subunit beta) [Cleaved into: Beta-hexosaminidase subunit beta chain B; Beta-hexosaminidase subunit beta chain A] | P07686; Q5URX0 |
| P07814 | Bifunctional glutamate/proline--tRNA ligase (Bifunctional aminoacyl-tRNA synthetase) (Cell proliferation-inducing gene 32 protein) (Glutamatyl-prolyl-tRNA synthetase) [Includes: Glutamate--tRNA ligase (EC 6.1.1.17) (Glutamyl-tRNA synthetase) (GluRS); Proline--tRNA ligase (EC 6.1.1.15) (Prolyl-tRNA synthetase)] | P07814; V9GYZ6 |
| H7C3X0 | Bifunctional protein NCOAT | O60502-4; H7C3X0; O60502; O60502-2; O60502-3 |
| Q96GW7 | Brevican core protein (Brain-enriched hyaluronan-binding protein) (BEHAB) (Chondroitin sulfate proteoglycan 7) | Q5T3I7; Q96GW7; Q96GW7-1 |
| F5H2F4 | C-1-tetrahydrofolate synthase, cytoplasmic | F5H2F4; P11586 |
| Q9Y376 | Calcium-binding protein 39 (MO25alpha) (Protein Mo25) | Q9Y376 |
| B7ZBJ4 | Calcium-binding protein 39-like | B7ZBJ4; Q5TAW7; Q9H9S4; Q9Y376 |
| E7ERY9 | Calcium-transporting ATPase (EC 3.6.3.8) | E7ERY9; P20020; P20020-2; P20020-3; P20020-4; P20020-5; P20020-6 |
| Q9HB71 | Calcyclin-binding protein (CacyBP) (hCacyBP) (S100A6-binding protein) (Siah-interacting protein) | Q9HB71; Q9HB71-3 |
| D6RAQ8 | Calnexin | P27824-2; D6RAQ8; D6RAU8; D6RB85; D6RDP7; H0Y9Q7; P27824 |
| P27797 | Calreticulin (CRP55) (Calregulin) (Endoplasmic reticulum resident protein 60) (ERp60) (HACBP) (grp60) | K7EJB9; K7EL50; P27796 |
| O94985 | Calsyntenin-1 (Alcadein-alpha) (Alc-alpha) (Alzheimer-related cadherin-like protein) | O94985-2 |

TABLE 2-continued

| Uniprot ID | Protein Name | All Uniprot matches |
|---|---|---|
| | (Non-classical cadherin XB31alpha) [Cleaved into: Soluble Alc-alpha (SAlc-alpha); CTF1-alpha (C-terminal fragment 1-alpha)] | |
| O43852 | Calumenin (Crocalbin) (IEF SSP 9302) | O43852; O43852-10; O43852-15; O43852-2; O43852-3; O43852-4; O43852-6; O43852-8 |
| P10644 | cAMP-dependent protein kinase type I-alpha regulatory subunit (Tissue-specific extinguisher 1) (TSE1) [Cleaved into: cAMP-dependent protein kinase type I-alpha regulatory subunit, N-terminally processed] | P10644 |
| H7BYW5 | cAMP-dependent protein kinase type I-beta regulatory subunit | H7BYW5; P10644; P31321 |
| H7C4A9 | cAMP-dependent protein kinase type II-alpha regulatory subunit | H7C4A9; P13861; Q9BUB1 |
| K7EID3 | cAMP-dependent protein kise type I-alpha regulatory subunit | K7EID3; K7EIE5; K7EJ40; K7EK41; K7ENR3; K7EPB2; K7ER48; P10644 |
| B1AK87 | Capping protein (Actin filament) muscle Z-line, beta, isoform CRA_a (F-actin-capping protein subunit beta) | B1AK87; B1AK88; P47756; P47756-2 |
| A8MTM1 | Carbonyl reductase [NADPH] 1 | A8MTM1; P16152-2; E9PQ63; P16152 |
| C9JE88 | Carboxypeptidase E | C9JE88; D6R930; D6RF88; P16870; P16870-2 |
| H3BSA1 | Casein kinase II subunit alpha | H3BSA1; H3BV19; P19784 |
| C9JZR2 | Catenin delta-1 | C9JZR2; E9PKY0; O60716; O60716-10; O60716-11; O60716-12; O60716-13; O60716-14; O60716-15; O60716-16; O60716-17; O60716-18; O60716-19; O60716-2; O60716-20; O60716-21; O60716-22; O60716-23; O60716-24; O60716-25; O60716-26; O60716-27; O60716-28; O60716-29; O60716-3; O60716-30; O60716-31; O60716-32; O60716-4; O60716-5; O60716-6; O60716-7; O60716-8; O60716-9 |
| P43235 | Cathepsin K (EC 3.4.22.38) (Cathepsin O) (Cathepsin O2) (Cathepsin X) | P43235; Q5QP40 |
| Q9UBR2 | Cathepsin Z (EC 3.4.18.1) (Cathepsin P) (Cathepsin X) | Q9UBR2 |
| F5GXJ9 | CD166 antigen | F5GXJ9; H7C543; Q13740; Q13740-2; Q13740-4 |
| Q9NZ45 | CDGSH iron-sulfur domain-containing protein 1 (MitoNEET) | Q9NZ45 |
| B3KRG5 | cDNA FLJ34201 fis, clone FCBBF3019714, highly similar to HETEROGENEOUS NUCLEAR RIBONUCLEOPROTEIN G | B3KRG5; H3BUY5; P38159; P38159-2; Q96E39 |
| B7Z514 | cDNA FLJ50601, highly similar to Glutathione synthetase (EC 6.3.2.3) | B7Z514; P48637 |
| B7Z3E2 | cDNA FLJ50777, highly similar to Serine/threonine-protein phosphatase 6 (EC 3.1.3.16) (cDNA, FLJ79426, highly similar to Serine/threonine-protein phosphatase 6 (EC 3.1.3.16)) | B7Z3E2; O00743; O00743-2; O00743-3 |
| B4DXI8 | cDNA FLJ51373, highly similar to 26S proteasome non-ATPase regulatory subunit 7 | B4DXI8; H3BNT7; H3BTM8; P51665 |
| B4DPJ8 | cDNA FLJ52344, highly similar to T-complex protein 1 subunit zeta (cDNA, FLJ79129, highly similar to T-complex protein 1 subunit zeta) | B4DPJ8; P40227; P40227-2 |
| B4DN60 | cDNA FLJ52703, highly similar to Asparaginyl-tRNA synthetase, cytoplasmic (EC6.1.1.22) | B4DN60; O43776 |
| B4DTM7 | cDNA FLJ53006, highly similar to Vinculin | B4DTM7; P18206; P18206-2; P18206-3 |
| B4DUC5 | cDNA FLJ53202, highly similar to Exportin-2 | B4DUC5; P55060; P55060-3; P55060-4 |
| B4DT31 | cDNA FLJ53425, highly similar to Far upstream element-binding protein 1 | B4DT31; E9PEB5; M0R0I5; Q92945; Q96AE4; Q96AE4-2; Q96I24; Q96I24-2 |
| B7Z2F4 | cDNA FLJ53873, highly similar to T-complex protein 1 subunit delta | B7Z2F4; B7Z9L0; P50991; P50991-2 |
| B4DX42 | cDNA FLJ54064, highly similar to Splicing factor 1 | B4DX42; Q15637; Q15637-2; Q15637-3; Q15637-4; Q15637-6; Q15637-7; Q15637-5 |
| B4DTC3 | cDNA FLJ54150, highly similar to Heterogeneous nuclear ribonucleoprotein D0 | B4DTC3; F5H6R6; H0YA96; Q14103; Q14103-2; Q14103-3; Q14103-4; H0Y8G5 |
| B4E2J1 | cDNA FLJ54240, highly similar to ATPase family AAA domain-containing protein 1 | B4E2J1; Q8NBU5 |
| B4DYV7 | cDNA FLJ54806, highly similar to Homo sapiens meningioma expressed antigen 5 (MGEA5), mRNA | B4DYV7; O60502-4; H7C3X0; O60502; O60502-2; O60502-3 |
| B4DG22 | cDNA FLJ56618, highly similar to Ribosomal protein S6 kinase alpha-3 (EC 2.7.11.1) | B4DG22; B7Z3B5; B7Z17; B7ZL90; E9PGT3; E9PRI4; F2Z2J1; F5GYC4; P51812; Q15349; Q15349-2; Q15349-3; Q15418; Q15418-2; Q15418-3; Q5SVM6; Q9UK32 |

TABLE 2-continued

| Uniprot ID | Protein Name | All Uniprot matches |
|---|---|---|
| B1APJ0 | cDNA FLJ57459, highly similar to Mitochondrial import inner membrane translocase subunit Tim23 | B1APJ0; E7EP42; E9PB91; O14925; Q5SRD1; S4R2X5 |
| B7Z8M7 | cDNA FLJ57768, highly similar to Ras-related protein Rab-1A | B7Z8M7; E7END7; P62820; P62820-2 |
| B4DDM6 | cDNA FLJ57899, highly similar to Mitotic checkpoint protein BUB3 | B4DDM6; J3QT28; O43684; O43684-2 |
| B4DIZ2 | cDNA FLJ57995, moderately similar to Ubiquitin-conjugating enzyme E2-25 kDa (EC 6.3.2.19) | B4DIZ2; D6RDM7; P61086; P61086-3 |
| B7Z1Z6 | cDNA FLJ58056, highly similar to Calcium/calmodulin-dependent protein kinase type II beta chain (EC 2.7.11.17) | D6R938; E9PBG7; E9PF82; Q13557; Q13557-10; Q13557-11; Q13557-12; Q13557-3; Q13557-4; Q13557-5; Q13557-6; Q13557-8; Q13557-9; B7Z1Z6; D6RHX9; E7EQE4; E9PBE8; H7BXS4; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q5SWX3; Q8WU40; Q9UQM7; Q9UQM7-2 |
| B4DLC0 | cDNA FLJ58476, highly similar to Poly(rC)-binding protein 2 | B4DLC0; B4DXP5; F8VRH0; F8VXH9; F8VZX2; Q15366-7; H3BRU6; Q15366; Q15366-2; Q15366-3; Q15366-4; Q15366-5; Q15366-6 |
| B7Z5N7 | cDNA FLJ58612, highly similar to Sec1 family domain-containing protein 1 | B7Z5N7; B7Z738; Q8WVM8; Q8WVM8-2; Q8WVM8-3 |
| B4DJ96 | cDNA FLJ59548, highly similar to Cisplatin resistance-associated overexpressed protein | B4DJ96; D6RDI2; J3KPP4; O95232 |
| B4DKM5 | cDNA FLJ60120, highly similar to Voltage-dependent anion-selective channel protein 2 (cDNA, FLJ78818, highly similar to Voltage-dependent anion-selective channel protein 2) | B4DKM5; P45880; P45880-1; P45880-2 |
| B4DH61 | cDNA FLJ60521, highly similar to Protein kinase-like protein C9orf96 | E9PKD5; E9PM69; P17980; R4GNH3; B4DH61; E9PLG2; E9PMD8; E9PN50 |
| A8K8G0 | cDNA FLJ75113 | A8K8G0; P51858; P51858-2; P51858-3 |
| B7Z9J8 | cDNA, FLJ78862, highly similar to Isocitrate dehydrogenase (cDNA, FLJ78950, highly similar to Isocitrate dehydrogenase) | B7Z9J8; H0YL72; H0YMU3; P50213; P50213-2 |
| Q9BY67 | Cell adhesion molecule 1 (Immunoglobulin superfamily member 4) (IgSF4) (Nectin-like protein 2) (NECL-2) (Spermatogenic immunoglobulin superfamily) (SgIgSF) (Synaptic cell adhesion molecule) (SynCAM) (Tumor suppressor in lung cancer 1) (TSLC-1) | Q9BY67; Q9BY67-2; Q9BY67-3; Q9BY67-4; Q9BY67-5; X5DQS5 |
| Q8NFZ8 | Cell adhesion molecule 4 (Immunoglobulin superfamily member 4C) (IgSF4C) (Nectin-like protein 4) (NECL-4) (TSLC1-like protein 2) | Q8NFZ8 |
| E7ETU3 | Cell division control protein 42 homolog | E7ETU3; P60953 |
| E7ETU3 | Cell division control protein 42 homolog* | E7ETU3; P60953; P60953-1; Q5JYX0 |
| E9PFZ2 | Ceruloplasmin | E9PFZ2; H7C5R1; P00450 |
| Q7LBR1 | Charged multivesicular body protein 1b (CHMP1.5) (Chromatin-modifying protein 1b) (CHMP1b) (Vacuolar protein sorting-associated protein 46-2) (Vps46-2) (hVps46-2) | Q7LBR1 |
| Q9H444 | Charged multivesicular body protein 4b (Chromatin-modifying protein 4b) (CHMP4b) (SNF7 homolog associated with Alix 1) (SNF7-2) (h5nf7-2) (Vacuolar protein sorting-associated protein 32-2) (Vps32-2) (hVps32-2) | Q9H444 |
| O00299 | Chloride intracellular channel protein 1 (Chloride channel ABP) (Nuclear chloride ion channel 27) (NCC27) (Regulatory nuclear chloride ion channel protein) (hRNCC) | O00299 |
| C9J050 | Choline-phosphate cytidylyltransferase A | C9J050; C9JEJ2; H7BZN1; H7C1T3; P49585; C9J2E1 |
| O95196 | Chondroitin sulfate proteoglycan 5 (Acidic leucine-rich EGF-like domain-containing brain protein) (Neuroglycan C) | O95196; O95196-2 |
| B8ZZ43 | Chromobox homolog 3 (HP1 gamma homolog, Drosophila), isoform CRA_b (Chromobox protein homolog 3) | B8ZZ43; C9JMM0; Q13185; S4R2Y4 |
| Q13185 | Chromobox protein homolog 3 (HECH) (Heterochromatin protein 1 homolog gamma) (HP1 gamma) (Modifier 2 protein) | Q13185; S4R2Y4 |
| F5GWX5 | Chromodomain-helicase-DNA-binding protein 4 | F5GWX5; Q12873; Q12873-2; Q12873-3; Q14839; Q14839-2 |

TABLE 2-continued

| Uniprot ID | Protein Name | All Uniprot matches |
|---|---|---|
| G5E968 | Chromogranin-A (CgA) (Pituitary secretory protein I) (SP-I) [Cleaved into: Vasostatin-1 (Vasostatin I); Vasostatin-2 (Vasostatin II); EA-92; ES-43; Pancreastatin; SS-18; WA-8; WE-14; LF-19; AL-11; GV-19; GR-44; ER-37] | G5E968; P10645 |
| B4DJV2 | Citrate synthase | B4DJV2; F8VPA1; F8VTT8; F8VX07; F8VX68; F8W1S4; F8W4S1; F8W642; H0YH82; O75390; F8VPF9; F8VRP1; F8VZK9 |
| Q00610 | Clathrin heavy chain 1 (Clathrin heavy chain on chromosome 17) (CLH-17) | J3KRF5; J3KS13; K7EJJ5; Q00610; Q00610-1 |
| Q14677 | Clathrin interactor 1 (Clathrin-interacting protein localized in the trans-Golgi region) (Clint) (Enthoprotin) (Epsin-4) (Epsin-related protein) (EpsinR) | Q14677; Q14677-2; Q14677-3 |
| F8WF69 | Clathrin light chain A | F8WF69; P09496; P09496-2; P09496-3; P09496-4 |
| P09497 | Clathrin light chain B (Lcb) | P09497; P09497-2 |
| I3L2B0 | Clustered mitochondria protein homolog | I3L2B0; K7EIG1; O75153 |
| E7ERK6 | Clusterin beta chain | E7ERK6; H0YC35; H0YLK8; P10909; P10909-2; P10909-3; P10909-4; P10909-5 |
| Q14019 | Coactosin-like protein | Q14019 |
| B4DZI8 | Coatomer protein complex, subunit beta 2 (Beta prime), isoform CRA_b (Coatomer subunit beta') (cD FLJ56271, highly similar to Coatomer subunit beta) | B4DZI8; P35606 |
| P53621 | Coatomer subunit alpha (Alpha-coat protein) (Alpha-COP) (HEP-COP) (HEPCOP) [Cleaved into: Xenin (Xenopsin-related peptide); Proxenin] | P53621; P53621-2 |
| B4DZI8 | Coatomer subunit beta# | B4DZI8; P35606 |
| F8VVA7 | Coatomer subunit zeta-1 | P61923-3; F8VVA7; P61923-4; F8VYK5; F8W651; P61923; P61923-2 |
| E9PK25 | Cofilin-1 | E9PK25; G3V1A4; P23528; E9PP50 |
| A6NNP5 | Coiled-coil domain-containing protein 169 | A6NNP5; A6NNP5-3; A6NNP5-4; A6NNP5-5; A6NNP5-6; E9PBZ7; H7C1A8; Q9GZT8; Q9GZT8-2; Q9NX45-3 |
| C9JRZ6 | Coiled-coil-helix-coiled-coil-helix domain-containing protein 3, mitochondrial | C9JRZ6; F8WAR4; Q9NX63 |
| E9PLT0 | Cold shock domain-containing protein E1 | E9PLT0; O75534-4; O75534; O75534-2; O75534-3 |
| P12109 | Collagen alpha-1(VI) chain | P12109 |
| Q5KU26 | Collectin-12 (Collectin placenta protein 1) (CL-P1) (hCL-P1) (Nurse cell scavenger receptor 2) (Scavenger receptor class A member 4) (Scavenger receptor with C-type lectin) | Q5KU26 |
| P01024 | Complement C3 (C3 and PZP-like alpha-2-macroglobulin domain-containing protein 1) [Cleaved into: Complement C3 beta chain; C3-beta-c (C3bc); Complement C3 alpha chain; C3a anaphylatoxin; Acylation stimulating protein (ASP) (C3adesArg); Complement C3b alpha' chain; Complement C3c alpha' chain fragment 1; Complement C3dg fragment; Complement C3g fragment; Complement C3d fragment; Complement C3f fragment; Complement C3c alpha' chain fragment 2] | M0QXZ3; P01023 |
| F5GXS0 | Complement C4-B | F5GXS0; P0C0L4; P0C0L4-2; P0C0L5 |
| F8WDX4 | Complement factor H | P08603; F8WDX4; P08603-2 |
| Q12860 | Contactin-1 (Glycoprotein gp135) (Neural cell surface protein F3) | Q12860; Q12860-2 |
| C9JFE4 | COP9 signalosome complex subunit 1 (G protein pathway suppressor 1, isoform CRA_b) | C9JFE4; J3KSA5; Q13098; Q13098-5; Q13098-6; Q13098-7 |
| C9JLV5 | COP9 signalosome complex subunit 3 | H7C3P9; J3KTQ1; J3QKR0; Q9UNS2; Q9UNS2-2; C9JLV5 |
| D6RAX7 | COP9 signalosome complex subunit 4 | D6RAX7; D6RFN0; Q9BT78; Q9BT78-2 |
| E5RHH5 | COP9 signalosome complex subunit 5 (SGN5) (Signalosome subunit 5) (EC 3.4.—.—) (Jun activation domain-binding protein 1) | E5RHH5; Q92905 |
| O75131 | Copine-3 (Copine III) | O75131 |
| O75367 | Core histone macro-H2A.1 (Histone macroH2A1) (mH2A1) (Histone H2A.y) (H2A/y) (Medulloblastoma antigen MU-MB-50.205) | O75367; O75367-2; O75367-3 |
| H3BRY3 | Coronin | H3BRY3; H3BTU6; P31146; H3BRJ1 |
| Q9BR76 | Coronin-1B (Coronin-2) | Q9BR76 |
| D6RAX2 | C-terminal-binding protein 1 | E7EPF8; E7ESU7; P56545; P56545-2; Q13363; Q13363-2; Q5SQP8; D6RAX2 |
| P17812 | CTP synthase 1 (EC 6.3.4.2) (CTP synthetase 1) (UTP--ammonia ligase 1) | P17812-2; P17812 |
| Q13616 | Cullin-1 (CUL-1) | Q13616 |
| Q13618 | Cullin-3 (CUL-3) | Q13618; Q13618-2; Q13618-3 |

TABLE 2-continued

| Uniprot ID | Protein Name | All Uniprot matches |
|---|---|---|
| A6NE76 | Cullin-4B | A6NE76; K4DI93; Q13620; Q13620-1; Q13620-3 |
| Q86VP6 | Cullin-associated NEDD8-dissociated protein 1 (Cullin-associated and neddylation-dissociated protein 1) (TBP-interacting protein of 120 kDa A) (TBP-interacting protein 120A) (p120 CAND1) | Q86VP6; Q86VP6-2 |
| P01034 | Cystatin-C (Cystatin-3) (Gamma-trace) (Neuroendocrine basic polypeptide) (Post-gamma-globulin) | P01034 |
| F5GWD2 | Cytochrome b-245 heavy chain | F5GWD2; F5GWU5; P04839; Q9Y5S8; Q9Y5S8-3 |
| P31930 | Cytochrome b-c1 complex subunit 1, mitochondrial (Complex III subunit 1) (Core protein I) (Ubiquinol-cytochrome-c reductase complex core protein 1) | P31930 |
| C9JFR7 | Cytochrome c | C9JFR7; P99999 |
| E7ENE7 | Cytochrome P450 2D6 | E7ENE7; P10635; E9PDB2; G3XAL0; P40926 |
| Q14204 | Cytoplasmic dynein 1 heavy chain 1 (Cytoplasmic dynein heavy chain 1) (Dynein heavy chain, cytosolic) | Q14204 |
| E7EQL5 | Cytoplasmic dynein 1 intermediate chain 2 | Q13409-7; E7EQL5; F8W8S0; Q13409; Q13409-2; Q13409-3; Q13409-5; Q13409-6; E7EV09 |
| H0YCF6 | Cytoskeleton-associated protein 5 | H0YEK7; Q14008; Q14008-2; Q14008-3; H0YCF6 |
| P28838 | Cytosol aminopeptidase (EC 3.4.11.1) (Leucine aminopeptidase 3) (LAP-3) (Leucyl aminopeptidase) (Peptidase S) (Proline aminopeptidase) (EC 3.4.11.5) (Prolyl aminopeptidase) | P28838; P28838-2; H0Y9Q0 |
| B4DUX0 | Cytosolic acyl coenzyme A thioester hydrolase (cDNA FLJ60167, highly similar to Cytosolic acyl coenzyme A thioester hydrolase(EC 3.1.2.2)) | B4DUX0; O00154; O00154-2; O00154-3; O00154-4; O00154-5; O00154-6; O00154-7; K7EKP8 |
| B7Z382 | Cytosolic purine 5'-nucleotidase | B7Z382; P49902; Q5JUV6 |
| P49902 | Cytosolic purine 5'-nucleotidase (EC 3.1.3.5) (Cytosolic 5'-nucleotidase II) | P49902-2; P49902; Q5JUV3; Q5JUV4 |
| C9J8U1 | Cytospin-A | F8WAN1; P35241; P35241-4; P35241-5; Q69YQ0; Q69YQ0-2; C9J8U1 |
| O43175 | D-3-phosphoglycerate dehydrogenase (3-PGDH) (EC 1.1.1.95) | O43175 |
| F6RFD5 | Destrin | F6RFD5; P60981; P60981-2 |
| Q9Y295 | Developmentally-regulated GTP-binding protein 1 (DRG-1) (Neural precursor cell expressed developmentally down-regulated protein 3) (NEDD-3) | Q9Y295 |
| B4DDD2 | Dihydrofolate reductase# | B4DDD2; P00374 |
| F2Z2E3 | Dihydrolipoyl dehydrogenase, mitochondrial | P09622-3; F2Z2E3; F8WDM5; P09622 |
| B3KW71 | Dihydropteridine reductase | B3KW71; P09417 |
| E9PD68 | Dihydropyrimidinase-related protein 1 | E9PD68; F5GWI3; H0YBT4; Q14194; Q14194-2; Q14195; Q14195-2; Q16555; Q16555-2 |
| E5RFU4 | Dihydropyrimidinase-related protein 2 | E5RFU4; E9PD68; Q14194; Q14194-2; Q16555; Q16555-2 |
| Q16555 | Dihydropyrimidinase-related protein 2 (DRP-2) (Collapsin response mediator protein 2) (CRMP-2) (N2A3) (Unc-33-like phosphoprotein 2) (ULIP-2) | Q16555; Q16555-2 |
| E7EWB4 | Dihydropyrimidise-related protein 5 | E7EWB4; Q9BPU6 |
| G3V180 | Dipeptidyl peptidase 3 (HCG2016942, isoform CRA_d) | G3V180; G3V1D3; Q9NY33; Q9NY33-4 |
| B4DTU4 | DNA ligase (EC 6.5.1.1) | B4DTU4; F5GZ28; M0R0Q7; P18858; Q2TB12 |
| Q9NRF9 | DNA polymerase epsilon subunit 3 (EC 2.7.7.7) (Arsenic-transactivated protein) (AsTP) (Chromatin accessibility complex 17 kDa protein) (CHRAC-17) (HuCHRAC17) (DNA polymerase II subunit 3) (DNA polymerase epsilon subunit p17) | Q9NRF9 |
| H0Y8E6 | DNA replication licensing factor MCM2 | H0Y8E6; P49736 |
| P11387 | DNA topoisomerase 1 (EC 5.99.1.2) (DNA topoisomerase I) | P11387 |
| E9PCY5 | DNA topoisomerase 2 (EC 5.99.1.3) | E9PCY5; P11388; P11388-2; P11388-3; P11388-4; Q02880; Q02880-2 |
| P31689 | DnaJ homolog subfamily A member 1 (DnaJ protein homolog 2) (HSDJ) (Heat shock 40 kDa protein 4) (Heat shock protein J2) (HSJ-2) (Human DnaJ protein 2) (hDj-2) | P31689; P31689-2 |
| O60884 | DnaJ homolog subfamily A member 2 (Cell cycle progression restoration gene 3 protein) (Dnj3) (Dj3) (HIRA-interacting protein 4) (Renal carcinoma antigen NY-REN-14) | O60884 |
| Q9H3Z4 | DnaJ homolog subfamily C member 5 (Cysteine string protein) (CSP) | Q9H3Z4; Q9H3Z4-2 |

TABLE 2-continued

| Uniprot ID | Protein Name | All Uniprot matches |
|---|---|---|
| H0Y368 | Dolichol-phosphate mannosyltransferase subunit 1 | H0Y368; O60762; Q5QPK2 |
| Q9P2X0 | Dolichol-phosphate mannosyltransferase subunit 3 (Dolichol-phosphate mannose synthase subunit 3) (DPM synthase subunit 3) (Dolichyl-phosphate beta-D-mannosyltransferase subunit 3) (Mannose-P-dolichol synthase subunit 3) (MPD synthase subunit 3) (Prostin-1) | Q9P2X0; Q9P2X0-2 |
| E7EWT1 | Dolichyl-diphosphooligosaccharide--protein glycosyltransferase 48 kDa subunit | E7EWT1; P39656; U3KQ84 |
| F8WF32 | Dolichyl-diphosphooligosaccharide--protein glycosyltransferase subunit 1 | P04843; F8WF32; B7Z4L4 |
| E9PI32 | Dolichyl-diphosphooligosaccharide--protein glycosyltransferase subunit STT3A (Oligosaccharyl transferase subunit STT3A) (STT3-A) (EC 2.4.99.18) (B5) (Integral membrane protein 1) (Transmembrane protein TMC) | E9PI32; E9PN73; P46977 |
| G5E9C7 | Dual-specificity mitogen-activated protein kinase kinase 2 (Mitogen-activated protein kinase kinase 2, isoform CRA_b) | P36507; Q02750; Q02750-2; G5E9C7 |
| Q9UJW0 | Dynactin subunit 4 (Dyn4) (Dynactin subunit p62) | E5RGG1; H9KVE0; Q9UJW0; Q9UJW0-2; Q9UJW0-2 |
| G8JLD5 | Dynamin-1-like protein | O00429-7; G8JLD5; O00429-8; O00429; O00429-2; O00429-3; O00429-4; O00429-5; O00429-6 |
| F8VRV5 | Dynein light chain 1, cytoplasmic | F8VRV5; F8VXL2; P63167 |
| E5RI87 | E3 ubiquitin-protein ligase RNF130 | E5RI87; Q86XS8-2; Q86XS8; F5H1R4; F5H4A3; K7EM85; K7ES98; Q92619; Q92619-2 |
| F5H012 | E3 ubiquitin-protein ligase TRIM21 | F5H012; P19474; P19474-2 |
| Q96C19 | EF-hand domain-containing protein D2 (Swiprosin-1) | Q96C19 |
| B4DVB8 | ELAV-like protein 1 (cD FLJ60076, highly similar to ELAV-like protein 1) | B4DVB8; M0QZR9; M0R055; Q15717 |
| H0YK49 | Electron transfer flavoprotein subunit alpha, mitochondrial | H0YK49; H0YNX6; P13804; P13804-2 |
| P38117 | Electron transfer flavoprotein subunit beta (Beta-ETF) | M0QY67; P38117; P38117-1 |
| P68104 | Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7) | P68104; Q05639; Q5VTE0 |
| C9JZW3 | Elongation factor 1-beta | C9JZW3; P24534 |
| B4DTG2 | Elongation factor 1-gamma# | B4DTG2; P26641 |
| P13639 | Elongation factor 2 (EF-2) | P13639 |
| C9IZ01 | Elongation factor G, mitochondrial | C9IZ01; Q96RP9; Q96RP9-2 |
| P49411 | Elongation factor Tu, mitochondrial (EF-Tu) (P43) | P49411 |
| Q9NZ08 | Endoplasmic reticulum aminopeptidase 1 (EC 3.4.11.—) (ARTS-1) (Adipocyte-derived leucine aminopeptidase) (A-LAP) (Aminopeptidase PILS) (Puromycin-insensitive leucyl-specific aminopeptidase) (PILS-AP) (Type 1 tumor necrosis factor receptor shedding aminopeptidase regulator) | Q9NZ08; Q9NZ08-2 |
| Q9BS26 | Endoplasmic reticulum resident protein 44 (ER protein 44) (ERp44) (Thioredoxin domain-containing protein 4) | Q9BS26 |
| Q969X5 | Endoplasmic reticulum-Golgi intermediate compartment protein 1 (ER-Golgi intermediate compartment 32 kDa protein) (ERGIC-32) | Q969X5; Q969X5-2 |
| P14625 | Endoplasmin (94 kDa glucose-regulated protein) (GRP-94) (Heat shock protein 90 kDa beta member 1) (Tumor rejection antigen 1) (gp96 homolog) | P14625 |
| O60869 | Endothelial differentiation-related factor 1 (EDF-1) (Multiprotein-bridging factor 1) (MBF1) | O60869; O60869-2; O60869-3 |
| H7C0S6 | Engulfment and cell motility protein 1 | H7C0S6; Q92556; Q92556-3 |
| G3V279 | Enhancer of rudimentary homolog | P84090; G3V279 |
| P30084 | Enoyl-CoA hydratase, mitochondrial (EC 4.2.1.17) (Enoyl-CoA hydratase 1) (Short-chain enoyl-CoA hydratase) (SCEH) | P30084 |
| B7Z6Q8 | Ephrin type-A receptor 4# | B7Z6Q8; E9PG71; P54764 |
| M0R2A0 | ER membrane protein complex subunit 10 | M0R2A0; Q5UCC4; Q5UCC4-2 |
| D6R9B1 | ETS-related transcription factor Elf-2 | D6R9B1 |
| P60842 | Eukaryotic initiation factor 4A-I (eIF-4A-I) (eIF4A-I) (EC 3.6.4.13) (ATP-dependent RNA helicase eIF4A-1) | J3KSZ0; J3KT12; J3KTB5; J3KTN0; J3QS69; P60842; P60842-1 |

TABLE 2-continued

| Uniprot ID | Protein Name | All Uniprot matches |
|---|---|---|
| E7EQG2 | Eukaryotic initiation factor 4A-II | E7EQG2; J3KSZ0; J3KT12; J3KTN0; J3QL43; J3QS69; P38919; P60842; P60842-2; Q14240; Q14240-2; Q9NZE6; J3QL52 |
| H3BR35 | Eukaryotic peptide chain release factor GTP-binding subunit ERF3A | H3BR35; P15170; P15170-2; P15170-3; Q8IYD1 |
| B7Z7P8 | Eukaryotic peptide chain release factor subunit 1 (cDNA FLJ56175, highly similar to Eukaryotic peptide chain release factor subunit1) | B7Z7P8; I3L492; P62495; Q96CG1 |
| P05198 | Eukaryotic translation initiation factor 2 subunit 1 (Eukaryotic translation initiation factor 2 subunit alpha) (eIF-2-alpha) (eIF-2A) (eIF-2alpha) | P05198 |
| P20042 | Eukaryotic translation initiation factor 2 subunit 2 (Eukaryotic translation initiation factor 2 subunit beta) (eIF-2-beta) | P20042 |
| P41091 | Eukaryotic translation initiation factor 2 subunit 3 (Eukaryotic translation initiation factor 2 subunit gamma X) (eIF-2-gamma X) (eIF-2gX) | P41091; Q2VIR3 |
| F5H335 | Eukaryotic translation initiation factor 3 subunit A (eIF3a) (Eukaryotic translation initiation factor 3 subunit 10) (eIF-3-theta) | F5H335; Q14152 |
| P55884 | Eukaryotic translation initiation factor 3 subunit B (eIF3b) (Eukaryotic translation initiation factor 3 subunit 9) (Prt1 homolog) (hPrt1) (eIF-3-eta) (eIF3 p110) (eIF3 p116) | P55884; P55884-2 |
| B0QYA4 | Eukaryotic translation initiation factor 3 subunit D | B0QYA4; B0QYA5; O15371-2; O15371; O15371-3 |
| E5RGA2 | Eukaryotic translation initiation factor 3 subunit E (eIF3e) (Eukaryotic translation initiation factor 3 subunit 6) (eIF-3 p48) | E5RGA2; E5RIT4; H0YBR5; P60228 |
| K7ENA8 | Eukaryotic translation initiation factor 3 subunit G | K7ENA8; K7EP16; O75821 |
| Q13347 | Eukaryotic translation initiation factor 3 subunit I (eIF3i) (Eukaryotic translation initiation factor 3 subunit 2) (TGF-beta receptor-interacting protein 1) (TRIP-1) (eIF-3-beta) (eIF3 p36) | Q13347 |
| O75822 | Eukaryotic translation initiation factor 3 subunit J (eIF3j) (Eukaryotic translation initiation factor 3 subunit 1) (eIF-3-alpha) (eIF3 p35) | O75822-2; O75822-3; O75822 |
| B0QY89 | Eukaryotic translation initiation factor 3 subunit L (eIF3l) (Eukaryotic translation initiation factor 3 subunit 6-interacting protein) (Eukaryotic translation initiation factor 3 subunit E-interacting protein) | B0QY89; B0QY90; Q9Y262; Q9Y262-2 |
| B4E2Q4 | Eukaryotic translation initiation factor 3 subunit M (cDNA FLJ54904, highly similar to Homo sapiens dendritic cell protein (hfl-B5), mRNA) | B4E2Q4; Q7L2H7; H0YCQ8 |
| E7EUU4 | Eukaryotic translation initiation factor 4 gamma 1 | E7EUU4; E7EX73; E9PGM1; Q04637; Q04637-3; Q04637-4; Q04637-5; Q04637-6; Q04637-7; Q04637-8; Q04637-9 |
| I3L397 | Eukaryotic translation initiation factor 5A-1 | I3L504; P63241; P63241-2; I3L397 |
| C9J4W5 | Eukaryotic translation initiation factor 5A-2 | C9J4W5; C9J7B5; F8WCJ1; I3L504; P63241; P63241-2; Q9GZV4; I3L397 |
| O43909 | Exostosin-like 3 (EC 2.4.1.223) (EXT-related protein 1) (Glucuronyl-galactosyl-proteoglycan 4-alpha-N-acetylglucosaminyltransferase) (Hereditary multiple exostoses gene isolog) (Multiple exostosis-like protein 3) (Putative tumor suppressor protein EXTL3) | O43909; O95502 |
| E7EQR4 | Ezrin | E7EQR4; P15311; P26038; P35241; P35241-4; P35241-5 |
| Q9Y5B9 | FACT complex subunit SPT16 (Chromatin-specific transcription elongation factor 140 kDa subunit) (FACT 140 kDa subunit) (FACTp140) (Facilitates chromatin transcription complex subunit SPT16) (hSPT16) | Q9Y5B9 |
| C9JUG7 | F-actin-capping protein subunit alpha-2 (CapZ alpha-2) | C9JUG7; F8W9N7; P47755; P47755-2 |
| B4DT31 | Far upstream element-binding protein 1 (cD FLJ53425, highly similar to Far upstream element-binding protein 1) | Q96AE4; B4DT31; E9PEB5; M0QYG1; M0R0C6; M0R251; M0R263; M0R3J3; Q92945; Q96AE4-2 |
| M0QXW7 | Far upstream element-binding protein 2 (FUSE-binding protein 2) (KH type-splicing regulatory protein) (KSRP) (p75) | M0QXW7; M0QYH3; M0R0I5; Q92945 |
| P15090 | Fatty acid-binding protein, adipocyte (Adipocyte lipid-binding protein) (ALBP) (Adipocyte-type fatty acid-binding protein) (A-FABP) (AFABP) (Fatty acid-binding protein 4) | P15090 |

TABLE 2-continued

| Uniprot ID | Protein Name | All Uniprot matches |
|---|---|---|
| E9PNW8 | Fatty acyl-CoA reductase 1 | E9PNW8; Q8WVX9 |
| O60907 | F-box-like/WD repeat-containing protein TBL1X (SMAP55) (Transducin beta-like protein 1X) (Transducin-beta-like protein 1, X-linked) | O60907; O60907-2; Q9BQ87; Q9BZK7 |
| H0YFT5 | Fermitin family homolog 3 | H0YFT5; Q86UX7; Q86UX7-2 |
| B1AHL2 | Fibulin-1 | B1AHL2; P23142-3; F8W7M9; P23142; P23142-2; P23142-4 |
| P21333 | Filamin-A (FLN-A) (Actin-binding protein 280) (ABP-280) (Alpha-filamin) (Endothelial actin-binding protein) (Filamin-1) (Non-muscle filamin) | F8WE98; O75369; O75369-2; O75369-3; O75369-4; O75369-5; O75369-6; O75369-8; O75369-9; P21333; P21333-2; Q14315; Q14315-2; Q5HY53 |
| A8MQB8 | Fragile X mental retardation protein 1 | A8MQB8; G3V0J0; Q06787-9; G8JLE9; Q06787; Q06787-2; Q06787-3; Q06787-4; Q06787-5; Q06787-6; Q06787-7; Q06787-8; Q8IXW7 |
| H3BQN4 | Fructose-bisphosphate aldolase (EC 4.1.2.13) | H3BQN4; H3BR68; J3KPS3; P04075; P04075-2 |
| A8MVZ9 | Fructose-bisphosphate aldolase C | A8MVZ9; C9J8F3; H3BMQ8; H3BPS8; H3BQN4; H3BR04; H3BU78; H3BUH7; J3KPS3; J3KSV6; J3QKP5; K7EKH5; P04075; P04075-2; P09972 |
| P09382 | Galectin-1 (Gal-1) (14 kDa laminin-binding protein) (HLBP14) (14 kDa lectin) (Beta-galactoside-binding lectin L-14-I) (Galaptin) (HBL) (HPL) (Lactose-binding lectin 1) (Lectin galactoside-binding soluble 1) (Putative MAPK-activating protein PM12) (S-Lac lectin 1) | P09382 |
| B7Z2X9 | Gamma-enolase (cD FLJ50150, highly similar to Gamma-enolase (EC 4.2.1.11)) | B7Z2X9; F5H0C8; F5H1C3; P09104 |
| E9PEV0 | Gamma-secretase C-termil fragment 59 | E9PEV0; E9PG40; P05067; P05067-10; P05067-11; P05067-4; P05067-6; P05067-8 |
| O60547 | GDP-mannose 4,6 dehydratase (EC 4.2.1.47) (GDP-D-mannose dehydratase) (GMD) | O60547; O60547-2 |
| Q8TEQ6 | Gem-associated protein 5 (Gemin5) | Q8TEQ6 |
| P13984 | General transcription factor IIF subunit 2 (EC 3.6.4.12) (ATP-dependent helicase GTF2F2) (General transcription factor IIF 30 kDa subunit) (Transcription initiation factor IIF subunit beta) (TFIIF-beta) (Transcription initiation factor RAP30) | P13984 |
| G3V4P8 | Glia maturation factor beta | G3V4P8; M0QYG8; M0QYJ8; M0R0C1; M0R1D2; O60234; P60983 |
| E7EM57 | Glucose-6-phosphate 1-dehydrogenase (EC 1.1.1.49) | E7EM57; E9PD92; P11413; P11413-2; P11413-3; E7EUI8 |
| K7EQ48 | Glucose-6-phosphate isomerase (EC 5.3.1.9) | K7EQ48; P06744; P06744-2 |
| K7ELL7 | Glucosidase 2 subunit beta | K7ELL7; P14314; P14314-2 |
| B3KV55 | Glutamate dehydrogenase 1, mitochondrial# | B3KV55; B4DGN5; P00367; P49448 |
| P00367 | Glutamate dehydrogenase 1, mitochondrial (GDH 1) (EC 1.4.1.3) | P00367; P49448 |
| O94925 | Glutaminase kidney isoform, mitochondrial (GLS) (EC 3.5.1.2) (K-glutaminase) (L-glutamine amidohydrolase) | O94925; O94925-3 |
| P47897 | Glutamine--tRNA ligase (EC 6.1.1.18) (Glutaminyl-tRNA synthetase) (GlnRS) | P47897-2; P47897 |
| O76003 | Glutaredoxin-3 (PKC-interacting cousin of thioredoxin) (PICOT) (PKC-theta-interacting protein) (PKCq-interacting protein) (Thioredoxin-like protein 2) | O76003 |
| K7EJ20 | Glutathione peroxidase | K7EJ20; K7EKX7; K7ENB4; K7ERP4; P36969; P36969-2; R4GNE4 |
| E9PHN6 | Glutathione S-transferase Mu 2 | E9PHN6; E9PHN7; E9PLF1; F6XZQ7; P21266; P28161; P28161-2; P46439; Q5T8Q9; Q5T8R1 |
| P78417 | Glutathione S-transferase omega-1 (GSTO-1) (EC 2.5.1.18) (Glutathione S-transferase omega 1-1) (GSTO 1-1) (Glutathione-dependent dehydroascorbate reductase) (EC 1.8.5.1) (Monomethylarsonic acid reductase) (MMA(V) reductase) (EC 1.20.4.2) (S-(Phenacyl)glutathione reductase) (SPG-R) | P78417; P78417-2; P78417-3; Q5TA01; Q5TA02 |
| E7EUT5 | Glyceraldehyde-3-phosphate dehydrogenase (GAPDH) (EC 1.2.1.12) (Peptidyl-cysteine S-nitrosylase GAPDH) (EC 2.6.99.—) | E7EUT5; P04406; P04406-2 |
| F5GYK7 | Glycerol-3-phosphate dehydrogenase, mitochondrial | P43304; P43304-2; F5GYK7 |
| P23434 | Glycine cleavage system H protein, mitochondrial (Lipoic acid-containing protein) | P23434 |
| P41250 | Glycine--tRNA ligase (EC 6.1.1.14) (Diedenosine tetraphosphate synthetase) (AP-4-A synthetase) (Glycyl-tRNA synthetase) (GlyRS) | H7C443; P41249 |

TABLE 2-continued

| Uniprot ID | Protein Name | All Uniprot matches |
|---|---|---|
| F2Z349 | Glycodelin | Q15431; P14618; F2Z349; H0Y4U4; H0Y6A4; H3BQ34; H3BTN5; P09466; P09466-2; P14618-2; P14618-3; Q504U3; Q5T6T6; Q5VXJ5 |
| B7Z806 | Glycogen [starch] synthase, muscle (cD FLJ53681, highly similar to Glycogen (starch) synthase, muscle (EC 2.4.1.11)) | B7Z806; F5H1N8; P13807; P13807-2 |
| F5H0U5 | Glycolipid transfer protein | F5H0U5; Q9NZD2 |
| B7Z403 | Glyoxalase domain-containing protein 4 (cDNA FLJ55095) | B7Z403; I3L3Q4; Q9HC38; Q9HC38-2; Q9HC38-3 |
| H3BM42 | Golgi apparatus protein 1 (Golgi apparatus protein 1, isoform CRA_c) | H3BM42; Q92896; Q92896-2; Q92896-3 |
| Q96CN9 | GRIP and coiled-coil domain-containing protein 1 (Golgi coiled-coil protein 1) | Q96CN9 |
| B4DJW4 | Group XV phospholipase A2 (cDNA FLJ58003, highly similar to 1-O-acylceramide synthase (EC 2.3.1.—)) | B4DJW4; H3BM47; H3BMU8; H3BPT3; Q8NCC3 |
| J3K138 | Growth factor receptor-bound protein 2 | P62993; J3KT38 |
| P62993 | Growth factor receptor-bound protein 2 (Adapter protein GRB2) (Protein Ash) (SH2/SH3 adapter GRB2) | P62993; P62993-2 |
| H0YDZ7 | Guanine deaminase | H0YDZ7; J3QSY3; Q5SZC3; Q5SZC6; Q9Y2T3; Q9Y2T3-2; Q9Y2T3-3 |
| H0YDG2 | Guanine nucleotide exchange factor VAV3 | H0YDG2; Q9UKW4; Q9UKW4-4 |
| B1AKQ8 | Guanine nucleotide-binding protein G(I)/G(S)/G(T) subunit beta-1 | F6UT28; P62873; B1AKQ8; P62873-2 |
| C9JIS1 | Guanine nucleotide-binding protein G(I)/G(S)/G(T) subunit beta-2 | C9JIS1; C9JXA5; C9JZN1; P62879 |
| D6R909 | Guanine nucleotide-binding protein subunit beta-2-like 1 | D6R909; D6R9L0; D6RAC2; D6RAU2; D6RBD0; D6REE5; D6RFX4; D6RGK8; D6RHH4; E9PD14; P63244; D6R9Z1; D6RFZ9 |
| Q9NY12 | H/ACA ribonucleoprotein complex subunit 1 (Nucleolar protein family A member 1) (snoRNP protein GAR1) | Q9NY12; Q9NY12-2 |
| A8MV53 | HCG2033702, isoform CRA_a (Suppressor of SWI4 1 homolog) | A8MV53; C9J3W3; Q9NQ55; Q9NQ55-2; Q9NQ55-3 |
| H3BQZ7 | HCG2044799 (Protein HNRNPUL2-BSCL2) | H3BQZ7; Q1KMD3 |
| P34931 | Heat shock 70 kDa protein 1-like (Heat shock 70 kDa protein 1L) (Heat shock 70 kDa protein 1-Hom) (HSP70-Hom) | P34931 |
| P34932 | Heat shock 70 kDa protein 4 (HSP70RY) (Heat shock 70-related protein APG-2) | P34932 |
| B4DY72 | Heat shock protein 105 kDa (cD FLJ52360, highly similar to Heat-shock protein 105 kDa) | B4DY72; B4DYH1; Q92598; Q92598-2; Q92598-3 |
| I3L0K7 | Heat shock protein 75 kDa, mitochondrial (TNF receptor-associated protein 1, isoform CRA_b) | P07900; P07900-2; P08238; Q86U12; Q12931-2; I3L0K7; I3L239; Q12931; F5H897 |
| P07900 | Heat shock protein HSP 90-alpha (Heat shock 86 kDa) (HSP 86) (HSP86) (Lipopolysaccharide-associated protein 2) (LAP-2) (LPS-associated protein 2) (Rel carcinoma antigen NY-REN-38) | G3V2J8; P07900; P07900-2; P08238; Q58FF6; Q58FF7; Q58FF8; Q5T9W8;; Q86U13 |
| E7EVW7 | Hematopoietic lineage cell-specific protein (Hematopoietic cell-specific LYN substrate 1) (LckBP1) (p75) | E7EVW7; P14317 |
| F5GWX2 | Heme-binding protein 1 | F5GWX2; Q9NRV9 |
| P69905 | Hemoglobin subunit alpha (Alpha-globin) (Hemoglobin alpha chain) | P69905 |
| E9PBW4 | Hemoglobin subunit gamma-2 | E9PBW4; P02100; P69891; P69892 |
| A8K8G0 | Hepatoma-derived growth factor (cD FLJ75113) | A8K8G0; P51858; P51858-2; P51858-3 |
| P51858 | Hepatoma-derived growth factor (HDGF) (High mobility group protein 1-like 2) (HMG-1L2) | P51858 |
| D6R9P3 | Heterogeneous nuclear ribonucleoprotein A/B | D6R9P3; D6RBZ0; D6RD18; Q99729-2; Q99729-3; Q99729; Q99729-4 |
| Q13151 | Heterogeneous nuclear ribonucleoprotein A0 (hnRNP A0) | Q13151 |
| P51991 | Heterogeneous nuclear ribonucleoprotein A3 (hnRNP A3) | P51991; P51991-2 |
| P52597 | Heterogeneous nuclear ribonucleoprotein F (hnRNP F) (Nucleolin-like protein mcs94-1) [Cleaved into: Heterogeneous nuclear ribonucleoprotein F, N-termilly processed] | P52597 |
| D6R9T0 | Heterogeneous nuclear ribonucleoprotein H | D6RAM1; D6RBM0; D6RDU3; D6RFM3; D6RIH9; D6RIT2; D6RIU0; D6RJ04; E5RGH4; E5RGV0; E7EQJ0; E9PCY7; G8JLB6; H0YAQ2; P31943; P55795; D6R9T0 |
| P61978 | Heterogeneous nuclear ribonucleoprotein K (hnRNP K) (Transformation up-regulated nuclear protein) (TUNP) | P61978; P61978-2; P61978-3; Q5T6W5; S4R359 |

TABLE 2-continued

| Uniprot ID | Protein Name | All Uniprot matches |
|---|---|---|
| M0QYQ7 | Heterogeneous nuclear ribonucleoprotein M | M0QZM1; P52272; P52272-2; M0QYQ7; M0R2T0; M0R019; M0R0N3 |
| F6UXX1 | Heterogeneous nuclear ribonucleoprotein Q | F6UXX1; O60506; O60506-2; O60506-3; O60506-4 |
| O60506 | Heterogeneous nuclear ribonucleoprotein Q (hnRNP Q) (Glycine- and tyrosine-rich RNA-binding protein) (GRY-RBP) (NS1-associated protein 1) (Synaptotagmin-binding, cytoplasmic RNA-interacting protein) | O60506; O60506-2; O60506-3; O60506-4; O60506-5 |
| B4DT28 | Heterogeneous nuclear ribonucleoprotein R (Heterogeneous nuclear ribonucleoprotein R, isoform CRA_a) (cDNA FLJ54544, highly similar to Heterogeneous nuclear ribonucleoprotein R) | B4DT28; O43390; O43390-2; O43390-3; O43390-4 |
| B4DSU6 | Heterogeneous nuclear ribonucleoproteins C1/C2 (cDNA FLJ52975, highly similar to Heterogeneous nuclear ribonucleoproteins C) | B4DSU6; B4DY08; G3V2S1; G3V2Q1; G3V3K6; G3V4C1; G3V4W0; G3V555; G3V575; G3V576; G3V5X6; O60812; P07910; P07910-2; P07910-4 |
| E7ENR4 | Hexokinase-1 | E7ENR4; P19367; P19367-2; P19367-3; P19367-4 |
| E9PB90 | Hexokinase-2 (EC 2.7.1.1) (Hexokinase type II) (HK II) (Muscle form hexokinase) | E9PB90; P52789 |
| P09429 | High mobility group protein B1 (High mobility group protein 1) (HMG-1) | P09429; Q5T7C4; Q5T7C6 |
| E7EQU1 | High mobility group protein B3 | E7EQU1; E7ES08; E9PES6; O15347 |
| F5H2A4 | High mobility group protein HMGI-C | F5H2A4; F5H2U8; P52926 |
| F8VNX0 | Histidine ammonia-lyase | P42357; F8VNX0; F8W0V1; P42357-2; P42357-3 |
| D6RC06 | Histidine triad nucleotide-binding protein 1 | D6RC06; D6RD60; D6RE99; D6REP8; P49773 |
| B3KWE1 | Histidine--tR ligase, cytoplasmic (Histidyl-tR synthetase, isoform CRA_a) (cD FLJ42841 fis, clone BRCOC2003213, highly similar to Histidyl-tR synthetase (EC 6.1.1.21)) | B3KWE1; B4DDD8; B4E1C5; C9JWK3; E7ETE2; P12081; P12081-2; P12081-3; P12081-4 |
| B3KWE1 | Histidine--tRNA ligase, cytoplasmic (Histidyl-tRNA synthetase, isoform CRA_a) (cDNA FLJ42841 fis, clone BRCOC2003213, highly similar to Histidyl-tRNA synthetase (EC 6.1.1.21)) | B3KWE1; B4DDD8; B4E1C5; P12081; P12081-2; P12081-3; P12081-4 |
| B3KRS5 | Histone deacetylase (EC 3.5.1.98) | B3KRS5; E5RFI6; E5RFP9; E5RG37; E5RGV4; E5RH52; E5RHE7; E5RJ04; H3BM24; J3KPW7; Q13547; Q5TEE2; Q92769 |
| Q13547 | Histone deacetylase 1 (HD1) (EC 3.5.1.98) | Q13547; Q5TEE2 |
| O75446 | Histone deacetylase complex subunit SAP30 (30 kDa Sin3-associated polypeptide) (Sin3 corepressor complex subunit SAP30) (Sin3-associated polypeptide p30) | O75446 |
| P07305 | Histone H1.0 (Histone H1') (Histone H1(0)) [Cleaved into: Histone H1.0, N-terminally processed] | P07305 |
| P10412 | Histone H1.4 (Histone H1b) (Histone H1s-4) | P10412; P16402; P16403; P22492; Q02539 |
| P16401 | Histone H1.5 (Histone H1a) (Histone H1b) (Histone H1s-3) | P16401; Q9UPA5 |
| B4DEB1 | Histone H3 | B4DEB1; K7EK07; K7EMV3; K7EP01; K7ES00; P68431; P84243; Q16695; Q6NXT2; Q71DI3 |
| P68431 | Histone H3.1 (Histone H3/a) (Histone H3/b) (Histone H3/c) (Histone H3/d) (Histone H3/f) (Histone H3/h) (Histone H3/i) (Histone H3/j) (Histone H3/k) (Histone H3/l) | P68431; Q16695; Q5TEC6; Q71DI3 |
| P62805 | Histone H4 | P62805 |
| E9PC52 | Histone-binding protein RBBP7 | E9PC52; Q16576; Q16576-2; Q5JP01 |
| C9JAJ9 | Histone-binding protein RBBP7 | C9JAJ9; E9PC52; E9PIC4; E9PNS2; E9PNS6; Q09028; Q09028-2; Q09028-3; Q16576; Q16576-2 |
| Q6NXR6 | Histone-lysine N-methyltransferase setd3 (SETD3 protein) | Q6NXR6; Q86TU7; Q86TU7-2; Q86TU7-3 |
| B7Z5N8 | Homeobox protein Hox-B3 (cDNA FLJ51054, highly similar to Homeobox protein Hox-B3) | B7Z5N8; B7ZAD0; F8VXG0; O43365; P14651; P31249 |
| F8WAQ7 | Hsc70-interacting protein (Hip) (Aging-associated protein 2) (Progesterone receptor-associated p48 protein) (Protein FAM10A1) (Putative tumor suppressor ST13) (Renal carcinoma antigen NY-REN-33) (Suppression of tumorigenicity 13 protein) | F8WAQ7; P50502; Q8NFI4; F6VDH7; H7C3I1 |
| Q01581 | Hydroxymethylglutaryl-CoA synthase, cytoplasmic (HMG-CoA synthase) (EC 2.3.3.10) (3-hydroxy-3-methylglutaryl coenzyme A synthase) | Q01581 |
| P00492 | Hypoxanthine-guanine phosphoribosyltransferase (HGPRT) (HGPRTase) (EC 2.4.2.8) | P00492 |

TABLE 2-continued

| Uniprot ID | Protein Name | All Uniprot matches |
|---|---|---|
| B7Z909 | Hypoxia up-regulated protein 1# | B7Z909; E9PJ21; E9PL22; Q9Y4L1 |
| B1P7G3 | ICSU (ISCU) | B1P7G3; B3KQ30; B4DNC9; F5H5N2; Q9H1K1; Q9H1K1-2 |
| P01876 | Ig alpha-1 chain C region | P01876; P01877 |
| P01857 | Ig gamma-1 chain C region | P01857 |
| P01859 | Ig gamma-2 chain C region | P01859 |
| P01765 | Ig heavy chain V-III region TIL | P01765; P01774; P01776; P01779 |
| P01764 | Ig heavy chain V-III region VH26 | P01764 |
| P01834 | Ig kappa chain C region | P01834 |
| P01596 | Ig kappa chain V-I region CAR | P01596; P01598 |
| P80748 | Ig lambda chain V-III region LOI | P80748 |
| P01714 | Ig lambda chain V-III region SH | P01714 |
| A0M8Q6 | Ig lambda-7 chain C region | A0M8Q6; B9A064; P0CG04 |
| O00629 | Importin subunit alpha-3 (Importin alpha Q1) (Qip1) (Karyopherin subunit alpha-4) | O00629 |
| O95373 | Importin-7 (Imp7) (Ran-binding protein 7) (RanBP7) | O95373 |
| E7ETK5 | Inosine-5'-monophosphate dehydrogenase 2 | E7ETK5; H0Y4R1; P12268 |
| E5RG13 | Inositol monophosphatase 1 | E5RG13; H0YBL1; P29218; P29218-3; E5RIP7 |
| O00425 | Insulin-like growth factor 2 mRNA-binding protein 3 (IGF2 mRNA-binding protein 3) (IMP-3) (IGF-II mRNA-binding protein 3) (KH domain-containing protein overexpressed in cancer) (hKOC) (VICKZ family member 3) | O00425; Q9NZI8 |
| Q9Y287 | Integral membrane protein 2B (Immature BRI2) (imBRI2) (Protein E25B) (Transmembrane protein BRI) (Bri) [Cleaved into: BRI2, membrane form (Mature BRI2) (mBRI2); BRI2 intracellular domain (BRI2 ICD); BRI2C, soluble form; Bri23 peptide (Bri2-23) (ABri23) (C-terminal peptide) (P23 peptide)] | Q9Y287-2; Q9Y287; U3KQL7 |
| A8MYE6 | Integrin beta | A8MYE6; P05107 |
| H7C4N8 | Integrin beta-1 | H7C4N8; P05556; P05556-2; P05556-3; P05556-4; P05556-5 |
| H0YG72 | Integrin-alpha FG-GAP repeat-containing protein 2 | H0YG72 |
| Q9BYX4 | Interferon-induced helicase C domain-containing protein 1 (EC 3.6.4.13) (Clinically amyopathic dermatomyositis autoantigen 140 kDa) (CADM-140 autoantigen) (Helicase with 2 CARD domains) (Helicard) (Interferon-induced with helicase C domain protein 1) (Melanoma differentiation-associated protein 5) (MDA-5) (Murabutide down-regulated protein) (RIG-I-like receptor 2) (RLR-2) (RNA helicase-DEAD box protein 116) | Q9BYX4 |
| Q12906 | Interleukin enhancer-binding factor 3 (Double-stranded R-binding protein 76) (DRBP76) (M-phase phosphoprotein 4) (MPP4) (Nuclear factor associated with dsR) (NFAR) (Nuclear factor of activated T-cells 90 kDa) (NF-AT-90) (Translatiol control protein 80) (TCP80) | Q12906; Q12906-2; Q12906-3; Q12906-4; Q12906-5; Q12906-6; Q12906-7 |
| Q9H1K1 | Iron-sulfur cluster assembly enzyme ISCU, mitochondrial (NifU-like N-terminal domain-containing protein) (NifU-like protein) | Q9H1K1; Q9H1K1-2 |
| C9JE02 | Isoamyl acetate-hydrolyzing esterase 1 homolog | C9JE02; H7C5G1; Q2TAA2 |
| O43837 | Isocitrate dehydrogenase [NAD] subunit beta, mitochondrial (EC 1.1.1.41) (Isocitric dehydrogenase subunit beta) (NAD(+)-specific ICDH subunit beta) | O43837; O43837-3; O43837-2 |
| B4DFL2 | Isocitrate dehydrogenase [NADP], mitochondrial# | B4DFL2; B4DSZ6; H0YL11; P48735 |
| H0YKD0 | Isocitrate dehydrogese [D] subunit alpha, mitochondrial | H0YKD0; H0YL72; H0YLI6; H0YM64; H0YNF8; P50213 |
| J3KR24 | Isoleucine--tR ligase, cytoplasmic (Isoleucine-tR synthetase, isoform CRA_d) | J3KR24; P41252; Q5TCC4 |
| Q13907 | Isopentenyl-diphosphate Delta-isomerase 1 (EC 5.3.3.2) (Isopentenyl pyrophosphate isomerase 1) (IPP isomerase 1) (IPPI1) | Q13907; Q13907-2 |
| H0YLC3 | Isovaleryl-CoA dehydrogenase, mitochondrial | H0YLC3; P26440; P26440-2 |
| P33176 | Kinesin-1 heavy chain (Conventional kinesin heavy chain) (Ubiquitous kinesin heavy chain) (UKHC) | P33176 |
| Q04760 | Lactoylglutathione lyase (EC 4.4.1.5) (Aldoketomutase) (Glyoxalase I) (Glx I) (Ketone-aldehyde mutase) (Methylglyoxalase) (S-D-lactoylglutathione methylglyoxal lyase) | Q04760; Q04760-2 |

TABLE 2-continued

| Uniprot ID | Protein Name | All Uniprot matches |
|---|---|---|
| A2T926 | Lamina-associated polypeptide 2, isoforms beta/gamma# | A2T926; G5E972; H0YJH7; P42166; P42167; P42167-2 |
| C9JES9 | Lamin-B receptor | C9JES9; C9JXK0; Q14739 |
| P20700 | Lamin-B1 | P20700 |
| E5RH50 | La-related protein 1 | Q6PKG0; Q6PKG0-3; E5RH50 |
| F8VNV1 | La-related protein 4 | F8VY40; F8W1Z5; Q71RC2; Q71RC2-2; Q71RC2-3; Q71RC2-4; Q71RC2-5; Q71RC2-6; Q71RC2-7; F8VNV1 |
| Q96AG4 | Leucine-rich repeat-containing protein 59 (Ribosome-binding protein p34) (p34) | Q96AG4 |
| B4DEH5 | Leukotriene A-4 hydrolase (cDNA FLJ51712, moderately similar to Leukotriene A-4 hydrolase (EC 3.3.2.6)) | B4DEH5; P09960; P09960-2; P09960-3; P09960-4 |
| F6S2S5 | LIM and SH3 domain protein 1 | F6S2S5; K7ESD6; Q14847; Q14847-2; Q14847-3; C9J9W2 |
| F5H5G1 | Limbic system-associated membrane protein | C9J5G3; F5H5G1; H3BLU2; Q13448 |
| I3L1H3 | Lipopolysaccharide-induced tumor necrosis factor-alpha factor | I3L1H3; Q99732 |
| P06858 | Lipoprotein lipase (LPL) (EC 3.1.1.34) | P06858 |
| A8MW50 | L-lactate dehydrogenase (EC 1.1.1.27) | A8MW50; F5H1S5; F5H245; F5H5G7; G3XAP5; P00338; P00338-2; P00338-3; P00338-4; P00338-5; P07195; P07864; Q6ZMR3 |
| P00338 | L-lactate dehydrogenase A chain (LDH-A) (EC 1.1.1.27) (Cell proliferation-inducing gene 19 protein) (LDH muscle subunit) (LDH-M) (Renal carcinoma antigen NY-REN-59) | P00338; P00338-3; P00338-4 |
| K7EJE8 | Lon protease homolog, mitochondrial (EC 3.4.21.—) (Lon protease-like protein) (Mitochondrial ATP-dependent protease Lon) (Serine protease 15) | P36776-3; K7EJE8; K7EKE6; K7ER27; P36776; P36776-2 |
| O60488 | Long-chain-fatty-acid--CoA ligase 4 (EC 6.2.1.3) (Long-chain acyl-CoA synthetase 4) (LACS 4) | O60488; O60488-2 |
| A8MYV2 | LUC7-like (S. cerevisiae) (LUC7-like (S. cerevisiae), isoform CRA_f) (Putative RNA-binding protein Luc7-like 1) | A8MYV2; B8ZZ10; Q96HJ9-2; Q9NQ29; Q9NQ29-2; Q9NQ29-3; Q9Y383; Q9Y383-2; Q9Y383-3 |
| P05455 | Lupus La protein (La autoantigen) (La ribonucleoprotein) (Sjoegren syndrome type B antigen) (SS-B) | P05455 |
| F8W6P5 | LVV-hemorphin-7 | F8W6P5; P68871 |
| O94772 | Lymphocyte antigen 6H (Ly-6H) | O94772; O94772-2 |
| B1ALG6 | Lymphoid-specific helicase | B1ALG6; Q9NRZ9; Q9NRZ9-2; Q9NRZ9-3; Q9NRZ9-4; Q9NRZ9-5; Q9NRZ9-6; Q9NRZ9-7; Q9NRZ9-8 |
| Q9HD34 | LYR motif-containing protein 4 | Q9HD34 |
| H3BPV7 | Lysine--tRNA ligase | H3BPV7; H3BVA8; J3KRL2; Q15046; Q15046-2 |
| B4DWL3 | Lysosome-associated membrane glycoprotein 1# | B4DWL3; P11279 |
| F8VV32 | Lysozyme C | F8VV32; P61626 |
| P40121 | Macrophage-capping protein (Actin regulatory protein CAP-G) | B8ZZL6; E7ENU9; P40121; P40121-1 |
| A2A2V1 | Major prion protein | A2A2V1; P04156; P04156-2 |
| G3XAL0 | Malate dehydrogenase (EC 1.1.1.37) | B9A041; C9JF79; P40925; P40925-2; P40925-3; C9JRL3 |
| F5GX14 | Malectin | F5H1S8; H0YG07; Q14165 |
| Q9ULC4 | Malignant T-cell-amplified sequence 1 (MCT-1) (Multiple copies T-cell malignancies) | Q9ULC4; Q9ULC4-2; Q9ULC4-3 |
| B7Z1L3 | Membrane-associated progesterone receptor component 1 | O15173; O15173-2; B7Z1L3; O00264 |
| P55145 | Mesencephalic astrocyte-derived neurotrophic factor (Arginine-rich protein) (Protein ARMET) | P55145 |
| P02795 | Metallothionein-2 (MT-2) (Metallothionein-2A) (Metallothionein-II) (MT-II) | P02795; P04732; P13640; P13640-2; P80297; Q8N339 |
| O94776 | Metastasis-associated protein MTA2 (Metastasis-associated 1-like 1) (MTA1-L1 protein) (p53 target protein in deacetylase complex) | O94776 |
| Q13505 | Metaxin-1 (Mitochondrial outer membrane import complex protein 1) | Q13505; Q13505-2; Q13505-3 |
| A6NC17 | Methionine--tR ligase, cytoplasmic | A6NC17; P56192 |
| P22033 | Methylmalonyl-CoA mutase, mitochondrial (MCM) (EC 5.4.99.2) (Methylmalonyl-CoA isomerase) | P22033 |
| K7EM59 | Methylthioribose-1-phosphate isomerase | Q9BV20; K7EM59 |
| A6NCE7 | Microtubule-associated proteins 1A/1B light chain 3 beta 2 (Microtubule-associated proteins 1A/1B light chain 3B-like) | A6NCE7; H3BTL1; Q9GZQ8 |

TABLE 2-continued

| Uniprot ID | Protein Name | All Uniprot matches |
|---|---|---|
| Q9Y3D6 | Mitochondrial fission 1 protein (FIS1 homolog) (hFis1) (Tetratricopeptide repeat protein 11) (TPR repeat protein 11) | Q9Y3D6 |
| K7EIT2 | Mitochondrial import inner membrane translocase subunit Tim13 (Translocase of inner mitochondrial membrane 13 homolog (Yeast), isoform CRA_b) | K7EIT2; Q9Y5L4 |
| Q9NS69 | Mitochondrial import receptor subunit TOM22 homolog (hTom22) (1C9-2) (Translocase of outer membrane 22 kDa subunit homolog) | Q9NS69 |
| O94826 | Mitochondrial import receptor subunit TOM70 (Mitochondrial precursor proteins import receptor) (Translocase of outer membrane 70 kDa subunit) | O94826 |
| B9A067 | Mitochondrial inner membrane protein | B9A067; C9J406; H7C463; Q16891; Q16891-2; Q16891-3; Q16891-4 |
| P28482 | Mitogen-activated protein kinase 1 (MAP kinase 1) (MAPK 1) (EC 2.7.11.24) (ERT1) (Extracellular signal-regulated kinase 2) (ERK-2) (MAP kinase isoform p42) (p42-MAPK) (Mitogen-activated protein kinase 2) (MAP kinase 2) (MAPK 2) | P28482; P28482-2 |
| Q9UKD2 | mRNA turnover protein 4 homolog | Q9UKD2 |
| H0YDS7 | MutS protein homolog 5 | H0YDS7 |
| O00499 | Myc box-dependent-interacting protein 1 (Amphiphysin II) (Amphiphysin-like protein) (Box-dependent myc-interacting protein 1) (Bridging integrator 1) | O00499-10; O00499-11; O00499-2; O00499-4; O00499-6; O00499-7; O00499-8; O00499-9 |
| P02689 | Myelin P2 protein (Peripheral myelin protein 2) | P02689; P05413; S4R371; S4R3A2 |
| J3QRS3 | Myosin regulatory light chain 12A (Myosin regulatory light chain MRCL3, isoform CRA_b) | J3QRS3; O14950; P19105 |
| F8W6L6 | Myosin-10 | F8W6L6; P35579; P35579-2; P35580; P35580-2; P35580-3; P35580-4; P35749; P35749-2; P35749-3; P35749-4; P35580-5 |
| F2Z2U8 | Myosin-14 | F2Z2U8; G8JLL9; P35579; P35749; P35749-2; P35749-3; P35749-4; Q7Z406; Q7Z406-2; Q7Z406-4; Q7Z406-5; Q7Z406-6 |
| P35579 | Myosin-9 (Cellular myosin heavy chain, type A) (Myosin heavy chain 9) (Myosin heavy chain, non-muscle IIa) (Non-muscle myosin heavy chain A) (NMMHC-A) (Non-muscle myosin heavy chain IIa) (NMMHC II-a) (NMMHC-IIA) | P35579; B1AH99; Q5BKV1 |
| B4DGT0 | N(G),N(G)-dimethylarginine dimethylaminohydrolase 1 (cDNA FLJ54083, highly similar to NG,NG-dimethylarginine dimethylaminohydrolase 1 (EC 3.5.3.18)) | B4DGT0; B4DYP1; O94760; O94760-2 |
| O43505 | N-acetyllactosaminide beta-1,3-N-acetylglucosaminyltransferase (EC 2.4.1.149) (I-beta-1,3-N-acetylglucosaminyltransferase) (iGnT) (Poly-N-acetyllactosamine extension enzyme) (UDP-GlcNAc:betaGal beta-1,3-N-acetylglucosaminyltransferase 1) | O43505 |
| Q9H0A0 | N-acetyltransferase 10 (EC 2.3.1.—) | Q9H0A0-2; Q9H0A0 |
| A8MZB2 | N-acetyltransferase 5 (ARD1 homolog, S. cerevisiae), isoform CRA_a (N-alpha-acetyltransferase 20) | A8MZB2; P61599; P61599-2 |
| A6NKZ2 | N-acylglucosamine 2-epimerase | A6NKZ2; P51606 |
| Q8NFW8 | N-acylneuraminate cytidylyltransferase (EC 2.7.7.43) (CMP-N-acetylneuraminic acid synthase) (CMP-NeuNAc synthase) | Q8NFW8 |
| P23368 | NAD-dependent malic enzyme, mitochondrial (NAD-ME) (EC 1.1.1.38) (Malic enzyme 2) | P23368; P23368-2 |
| E7EMD0 | NADPH--cytochrome P450 reductase | E7EMD0; E7EPN3; E7EVY7; F5H468; H0Y4R2; P16435 |
| Q9BXJ9 | N-alpha-acetyltransferase 15, NatA auxiliary subunit (Gastric cancer antigen Ga19) (N-terminal acetyltransferase) (NMDA receptor-regulated protein 1) (Protein tubedown-1) (Tbdn100) | Q9BXJ9; Q9BXJ9-4 |
| B0AZT5 | N-alpha-acetyltransferase 50 (cDNA FLJ51877, highly similar to Homo sapiens Mak3 homolog (MAK3), mRNA) (cDNA, FLJ79525, highly similar to Homo sapiens Mak3 homolog (MAK3), mRNA) | B0AZT5; C9J5D1; E7EQ69; Q9GZZ1; Q9GZZ1-2 |
| B1AKJ5 | Nardilysin (Nardilysin (N-arginine dibasic convertase), isoform CRA_d) | B1AKJ5; F5H7V1; G3V1R5; O43847; O43847-2 |

TABLE 2-continued

| Uniprot ID | Protein Name | All Uniprot matches |
|---|---|---|
| E9PAV3 | Nascent polypeptide-associated complex subunit alpha, muscle-specific form (Alpha-NAC, muscle-specific form) (skNAC) | E9PAV3; E9PAV3-2; F8VNW4; F8VZ58; F8VZJ2; F8W0W4; F8W1N5; H0YHX9; Q13765 |
| F8W050 | Nck-associated protein 1-like | F8W050; P55160; P55160-2 |
| H7BYX6 | Neural cell adhesion molecule 1 | H7BYX6; P13591; P13591-1; P13591-3; P13591-4; P13591-5; R4GMN9; S4R389; S4R3Z6 |
| H9KV31 | Neural cell adhesion molecule 2 | H9KV31; O15394 |
| O00533 | Neural cell adhesion molecule L1-like protein (Close homolog of L1) [Cleaved into: Processed neural cell adhesion molecule L1-like protein] | C9J905; C9JW79; O00533; O00533-2; C9JH36 |
| E7ERL8 | Neurexin-1-beta | E7ERL8; F5GYC7; F8WB18; Q9ULB1; Q9ULB1-2; Q9ULB1-3; H0YJL2; Q9Y4C0; Q9Y4C0-4 |
| Q9Y4C0 | Neurexin-3 (Neurexin III-alpha) (Neurexin-3-alpha) | Q9Y4C0; Q9Y4C0-4 |
| Q9HDB5 | Neurexin-3-beta (Neurexin III-beta) [Cleaved into: Neurexin-3-beta, soluble form; Neurexin-3-beta, C-terminal fragment (NRXN3-CTF)] | Q9HDB5; Q9HDB5-2; Q9HDB5-3; Q9HDB5-4; Q9Y4C0; Q9Y4C0-3; Q9Y4C0-4 |
| Q09666 | Neuroblast differentiation-associated protein AHNAK (Desmoyokin) | Q09666 |
| P29120 | Neuroendocrine convertase 1 (NEC 1) (EC 3.4.21.93) (Prohormone convertase 1) (Proprotein convertase 1) (PC1) | P29120; P29120-2 |
| D6RBU5 | Neurofascin | D6RBU5; F8W791; F8W792; F8W8X7; F8W9B6; F8WAT1; H7BY57; J3QSX2; O94856; O94856-10; O94856-11; O94856-12; O94856-13; O94856-2; O94856-3; O94856-4; O94856-5; O94856-6; O94856-7; O94856-8; O94856-9; X6RKN2 |
| O95502 | Neuronal pentraxin receptor | O95502 |
| Q15818 | Neuronal pentraxin-1 (NP1) (Neuronal pentraxin I) (NP-I) | Q15818 |
| Q5BLP8 | Neuropeptide-like protein C4orf48 | Q5BLP8; Q5BLP8-2; X6RBU3 |
| B7Z1I4 | Neurotrimin (cDNA FLJ57258, highly similar to Neurotrimin) | B7Z1I4; B7Z1Z5; F8VTR5; Q9P121; Q9P121-2; Q9P121-3; Q9P121-4 |
| E9PKU7 | Neutral alpha-glucosidase AB | E9PKU7; F5H6X6; Q14697; Q14697-2 |
| Q96TA1 | Niban-like protein 1 (Meg-3) (Melanoma invasion by ERK) (MINERVA) (Protein FAM129B) | Q96TA1; Q96TA1-2 |
| P35228 | Nitric oxide synthase, inducible (EC 1.14.13.39) (Hepatocyte NOS) (HEP-NOS) (Inducible NO synthase) (Inducible NOS) (iNOS) (NOS type II) (Peptidyl-cysteine S-nitrosylase NOS2) | P35228; P35228-2 |
| J3KN36 | Nodal modulator 3 | J3KN36; P69849; Q15155; Q5JPE7; Q5JPE7-2 |
| P05204 | Non-histone chromosomal protein HMG-17 (High mobility group nucleosome-binding domain-containing protein 2) | P05204 |
| Q9Y266 | Nuclear migration protein nudC (Nuclear distribution protein C homolog) | Q9Y266 |
| Q12769 | Nuclear pore complex protein Nup160 (160 kDa nucleoporin) (Nucleoporin Nup160) | Q12769 |
| H3BPA9 | Nuclear pore complex protein Nup93 | H3BVG0; Q8N1F7; Q8N1F7-2; H3BPA9 |
| H3BRV9 | Nuclear transport factor 2 | H3BRV9; P61970 |
| Q02818 | Nucleobindin-1 (CALNUC) | H7BZI1; Q02818 |
| B7Z7A3 | Nucleolar GTP-binding protein 1# | B7Z7A3; Q5T3R7; Q9BZE4 |
| H0YDU4 | Nucleolar protein 56 | H0YDU4; O00567; Q5JXT2 |
| H7BZ72 | Nucleolar protein 58 | H7BZ72; Q9Y2X3 |
| Q9NR30 | Nucleolar RNA helicase 2 (EC 3.6.4.13) (DEAD box protein 21) (Gu-alpha) (Nucleolar RNA helicase Gu) (Nucleolar RNA helicase II) (RH II/Gu) | Q9NR30; Q9NR30-2 |
| E9PKP7 | Nucleolar transcription factor 1 | E9PKP7; P17480; P17480-2 |
| P19338 | Nucleolin (Protein C23) | P19338 |
| H7BYF2 | Nucleoporin p58/p45 | H7BYF2; Q5JRG1; Q9BVL2; Q9BVL2-2; Q9BVL2-3 |
| P12270 | Nucleoprotein TPR (Megator) (NPC-associated intranuclear protein) (Translocated promoter region protein) | P12270 |
| E7ERL0 | Nucleoside diphosphate kinase A | E7ERL0; F6XY72; J3KPD9; O60361; P15531; P15531-2; P22392; P22392-2; Q32Q12; C9K028 |
| B3KNT8 | Nucleosome assembly protein 1-like 1 | B3KNT8; B7Z9C2; F5H4R6; F8VRJ2; F8VV59; F8VVB5; F8VY35; F8W020; F8W0J6; F8W118; F8W543; H0YH88; H0YHC3; H0YIV4; P55209 |
| C9JZI7 | Nucleosome assembly protein 1-like 4 | C9JZI7; H0YCI4; Q99733; Q99733-2 |
| E5RFP0 | NudC domain-containing protein 2 | E5RFP0; Q8WVJ2 |
| Q14982 | Opioid-binding protein/cell adhesion molecule (OBCAM) (OPCML) (Opioid-binding cell adhesion molecule) (IgLON family member 1) | Q14982-4; Q14982; Q14982-2; Q14982-3 |

TABLE 2-continued

| Uniprot ID | Protein Name | All Uniprot matches |
|---|---|---|
| Q92882 | Osteoclast-stimulating factor 1 | Q92882 |
| D6R9C5 | Osteopontin | D6R9C5; P10451; P10451-2; P10451-3; P10451-4; P10451-5 |
| B1AKJ6 | Oxysterol-binding protein | B1AKJ6; E9PJW9; J3KPA3; Q96SU4; Q96SU4-2; Q96SU4-3; Q96SU4-4; Q96SU4-5; Q96SU4-6; Q96SU4-7 |
| P19021 | Peptidyl-glycine alpha-amidating monooxygese (PAM) [Includes: Peptidylglycine alpha-hydroxylating monooxygese (PHM) (EC 1.14.17.3); Peptidyl-alpha-hydroxyglycine alpha-amidating lyase (EC 4.3.2.5) (Peptidylamidoglycolate lyase) (PAL)] | P19021; P19021-2; P19021-3; P19021-4; P19021-5; P19021-6 |
| A2BFH1 | Peptidyl-prolyl cis-trans isomerase A-like 4G (PPlase A-like 4G) (EC 5.2.1.8) (Peptidylprolyl cis-trans isomerase A-like 4) | A2BFH1; C9J5S7; F5H284; F8WE65; P62937; Q9Y536 |
| H0Y8J0 | Peptidyl-prolyl cis-trans isomerase D (PPlase D) (EC 5.2.1.8) (40 kDa peptidyl-prolyl cis-trans isomerase) (Cyclophilin-40) (CYP-40) (Cyclophilin-related protein) (Rotamase D) | Q08752; H0Y8J0 |
| P30405 | Peptidyl-prolyl cis-trans isomerase F, mitochondrial (PPlase F) (EC 5.2.1.8) (Cyclophilin D) (CyP-D) (CypD) (Cyclophilin F) (Mitochondrial cyclophilin) (CyP-M) (Rotamase F) | P30405 |
| P62942 | Peptidyl-prolyl cis-trans isomerase FKBP1A (PPlase FKBP1A) (EC 5.2.1.8) (12 kDa FK506-binding protein) (12 kDa FKBP) (FKBP-12) (Calstabin-1) (FK506-binding protein 1A) (FKBP-1A) (Immunophilin FKBP12) (Rotamase) | P62942 |
| P26885 | Peptidyl-prolyl cis-trans isomerase FKBP2 (PPlase FKBP2) (EC 5.2.1.8) (13 kDa FK506-binding protein) (13 kDa FKBP) (FKBP-13) (FK506-binding protein 2) (FKBP-2) (Immunophilin FKBP13) (Rotamase) | P26885 |
| G3V5F2 | Peptidyl-prolyl cis-trans isomerase FKBP3 | G3V5F2; Q00688 |
| K7EN45 | Peptidyl-prolyl cis-trans isomerase NIMA-interacting 1 | K7EN45; Q13526 |
| Q15269 | Periodic tryptophan protein 2 homolog | Q15269 |
| P32119 | Peroxiredoxin-2 (EC 1.11.1.15) (Natural killer cell-enhancing factor B) (NKEF-B) (PRP) (Thiol-specific antioxidant protein) (TSA) (Thioredoxin peroxidase 1) (Thioredoxin-dependent peroxide reductase 1) | P32119; Q06830 |
| H7C3T4 | Peroxiredoxin-4 (EC 1.11.1.15) (Antioxidant enzyme AOE372) (AOE37-2) (Peroxiredoxin IV) (Prx-IV) (Thioredoxin peroxidase AO372) (Thioredoxin-dependent peroxide reductase A0372) | H7C3T4; Q06830; Q13162 |
| P30041 | Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12) | P30041 |
| Q8WW12 | PEST proteolytic signal-containing nuclear protein (PCNP) (PEST-containing nuclear protein) | Q8WW12; Q8WW12-2 |
| Q7RTV0 | PHD finger-like domain-containing protein 5A (PHD finger-like domain protein 5A) (Splicing factor 3B-associated 14 kDa protein) (SF3b14b) | Q7RTV0 |
| F8VVM2 | Phosphate carrier protein, mitochondrial | F8VVM2; Q00325; Q00325-2 |
| P30086 | Phosphatidylethanolamine-binding protein 1 (PEBP-1) (HCNPpp) (Neuropolypeptide h3) (Prostatic-binding protein) (Raf kinase inhibitor protein) (RKIP) [Cleaved into: Hippocampal cholinergic neurostimulating peptide (HCNP)] | P30086 |
| Q96S96 | Phosphatidylethanolamine-binding protein 4 (PEBP-4) (hPEBP4) (Protein cousin-of-RKIP 1) | Q96S96 |
| F5GWE5 | Phosphatidylinositol transfer protein alpha isoform | F5GWE5; I3L459; I3L4H1; Q00169 |
| E9PJT1 | Phosphatidylinositol-binding clathrin assembly protein | E9PJT1; E9PK13; Q13492; Q13492-2; Q13492-3; Q13492-5 |
| B4DW73 | Phosphoenolpyruvate carboxykinase [GTP], mitochondrial (cDNA FLJ50710, highly similar to Phosphoenolpyruvate carboxykinase (GTP), | H0YM31; Q16822; Q16822-2; B4DW73; H0YML5 |

TABLE 2-continued

| Uniprot ID | Protein Name | All Uniprot matches |
|---|---|---|
| | mitochondrial (EC 4.1.1.32)) (cDNA, FLJ79105, highly similar to Phosphoenolpyruvate carboxykinase (GTP), mitochondrial (EC 4.1.1.32)) | |
| E7ERH5 | Phosphoglycerate kinase 1 | E7ERH5; P00558 |
| P15259 | Phosphoglycerate mutase 2 (EC 3.1.3.13) (EC 5.4.2.11) (EC 5.4.2.4) (BPG-dependent PGAM 2) (Muscle-specific phosphoglycerate mutase) (Phosphoglycerate mutase isozyme M) (PGAM-M) | P15259; P18669; Q8N0Y7 |
| C9JDH0 | Phosphoribosyl pyrophosphate synthase-associated protein 2 | C9JDH0; C9JDU5; C9JJS3; C9K0K7; E7EPA1; E7EW35; I3L164; I3L331; O60256; O60256-3 |
| E9PBS1 | Phosphoribosylaminoimidazole carboxylase | E9PBS1; P22234; P22234-2 |
| F8WEF0 | Phosphoribosylaminoimidazolecarboxamide formyltransferase | C9JLK0; F5GWY2; P31939; P31939-1 |
| Q9Y617 | Phosphoserine aminotransferase (EC 2.6.1.52) (Phosphohydroxythreonine aminotransferase) (PSAT) | Q9Y617; Q9Y617-2 |
| I3L4N7 | Pigment epithelium-derived factor | I3L4N7; P36955 |
| F5GZA6 | PILR alpha-associated neural protein | Q8IYJ0; Q8IYJ0-2; F5GZA6; F5H0N9; F5H191 |
| Q9H307 | Pinin (140 kDa nuclear and cell adhesion-related phosphoprotein) (Desmosome-associated protein) (Domain-rich serine protein) (DRS protein) (DRSP) (Melanoma metastasis clone A protein) (Nuclear protein SDK3) (SR-like protein) | Q9H307; Q9H307-2 |
| B4E1F0 | Plasma protease C1 inhibitor# | B4E1F0; B4E1H2; E9PGN7; H9KV48; P05155 |
| Q8NC51 | Plasminogen activator inhibitor 1 RNA-binding protein (PAI1 RNA-binding protein 1) (PAI-RBP1) (SERPINE1 mRNA-binding protein 1) | Q8NC51; Q8NC51-2; Q8NC51-3; Q8NC51-4 |
| P13796 | Plastin-2 (L-plastin) (LC64P) (Lymphocyte cytosolic protein 1) (LCP-1) | P13796 |
| B4DGB4 | Plastin-3# | B4DGB4; B4DI60; B7Z6M1; F8W8D8; P13797 |
| P08567 | Pleckstrin (Platelet 47 kDa protein) (p47) | P08567 |
| Q15149 | Plectin (PCN) (PLTN) (Hemidesmosomal protein 1) (HD1) (Plectin-1) | Q15149; Q15149-2; Q15149-3; Q15149-4; Q15149-5; Q15149-6; Q15149-7; Q15149-8; Q15149-9 |
| Q15365 | Poly(rC)-binding protein 1 (Alpha-CP1) (Heterogeneous nuclear ribonucleoprotein E1) (hnRNP E1) (Nucleic acid-binding protein SUB2.3) | Q15365 |
| E7EQV3 | Polyadenylate-binding protein 1 | E7EQV3; E7ERJ7; H0YAS6; H0YAS7; H0YB75; H0YC10; P11940; P11940-2; Q9H361 |
| B4DEH8 | Polyadenylate-binding protein 2 (cDNA FLJ57714, highly similar to Poly(A)-binding protein 2) | B4DEH8; G3V4T2; H0YJH9; Q86U42; Q86U42-2; Q92843-2 |
| C9J2C3 | Polypeptide N-acetylgalactosaminyltransferase 3 | C9J2C3; Q14435; Q14435-2; Q8NCL4; S4R3S5 |
| K7EKJ7 | Polypyrimidine tract-binding protein 1 | K7EKJ7; K7ELW5; K7ES59; P26599; P26599-2; P26599-3 |
| A5A3E0 | POTE ankyrin domain family member F (ANKRD26-like family C member 1B) (Chimeric POTE-actin protein) | A5A3E0; I3L1U9; P0CG38; P0CG39; P60709; P62736; P63261; P63267; P63267-2; P68032; P68133; Q562R1; Q5T8M7; Q6S8J3; Q9BYX7; I3L4N8; F5H6T1; P61160; P61160-2; B4DXP9; F5H3I4; P61163; R4GMT0 |
| E5RGS4 | Prefoldin subunit 1 | E5RGS4; O60925 |
| Q9UHV9 | Prefoldin subunit 2 | Q9UHV9 |
| F5H2A7 | Prefoldin subunit 3 | F5H2A7; P61758 |
| A2AB88 | Prefoldin subunit 6 | A2AB88; O15212 |
| P02545 | Prelamin-A/C [Cleaved into: Lamin-A/C (70 kDa lamin) (Renal carcinoma antigen NY-REN-32)] | H0YAB0; P02545; P02545-2; P02545-3; P02545-4; P02545-5; P02545-6; Q5TCI9 |
| O75400 | Pre-mRNA-processing factor 40 homolog A (Fas ligand-associated factor 1) (Formin-binding protein 11) (Formin-binding protein 3) (Huntingtin yeast partner A) (Huntingtin-interacting protein 10) (HIP-10) (Huntingtin-interacting protein A) (Renal carcinoma antigen NY-REN-6) | O75400; O75400-2; O75400-3 |
| I3L3Z8 | Pre-mRNA-processing-splicing factor 8 | I3L3Z8; Q6P2Q9 |
| Q92620 | Pre-mRNA-splicing factor ATP-dependent RNA helicase PRP16 (EC 3.6.4.13) (ATP-dependent RNA helicase DHX38) (DEAH box protein 38) | Q92620 |
| Q8IY81 | pre-rRNA processing protein FTSJ3 (EC 2.1.1.—) (2'-O-ribose RNA methyltransferase SPB1 homolog) (Protein ftsJ homolog 3) (Putative rRNA methyltransferase 3) | Q8IY81 |
| Q5JRX3 | Presequence protease, mitochondrial (hPreP) (EC 3.4.24.—) (Pitrilysin metalloproteinase 1) (Metalloprotease 1) (hMP1) | Q5JRX3; Q5JRX3-2; Q5JRX3-3 |

TABLE 2-continued

| Uniprot ID | Protein Name | All Uniprot matches |
|---|---|---|
| C9JMU5 | Probable ATP-dependent R helicase DDX17 | C9JMU5; H3BLZ8; Q92841; Q92841-1; Q92841-2; Q92841-3 |
| B4DLW8 | Probable ATP-dependent R helicase DDX5 (cD FLJ59339, highly similar to Probable ATP-dependent R helicase DDX5 (EC 3.6.1.—)) | B4DLW8; J3KRX8; J3KTA4; J3QKN9; J3QR02; J3QRQ7; P17844 |
| Q9BUQ8 | Probable ATP-dependent RNA helicase DDX23 (EC 3.6.4.13) (100 kDa U5 snRNP-specific protein) (DEAD box protein 23) (PRP28 homolog) (U5-100 kD) | Q9BUQ8 |
| Q9UKR5 | Probable ergosterol biosynthetic protein 28 | Q9UKR5 |
| A2RTX5 | Probable threonine--tRNA ligase 2, cytoplasmic (EC 6.1.1.3) (Threonyl-tRNA synthetase) (ThrRS) (Threonyl-tRNA synthetase-like protein 2) | A2RTX5; A2RTX5-2; E7ERI3; G3XAN9; P26639; P26639-2 |
| B4DR87 | Procollagen-lysine, 2-oxoglutarate 5-dioxygenase 1# | B4DR87; Q02809 |
| C9JU11 | Procollagen-lysine, 2-oxoglutarate 5-dioxygenase 3 | C9JU11; H7C2A8; O60568 |
| K7EJ44 | Profilin 1, isoform CRA_b (Profilin-1) | K7EJ44; P07737 |
| Q8WUM4 | Programmed cell death 6-interacting protein (PDCD6-interacting protein) (ALG-2-interacting protein 1) (ALG-2-interacting protein X) (Hp95) | Q8WUM4; Q8WUM4-2; C9IZF9; F8WBR8; F8WEQ8 |
| K7ESJ4 | Programmed cell death protein 5 | K7ESJ4; O14737; Q3HM38 |
| C9JW96 | Prohibitin | C9JW96; C9JZ20; E7ESE2; E9PCW0; P35232 |
| F5GWA7 | Prohibitin-2 | F5GWA7; F5GY37; J3KPX7; Q99623 |
| F8VR77 | Proliferation-associated protein 2G4 (Cell cycle protein p38-2G4 homolog) (hG4-1) (ErbB3-binding protein 1) | F8VR77; Q9UQ80 |
| P48147 | Prolyl endopeptidase (PE) (EC 3.4.21.26) (Post-proline cleaving enzyme) | P48147 |
| Q9UHG2 | ProSAAS (Proprotein convertase subtilisin/kexin type 1 inhibitor) (Proprotein convertase 1 inhibitor) (pro-SAAS) [Cleaved into: KEP; Big SAAS (b-SAAS); Little SAAS (I-SAAS) (N-proSAAS); Big PEN-LEN (b-PEN-LEN) (SAAS CT(1-49)); PEN; Little LEN (I-LEN); Big LEN (b-LEN) (SAAS CT(25-40))] | Q9UHG2 |
| O15354 | Prosaposin receptor GPR37 (Endothelin B receptor-like protein 1) (ETBR-LP-1) (G-protein coupled receptor 37) (Parkin-associated endothelin receptor-like receptor) (PAELR) | O15354 |
| Q16186 | Proteasomal ubiquitin receptor ADRM1 (110 kDa cell membrane glycoprotein) (Gp110) (Adhesion-regulating molecule 1) (ARM-1) (Proteasome regulatory particle non-ATPase 13) (hRpn13) (Rpn13 homolog) | Q16186 |
| B4DEV8 | Proteasome subunit alpha type (EC 3.4.25.1) | B4DEV8; F5GX11; P25786; P25786-2 |
| F5GX11 | Proteasome subunit alpha type-1 | F5GX11; P25786; P25786-2 |
| G3V4X5 | Proteasome subunit alpha type-3 (EC 3.4.25.1) (Macropain subunit C8) (Multicatalytic endopeptidase complex subunit C8) (Proteasome component C8) | G3V4X5; P25788; P25788-2 |
| H0YN18 | Proteasome subunit alpha type-4 | H0YN18; P25789; P25789-2 |
| P28066 | Proteasome subunit alpha type-5 (EC 3.4.25.1) (Macropain zeta chain) (Multicatalytic endopeptidase complex zeta chain) (Proteasome zeta chain) | P28066; P28066-2 |
| H0Y586 | Proteasome subunit alpha type-7 | H0Y586; O14818; O14818-2; Q8TAA3; Q8TAA3-2; Q8TAA3-5 |
| P20618 | Proteasome subunit beta type-1 (EC 3.4.25.1) (Macropain subunit C5) (Multicatalytic endopeptidase complex subunit C5) (Proteasome component C5) (Proteasome gamma chain) | P20618 |
| P49721 | Proteasome subunit beta type-2 (EC 3.4.25.1) (Macropain subunit C7-I) (Multicatalytic endopeptidase complex subunit C7-I) (Proteasome component C7-I) | P49721 |
| J3KRR2 | Proteasome subunit beta type-3 | J3KRR2; J3KSM3; J3QKR3; P49720 |
| P28070 | Proteasome subunit beta type-4 (EC 3.4.25.1) (26 kDa prosomal protein) (HsBPROS26) (PROS-26) (Macropain beta chain) (Multicatalytic endopeptidase complex beta chain) (Proteasome beta chain) (Proteasome chain 3) (HsN3) | P28070 |
| P28074 | Proteasome subunit beta type-5 (EC 3.4.25.1) (Macropain epsilon chain) (Multicatalytic endopeptidase complex epsilon chain) | P28074; P28074-3 |

TABLE 2-continued

| Uniprot ID | Protein Name | All Uniprot matches |
|---|---|---|
| | (Proteasome chain 6) (Proteasome epsilon chain) (Proteasome subunit MB1) (Proteasome subunit X) | |
| E9PIX6 | Protein arginine N-methyltransferase 1 | E9PIX6; E9PKG1; E9PQ98; H7C2I1; Q99873; Q99873-2; Q99873-3; Q99873-4 |
| O14744 | Protein arginine N-methyltransferase 5 (EC 2.1.1.—) (72 kDa ICIn-binding protein) (Histone-arginine N-methyltransferase PRMT5) (EC 2.1.1.125) (Jak-binding protein 1) (Shk1 kinase-binding protein 1 homolog) (SKB1 homolog) (SKB1Hs) [Cleaved into: Protein arginine N-methyltransferase 5, N-terminally processed] | O14744; O14744-2 |
| F8WCF6 | Protein ARPC4-TTLL3 | F8WCF6; F8WDD7; P59998; P59998-2; P59998-3 |
| C9JNV2 | Protein BUD31 homolog | C9JNV2; P41223; P41223-2 |
| Q9BT09 | Protein canopy homolog 3 (CTG repeat protein 4a) (Expanded repeat-domain protein CAG/CTG 5) (Protein associated with TLR4) (Trinucleotide repeat-containing gene 5 protein) | Q9BT09 |
| Q9UKY7 | Protein CDV3 homolog | Q9UKY7; Q9UKY7-2 |
| Q5TDH0 | Protein DDI1 homolog 2 | Q5TDH0; Q5TDH0-2; Q5TDH0-3 |
| B4DFG0 | Protein DEK (cD FLJ53031, highly similar to Protein DEK) | B4DFG0; D6R9L5; P35659 |
| G5EA52 | Protein disulfide isomerase family A, member 3, isoform CRA_b (Protein disulfide-isomerase A3) | G5EA52; P30101 |
| I3L312 | Protein disulfide-isomerase | I3L312; I3L3P5; P07237 |
| P13667 | Protein disulfide-isomerase A4 (EC 5.3.4.1) (Endoplasmic reticulum resident protein 70) (ER protein 70) (ERp70) (Endoplasmic reticulum resident protein 72) (ER protein 72) (ERp-72) (ERp72) | P13667 |
| Q15084 | Protein disulfide-isomerase A6 (EC 5.3.4.1) (Endoplasmic reticulum protein 5) (ER protein 5) (ERp5) (Protein disulfide isomerase P5) (Thioredoxin domain-containing protein 7) | Q15084-5; Q15084-3; Q15084-4; Q15084; Q15084-2 |
| K7ELW0 | Protein DJ-1 | Q99497; K7ELW0 |
| Q5VUD6 | Protein FAM69B | Q5VUD6; Q5VUD6-2 |
| Q13045 | Protein flightless-1 homolog | Q13045; Q13045-2; Q13045-3 |
| F8VVB6 | Protein kinase C-binding protein NELL2 | F8VVB6; Q99435; Q99435-2; Q99435-3; Q99435-4 |
| F8VVB6 | Protein kise C-binding protein NELL2 | F8VVB6; Q99435; Q99435-2; Q99435-3; Q99435-4 |
| B4E2N0 | Protein LZIC# | B4E2N0; K7ES95; Q8WZA0 |
| E9PL57 | Protein NEDD8-MDP1 | E9PL57; E9PS38; F8VSA6; H3BP08; H3BTT7; Q15011; Q15011-2; Q15011-3; Q15011-4; Q15843; S4R3E9 |
| F6XY72 | Protein NME1-NME2 | F6XY72; O60361; P22392; P22392-2; Q32Q12 |
| Q9BVG4 | Protein PBDC1 (Polysaccharide biosynthesis domain-containing protein 1) | A6NDF3; P11532; E9PDN5; P11532-4; Q4G0X0; Q9BVG5 |
| O15355 | Protein phosphatase 1G (EC 3.1.3.16) (Protein phosphatase 1C) (Protein phosphatase 2C isoform gamma) (PP2C-gamma) (Protein phosphatase magnesium-dependent 1 gamma) | O15355 |
| E7EVG2 | Protein polybromo-1 | E7EVG2; H0Y5B5; Q86U86; Q86U86-2; Q86U86-3; Q86U86-4; Q86U86-5; Q86U86-6; Q86U86-7; Q86U86-8; Q86U86-9 |
| Q9P258 | Protein RCC2 (RCC1-like protein TD-60) (Telophase disk protein of 60 kDa) | Q9P258 |
| O15258 | Protein RER1 | O15258; Q5T091; Q5T092 |
| H0Y3V9 | Protein RPL36A-HNRNPH2 | H0Y3V9; H0Y5B4; H7BY91; H7BZ11; J3KQN4; P83881 |
| Q14690 | Protein RRP5 homolog (NF-kappa-B-binding protein) (NFBP) (Programmed cell death protein 11) | Q14690 |
| P60903 | Protein S100-A10 (Calpactin I light chain) (Calpactin-1 light chain) (Cellular ligand of annexin II) (S100 calcium-binding protein A10) (p10 protein) (p11) | P60903 |
| P26447 | Protein S100-A4 (Calvasculin) (Metastasin) (Placental calcium-binding protein) (Protein Mts1) (S100 calcium-binding protein A4) | P26447 |
| Q01105 | Protein SET (HLA-DR-associated protein II) (Inhibitor of granzyme A-activated Dse) (IGAAD) (PHAPII) (Phosphatase 2A inhibitor I2PP2A) (I-2PP2A) (Template-activating factor I) (TAF-I) | Q01105; Q01105-2; Q01105-3; Q01105-4 |
| P0DME0 | Protein SETSIP (SET pseudogene protein 18) (SET similar protein) (Similar to SET translocation protein) | Q01105; Q01105-2; Q01105-3; Q01105-4; P0DME0 |

TABLE 2-continued

| Uniprot ID | Protein Name | All Uniprot matches |
|---|---|---|
| A6NIF9 | Protein transport protein Sec61 subunit alpha isoform 2 | A6NIF9; A6NK38; B4DR61; C9JJV4; C9JXC6; F2Z2C7; F8W776; H7C069; H7C1Q9; P61619; Q8TC24; Q9H9S3; Q9H9S3-2; Q9H9S3-3 |
| B7Z972 | Protein-L-isoaspartate O-methyltransferase (EC 2.1.1.77) | B7Z972; C9J0F2; H7BY58; P22061; P22061-2 |
| H0Y6Z4 | Protein-methionine sulfoxide oxidase MICAL1 | H0Y6Z4; Q8TDZ2; Q8TDZ2-2; Q8TDZ2-4 |
| H0YA52 | Pterin-4-alpha-carbinolamine dehydratase 2 | H0YA52; P61457; Q9H0N5 |
| K7ENC1 | Purine-rich element-binding protein gamma | Q00577; Q96QR8; Q9H598; K7ENC1; Q9UJV8; Q9UJV8-2 |
| B7Z463 | Puromycin-sensitive aminopeptidase# | B7Z463; E9PLK3; P55786 |
| B2RPK0 | Putative high mobility group protein B1-like 1 (High mobility group protein B1 pseudogene 1) (Putative high mobility group protein 1-like 1) (HMG-1L1) | B2RPK0; P09429; P23497; Q5T7C0; Q5T7C4; Q5T7C6 |
| A6NI72 | Putative neutrophil cytosol factor 1B (NCF-1B) (Putative SH3 and PX domain-containing protein 1B) | A6NI72; C9J155; P14598; P14598-2 |
| A2A3N6 | Putative PIP5K1A and PSMD4-like protein (PIP5K1A-PSMD4) | A2A3N6; A6PVX3; P55036; P55036-2; Q5VWC4 |
| O43143 | Putative pre-mRNA-splicing factor ATP-dependent RNA helicase DHX15 (EC 3.6.4.13) (ATP-dependent RNA helicase #46) (DEAH box protein 15) | O43143 |
| P98179 | Putative RNA-binding protein 3 (RNA-binding motif protein 3) (RNPL) | P98179 |
| A8MWD9 | Putative small nuclear ribonucleoprotein G-like protein 15 | A8MWD9; C9JVQ0; P62308 |
| H3BQ34 | Pyruvate kinase (EC 2.7.1.40) | H3BQ34; H3BTN5; P14618; P14618-2; P14618-3 |
| P30613 | Pyruvate kinase PKLR (EC 2.7.1.40) (Pyruvate kinase 1) (Pyruvate kinase isozymes L/R) (R-type/L-type pyruvate kinase) (Red cell/liver pyruvate kinase) | P30613; P30613-2 |
| E9PNV3 | Radixin | P35241; P35241-3; P35241-5; E9PNV3 |
| C9JDM3 | Ran-specific GTPase-activating protein | C9JIC6; C9JJ34; C9JXG8; P43487; C9JDM3; C9JGV6; P43487-2 |
| E5RH42 | Ras GTPase-activating protein-binding protein 1 | E5RH42; E5RI46; E5RIF8; E5RIZ6; E5RJU8; Q13283; Q5HYE9 |
| H0YLE8 | Ras GTPase-activating-like protein IQGAP1 | H0YLE8; P46940 |
| B1AH77 | Ras-related C3 botulinum toxin substrate 1 (Cell migration-inducing gene 5 protein) (Ras-like protein TC25) (p21-Rac1) | B1AH77; B1AH80; P15153; P63000; P63000-2; B1AH78 |
| P61026 | Ras-related protein Rab-10 | P61026 |
| Q6IQ22 | Ras-related protein Rab-12 | Q6IQ22 |
| P51153 | Ras-related protein Rab-13 (Cell growth-inhibiting gene 4 protein) | P51153; P61026 |
| P61106 | Ras-related protein Rab-14 | P61106; X6RFL8 |
| E9PKL7 | Ras-related protein Rab-2A | E9PKL7; H0YD31; P61019; P61019-2 |
| F5H157 | Ras-related protein Rab-35 | F5H157; Q15286 |
| F8VSF8 | Ras-related protein Rab-5C | F8VVK3; K7ERI8; K7ERQ8; P51148; P51148-2; F8VWU4; F8VSF8 |
| C9IZZ0 | Ras-related protein Rab-7a | C9IZZ0; C9J4S4; C9J4V0; C9J592; C9J7D1; C9J8S3; P51149 |
| B4DEK7 | Ras-related protein Rab-8A# | B4DEK7; B7Z8M7; E7END7; E7ETK2; E9PLD0; F5GY21; H0YL94; H0YLJ8; H0YMN7; H0YNE9; P51153; P59190; P59190-2; P61006; P61026; P62820; P62820-2; P62820-3; Q92928; Q92930; Q9H0U4; F5H157; Q15286; Q15286-2 |
| H7C3P7 | Ras-related protein Ral-A | H7C3P7; P11233 |
| E7ESV4 | Ras-related protein Rap-1b | E7ESV4; F5GWU8; F5GX62; F5GYB5; F5GYH7; F5H004; F5H077; F5H0B7; F5H491; F5H4H0; F5H500; F5H6R7; F5H7Y6; F8WBC0; P61224; P61224-2; P61224-3; P61224-4; P62834 |
| A6NIZ1 | Ras-related protein Rap-1b-like protein | A6NIZ1; E7ESV4; F5GWU8; F5GX62; F5GYB5; F5GYH7; F5H004; F5H0B7; F5H491; F5H4H0; F5H500; F5H6R7; F5H7Y6; P61224; P61224-2; P61224-3; P62834; F5H077 |
| Q96PK6 | R-binding protein 14 (Paraspeckle protein 2) (PSP2) (R-binding motif protein 14) (RRM-containing coactivator activator/modulator) (Syptotagmin-interacting protein) (SYT-interacting protein) | Q96PK6 |
| D6R9K7 | R-binding protein 4 | D6R9K7; E9PB51; E9PLB0; E9PM61; J3QRR5; Q9BQ04; Q9BWF3; Q9BWF3-2; Q9BWF3-3; Q9BWF3-4; U3KQD5 |
| H3BPE7 | R-binding protein FUS | H3BPE7; P35637; P35637-2; K7EPT6; Q92804; Q92804-2 |

TABLE 2-continued

| Uniprot ID | Protein Name | All Uniprot matches |
|---|---|---|
| P23471 | Receptor-type tyrosine-protein phosphatase zeta (R-PTP-zeta) (EC 3.1.3.48) (Protein-tyrosine phosphatase receptor type Z polypeptide 1) (Protein-tyrosine phosphatase receptor type Z polypeptide 2) (R-PTP-zeta-2) | P23471-3; P23471; P23471-2 |
| J3KQ66 | Reelin | J3KQ66; P78509; P78509-2; P78509-3 |
| A2A2M0 | Regulation of nuclear pre-mRNA domain-containing protein 1B | A2A2M0; Q9NQG5 |
| Q92900 | Regulator of nonsense transcripts 1 (EC 3.6.4.—) (ATP-dependent helicase RENT1) (Nonsense mR reducing factor 1) (NORF1) (Up-frameshift suppressor 1 homolog) (hUpf1) | Q92900; Q92900-2 |
| Q86UN3 | Reticulon-4 receptor-like 2 (Nogo receptor-like 3) (Nogo-66 receptor homolog 1) (Nogo-66 receptor-related protein 2) (NgR2) | Q86UN3 |
| B7Z6Z4 | Retinal cone rhodopsin-sensitive cGMP 3',5'-cyclic phosphodiesterase subunit gamma (cDNA FLJ56329, highly similar to Myosin light polypeptide 6) | B7Z6Z4; F8VPF3; F8W1I5; F8W1R7; G3V1V0; G8JLA2; J3KND3; P14649; P60660; P60660-2 |
| I3L2N6 | Retinoid-inducible serine carboxypeptidase | I3L2N6; I3L4Z3; Q9HB40; Q9HB40-2 |
| J3KNF6 | RGM domain family member B | J3KNF6; Q6NW40 |
| J3KTF8 | Rho GDP-dissociation inhibitor 1 | J3QQX2; P52565; J3KTF8 |
| F5H2R5 | Rho GDP-dissociation inhibitor 2 | F5H2R5; F5H6Q0; H0YGX7; P52566; F5H3P3 |
| E9PNR6 | Rho GTPase-activating protein 1 | E9PNR6; H0YE29; Q07960 |
| Q5TBB1 | Ribonuclease H2 subunit B (RNase H2 subunit B) (Aicardi-Goutieres syndrome 2 protein) (AGS2) (Deleted in lymphocytic leukemia 8) (Ribonuclease HI subunit B) | Q5TBB1-2; Q5TBB1 |
| E9PAU2 | Ribonucleoprotein PTB-binding 1 | E9PAU2; Q8IY67-2 |
| E7ENU7 | Ribosomal protein L15 | E7ENU7; E7EQV9; P61313 |
| B1AXG1 | Ribosomal protein S6 kinase alpha-3 | B7Z3B5; D6R910; F2Z2J1; J3KRK0; J3QLK5; Q15349; Q15349-2; Q15349-3; Q5TI62; Q86UE8; Q86UE8-2; Q86UE8-3; Q9UKI8; Q9UKI8-2; Q9UKI8-3; Q9UKI8-4; Q9UKI8-5; B1AXG1; B4DG22; B7ZB17; B7ZL90; E7ERL6; E7EWQ5; E9PGT3; E9PRI4; F5GYC4; F8WAQ9; J3QT34; O15021; O15021-1; O15021-2; O15021-3; O60307; P51812; Q15418; Q15418-2; Q15418-3; Q6P0Q8; Q6P0Q8-2; Q96GX5; Q96GX5-2; Q96GX5-3; Q9UK32; Q9Y2H9; V9GXZ1 |
| Q9Y3A5 | Ribosome maturation protein SBDS (Shwachman-Bodian-Diamond syndrome protein) | Q9Y3A5 |
| Q5VXN0 | Ribosome production factor 2 homolog | Q5VXN0; Q9H7B2 |
| F8W7S5 | Ribosome-binding protein 1 | F8W7S5; Q9P2E9; Q9P2E9-2; Q9P2E9-3 |
| Q96PK6 | RNA-binding protein 14 (Paraspeckle protein 2) (PSP2) (RNA-binding motif protein 14) (RRM-containing coactivator activator/modulator) (Synaptotagmin-interacting protein) (SYT-interacting protein) | Q96PK6; Q96PK6-2 |
| H3BPE7 | RNA-binding protein FUS | H3BPE7; P35637; P35637-2 |
| Q9NRX1 | RNA-binding protein PNO1 | Q9NRX1 |
| Q5QPL9 | RNA-binding protein Raly | Q5QPL9; Q9UKM9; Q9UKM9-2; Q5QPM0 |
| M0QXL5 | rR 2'-O-methyltransferase fibrillarin | M0QXL5; M0R0P1; M0R1H0; M0R299; M0R2B0; M0R2Q4; M0R2U2; P22087 |
| M0QXL5 | rRNA 2'-O-methyltransferase fibrillarin | M0QXL5; M0R0P1; M0R1H0; M0R299; M0R2B0; M0R2Q4; M0R2U2; P22087 |
| A6NHQ2 | rRNA/tRNA 2'-O-methyltransferase fibrillarin-like protein 1 (EC 2.1.1.—) (Protein-glutamine methyltransferase) | M0QXL5; M0R0P1; M0R299; M0R2Q4; P22087; A6NHQ2; R4GMW7 |
| Q5JTH9 | RRP12-like protein | Q5JTH9; Q5JTH9-2; Q5JTH9-3 |
| E7ETR0 | RuvB-like 1 | E7ETR0; H7C4G5; H7C4I3; Q9Y265; Q9Y265-2 |
| H7BXE3 | SAFB-like transcription modulator | H7BXE3; Q9NWH9 |
| B1AVU8 | Saposin-D | B1AVU8; C9JIZ6; P07602; P07602-2; P07602-3 |
| H7C5W9 | Sarcoplasmic/endoplasmic reticulum calcium ATPase 2 | H7C5W9; P16615; P16615-2; P16615-3; P16615-4; P16615-5; Q93084; Q93084-2; Q93084-3; Q93084-4; Q93084-5; Q93084-6; Q93084-7 |
| E9PAV3 | scent polypeptide-associated complex subunit alpha, muscle-specific form (Alpha-C, muscle-specific form) (skC) | E9PAV3; F8VNW4; F8VZJ2; F8W0W4; F8W1N5; H0YHX9; Q13765; Q13765-2 |
| P05060 | Secretogranin-1 (Chromogranin-B) (CgB) (Secretogranin I) (SgI) [Cleaved into: GAWK peptide; CCB peptide] | P05060 |
| P13521 | Secretogranin-2 (Chromogranin-C) (Secretogranin II) (SgII) [Cleaved into: Secretoneurin (SN)] | P13521 |

TABLE 2-continued

| Uniprot ID | Protein Name | All Uniprot matches |
|---|---|---|
| Q8WXD2 | Secretogranin-3 (Secretogranin III) (SgIII) | Q8WXD2 |
| C9JQI2 | Secretoneurin | P13521; C9JQI2 |
| B0QYH4 | Seizure 6-like protein | B0QYH4; B0QYH5; Q9BYH1; Q9BYH1-2; Q9BYH1-3; Q9BYH1-4; Q9BYH1-5; Q9BYH1-6; Q9BYH1-7 |
| F5GYX3 | Semaphorin-7A | F5GYX3; O75326; O75326-2 |
| B5MCX3 | Septin-2 | B5MCX3; H7C2Y0; Q15019; Q15019-2 |
| E7EPK1 | Septin-7 | E7EPK1; E7ES33; G3V1Q4; Q16181; Q16181-2; Q5JXL7 |
| K7EIE4 | Septin-9 | K7EIE4; K7EK18; K7EL40; K7ELJ9; K7EQD7; K7ER52; Q9UHD8; Q9UHD8-2; Q9UHD8-3; Q9UHD8-4; Q9UHD8-5; Q9UHD8-7; Q9UHD8-8; Q9UHD8-9 |
| G3V241 | Serine hydroxymethyltransferase, mitochondrial | P34897; P34897-2; P34897-3; G3V241; G3V2E4; G3V2W0; G3V3Y8; G3V4T0; G3V4W5; G3V4X0; G3V540; G3V5L0 |
| Q92743 | Serine protease HTRA1 (EC 3.4.21.—) (High-temperature requirement A serine peptidase 1) (L56) (Serine protease 11) | Q92743 |
| B4E241 | Serine/arginine-rich splicing factor 3# | B4E241; P84103 |
| J3KSW7 | Serine/arginine-rich-splicing factor 1 | J3KSW7; J3KTL2; J3QQV5; Q07955; Q07955-2; Q07955-3 |
| C9JAB2 | Serine/arginine-rich-splicing factor 7 | C9JAB2; Q16629; Q16629-2; Q16629-3; Q16629-4 |
| O94804 | Serine/threonine-protein kinase 10 (EC 2.7.11.1) (Lymphocyte-oriented kinase) | O94804; Q9H2G2; Q9H2G2-2 |
| Q13177 | Serine/threonine-protein kise PAK 2 (EC 2.7.11.1) (Gamma-PAK) (PAK65) (S6/H4 kise) (p21-activated kise 2) (PAK-2) (p58) [Cleaved into: PAK-2p27 (p27); PAK-2p34 (p34) (C-t-PAK2)] | Q13177 |
| B1AKS5 | Serine/threonine-protein kise PAK 3 | Q13177; B1AKS5; O75914; O75914-2; O75914-3; O75914-4 |
| E9PMD7 | Serine/threonine-protein phosphatase (EC 3.1.3.16) | E9PMD7; F8VYE8; F8W0W8; P36873; P36873-2; P62136; P62136-2; P62136-3; P62140 |
| E5RFR9 | Serine/threonine-protein phosphatase 2A 55 kDa regulatory subunit B alpha isoform | E5RFR9; P63151; P63151-2; Q9Y2T4; Q9Y2T4-2; Q9Y2T4-3; Q9Y2T4-4 |
| B3KQV6 | Serine/threonine-protein phosphatase 2A 65 kDa regulatory subunit A alpha isoform (cD FLJ33169 fis, clone ADRGL2000384, highly similar to Serine/threonine-protein phosphatase 2A 65 kDa regulatory subunit A alpha isoform) | B3KQV6; C9J9C1; F5H3X9; J3KR29; P30153; P30154; P30154-2; P30154-3; P30154-4 |
| A6PVN5 | Serine/threonine-protein phosphatase 2A activator | A6PVN5; A6PVN9; B4DZF8; H0Y562; H0Y6E5; Q15257; Q15257-2; Q15257-3; Q15257-4 |
| Q08209 | Serine/threonine-protein phosphatase 2B catalytic subunit alpha isoform (EC 3.1.3.16) (CAM-PRP catalytic subunit) (Calmodulin-dependent calcineurin A subunit alpha isoform) | Q08209-2; Q08209-3 |
| B4DNJ6 | Serine-threonine kinase receptor-associated protein (cDNA FLJ51909, highly similar to Serine-threonine kinase receptor-associatedprotein) | B4DNJ6; Q9Y3F4 |
| P49591 | Serine--tR ligase, cytoplasmic (EC 6.1.1.11) (Seryl-tR synthetase) (SerRS) (Seryl-tR(Ser/Sec) synthetase) | P49591; Q5T507 |
| J3KN47 | Serotransferrin | C9JVG0; J3KN47; P02786 |
| C9JTJ8 | Serpin B8 | C9JTJ8; C9JVA8; H7BXK7; P35237; P50452; P50452-2 |
| Q9BXP5 | Serrate RNA effector molecule homolog (Arsenite-resistance protein 2) | H7C3A1; Q9BXP5; Q9BXP5-2; Q9BXP5-3; Q9BXP5-4; Q9BXP5-4 |
| B7WNR0 | Serum albumin | B7WNR0; C9JKR2; H7C013; P02768; P02768-2 |
| C9JZ99 | Serum paraoxonase/lactonase 3 | C9JZ99; F8WD41; Q15166; F5H4W9; P27169 |
| P10768 | S-formylglutathione hydrolase (FGH) (EC 3.1.2.12) (Esterase D) (Methylumbelliferyl-acetate deacetylase) (EC 3.1.1.56) | P10768 |
| O75368 | SH3 domain-binding glutamic acid-rich-like protein | O75368 |
| H0YKT4 | Signal peptidase complex catalytic subunit SEC11A | P67812-4; P67812-3; H0YKT4; H0YNG3; P67812; P67812-2 |
| E9PI68 | Signal peptidase complex subunit 2 | E9PI68; E9PL01; H0YE04; Q15005 |
| G3V346 | Signal recognition particle 54 kDa protein | G3V3L9; G3V480; P61011; G3V346 |
| H0Y9L6 | Sister chromatid cohesion protein PDS5 homolog A | H0Y9L6; Q29RF7 |

TABLE 2-continued

| Uniprot ID | Protein Name | All Uniprot matches |
|---|---|---|
| Q5T0V3 | Slit homolog 1 protein | Q5T0V3 |
| K7EJB5 | Small nuclear ribonucleoprotein Sm D2 | P62316; P62316-2; K7EJB5 |
| B3KVR1 | Small nuclear ribonucleoprotein-associated protein N# | B3KVR1; J3KRY3; J3QLE5; P14678; P14678-2; P14678-3; P63162; S4R3P3 |
| B4DUC8 | S-methyl-5'-thioadenosine phosphorylase (EC 2.4.2.28) (5'-methylthioadenosine phosphorylase) | B4DUC8; F2Z2F3; J3QSB7; Q13126; Q13126-2; Q13126-3; Q13126-4; Q13126-5; Q13126-6; Q13126-7 |
| B8ZZ67 | SMT3 suppressor of mif two 3 homolog 1 (Yeast), isoform CRA_b (Small ubiquitin-related modifier 1) | B8ZZ67; B8ZZN6; P63165; P63165-2 |
| G3V3A4 | SNW domain-containing protein 1 | G3V3A4; G3V4X8; Q13573 |
| P05023 | Sodium/potassium-transporting ATPase subunit alpha-1 (Na(+)/K(+) ATPase alpha-1 subunit) (EC 3.6.3.9) (Sodium pump subunit alpha-1) | P05023; P05023-2; P05023-3; P05023-4 |
| B1AKY9 | Sodium/potassium-transporting ATPase subunit alpha-2 | B1AKY9; M0R116; P05023; P05023-2; P05023-3; P05023-4; P13637; P13637-2; P13637-3; P20648; P50993 |
| M0R116 | Sodium/potassium-transporting ATPase subunit alpha-3 | M0R116; P05023; P05023-3; P05023-4; P13637; P13637-2; P13637-3; Q5TC05 |
| F8VX04 | Sodium-coupled neutral amino acid transporter 1 | F8VX04; Q9H2H9 |
| P61278 | Somatostatin (Growth hormone release-inhibiting factor) [Cleaved into: Somatostatin-28; Somatostatin-14] | P61278 |
| C9J0K6 | Sorcin | P30626-3; C9J0K6; P30626; P30626-2 |
| B4DJS7 | Sorting nexin 6, isoform CRA_e (cDNA FLJ58001, highly similar to Sorting nexin-6) | B4DJS7; Q9UNH7; Q9UNH7-2 |
| Q9UMY4 | Sorting nexin-12 | Q9UMY4; Q9UMY4-2 |
| B4DEK4 | Sorting nexin-2 | B4DEK4; O60749; E9PS65; H7C5W5; P41219; P41219-2 |
| Q96L92 | Sorting nexin-27 | Q96L92; Q96L92-3 |
| O60493 | Sorting nexin-3 (Protein SDP3) | O60493; O60493-3; O60493-4 |
| G3V2U1 | Sorting nexin-6 | G3V5X9; Q9UNH7; G3V2U1; G3V4Z5; H0YJF8 |
| E5RK62 | SPARC | E5RK62; F5GY03; P09486 |
| C9JJR8 | SPARC-like protein 1 | C9JJR8; D6RA29; F5H331; F5H4Y3; Q14515; E9PC64 |
| Q9H4F8 | SPARC-related modular calcium-binding protein 1 (Secreted modular calcium-binding protein 1) (SMOC-1) | Q9H4F8; Q9H4F8-2 |
| E5RJR5 | S-phase kinase-associated protein 1 | E5RJR5; P63208 |
| O75533 | Splicing factor 3B subunit 1 (Pre-mRNA-splicing factor SF3b 155 kDa subunit) (SF3b155) (Spliceosome-associated protein 155) (SAP 155) | H7C341; O75534 |
| Q15393 | Splicing factor 3B subunit 3 (Pre-mR-splicing factor SF3b 130 kDa subunit) (SF3b130) (STAF130) (Spliceosome-associated protein 130) (SAP 130) | Q15393; Q15393-2 |
| Q15427 | Splicing factor 3B subunit 4 (Pre-mRNA-splicing factor SF3b 49 kDa subunit) (SF3b50) (Spliceosome-associated protein 49) (SAP 49) | Q15427 |
| H0Y6J6 | Splicing factor 45 | H0Y6J6; Q5W010; Q5W011; Q5W012; Q96I25 |
| K7ENG2 | Splicing factor U2AF 65 kDa subunit | K7ENG2; P26368; P26368-2 |
| P23246 | Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor) | P23246; P23246-2 |
| Q9HCB6 | Spondin-1 (F-spondin) (Vascular smooth muscle cell growth-promoting factor) | Q9HCB6 |
| Q7KZF4 | Staphylococcal nuclease domain-containing protein 1 (100 kDa coactivator) (EBNA2 coactivator p100) (Tudor domain-containing protein 11) (p100 co-activator) | H7C597; Q7KZF3 |
| P16949 | Stathmin (Leukemia-associated phosphoprotein p18) (Metablastin) (Oncoprotein 18) (Op18) (Phosphoprotein p19) (pp19) (Prosolin) (Protein Pr22) (pp17) | P16949; P16949-2; A2A2D1 |
| P38646 | Stress-70 protein, mitochondrial (75 kDa glucose-regulated protein) (GRP-75) (Heat shock 70 kDa protein 9) (Mortalin) (MOT) (Peptide-binding protein 74) (PBP74) | P38646 |
| F5GXD8 | Stress-induced-phosphoprotein 1 (STI1) (Hsc70/Hsp90-organizing protein) (Hop) (Renal carcinoma antigen NY-REN-11) (Transformation-sensitive protein IEF SSP 3521) | F5GXD8; P31948-3; F5H783; P31948-2; P31948 |

TABLE 2-continued

| Uniprot ID | Protein Name | All Uniprot matches |
|---|---|---|
| Q14683 | Structural maintenance of chromosomes protein 1A (SMC protein 1A) (SMC-1-alpha) (SMC-1A) (Sb1.8) | Q14683 |
| D6RFM5 | Succinate dehydrogenase [ubiquinone] flavoprotein subunit, mitochondrial | D6RFM5; P31040-2; P31040; P31040-3 |
| H7C233 | Succinyl-CoA ligase [ADP/GDP-forming] subunit alpha, mitochondrial | H7C233; P53597 |
| P55809 | Succinyl-CoA:3-ketoacid coenzyme A transferase 1, mitochondrial (EC 2.8.3.5) (3-oxoacid CoA-transferase 1) (Somatic-type succinyl-CoA:3-oxoacid CoA-transferase) (SCOT-s) | P55809 |
| O75683 | Surfeit locus protein 6 | O75683 |
| C9K0U0 | SUZ domain-containing protein 1 | C9K0U0; F8WEE8; Q7Z422; Q7Z422-2; Q7Z422-3; Q7Z422-4 |
| F8VXC8 | SWI/SNF complex subunit SMARCC2 | F8VXC8; Q8TAQ2; Q8TAQ2-2; Q8TAQ2-3; Q92922 |
| O60264 | SWI/SNF-related matrix-associated actin-dependent regulator of chromatin subfamily A member 5 (SWI/SNF-related matrix-associated actin-dependent regulator of chromatin A5) (EC 3.6.4.—) (Sucrose nonfermenting protein 2 homolog) (hSNF2H) | O60264; P28370; P28370-2 |
| O15498 | Synaptobrevin homolog YKT6 (EC 2.3.1.—) | O15498 |
| Q9H7C4 | Syncoilin (Syncoilin intermediate filament 1) (Syncoilin-1) | Q9H7C4 |
| B1AJQ6 | Syntaxin-12 | B1AJQ6; Q86Y82 |
| O15400 | Syntaxin-7 | O15400; O15400-2 |
| I3L305 | Syntaxin-8 | I3L305; Q9UNK0 |
| P61764 | Syntaxin-binding protein 1 (MUNC18-1) (N-Sec1) (Protein unc-18 homolog 1) (Unc18-1) (Protein unc-18 homolog A) (Unc-18A) (p67) | P61764; P61764-2 |
| Q5TCU6 | Talin-1 | Q9Y490; Q5TCU6 |
| H0YMT1 | Talin-2 | H0YMT1; Q5TCU6; Q9Y490; Q9Y4G6 |
| E7EQR6 | T-complex protein 1 subunit alpha | E7EQR6; F5H282; P17987 |
| F5GWF6 | T-complex protein 1 subunit beta | F5GWF6; F8VQ14; P78371; P78371-2 |
| B7ZAR1 | T-complex protein 1 subunit epsilon (cDNA, FLJ79275, highly similar to T-complex protein 1 subunit epsilon) | P48643-2; B7ZAR1; E7ENZ3; E9PCA1; P48643 |
| B4DUR8 | T-complex protein 1 subunit gamma (cD FLJ57603, highly similar to T-complex protein 1 subunit gamma) (cD, FLJ78822, highly similar to T-complex protein 1 subunit gamma) (cD, FLJ79286, highly similar to T-complex protein 1 subunit gamma) | E9PM09; E9PRC8; P49368; P49368-2; Q5SZW8; Q5SZX6; Q5SZX8 |
| P50990 | T-complex protein 1 subunit theta (TCP-1-theta) (CCT-theta) (Renal carcinoma antigen NY-REN-15) | P50990-2; P50990-3; P50990 |
| P10599 | Thioredoxin (Trx) (ATL-derived factor) (ADF) (Surface-associated sulphydryl protein) (SASP) | P10599; P10599-2 |
| P30048 | Thioredoxin-dependent peroxide reductase, mitochondrial (EC 1.11.1.15) (Antioxidant protein 1) (AOP-1) (HBC189) (Peroxiredoxin III) (Prx-III) (Peroxiredoxin-3) (Protein MER5 homolog) | P30048-2; P30048 |
| K7EKG2 | Thioredoxin-like protein 1 | K7EKG2; K7EPB7; O43396 |
| E9PB61 | THO complex subunit 4 | E9PB61; Q86V81 |
| D6R9F8 | Threonine--tR ligase, cytoplasmic | P26639; P26639-2; D6R9F8; D6RBR8; D6RCA5; D6RDJ6 |
| C9JV37 | Thrombin light chain | C9JV37; E9PIT3; P00734 |
| E9PIM6 | Thy-1 membrane glycoprotein | E9PNQ8; P04216; E9PIM6 |
| B8ZZA1 | Thymosin alpha-1 | B8ZZA1; B8ZZQ6; B8ZZW7; H7C2N1; P06454; P06454-2 |
| O75663 | TIP41-like protein (Putative MAPK-activating protein PM10) (Type 2A-interacting protein) (TIP) | O75663; O75663-2 |
| Q08J23 | tR (cytosine(34)-C(5))-methyltransferase (EC 2.1.1.203) (Myc-induced SUN domain-containing protein) (Misu) (NOL1/NOP2/Sun domain family member 2) (Substrate of AIM1/Aurora kise B) (tR (cytosine-5-)-methyltransferase) (tR methyltransferase 4 homolog) (hTrm4) | Q08J23; Q08J23-2 |
| C9J338 | TRAF2 and NCK-interacting protein kise | C9J338; E7EN19; E7ENQ1; E7ESS2; F5H5M9; F5H865; G3XAA2; G5E948; H7C360; I3L2I2; O95819; O95819-2; O95819-3; O95819-4; O95819-5; Q8N4C8; Q8N4C8-2; Q8N4C8-3; Q8N4C8-4; Q8N4C8-5; Q9UKE5; Q9UKE5-2; Q9UKE5-3; Q9UKE5-4; Q9UKE5-5; Q9UKE5-6; Q9UKE5-7; Q9UKE5-8 |

TABLE 2-continued

| Uniprot ID | Protein Name | All Uniprot matches |
|---|---|---|
| P37837 | Transaldolase (EC 2.2.1.2) | P37837 |
| B5MBX2 | Transcobalamin-2 | B5MBX2; P20062; P20062-2; C9J6W9 |
| B8ZZU8 | Transcription elongation factor B (SIII), polypeptide 2 (18 kDa, elongin B), isoform CRA_b (Transcription elongation factor B polypeptide 2) | B8ZZU8; I3L0M9; Q15370; Q15370-2 |
| E5RHG8 | Transcription elongation factor B polypeptide 1 | E5RHG8; Q15369; Q15369-2 |
| O15391 | Transcription factor YY2 (Yin and yang 2) (YY-2) (Zinc finger protein 631) | O15391; P25490 |
| F2Z2U4 | Transformation/transcription domain-associated protein | Q9BPX3; O75083; O75083-3; Q8WZ42; F2Z2U4; H0Y4W2; Q8WZ42-10; Q8WZ42-11; Q8WZ42-12; Q8WZ42-13; Q8WZ42-2; Q8WZ42-3; Q8WZ42-4; Q8WZ42-5; Q8WZ42-7; Q8WZ42-8; Q8WZ42-9; Q9Y4A5; Q9Y4A5-2 |
| E7EMZ9 | Transforming acidic coiled-coil-containing protein 2 | O95359; E7EMZ9; E9PBC6; O95359-3 |
| C9JNR4 | Transforming protein RhoA | C9JNR4; C9JX21; E9PN11; E9PQH6; P08134; P61586; Q5JR05; Q5JR07; Q5JR08 |
| P55072 | Transitional endoplasmic reticulum ATPase (TER ATPase) (EC 3.6.4.6) (15S Mg(2+)-ATPase p97 subunit) (Valosin-containing protein) (VCP) | P55072 |
| B4E022 | Transketolase (cDNA FLJ56274, highly similar to Transketolase (EC 2.2.1.1)) | B4E022; P29401; P29401-2 |
| Q92616 | Translational activator GCN1 (HsGCN1) (GCN1-like protein 1) | Q92616 |
| E9PGT1 | Translin | E9PGT1; Q15631 |
| Q5TB53 | Transmembrane 9 superfamily member 3 | Q9HD45; Q5TB53 |
| Q92544 | Transmembrane 9 superfamily member 4 | Q92544 |
| G3V2K7 | Transmembrane emp24 domain-containing protein 10 (21 kDa transmembrane-trafficking protein) (S31III125) (S31I125) (Tmp-21-I) (Transmembrane protein Tmp21) (p23) (p24 family protein delta-1) (p24delta1) (p24delta) | G3V2K7; P49755 |
| E7EQ72 | Transmembrane emp24 domain-containing protein 2 | E7EQ72; Q15363 |
| Q7Z7H5 | Transmembrane emp24 domain-containing protein 4 (Endoplasmic reticulum stress-response protein 25) (ERS25) (GMP25iso) (Putative NF-kappa-B-activating protein 156) (p24 family protein alpha-3) (p24alpha3) | Q7Z7H5; Q7Z7H5-2; Q7Z7H5-3; F8W7F7 |
| P40939 | Trifunctional enzyme subunit alpha, mitochondrial (78 kDa gastrin-binding protein) (TP-alpha) [Includes: Long-chain enoyl-CoA hydratase (EC 4.2.1.17); Long chain 3-hydroxyacyl-CoA dehydrogenase (EC 1.1.1.211)] | H0YFD6; P40938 |
| P29144 | Tripeptidyl-peptidase 2 (TPP-2) (EC 3.4.14.10) (Tripetidyl aminopeptidase) (Tripeptidyl-peptidase II) (TPP-II) | P29144; Q5VZU9 |
| B7Z596 | Tropomyosin alpha-1 chain (cDNA FLJ55130, highly similar to Rattus norvegicus tropomyosin 1, alpha (Tpm1), transcript variant 8, mRNA) | B7Z596; F5H7S3; H0YK20; H0YK48; H0YKX5; H0YL42; H0YL52; H0YNC7; H7BYY1; J3KN67; K7EMU5; K7ENT6; K7EP68; K7EPV9; K7ERG3; P06753; P06753-2; P06753-3; P06753-4; P06753-5; P07951; P07951-2; P07951-3; P09493; P09493-10; P09493-2; P09493-3; P09493-4; P09493-5; P09493-6; P09493-7; P09493-8; P09493-9; P67936; P67936-2; Q5TCU3; Q5TCU8; P06753-6; Q5VU59; Q5VU61; P06753-7; Q6ZN40; U3KQK2 |
| J3KN67 | Tropomyosin alpha-3 chain | J3KN67; P06753-2; P06753-3; P06753-6; Q5VU59; Q5VU61 |
| K7EPB9 | Tropomyosin alpha-4 chain | K7EPB9; P67936; P67936-2 |
| F5H5D3 | Tubulin alpha-1C chain | F5H5D3; F8VQQ4; F8VRK0; F8VRZ4; F8VS66; F8VWV9; F8VX09; P68363; Q71U36; Q71U36-2; Q9BQE3; F8VVB9; P68363-2 |
| C9JDS9 | Tubulin alpha-4A chain | P68366-2; C9JDS9; C9JEV8; C9JJQ8; C9JQ00; F5H5D3; F8VQQ4; P68363; P68366; Q13748; Q13748-2; Q71U36; Q71U36-2; Q9BQE3 |
| P07437 | Tubulin beta chain (Tubulin beta-5 chain) | P07437; P68371; Q13885; Q5JP53; Q5ST81; Q9BVA1 |
| Q13885 | Tubulin beta-2A chain (Tubulin beta class IIa) | Q13885 |
| P68371 | Tubulin beta-4B chain (Tubulin beta-2 chain) (Tubulin beta-2C chain) | P68371 |

TABLE 2-continued

| Uniprot ID | Protein Name | All Uniprot matches |
|---|---|---|
| A6PVU8 | Tuftelin | H0Y5R1; Q13029; Q13029-2; Q13029-3; Q5THJ1; Q8WYA1; Q8WYA1-2; Q8WYA1-3; Q8WYA1-4; Q8WYA1-5; Q8WYA1-6; Q8WYA1-7; Q8WYA1-8; Q8WYA1-9; A6PVU8; F5H607; Q9NNX1; Q9NNX1-2; Q9NNX1-3 |
| E5RFR7 | Tumor protein D52 | E5RFR7; F5H0B0; H0YC44; P55327; P55327-2; P55327-3; P55327-4; P55327-5; P55327-6; P55327-7; P55327-8 |
| F5H442 | Tumor susceptibility gene 101 protein | F5H442; Q99816 |
| Q86UY0 | TXNDC5 protein (Thioredoxin domain-containing protein 5) | Q86UY0; Q8NBS9; Q8NBS9-2 |
| Q06187 | Tyrosine-protein kinase BTK (EC 2.7.10.2) (Agammaglobulinemia tyrosine kinase) (ATK) (B-cell progenitor kinase) (BPK) (Bruton tyrosine kinase) | Q06187; Q06187-2; Q5JY90 |
| P78324 | Tyrosine-protein phosphatase non-receptor type substrate 1 (SHP substrate 1) (SHPS-1) (Brain Ig-like molecule with tyrosine-based activation motifs) (Bit) (CD172 antigen-like family member A) (Inhibitory receptor SHPS-1) (Macrophage fusion receptor) (MyD-1 antigen) (Signal-regulatory protein alpha-1) (Sirp-alpha-1) (Signal-regulatory protein alpha-2) (Sirp-alpha-2) (Signal-regulatory protein alpha-3) (Sirp-alpha-3) (p84) (CD antigen CD172a) | P78324; P78324-2; P78324-4; Q5TFQ8 |
| P54577 | Tyrosine--tRNA ligase, cytoplasmic (EC 6.1.1.1) (Tyrosyl-tRNA synthetase) (TyrRS) [Cleaved into: Tyrosine--tRNA ligase, cytoplasmic, N-terminally processed] | P54577 |
| P08621 | U1 small nuclear ribonucleoprotein 70 kDa (U1 snRNP 70 kDa) (U1-70K) (snRNP70) | P08621; P08621-2; P08621-4 |
| B4E0P5 | U5 small nuclear ribonucleoprotein 200 kDa helicase (cDNA FLJ56901, highly similar to U5 small nuclear ribonucleoprotein 200 kDa helicase (EC 3.6.1.—)) | B4E0P5; O75643 |
| B4DQJ1 | U5 small nuclear ribonucleoprotein 40 kDa protein# | B4DQJ1; Q96DI7; Q9NSS8 |
| H0YDS0 | Ubiquilin-1 | H0YDS0; Q9NRR5; Q9UMX0; Q9UMX0-2 |
| B4DV12 | Ubiquitin (cDNA FLJ51326, highly similar to Homo sapiens ubiquitin B (UBB), mRNA) | B4DV12; F5GXK7; F5GYU3; F5GZ39; F5H041; F5H265; F5H2Z3; F5H388; J3QKN0; J3QLP7; J3QRK5; J3QS39; J3QSA3; J3QTR3; K7EMA8; M0R1M6; M0R1V7; M0R2S1; P0CG47; P0CG48; P62979; P62987; Q96C32; F5H6Q2; F5H747 |
| P45974 | Ubiquitin carboxyl-termil hydrolase 5 (EC 3.4.19.12) (Deubiquititing enzyme 5) (Isopeptidase T) (Ubiquitin thioesterase 5) (Ubiquitin-specific-processing protease 5) | P45974; P45974-2 |
| P45974 | Ubiquitin carboxyl-terminal hydrolase 5 (EC 3.4.19.12) (Deubiquitinating enzyme 5) (Isopeptidase T) (Ubiquitin thioesterase 5) (Ubiquitin-specific-processing protease 5) | P45974; P45974-2 |
| F5GYJ8 | Ubiquitin thioesterase OTUB1 | F5GYJ8; F5GYN4; F5H6Q1; J3KR44; Q96FW1 |
| F8W726 | Ubiquitin-associated protein 2-like | F8W726; Q14157; Q14157-1; Q14157-3; Q14157-4; Q14157-5; Q5VU77; Q5VU78; Q5VU79; Q5VU80; Q5VU81 |
| B4DIZ2 | Ubiquitin-conjugating enzyme E2 K (cD FLJ57995, moderately similar to Ubiquitin-conjugating enzyme E2-25 kDa (EC 6.3.2.19)) | B4DIZ2; D6RDM7; P61086; P61086-2 |
| P68036 | Ubiquitin-conjugating enzyme E2 L3 (EC 6.3.2.19) (L-UBC) (UbcH7) (Ubiquitin carrier protein L3) (Ubiquitin-conjugating enzyme E2-F1) (Ubiquitin-protein ligase L3) | P68036; P68036-2; P68036-3 |
| F8VSD4 | Ubiquitin-conjugating enzyme E2 N | F8VSD4; F8VV71; F8VZ29; P61088; Q5JXB2 |
| P22314 | Ubiquitin-like modifier-activating enzyme 1 (Protein A1S9) (Ubiquitin-activating enzyme E1) | P22314; Q5JRR6; P22314-2 |
| Q3KQV9 | UDP-N-acetylhexosamine pyrophosphorylase-like protein 1 (EC 2.7.7.—) | Q3KQV9 |
| F8W810 | Uncharacterized protein | F8W810; H7BZU1; P41091; Q2VIR3; Q2VIR3-2 |
| H3BML4 | Uncharacterized protein | H3BML4; H3BRP9; H3BV43; H9KV29; O00241; O00241-2; P78324; P78324-2 |
| B4DUC5 | Uncharacterized protein (cD FLJ53202, highly similar to Exportin-2) | B4DUC5; P55060; P55060-3; P55060-4 |
| B4DWJ2 | Uncharacterized protein (cD FLJ54314, highly similar to Glutaminyl-tR synthetase (EC 6.1.1.18)) | B4DWJ2; P47897 |

TABLE 2-continued

| Uniprot ID | Protein Name | All Uniprot matches |
|---|---|---|
| Q9UKN7 | Unconventional myosin-XV (Unconventional myosin-15) | Q9UKN7 |
| Q969H8 | UPF0556 protein C19orf10 (Interleukin-25) (IL-25) (Stromal cell-derived growth factor SF20) | Q969H8 |
| E7EUC7 | UTP--glucose-1-phosphate uridylyltransferase | C9JQU9; C9JUW1; C9JWG0; E7EUC7; F2Z3H1; Q16851; Q16851-2; C9JNZ1; C9JTZ5; C9JVG2 |
| K7ELW1 | UV excision repair protein RAD23 homolog A | K7ELW1; K7ENJ0; P54725; P54725-2; P54727; Q5W0S4; Q5W0S5; P54725-3 |
| P54727 | UV excision repair protein RAD23 homolog B (HR23B) (hHR23B) (XP-C repair-complementing complex 58 kDa protein) (p58) | P54727; Q5W0S4; Q5W0S5 |
| O75436 | Vacuolar protein sorting-associated protein 26A (Vesicle protein sorting 26A) (hVPS26) | O75436; O75436-2; S4R3Q6; S4R2Y3 |
| F8VXU5 | Vacuolar protein sorting-associated protein 29 | F8VXU5; Q05DG7; Q9UBQ0; Q9UBQ0-2 |
| Q96QK1 | Vacuolar protein sorting-associated protein 35 (hVPS35) (Maternal-embryonic 3) (Vesicle protein sorting 35) | Q96QK1 |
| P26640 | Valine--tRNA ligase (EC 6.1.1.9) (Protein G7a) (Valyl-tRNA synthetase) (ValRS) | P26640 |
| H3BPZ1 | Very-long-chain (3R)-3-hydroxyacyl-CoA dehydratase 3 | H3BPZ1; H3BS72; Q9P035 |
| Q9P0L0 | Vesicle-associated membrane protein-associated protein A (VAMP-A) (VAMP-associated protein A) (VAP-A) (33 kDa VAMP-associated protein) (VAP-33) | Q9P0L0; Q9P0L0-2 |
| E5RK64 | Vesicle-associated membrane protein-associated protein B/C | E5RK64; O95292; O95292-2 |
| D6RBV2 | Vesicular integral-membrane protein VIP36 | D6RBV2; D6RDX1; Q12907; D6RIU4 |
| H0Y394 | Vigilin | H0Y394; Q00341; Q00341-2 |
| P08670 | Vimentin | P08670 |
| P18206 | Vinculin (Metavinculin) (MV) | P18206; P18206-2; Q5JQ13 |
| P21796 | Voltage-dependent anion-selective channel protein 1 (VDAC-1) (hVDAC1) (Outer mitochondrial membrane protein porin 1) (Plasmalemmal porin) (Porin 31HL) (Porin 31HM) | P21796 |
| A2A3S1 | Voltage-dependent anion-selective channel protein 2 | A2A3S1; P45880; P45880-1; P45880-2; Q5JSD1; Q5JSD2 |
| A6NLU5 | V-set and transmembrane domain-containing protein 2B | A6NLU5 |
| B7Z1R5 | V-type proton ATPase catalytic subunit A# | B7Z1R5; C9JVW8; P38606; C9JA17 |
| E7EV59 | V-type proton ATPase subunit C 1 (V-ATPase subunit C 1) (Vacuolar proton pump subunit C 1) | E7EV59; P21283; Q8NEY4; Q8NEY4-2 |
| G3V2S6 | V-type proton ATPase subunit D | G3V2S6; G3V559; H0YJ55; H0YJS0; Q9Y5K8 |
| P36543 | V-type proton ATPase subunit E 1 (V-ATPase subunit E 1) (V-ATPase 31 kDa subunit) (p31) (Vacuolar proton pump subunit E 1) | P36543; P36543-3; Q96A05; C9J8H1; P36543-2 |
| Q15904 | V-type proton ATPase subunit S1 (V-ATPase subunit S1) (Protein XAP-3) (V-ATPase Ac45 subunit) (V-ATPase S1 accessory protein) (Vacuolar proton pump subunit S1) | Q15904 |
| O75083 | WD repeat-containing protein 1 (Actin-interacting protein 1) (AIP1) (NORI-1) | D6RD66; O75083; O75083-3 |
| Q9UNX4 | WD repeat-containing protein 3 | Q9UNX4 |
| Q96MR6 | WD repeat-containing protein 65 | Q96MR6 |
| Q6ZMY6 | WD repeat-containing protein 88 (PQQ repeat and WD repeat-containing protein) | Q6ZMY6; Q6ZMY6-2 |
| G8JLB2 | Xaa-Pro aminopeptidase 1# | G8JLB2; Q5T6H2; Q5T6H7; Q9NQW7; Q9NQW7-2; Q9NQW7-3 |
| P12955 | Xaa-Pro dipeptidase (X-Pro dipeptidase) (EC 3.4.13.9) (Imidodipeptidase) (Peptidase D) (Proline dipeptidase) (Prolidase) | P12955; P12955-2; P12955-3 |
| P17040 | Zinc finger and SCAN domain-containing protein 20 (Zinc finger protein 31) (Zinc finger protein 360) (Zinc finger protein KOX29) | P17040-4 |
| Q96NC0 | Zinc finger matrin-type protein 2 | Q96NC0; R4GNG8 |
| Q96KM6 | Zinc finger protein 512B | Q96KM6 |
| H3BQQ2 | Zinc finger protein 598 | H3BQQ2; Q86UK7; Q86UK7-2; Q86UK7-3 |

Table 2 discloses proteins whose peptides were found to be regulated by at least 60% in the CSF of AD patients compared to CSF of non-AD subjects. Uniprot ID=annotated ID during data search; Protein names=protein name/s given to matched sequence; All Uniprot matches=All Uniprot IDs that match to the peptide sequence detected at the time of invention. Hash (#) indicates those proteins that were annotated as "merged with ###" and which have been re-searched in Uniprot. Asterisk (*) indicates those proteins which were annotated as deleted as the entry has been removed from Uniprot (due to redundancy).

In one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, or at least two or more, optionally at least three or all biomarkers selected from the group of Apolipoprotein E, Secretogranin-1, Serine/threonine-protein phosphatase 2A 65 kDa regulatory subunit A alpha isoform, Cytoplasmic dynein 1 heavy chain 1, RuvB-like 1, cDNA FLJ54806, Alpha-1-acid glycoprotein 2, Ras-related protein Rab-13, Serum albumin and Pigment epithelium-derived factor.

The biomarker panel may comprise phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, optionally two or more biomarkers selected from Table 1 and/or Table 2 and/or Table 3 or fragments thereof.

TABLE 3

| Uniprot ID | Protein Name | All Uniprot matches |
| --- | --- | --- |
| P61981 | 14-3-3 protein gamma (Protein kinase C inhibitor protein 1) (KCIP-1) [Cleaved into: 14-3-3 protein gamma, N-terminally processed] | P61981 |
| E9PG15 | 14-3-3 protein theta | E9PG15; P27348 |
| E9PL38 | 26S proteasome non-ATPase regulatory subunit 13 | E9PL38; H0YD73; J3KNQ3; Q9UNM6; Q9UNM6-2 |
| E9PS50 | 40S ribosomal protein S13 | E9PS50; J3KMX5; P62277 |
| P47914 | 60S ribosomal protein L29 (Cell surface heparin-binding protein HIP) | P47914 |
| P62424 | 60S ribosomal protein L7a (PLA-X polypeptide) (Surfeit locus protein 3) | P62424; Q5T8U2 |
| E7EMM4 | Acid ceramidase | E7EMM4; E7ERV9; Q13510; Q13510-2; Q13510-3 |
| B7Z683 | Active breakpoint cluster region-related protein (cDNA FLJ54747, highly similar to Active breakpoint cluster region-related protein) | B7Z683; I3L0R7; Q12979; Q12979-2; Q12979-4 |
| P43652 | Afamin (Alpha-albumin) (Alpha-Alb) | P43652 |
| P02763 | Alpha-1-acid glycoprotein 1 (AGP 1) (Orosomucoid-1) (OMD 1) | P02763 |
| P19652 | Alpha-1-acid glycoprotein 2 (AGP 2) (Orosomucoid-2) (OMD 2) | P19652 |
| G3V3A0 | Alpha-1-antichymotrypsin (Serpin peptidase inhibitor, clade A (Alpha-1 antiproteinase, antitrypsin), member 3, isoform CRA_a) | G3V3A0; P01011 |
| P04217 | Alpha-1B-glycoprotein (Alpha-1-B glycoprotein) | P04217; P04217-2 |
| P50995 | Annexin A11 (56 kDa autoantigen) (Annexin XI) (Annexin-11) (Calcyclin-associated annexin 50) (CAP-50) | P50995-2; P50995 |
| P01008 | Antithrombin-III (ATIII) (Serpin C1) | P01008 |
| B3KNW1 | AP-1 complex subunit gamma-1 (cDNA FLJ30560 fis, clone BRAWH2004217, highly similar to AP-1 complex subunit gamma-1) | B3KNW1; B3KXW5; J3KQU9; O43747; O43747-2 |
| P02647 | Apolipoprotein A-I (Apo-AI) (ApoA-I) (Apolipoprotein A1) [Cleaved into: Proapolipoprotein A-I (ProapoA-I); Truncated apolipoprotein A-I (Apolipoprotein A-I(1-242))] | P02647 |
| P02652 | Apolipoprotein A-II (Apo-AII) (ApoA-II) (Apolipoprotein A2) [Cleaved into: Proapolipoprotein A-II (ProapoA-II); Truncated apolipoprotein A-II (Apolipoprotein A-II(1-76))] | P02652; V9GYC1; V9GYG9; V9GYM3; V9GYS1 |
| P06727 | Apolipoprotein A-IV (Apo-AIV) (ApoA-IV) (Apolipoprotein A4) | P06727 |
| P04114 | Apolipoprotein B-100 (Apo B-100) [Cleaved into: Apolipoprotein B-48 (Apo B-48)] | P04114 |
| B4DG16 | Asparagine--tRNA ligase, cytoplasmic# | B4DG16; K7EIU7; K7EJ19; K7EPK2; K7EQ35; O43776 |
| P25705 | ATP synthase subunit alpha, mitochondrial | P25705-3; P25705; P25705-2; K7EK77; P25705-3; K7EQH4; K7ERX7; P25705; P25705-2; K7EJP1 |
| C9JHK9 | ATP-binding cassette sub-family F member 2 | C9JHK9; C9JZV3; Q75MJ1; Q9UG63 |
| B4E3P0 | ATP-citrate synthase (cD FLJ55447, highly similar to ATP-citrate synthase (EC 2.3.3.8)) | B4E3P0; K7EIE7; P53396; P53396-2 |
| O14497 | AT-rich interactive domain-containing protein 1A (ARID domain-containing protein 1A) (B120) (BRG1-associated factor 250) (BAF250) (BRG1-associated factor 250a) (BAF250A) (Osa homolog 1) (hOSA1) (SWI-like protein) | O14497; O14497-2 |

TABLE 3-continued

| Uniprot ID | Protein Name | All Uniprot matches |
|---|---|---|
| | (SWI/SNF complex protein p270) (SWI/SNF-related, matrix-associated, actin-dependent regulator of chromatin subfamily F member 1) (hELD) | |
| A2A296 | BAG family molecular chaperone regulator 2 | A2A296; B4DXE2; O95816 |
| P02749 | Beta-2-glycoprotein 1 (APC inhibitor) (Activated protein C-binding protein) (Anticardiolipin cofactor) (Apolipoprotein H) (Apo-H) (Beta-2-glycoprotein I) (B2GPI) (Beta(2)GPI) | J3QLI0; J3QRN2; P02748 |
| P07814 | Bifunctiol glutamate/proline--tR ligase (Bifunctiol aminoacyl-tR synthetase) (Cell proliferation-inducing gene 32 protein) (Glutamatyl-prolyl-tR synthetase) [Includes: Glutamate--tR ligase (EC 6.1.1.17) (Glutamyl-tR synthetase) (GluRS); Proline--tR ligase (EC 6.1.1.15) (Prolyl-tR synthetase)] | P07814 |
| A6NJ33 | Butyrophilin-like protein 9* | A6NJ33; B7Z4Y8; Q6UXG8; Q6UXG8-2; Q6UXG8-3 |
| D6R938 | Calcium/calmodulin-dependent protein kinase (CaM kinase) II delta, isoform CRA_e (Calcium/calmodulin-dependent protein kinase type II subunit delta) | D6R938; E9PBG7; E9PF82; H0Y9J2; Q13557; Q13557-10; Q13557-11; Q13557-12; Q13557-3; Q13557-4; Q13557-5; Q13557-6; Q13557-8; Q13557-9 |
| P27824 | Calnexin (IP90) (Major histocompatibility complex class I antigen-binding protein p88) (p90) | P27824-2; P27824 |
| E7EU96 | Casein kinase II subunit alpha | E7EU96; P68400; P68400-2; Q8NEV1 |
| B3KXW5 | cDNA FLJ46199 fis, clone TESTI4007965, highly similar to AP-1 complex subunit gamma-1 | B3KXW5; J3KQU9; O43747; O43747-2 |
| B4DIZ2 | cDNA FLJ57995, moderately similar to Ubiquitin-conjugating enzyme E2-25 kDa (EC 6.3.2.19) | B4DIZ2; D6RDM7; P61086; P61086-3 |
| P00450 | Ceruloplasmin (EC 1.16.3.1) (Ferroxidase) | H7C5R1; P00450 |
| M0R1L7 | Charged multivesicular body protein 2a | M0R1L7; M0R1T5; O43633 |
| F5H5N6 | Clathrin heavy chain 2 | F5H5N6; J3KR87; J3KS13; J3KSQ2; P53675; P53675-2; Q00610; Q00610-2 |
| P09496 | Clathrin light chain A (Lca) | P09496-2; P09496-5 |
| E9PK25 | Cofilin-1 | P23528; Q9Y281; E9PK25; E9PP50; E9PQB7; F6RFD5; G3V1A4; P60981; P60981-2; Q9Y281-3 |
| P02452 | Collagen alpha-1(I) chain (Alpha-1 type I collagen) | P02452 |
| P08572 | Collagen alpha-2(IV) chain [Cleaved into: Canstatin] | P08572 |
| P01024 | Complement C3 (C3 and PZP-like alpha-2-macroglobulin domain-containing protein 1) [Cleaved into: Complement C3 beta chain; C3-beta-c (C3bc); Complement C3 alpha chain; C3a anaphylatoxin; Acylation stimulating protein (ASP) (C3adesArg); Complement C3b alpha' chain; Complement C3c alpha' chain fragment 1; Complement C3dg fragment; Complement C3g fragment; Complement C3d fragment; Complement C3f fragment; Complement C3c alpha' chain fragment 2] | M0QYC8; P01024 |
| F5GXS0 | Complement C4-B | F5GXS0; P0C0L4; P0C0L4-2; P0C0L5 |
| P07357 | Complement component C8 alpha chain (Complement component 8 subunit alpha) | P07357 |
| P08603 | Complement factor H (H factor 1) | P08603 |
| B1AKG0 | Complement factor H-related protein 1 | B1AKG0; P08603; Q03591 |
| H3BRY3 | Coronin | H3BRY3; P31146 |
| F8W872 | Cyclin-dependent kise 10 | F8W872; H3BT74; Q15131; Q15131-2; Q15131-3; Q15131-4 |
| O43175 | D-3-phosphoglycerate dehydrogenase (3-PGDH) (EC 1.1.1.95) | O43175; Q5SZU1 |
| B7WPD1 | Doublecortin domain-containing protein 1* | B7WPD1; M0R2J8 |
| E7EMD0 | DPH--cytochrome P450 reductase | E7EMD0; E7EPN3; E7EVY7; F5H468; H0Y4R2; P16435 |
| P49792 | E3 SUMO-protein ligase RanBP2 (EC 6.3.2.—) (358 kDa nucleoporin) (Nuclear pore complex protein Nup358) (Nucleoporin Nup358) (Ran-binding protein 2) (RanBP2) (p270) | P49792 |
| E9PK01 | Elongation factor 1-delta | E9PK01; E9PQC9; E9PQZ1; E9PRY8; H0YE58; H0YE72; P29692; P29692-2; P29692-3; P29692-4 |
| P13639 | Elongation factor 2 (EF-2) | P13639 |
| E7EQG2 | Eukaryotic initiation factor 4A-II | E7EQG2; J3KSN7; J3KT12; J3KTB5; J3QL43; J3QLN6; J3QR64; P60842; P60842-2; Q14240; Q14240-2; J3KS25; J3QKZ9 |

TABLE 3-continued

| Uniprot ID | Protein Name | All Uniprot matches |
|---|---|---|
| P05198 | Eukaryotic translation initiation factor 2 subunit 1 (Eukaryotic translation initiation factor 2 subunit alpha) (eIF-2-alpha) (eIF-2A) (eIF-2alpha) | P05198 |
| Q8IXL6 | Extracellular serine/threonine protein kinase FAM20C (EC 2.7.11.1) (Dentin matrix protein 4) (DMP-4) (Golgi-enriched fraction casein kinase) (GEF-CK) (Protein FAM20C) | Q8IXL6 |
| Q01469 | Fatty acid-binding protein, epidermal (Epidermal-type fatty acid-binding protein) (E-FABP) (Fatty acid-binding protein 5) (Psoriasis-associated fatty acid-binding protein homolog) (PA-FABP) | Q01469 |
| G3V0F2 | Ferredoxin reductase, isoform CRA_c (DPH: adrenodoxin oxidoreductase, mitochondrial) | G3V0F2; J3QQX3; P22570; P22570-2; P22570-3; P22570-4; P22570-5; P22570-6; P22570-7 |
| E9PPQ4 | Ferritin | E9PPQ4; E9PRK8; G3V192; G3V1D1; P02794 |
| D6REL8 | Fibrinogen beta chain | D6REL8; P02675 |
| J3KTJ6 | Gamma-soluble NSF attachment protein | J3KTJ6; Q99747 |
| B7Z403 | Glyoxalase domain-containing protein 4 (cD FLJ55095) | B7Z403; Q9HC38; Q9HC38-2 |
| A8MTJ3 | Guanine nucleotide-binding protein G(t) subunit alpha-3 (Gustducin alpha-3 chain) | A8MTJ3; P04899-5; P04899-6; F5GZL8; P04899; P04899-2; P04899-3; P04899-4; P08754; P11488; P19087; P38405-3; P63096; P63096-2 |
| P00739 | Haptoglobin-related protein | P00739; P00739-2 |
| Q92598 | Heat shock protein 105 kDa (Antigen NY-CO-25) (Heat shock 110 kDa protein) | Q92598-4; Q92598; Q92598-2; Q92598-3; R4GN69 |
| I3L0K7 | Heat shock protein 75 kDa, mitochondrial (TNF receptor-associated protein 1, isoform CRA_b) | Q12931-2; I3L0K7; I3L239; Q12931 |
| P68871 | Hemoglobin subunit beta (Beta-globin) (Hemoglobin beta chain) [Cleaved into: LVV-hemorphin-7; Spinorphin] | P68871 |
| P02790 | Hemopexin (Beta-1B-glycoprotein) | P02790 |
| P61978 | Heterogeneous nuclear ribonucleoprotein K (hnRNP K) (Transformation up-regulated nuclear protein) (TUNP) | P61978; P61978-2; P61978-3; Q5T6W1; Q5T6W2; Q5T6W5 |
| B4DT28 | Heterogeneous nuclear ribonucleoprotein R (Heterogeneous nuclear ribonucleoprotein R, isoform CRA_a) (cD FLJ54544, highly similar to Heterogeneous nuclear ribonucleoprotein R) | B4DT28; O43390; O43390-2; O43390-3; S4R3J4 |
| P01861 | Ig gamma-4 chain C region | P01861 |
| P23083 | Ig heavy chain V-I region V35 | P23083 |
| F8WAR6 | Kinesin-like protein KIF3C | F8WAR6; F8WER6; O14782 |
| Q04760 | Lactoylglutathione lyase (EC 4.4.1.5) (Aldoketomutase) (Glyoxalase I) (Glx I) (Ketone-aldehyde mutase) (Methylglyoxalase) (S-D-lactoylglutathione methylglyoxal lyase) | Q04760; Q04760-2 |
| E9PBF6 | Lamin-B1 | E9PBF6; P20700 |
| Q92615 | La-related protein 4B (La ribonucleoprotein domain family member 4B) (La ribonucleoprotein domain family member 5) (La-related protein 5) | Q92615 |
| P51884 | Lumican (Keratan sulfate proteoglycan lumican) (KSPG lumican) | P51884 |
| F8W6P5 | LVV-hemorphin-7 | F8W6P5; P68871 |
| Q7Z7M0 | Multiple epidermal growth factor-like domains protein 8 (Multiple EGF-like domains protein 8) (Epidermal growth factor-like protein 4) (EGF-like protein 4) | Q7Z7M0; Q7Z7M0-2 |
| B4DYH8 | N-acetylglucosamine-6-sulfatase# | B4DYH8; F6S8M0; H0YFA9; H7C3P4; P15586; F5H4C6 |
| O43505 | N-acetyllactosaminide beta-1,3-N-acetylglucosaminyltransferase (EC 2.4.1.149) (I-beta-1,3-N-acetylglucosaminyltransferase) (iGnT) (Poly-N-acetyllactosamine extension enzyme) (UDP-GlcNAc:betaGal beta-1,3-N-acetylglucosaminyltransferase 1) | O43505 |
| Q96PD5 | N-acetylmuramoyl-L-alanine amidase (EC 3.5.1.28) (Peptidoglycan recognition protein 2) (Peptidoglycan recognition protein long) (PGRP-L) | Q96PD5; Q96PD5-2 |
| O00567 | Nucleolar protein 56 (Nucleolar protein 5A) | O00567; Q5JXT2 |
| H7BY16 | Nucleolin | P19338; H7BY16 |
| A8MXH2 | Nucleosome assembly protein 1-like 4 | A8MXH2; B3KNT8; B3KV44; B7Z9C2; C9J6D1; C9JZI7; E9PJJ2; E9PKT8; E9PNJ7; E9PNW0; E9PS34; F5H4R6; F5HFY4; F8VRJ2; F8VUX1; F8VV59; F8VVB5; F8VXI6; F8VY35; F8W020; F8W0J6; F8W118; F8W543; H0YH88; H0YHC3; H0YIV4; P55209; Q99733 |

TABLE 3-continued

| Uniprot ID | Protein Name | All Uniprot matches |
|---|---|---|
| B4E1F0 | Plasma protease C1 inhibitor# | B4E1F0; B4E1H2; E9PGN7; P05155 |
| P00747 | Plasminogen (EC 3.4.21.7) [Cleaved into: Plasmin heavy chain A; Activation peptide; Angiostatin; Plasmin heavy chain A, short form; Plasmin light chain B] | P00747 |
| Q15149 | Plectin (PCN) (PLTN) (Hemidesmosomal protein 1) (HD1) (Plectin-1) | Q15149; Q15149-2; Q15149-3; Q15149-4; Q15149-5; Q15149-6; Q15149-7; Q15149-8; Q15149-9 |
| O75051 | Plexin-A2 (Semaphorin receptor OCT) | O75051 |
| H0YAB0 | Prelamin-A/C | H0YAB0; P02545; P02545-2; P02545-3; P02545-4; P02545-5; P02545-6; Q5TCI8 |
| I3L1Q5 | Pre-rRNA-processing protein TSR1 homolog | I3L1Q5; Q2NL82 |
| H0Y7L7 | Presequence protease, mitochondrial | H0Y7L7; Q5JRX3; Q5JRX3-2; Q5JRX3-3 |
| E9PIF2 | Probable ATP-dependent RNA helicase DDX10 | E9PIF2; Q13206 |
| B4DLW8 | Probable ATP-dependent RNA helicase DDX5# | B4DLW8; C9JMU5; H3BLZ8; J3KRZ1; J3KTA4; J3QRQ7; P17844; Q92841; Q92841-1; Q92841-2; Q92841-3 |
| Q7Z4N8 | Prolyl 4-hydroxylase subunit alpha-3 (4-PH alpha-3) (EC 1.14.11.2) (Procollagen-proline, 2-oxoglutarate-4-dioxygenase subunit alpha-3) | Q7Z4N8-3 |
| P02760 | Protein AMBP [Cleaved into: Alpha-1-microglobulin (Protein HC) (Alpha-1 microglycoprotein) (Complex-forming glycoprotein heterogeneous in charge); Inter-alpha-trypsin inhibitor light chain (ITI-LC) (Bikunin) (EDC1) (HI-30) (Uronic-acid-rich protein); Trypstatin] | P02760; S4R471 |
| K7ER74 | Protein APOC4-APOC2 | K7ER74; P02655; Q6P163 |
| Q6ZSJ9 | Protein shisa-6 homolog | Q6ZSJ9; Q6ZSJ9-2; Q6ZSJ9-3 |
| Q9BVV6-3 | Protein TALPID3 | Q9BVV6-3 |
| B7Z972 | Protein-L-isoaspartate O-methyltransferase (EC 2.1.1.77) | B7Z972; H7BY58; P22061; P22061-2 |
| P59074 | Putative charged multivesicular body protein 4B-like protein CHMP4BP1 (Charged multivesicular body protein 4B pseudogene 1) | Q9H444; P59074 |
| O60361 | Putative nucleoside diphosphate kinase (NDK) (NDP kinase) (EC 2.7.4.6) | O60361; P22392; P22392-2; Q32Q12 |
| D6RHH8 | Rap1 GTPase-GDP dissociation stimulator 1 | D6RHZ7; P52306; P52306-2; P52306-3; P52306-4; P52306-5; P52306-6; D6RHH8 |
| P46940 | Ras GTPase-activating-like protein IQGAP1 (p195) | P46940 |
| E7END7 | Ras-related protein Rab-1A | E7END7; P62820 |
| P62834 | Ras-related protein Rap-1A (C21KG) (G-22K) (GTP-binding protein smg p21A) (Ras-related protein Krev-1) | P62834 |
| E7ENU7 | Ribosomal protein L15 | E7ENU7; E7EQV9; E7EX53; P61313; P61313-2 |
| B3KQ59 | RuvB-like 2# | B3KQ59; M0R0Y3; Q9Y230 |
| F8VZQ9 | SAP domain-containing ribonucleoprotein | F8VZQ9; H0YHG0; P82979; Q567R9 |
| B5MCX3 | Septin-2 | B5MCX3; H7C2Y0; Q15019; Q15019-2; Q15019-3 |
| J3KN47 | Serotransferrin* | J3KN47; P02787 |
| B7WNR0 | Serum albumin | B7WNR0; C9JKR2; D6RHD5; H0YA55; P02768; P02768-2 |
| F5H4W9 | Serum paraoxonase/arylesterase 1* | F5H4W9; P27169 |
| F8WF42 | Serum paraoxonase/arylesterase 1 | F8WF42; P27169 |
| B0FWH5 | Sex hormone binding globulin (Sex hormone-binding globulin) | B0FWH5; B0FWH6; B0FWH7; B4DYU0; I3L0M1; I3L145; I3L1C1; I3L1G4; I3L1J1; I3L2F1; I3L2X4; I3L4B9; P04278; P04278-2; P04278-3; P04278-4; P04278-5 |
| G3V2B9 | Short peptide from AAT | G3V2B9; P01009; P01009-2; P01009-3 |
| A6NKH4 | Sorting nexin-1* | A6NKH4; H0YK42; Q13596; Q13596-2; Q13596-3 |
| Q15459 | Splicing factor 3A subunit 1 (SF3a120) (Spliceosome-associated protein 114) (SAP 114) | Q15459-2; Q15459 |
| D6RFM5 | Succinate dehydrogenase [ubiquinone] flavoprotein subunit, mitochondrial | D6RFM5; P31040-2; P31040; P31040-3 |
| F5GXC8 | Succinyl-CoA ligase [ADP-forming] subunit beta, mitochondrial* | F5GXC8; Q5T9Q5; Q9P2R7; Q9P2R7-2 |
| Q5TCU6 | Talin-1 | Q9Y490; Q5TCU6; Q9Y4G6 |
| B7ZAR1 | T-complex protein 1 subunit epsilon (cDNA, FLJ79275, highly similar to T-complex protein 1 subunit epsilon) | P48643-2; B7ZAR1; E7ENZ3; E9PCA1; P48643 |

TABLE 3-continued

| Uniprot ID | Protein Name | All Uniprot matches |
| --- | --- | --- |
| B4DUR8 | T-complex protein 1 subunit gamma (cD FLJ57603, highly similar to T-complex protein 1 subunit gamma) (cD, FLJ78822, highly similar to T-complex protein 1 subunit gamma) (cD, FLJ79286, highly similar to T-complex protein 1 subunit gamma) | B4DUR8; E9PRC8; P49368; Q5SZX6; Q5SZX9 |
| E9PHK0 | Tetranectin | E9PHK0; P05452 |
| E7EQ72 | Transmembrane emp24 domain-containing protein 2 | E7EQ72; F5GX39; Q15363 |
| K7EJI9 | Truncated apolipoprotein C-I | K7EJI9; K7ELM9; K7EPF9; K7ERI9; P02654; K7EKP1 |
| G3V2J9 | Tubulin polyglutamylase TTLL5 | G3V2J9; Q6EMB2; Q6EMB2-3 |
| Q9UIG0 | Tyrosine-protein kinase BAZ1B (EC 2.7.10.2) (Bromodomain adjacent to zinc finger domain protein 1B) (Williams syndrome transcription factor) (Williams-Beuren syndrome chromosomal region 10 protein) (Williams-Beuren syndrome chromosomal region 9 protein) (hWALp2) | Q9UIG0; Q9UIG0-2 |
| B4E1Z4 | Uncharacterized protein (cDNA FLJ55673, highly similar to Complement factor B (EC 3.4.21.47)) | B4E1Z4; E7ETN3; H7C5H1; P00751 |
| H0Y426 | Valine--tRNA ligase | H0Y426; P26640 |
| C9J8H1 | V-type proton ATPase subunit E 1 | C9J8H1; P36543; P36543-2; P36543-3 |
| E9PB87 | WAS/WASL-interacting protein family member 1 | E9PB87; O43516; O43516-2; O43516-3 |
| Q06732 | Zinc finger protein 33B (Zinc finger protein 11B) (Zinc finger protein KOX2) | Q32M84; Q32M84-2; Q06732 |
| C9JEV0 | Zinc-alpha-2-glycoprotein | C9JEV0; P25311 |

Table 3 discloses proteins whose peptides were found to be down-regulated by at least 60% in the CSF of AD patients compared to CSF of non-AD subjects. Uniprot ID=annotated ID during data search; Protein names=protein name/s given to matched sequence; All Uniprot matches=All Uniprot IDs that match to the peptide sequence detected at the time of invention. Hash (#) indicates those proteins that were annotated as "merged with ###" and which have been re-searched in Uniprot. Asterisk (*) indicates those proteins which were annotated as deleted as the entry has been removed from Uniprot (due to redundancy).

In one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, or at least two or more, optionally at least three or all biomarkers selected from the group of ubiquitin carboxy-terminal hydrolase L1, vitamin D binding protein Peroxiredoxin-1, MARCKS-related protein, Moesin, Actin, Protein TMSB4XP4, ApoE, Gelsolin, Secretogranin, Albumin and complement proteins, Apolipoprotein E, Secretogranin-1, Serine/threonine-protein phosphatase 2A 65 kDa regulatory subunit A alpha isoform, Cytoplasmic dynein 1 heavy chain 1, RuvB-like 1, cDNA FLJ54806, Alpha-1-acid glycoprotein 2, Ras-related protein Rab-13, Serum albumin and Pigment epithelium-derived factor or fragments thereof.

The biomarker panel may comprise phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, optionally two or more biomarkers selected from Table 1 and/or Table 2 and/or Table 3 and/or Table 4 or fragments thereof.

TABLE 4

| Uniprot ID | Protein Name | All Uniprot matches |
| --- | --- | --- |
| I3L0S5 | 76 kDa lysosomal alpha-glucosidase | I3L0S5; I3L3L3; P10253 |
| P42684 | Abelson tyrosine-protein kinase 2 (EC 2.7.10.2) (Abelson murine leukemia viral oncogene homolog 2) (Abelson-related gene protein) (Tyrosine-protein kinase ARG) | P42684; P42684-10; P42684-2; P42684-3; P42684-4; P42684-5; P42684-6; P42684-7; P42684-8 |
| G5E951 | ADAM metallopeptidase domain 22, isoform CRA_I (Disintegrin and metalloproteinase domain-containing protein 22) | E7EPF1; F8WAD8; G5E951; Q9P0K1; Q9P0K1-2; Q9P0K1-3; Q9P0K1-4; Q9P0K1-5 |
| Q9UKB5 | Adherens junction-associated protein 1 (Membrane protein shrew-1) | Q9UKB5 |
| Q12955 | Ankyrin-3 (ANK-3) (Ankyrin-G) | Q12955; Q12955-4; Q12955-5 |
| Q6P163 | APOC2 protein (Apolipoprotein C-II) | P02655; K7ER74; Q6P163 |
| P02654 | Apolipoprotein C-I (Apolipoprotein C1) [Cleaved into: Truncated apolipoprotein C-I] | K7EJI9; K7ELM9; K7EPF9; K7ERI9; P02654 |
| P02655 | Apolipoprotein C-II (Apo-CII) (ApoC-II) (Apolipoprotein C2) | P02655; K7ER74 |
| P02656 | Apolipoprotein C-III (Apo-CIII) (ApoC-III) (Apolipoprotein C3) | P02656; B0YIW2 |
| P17174 | Aspartate aminotransferase, cytoplasmic (cAspAT) (EC 2.6.1.1) (EC 2.6.1.3) (Cysteine aminotransferase, cytoplasmic) (Cysteine transaminase, cytoplasmic) (cCAT) (Glutamate oxaloacetate transaminase 1) (Transaminase A) | P17174; B7Z7E9 |

TABLE 4-continued

| Uniprot ID | Protein Name | All Uniprot matches |
|---|---|---|
| P35613 | Basigin (5F7) (Collagenase stimulatory factor) (Extracellular matrix metalloproteinase inducer) (EMMPRIN) (Leukocyte activation antigen M6) (OK blood group antigen) (Tumor cell-derived collagenase stimulatory factor) (TCSF) (CD antigen CD147) | P35613; P35613-2; P35613-3; P35613-4 |
| Q96JF0 | Beta-galactoside alpha-2,6-sialyltransferase 2 (Alpha 2,6-ST 2) (EC 2.4.99.1) (CMP-N-acetylneuraminate-beta-galactosamide-alpha-2, 6-sialyltransferase 2) (ST6Gal II) (ST6GalII) (hST6Gal II) (Sialyltransferase 2) | Q96JF0; Q96JF0-2 |
| H3BP20 | Beta-hexosaminidase (EC 3.2.1.52) | E9PGL4; H3BP20; H3BS10; P06865 |
| P06865 | Beta-hexosaminidase subunit alpha (EC 3.2.1.52) (Beta-N-acetylhexosaminidase subunit alpha) (Hexosaminidase subunit A) (N-acetyl-beta-glucosaminidase subunit alpha) | E9PGL4; H3BP20; H3BS10; P06865 |
| A2A3C1 | Brain-specific angiogenesis inhibitor 2 | A2A3C1; A2A3C2; A2A3C3; A2A3C4; A2A3C6; E9PND1; O60241; O60241-2; O60241-3; O60241-4 |
| Q32M84 | BTB/POZ domain-containing protein 16 | Q06732; Q32M84; Q32M84-2 |
| Q9HCU4 | Cadherin EGF LAG seven-pass G-type receptor 2 (Cadherin family member 10) (Epidermal growth factor-like protein 2) (EGF-like protein 2) (Flamingo homolog 3) (Multiple epidermal growth factor-like domains protein 3) (Multiple EGF-like domains protein 3) | Q9HCU4 |
| Q5SWX3 | Calcium/calmodulin-dependent protein kinase (CaM kinase) II gamma, isoform CRA_n (Calcium/calmodulin-dependent protein kinase type II subunit gamma) | Q9Y266; B7Z1Z6; D6R938; E9PBG7; E9PF82; H0Y6G2; H0Y9C2; H0Y9J2; H7C394; Q13217; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q13557; Q13557-10; Q13557-11; Q13557-12; Q13557-3; Q13557-4; Q13557-5; Q13557-6; Q13557-8; Q13557-9; Q5SWX3; Q8WU40; Q9UQM7; Q9UQM7-2 |
| Q6P2M8 | Calcium/calmodulin-dependent protein kinase type 1B (EC 2.7.11.17) (CaM kinase I beta) (CaM kinase IB) (CaM-KI beta) (CaMKI-beta) (Pregnancy up-regulated non-ubiquitously-expressed CaM kinase) | Q6P2M8; Q6P2M8-2; Q6P2M8-3; Q6P2M8-5; Q6P2M8-6 |
| Q9UQM7 | Calcium/calmodulin-dependent protein kinase type II subunit alpha (CaM kinase II subunit alpha) (CaMK-II subunit alpha) (EC 2.7.11.17) | Q9Y266; B7Z1Z6; D6R938; E9PBG7; E9PF82; H0Y6G2; H0Y9C2; H0Y9J2; H7C394; Q13217; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q13557; Q13557-10; Q13557-11; Q13557-12; Q13557-3; Q13557-4; Q13557-5; Q13557-6; Q13557-8; Q13557-9; Q5SWX3; Q8WU40; Q9UQM7; Q9UQM7-2 |
| Q13554 | Calcium/calmodulin-dependent protein kinase type II subunit beta (CaM kinase II subunit beta) (CaMK-II subunit beta) (EC 2.7.11.17) | Q9Y266; B7Z1Z6; D6R938; E9PBG7; E9PF82; H0Y6G2; H0Y9C2; H0Y9J2; H7C394; Q13217; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q13557; Q13557-10; Q13557-11; Q13557-12; Q13557-3; Q13557-4; Q13557-5; Q13557-6; Q13557-8; Q13557-9; Q5SWX3; Q8WU40; Q9UQM7; Q9UQM7-2 |
| Q13555 | Calcium/calmodulin-dependent protein kinase type II subunit gamma (CaM kinase II subunit gamma) (CaMK-II subunit gamma) (EC 2.7.11.17) | Q9Y266; B7Z1Z6; D6R938; E9PBG7; E9PF82; H0Y6G2; H0Y9C2; H0Y9J2; H7C394; Q13217; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q13557; Q13557-10; Q13557-11; Q13557-12; Q13557-3; Q13557-4; Q13557-5; Q13557-6; Q13557-8; Q13557-9; Q5SWX3; Q8WU40; Q9UQM7; Q9UQM7-2 |

TABLE 4-continued

| Uniprot ID | Protein Name | All Uniprot matches |
|---|---|---|
| Q9BQT9 | Calsyntenin-3 (Alcadein-beta) (Alc-beta) | Q9BQT9; Q9BQT9-2 |
| Q5T8F0 | Cathepsin L1 | P07711; Q5T8F0 |
| P25774 | Cathepsin S (EC 3.4.22.27) | P25774; P25774-2; U3KQE7 |
| Q8N3J6 | Cell adhesion molecule 2 (Immunoglobulin superfamily member 4D) (IgSF4D) (Nectin-like protein 3) (NECL-3) (Synaptic cell adhesion molecule 2) (SynCAM 2) | Q8N3J6; Q8N3J6-2; Q8N3J6-3 |
| Q8N126 | Cell adhesion molecule 3 (Brain immunoglobulin receptor) (Immunoglobulin superfamily member 4B) (IgSF4B) (Nectin-like protein 1) (NECL-1) (Synaptic cell adhesion molecule 3) (SynCAM3) (TSLC1-like protein 1) (TSLL1) | Q8N126; Q8N126-2; Q8N126-3 |
| G3V2Y8 | Cerebellin-3 (HCG40197) | G3V2Y8; Q6UW01 |
| Q9NTU7 | Cerebellin-4 (Cerebellin-like glycoprotein 1) | Q9NTU7 |
| C9J0A7 | Charged multivesicular body protein 2b | C9J0A7 |
| P06307 | Cholecystokinin (CCK) [Cleaved into: Cholecystokinin-58 (CCK58); Cholecystokinin-58 desnonopeptide ((1-49)-CCK58); Cholecystokinin-39 (CCK39); Cholecystokinin-33 (CCK33); Cholecystokinin-25 (CCK25); Cholecystokinin-18 (CCK18); Cholecystokinin-12 (CCK12); Cholecystokinin-8 (CCK8); Cholecystokinin-7 (CCK7); Cholecystokinin-5 (CCK5)] | P06307 |
| Q16568 | Cocaine- and amphetamine-regulated transcript protein [Cleaved into: CART(1-39); CART(42-89)] | Q16568 |
| Q9BXJ4 | Complement C1q tumor necrosis factor-related protein 3 (Collagenous repeat-containing sequence 26 kDa protein) (CORS26) (Secretory protein CORS26) | E9PGA6; Q9BXJ4; Q9BXJ4-2; Q9BXJ4-3 |
| Q9C0A0 | Contactin-associated protein-like 4 (Cell recognition molecule Caspr4) | E9PDN6; F5H107; Q9C0A0; Q9C0A0-2 |
| Q9UBP4 | Dickkopf-related protein 3 (Dickkopf-3) (Dkk-3) (hDkk-3) | F6SYF8; Q9UBP4 |
| Q9P0K1 | Disintegrin and metalloproteinase domain-containing protein 22 (ADAM 22) (Metalloproteinase-disintegrin ADAM22-3) (Metalloproteinase-like, disintegrin-like, and cysteine-rich protein 2) | E7EPF1; F8WAD8; G5E951; Q9P0K1; Q9P0K1-2; Q9P0K1-3; Q9P0K1-4; Q9P0K1-5 |
| Q9UJA3 | DNA helicase MCM8 (EC 3.6.4.12) (Minichromosome maintenance 8) | Q9UJA3; Q9UJA3-2; Q9UJA3-3; Q9UJA3-4 |
| Q13217 | DnaJ homolog subfamily C member 3 (Endoplasmic reticulum DNA J domain-containing protein 6) (ER-resident protein ERdj6) (ERdj6) (Interferon-induced, double-stranded RNA-activated protein kinase inhibitor) (Protein kinase inhibitor of 58 kDa) (Protein kinase inhibitor p58) | Q9Y266; B7Z1Z6; D6R938; E9PBG7; E9PF82; H0Y6G2; H0Y9C2; H0Y9J2; H7C394; Q13217; Q13554; Q13554-2; Q13554-3; Q13554-4; Q13554-5; Q13554-6; Q13554-7; Q13554-8; Q13555; Q13555-10; Q13555-2; Q13555-3; Q13555-4; Q13555-5; Q13555-6; Q13555-7; Q13555-8; Q13555-9; Q13557; Q13557-10; Q13557-11; Q13557-12; Q13557-3; Q13557-4; Q13557-5; Q13557-6; Q13557-8; Q13557-9; Q5SWX3; Q8WU40; Q9UQM7; Q9UQM7-2 |
| Q9P225 | Dynein heavy chain 2, axonemal (Axonemal beta dynein heavy chain 2) (Ciliary dynein heavy chain 2) (Dynein heavy chain domain-containing protein 3) | P10645; Q9P225; Q9P225-2; Q9P225-3; O60741; Q9P1Z3; Q9UL51; Q9Y3Q4 |
| J3KQG3 | EPH receptor A10, isoform CRA_b (Ephrin type-A receptor 10) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |
| Q6NVW1 | EPHB2 protein (Ephrin type-B receptor 2) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |
| Q5JZY3 | Ephrin type-A receptor 10 (EC 2.7.10.1) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |
| P54764 | Ephrin type-A receptor 4 (EC 2.7.10.1) (EPH-like kinase 8) (EK8) (hEK8) (Tyrosine-protein kinase TYRO1) (Tyrosine-protein kinase receptor SEK) | B7Z6Q8; E9PG71; P54764 |
| P54756 | Ephrin type-A receptor 5 (EC 2.7.10.1) (Brain-specific kinase) (EPH homology kinase 1) (EHK-1) (EPH-like kinase 7) (EK7) (hEK7) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |

TABLE 4-continued

| Uniprot ID | Protein Name | All Uniprot matches |
|---|---|---|
| Q15375 | Ephrin type-A receptor 7 (EC 2.7.10.1) (EPH homology kinase 3) (EHK-3) (EPH-like kinase 11) (EK11) (hEK11) | Q15375; Q15375-2; Q15375-4; Q15375-5 |
| P29322 | Ephrin type-A receptor 8 (EC 2.7.10.1) (EPH- and ELK-related kinase) (EPH-like kinase 3) (EK3) (hEK3) (Tyrosine-protein kinase receptor EEK) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |
| P29323 | Ephrin type-B receptor 2 (EC 2.7.10.1) (Developmentally-regulated Eph-related tyrosine kinase) (ELK-related tyrosine kinase) (EPH tyrosine kinase 3) (EPH-like kinase 5) (EK5) (hEK5) (Renal carcinoma antigen NY-REN-47) (Tyrosine-protein kinase TYROS) (Tyrosine-protein kinase receptor EPH-3) | F8VP57; F8W9W0; J3KQG3; P29322; P29322-2; P54756; P54756-2; P54756-3; Q15375; Q15375-2; Q15375-3; Q15375-4; Q15375-5; Q5JZY3; Q5JZY3-2; Q5JZY3-3; B1AKC9; P29323; P29323-2; P29323-3; Q6NVW1 |
| P52797 | Ephrin-A3 (EFL-2) (EHK1 ligand) (EHK1-L) (EPH-related receptor tyrosine kinase ligand 3) (LERK-3) | B4DXG7; P52797 |
| B4DXG7 | Ephrin-A3 (Uncharacterized protein) (cDNA FLJ57652, highly similar to Ephrin-A3) | B4DXG7; P52797 |
| P52799 | Ephrin-B2 (EPH-related receptor tyrosine kinase ligand 5) (LERK-5) (HTK ligand) (HTK-L) | P52799 |
| Q9UBQ6 | Exostosin-like 2 (EC 2.4.1.223) (Alpha-1,4-N-acetylhexosaminyltransferase EXTL2) (Alpha-GalNAcT EXTL2) (EXT-related protein 2) (Glucuronyl-galactosyl-proteoglycan 4-alpha-N-acetylglucosaminyltransferase) [Cleaved into: Processed exostosin-like 2] | C9JEG3; F5GZK1; Q9UBQ6 |
| J3KNT4 | Fibroblast growth factor receptor (EC 2.7.10.1) | E7EU09; J3KNT4; P11362; P11362-10; P11362-11; P11362-12; P11362-13; P11362-14; P11362-16; P11362-18; P11362-19; P11362-2; P11362-20; P11362-21; P11362-3; P11362-4; P11362-5; P11362-6; P11362-7; P11362-8; P11362-9; E9PNM3; E9PKF2; E9PKV7; E9PN14 |
| P11362 | Fibroblast growth factor receptor 1 (FGFR-1) (EC 2.7.10.1) (Basic fibroblast growth factor receptor 1) (BFGFR) (bFGF-R-1) (Fms-like tyrosine kinase 2) (FLT-2) (N-sam) (Proto-oncogene c-Fgr) (CD antigen CD331) | E7EU09; J3KNT4; P11362; P11362-10; P11362-11; P11362-12; P11362-13; P11362-14; P11362-16; P11362-18; P11362-19; P11362-2; P11362-20; P11362-21; P11362-3; P11362-4; P11362-5; P11362-6; P11362-7; P11362-8; P11362-9; E9PNM3; E9PKF2; E9PKV7; E9PN14 |
| Q6MZW2 | Follistatin-related protein 4 (Follistatin-like protein 4) | Q6MZW2; Q6MZW2-3 |
| O00451 | GDNF family receptor alpha-2 (GDNF receptor alpha-2) (GDNFR-alpha-2) (GFR-alpha-2) (GDNF receptor beta) (GDNFR-beta) (Neurturin receptor alpha) (NRTNR-alpha) (NTNR-alpha) (RET ligand 2) (TGF-beta-related neurotrophic factor receptor 2) | E5RGR6; O00451; O00451-2; O00451-3 |
| P14314 | Glucosidase 2 subunit beta (80K-H protein) (Glucosidase II subunit beta) (Protein kinase C substrate 60.1 kDa protein heavy chain) (PKCSH) | K7ELL7; P14314; P14314-2 |
| Q16769 | Glutaminyl-peptide cyclotransferase (EC 2.3.2.5) (Glutaminyl cyclase) (QC) (sQC) (Glutaminyl-tRNA cyclotransferase) (Glutamyl cyclase) (EC) | Q16769 |
| B4DK85 | Glutaryl-CoA dehydrogenase, mitochondrial (cDNA FLJ59559, highly similar to Glutaryl-CoA dehydrogenase, mitochondrial (EC 1.3.99.7)) | B4DK85; K7ESA6; Q92947; Q92947-2; P13521 |
| Q5VW52 | Glycerol-3-phosphate acyltransferase 1, mitochondrial (Glycerol-3-phosphate acyltransferase, mitochondrial, isoform CRA_a) | Q5VW52; Q9HCL2 |
| O60812 | Heterogeneous nuclear ribonucleoprotein C-like 1 (hnRNP C-like-1) (hnRNP core protein C-like 1) | O60812 |
| P04233 | HLA class II histocompatibility antigen gamma chain (HLA-DR antigens-associated invariant chain) (Ia antigen-associated invariant chain) (Ii) (p33) (CD antigen CD74) | H0YBZ2; P04233 |
| Q86YZ3 | Hornerin | Q86YZ3 |
| Q9Y4L1 | Hypoxia up-regulated protein 1 (150 kDa oxygen-regulated protein) (ORP-150) (170 kDa glucose-regulated protein) (GRP-170) | E9PL22; Q9Y4L1 |
| P22304 | Iduronate 2-sulfatase (EC 3.1.6.13) (Alpha-L-iduronate sulfate sulfatase) (Idursulfase) [Cleaved into: Iduronate 2-sulfatase 42 kDa chain; Iduronate 2-sulfatase 14 kDa chain] | P22304; P22304-2; P22304-3 |
| P04433 | Ig kappa chain V-III region VG | P04433 |
| P06316 | Ig lambda chain V-I region BL2 | P01702; P06316 |
| P01702 | Ig lambda chain V-I region NIG-64 | P01702; P06316 |

TABLE 4-continued

| Uniprot ID | Protein Name | All Uniprot matches |
| --- | --- | --- |
| P04220 | Ig mu heavy chain disease protein (BOT) | P04220 |
| B9A064 | Immunoglobulin lambda-like polypeptide 5 (G lambda-1) (Germline immunoglobulin lambda 1) | B9A064; P0CG05 |
| Q15111 | Inactive phospholipase C-like protein 1 (PLC-L1) (Phospholipase C-deleted in lung carcinoma) (Phospholipase C-related but catalytically inactive protein) (PRIP) | H3BUD4; Q15111; Q15111-2 |
| Q9UMF0 | Intercellular adhesion molecule 5 (ICAM-5) (Telencephalin) | Q9UMF0 |
| P01579 | Interferon gamma (IFN-gamma) (Immune interferon) | P01579; P14618; P14618-2 |
| Q9NS87 | Kinesin-like protein KIF15 (Kinesin-like protein 2) (hKLP2) (Kinesin-like protein 7) (Serologically defined breast cancer antigen NY-BR-62) | C9JKA9; Q9NS87; Q9NS87-2; Q9NS87-3; Q9NS87-4 |
| P24043 | Laminin subunit alpha-2 (Laminin M chain) (Laminin-12 subunit alpha) (Laminin-2 subunit alpha) (Laminin-4 subunit alpha) (Merosin heavy chain) | P24043 |
| Q8N2S1 | Latent-transforming growth factor beta-binding protein 4 (LTBP-4) | E7EUU1; Q8N2S1-2; Q8N2S1; E7ENG9; F5GXC9; M0QZX0; Q8N2S1-3 |
| O94910 | Latrophilin-1 (Calcium-independent alpha-latrotoxin receptor 1) (CIRL-1) (Lectomedin-2) | O94910; O94910-2 |
| P07195 | L-lactate dehydrogenase B chain (LDH-B) (EC 1.1.1.27) (LDH heart subunit) (LDH-H) (Renal carcinoma antigen NY-REN-46) | P07195 |
| P10253 | Lysosomal alpha-glucosidase (EC 3.2.1.20) (Acid maltase) (Aglucosidase alfa) [Cleaved into: 76 kDa lysosomal alpha-glucosidase; 70 kDa lysosomal alpha-glucosidase] | I3L0S5; I3L3L3; P10253 |
| E9PGC8 | MAP1 light chain LC2 | E9PGC8; J3KPX8; P78559; P78559-2 |
| Q8TBP5 | Membrane protein FAM174A (Hepatitis C virus NS5A-transactivated protein 6) (HCV NS5A-transactivated protein 6) (Transmembrane protein 157) | Q8TBP5 |
| P04731 | Metallothionein-1A (MT-1A) (Metallothionein-IA) (MT-IA) | H3BSF1; P02795; P04731; P13640; P13640-2; P80294; P80297 |
| H3BSF1 | Metallothionein-1G | H3BSF1; P02795; P04731; P13640; P13640-2; P80294; P80297 |
| P80294 | Metallothionein-1H (MT-1H) (Metallothionein-0) (MT-0) (Metallothionein-IH) (MT-IH) | H3BSF1; P02795; P04731; P13640; P13640-2; P80294; P80297 |
| P78559 | Microtubule-associated protein 1A (MAP-1A) (Proliferation-related protein p80) [Cleaved into: MAP1A heavy chain; MAP1 light chain LC2] | E9PGC8; J3KPX8; P78559; P78559-2 |
| H0Y786 | Nebulin | P20929; F8WCL5; F8WCP0; H0Y786; J3QK84 |
| Q9NQX5 | Neural proliferation differentiation and control protein 1 (NPDC-1) | Q5SPY9; Q9NQX5 |
| O14594 | Neurocan core protein (Chondroitin sulfate proteoglycan 3) | O14594 |
| Q9BYT8 | Neurolysin, mitochondrial (EC 3.4.24.16) (Angiotensin-binding protein) (Microsomal endopeptidase) (MEP) (Mitochondrial oligopeptidase M) (Neurotensin endopeptidase) | E9PCB6; H0YAK4; Q9BYT8 |
| P17677 | Neuromodulin (Axonal membrane protein GAP-43) (Growth-associated protein 43) (Neural phosphoprotein B-50) (pp46) | P17677; P17677-2 |
| P47972 | Neuronal pentraxin-2 (NP2) (Neuronal pentraxin II) (NP-II) | P47972 |
| Q99574 | Neuroserpin (Peptidase inhibitor 12) (PI-12) (Serpin I1) | Q99574; C9JDY5; C9JQU9 |
| P14543 | Nidogen-1 (NID-1) (Entactin) | P14543; P14543-2 |
| Q7Z6G3 | N-terminal EF-hand calcium-binding protein 2 (EF-hand calcium-binding protein 2) (Neuronal calcium-binding protein 2) (Synaptotagmin-interacting protein 2) (Stip-2) | H3BPH6; H3BTW2; Q7Z6G3 |
| Q5VST9 | Obscurin (EC 2.7.11.1) (Obscurin-RhoGEF) (Obscurin-myosin light chain kinase) (Obscurin-MLCK) | P01009; A6NGQ3; F8W8T3; H3BPX2; H3BQA7; H7BY31; Q5VST9; Q5VST9-2; Q5VST9-3; Q5VST9-5; Q5VST9-6 |
| Q96CV9 | Optineurin (E3-14.7K-interacting protein) (FIP-2) (Huntingtin yeast partner L) (Huntingtin-interacting protein 7) (HIP-7) (Huntingtin-interacting protein L) (NEMO-related protein) (Optic neuropathy-inducing protein) (Transcription factor IIIA-interacting protein) (TFIIIA-IntP) | P06727; Q96CV9; Q96CV9-2; Q96CV9-3 |
| G5E956 | Outer dense fiber of sperm tails 2-like, isoform CRA_a (Outer dense fiber protein 2-like) | G5E956; H0YD68; Q9ULJ1; Q9ULJ1-2; Q9ULJ1-3; Q9ULJ1-4; Q9ULJ1-5; Q9ULJ1-6 |
| H0YD68 | Outer dense fiber protein 2-like | G5E956; H0YD68; Q9ULJ1; Q9ULJ1-2; Q9ULJ1-3; Q9ULJ1-4; Q9ULJ1-5; Q9ULJ1-6 |

TABLE 4-continued

| Uniprot ID | Protein Name | All Uniprot matches |
|---|---|---|
| H3BUD4 | Phosphoinositide phospholipase C (EC 3.1.4.11) | H3BUD4; Q15111; Q15111-2 |
| Q8IV08 | Phospholipase D3 (PLD 3) (EC 3.1.4.4) (Choline phosphatase 3) (HindIII K4L homolog) (Hu-K4) (Phosphatidylcholine-hydrolyzing phospholipase D3) | E2QRG1; M0R1F7; M0R2W7; Q8IV08 |
| Q9BTY2 | Plasma alpha-L-fucosidase (EC 3.2.1.51) (Alpha-L-fucoside fucohydrolase 2) (Alpha-L-fucosidase 2) | Q9BTY2 |
| O60741 | Potassium/sodium hyperpolarization-activated cyclic nucleotide-gated channel 1 (Brain cyclic nucleotide-gated channel 1) (BCNG-1) | P10645; Q9P225; Q9P225-2; Q9P225-3; O60741; Q9P1Z3; Q9UL51; Q9Y3Q4 |
| Q9UL51 | Potassium/sodium hyperpolarization-activated cyclic nucleotide-gated channel 2 (Brain cyclic nucleotide-gated channel 2) (BCNG-2) | P10645; Q9P225; Q9P225-2; Q9P225-3; O60741; Q9P1Z3; Q9UL51; Q9Y3Q4 |
| Q9P1Z3 | Potassium/sodium hyperpolarization-activated cyclic nucleotide-gated channel 3 | P10645; Q9P225; Q9P225-2; Q9P225-3; O60741; Q9P1Z3; Q9UL51; Q9Y3Q4 |
| Q9Y3Q4 | Potassium/sodium hyperpolarization-activated cyclic nucleotide-gated channel 4 | P10645; Q9P225; Q9P225-2; Q9P225-3; O60741; Q9P1Z3; Q9UL51; Q9Y3Q4 |
| E7EQY3 | Pregnancy-specific beta-1-glycoprotein 5 | E7EQY3; P11464-4 |
| A4D1T9 | Probable inactive serine protease 37 (Probable inactive trypsin-X2) | A4D1T9 |
| P09668 | Pro-cathepsin H [Cleaved into: Cathepsin H mini chain; Cathepsin H (EC 3.4.22.16); Cathepsin H heavy chain; Cathepsin H light chain] | P09668 |
| F5GZK1 | Processed exostosin-like 2 | C9JEG3; F5GZK1; Q9UBQ6 |
| P51888 | Prolargin (Proline-arginine-rich end leucine-rich repeat protein) | P51888 |
| Q5FWE3 | Proline-rich transmembrane protein 3 | Q5FWE3; Q5FWE3-3 |
| P01303 | Pro-neuropeptide Y [Cleaved into: Neuropeptide Y (Neuropeptide tyrosine) (NPY); C-flanking peptide of NPY (CPON)] | P01303 |
| P48745 | Protein NOV homolog (NovH) (CCN family member 3) (Insulin-like growth factor-binding protein 9) (IBP-9) (IGF-binding protein 9) (IGFBP-9) (Nephroblastoma-overexpressed gene protein homolog) | P48745 |
| G3XAD5 | Protein tyrosine phosphatase, receptor type, D, isoform CRA_c (Receptor-type tyrosine-protein phosphatase delta) | F5GWR7; F5GWT7; F5GWY7; G3XAD5; G3XAE2; P23468; P23468-2; P23468-3; P23468-4; P23468-5; P23468-6 |
| G3XAE2 | Protein tyrosine phosphatase, receptor type, D, isoform CRA_f (Receptor-type tyrosine-protein phosphatase delta) | F5GWR7; F5GWT7; F5GWY7; G3XAD5; G3XAE2; P23468; P23468-2; P23468-3; P23468-4; P23468-5; P23468-6 |
| F5GWR7 | Receptor-type tyrosine-protein phosphatase delta | F5GWR7; F5GWT7; F5GWY7; G3XAD5; G3XAE2; P23468; P23468-2; P23468-3; P23468-4; P23468-5; P23468-6 |
| P23470 | Receptor-type tyrosine-protein phosphatase gamma (Protein-tyrosine phosphatase gamma) (R-PTP-gamma) (EC 3.1.3.48) | P23470; P23470-2 |
| Q92932 | Receptor-type tyrosine-protein phosphatase N2 (R-PTP-N2) (EC 3.1.3.48) (Islet cell autoantigen-related protein) (IAR) (ICAAR) (Phogrin) | E7EM83; Q92932; Q92932-2; Q92932-3; Q92932-4 |
| Q96B86 | Repulsive guidance molecule A (RGM domain family member A) | F5GZU6; F5H7G2; G3V518; Q96B86; Q96B86-2 |
| G3V1D7 | Reticulon 4 receptor-like 2, isoform CRA_a (Reticulon-4 receptor-like 2) | G3V1D7; Q86UN3; Q86UN3-2 |
| Q9BZR6 | Reticulon-4 receptor (Nogo receptor) (NgR) (Nogo-66 receptor) | H7C0V4; H7C215; Q9BZR6 |
| Q6P5S7 | Ribonuclease kappa (RNase K) (RNase kappa) (EC 3.1.—.—) | F8W1G5; H0YHM1; H0YIM4; H0YIU3; I3L285; Q6P5S7 |
| Q99985 | Semaphorin-3C (Semaphorin-E) (Sema E) | F5H1Z7; Q99985 |
| Q6P3R8 | Serine/threonine-protein kinase Nek5 (EC 2.7.11.1) (Never in mitosis A-related kinase 5) (NimA-related protein kinase 5) | E9PIX7; Q6P3R8 |
| E9PQD6 | Serum amyloid A protein | E9PQD6; E9PR14; G3V1D9; P0DJI8; P0DJI9; P0DJI9-2 |
| P0DJI8 | Serum amyloid A-1 protein (SAA) [Cleaved into: Amyloid protein A (Amyloid fibril protein AA); Serum amyloid protein A(2-104); Serum amyloid protein A(3-104); Serum amyloid protein A(2-103); Serum amyloid protein A(2-102); Serum amyloid protein A(4-101)] | E9PQD6; E9PR14; G3V1D9; P0DJI8; P0DJI9; P0DJI9-2 |
| P0DJI9 | Serum amyloid A-2 protein (SAA2) | E9PQD6; E9PR14; G3V1D9; P0DJI8; P0DJI9; P0DJI9-2 |
| Q5TFQ8 | Signal-regulatory protein beta-1 isoform 3 (SIRP-beta-1 isoform 3) | P78324; P78324-2; P78324-4; Q5TFQ8 |
| Q8VWQ1 | Soluble calcium-activated nucleotidase 1 (SCAN-1) (EC 3.6.1.6) (Apyrase homolog) (Putative MAPK-activating protein PM09) (Putative NF-kappa-B-activating protein 107) | K7EN15; Q8VWQ1; Q8VWQ1-2 |

TABLE 4-continued

| Uniprot ID | Protein Name | All Uniprot matches |
|---|---|---|
| A8MXT8 | Sulfhydryl oxidase 1 | O00391; O00391-2; A8MXT8 |
| H7C2K7 | Sushi domain-containing protein 5 | H7C2K7; O60279 |
| Q92752 | Tenascin-R (TN-R) (Janusin) (Restrictin) | Q92752; Q92752-2 |
| D6RAM7 | Testican-1 | D6RAM7; Q08629 |
| Q03167 | Transforming growth factor beta receptor type 3 (TGF-beta receptor type 3) (TGFR-3) (Betaglycan) (Transforming growth factor beta receptor III) (TGF-beta receptor type III) | E9PKY4; Q03167; Q03167-2 |
| Q3YBM2 | Transmembrane protein 176B (Protein LR8) | Q3YBM2; Q3YBM2-2 |
| O95407 | Tumor necrosis factor receptor superfamily member 6B (Decoy receptor 3) (DcR3) (Decoy receptor for Fas ligand) (M68) | Q06481; O95407; Q06481-3; Q06481-6 |
| P30530 | Tyrosine-protein kinase receptor UFO (EC 2.7.10.1) (AXL oncogene) | P30530; P30530-2 |
| F5H7E1 | Uncharacterized protein | P19827; F5H7E1 |
| E9PGA6 | Uncharacterized protein | E9PGA6; Q9BXJ4; Q9BXJ4-2; Q9BXJ4-3 |
| M0QY22 | Uncharacterized protein | M0QY22 |
| C9JPP7 | Uncharacterized protein C1orf87 | C9JPP7; Q8N0U7; Q8N0U7-2; Q8N0U7-3 |
| Q13459 | Unconventional myosin-IXb (Unconventional myosin-9b) | M0R0P8; M0R300; Q13459; Q13459-2 |
| E9PAT2 | UPF0606 protein KIAA1549L | E9PAT2; H0YDE5; Q6ZVL6; Q6ZVL6-2 |
| Q6EMK4 | Vasorin (Protein slit-like 2) | Q6EMK4 |
| Q9UPU3 | VPS10 domain-containing receptor SorCS3 | Q9UPU3 |
| Q9HC57 | WAP four-disulfide core domain protein 1 (Prostate stromal protein ps20) (ps20 growth inhibitor) | Q9HC57 |
| Q86Y38 | Xylosyltransferase 1 (EC 2.4.2.26) (Peptide O-xylosyltransferase 1) (Xylosyltransferase I) (XT-I) (XylT-I) | Q86Y38 |
| F8VRY0 | Zinc finger protein 385A | F8VRY0; F8VSJ1; F8VVW6; F8VY43; Q96PM9-1; Q96PM9-2 |

Table 4 discloses proteins whose peptides were found to be regulated by at least 60% in the CSF of AD patients compared to non-AD CSF when compared in a proteomics study without calibrator. Significance is not considered here. Same 6 CSF samples as in all calibrator studies. Column 1=annotated ID during data search. Middle column=protein name/s given to matched sequence. Final column=All Uniprot IDs that match to the peptide sequence detected at time of invention.

The biomarker panel may comprise phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and at least one, optionally two or more biomarkers selected from Table 1 and/or Table 2 and/or Table 3 and/or Table 4 and/or Table 2 or fragments thereof.

The biomarkers disclosed herein may be upregulated in the CSF of AD patients versus control like dynactin subunit-1 or may be down-regulated in the CSF patients versus control like cofilin-1.

Accordingly, in one embodiment the biomarker panel comprises phosphoglucomutase 1 comprising or having the amino acid sequence of SEQ ID NO:1 or an isoform or a variant or a fragment thereof; and/or thymosin beta-4 comprising or having the amino acid sequence of SEQ ID NO:2 or a variant or a fragment thereof; and cofilin-1 or a fragment thereof (e.g. a fragment having SEQ ID NO: 38) and/or dynactin subunit 1 or a fragment thereof (e.g. a fragment having SEQ ID NO: 37).

Optionally, the biomarker panel may also comprise at least one, or at least two or more, optionally at least three or all biomarkers selected from the group of ubiquitin carboxyterminal hydrolase L1, vitamin D binding protein Peroxiredoxin-1, MARCKS-related protein, Moesin, Actin, Protein TMSB4XP4, ApoE, Gelsolin, Secretogranin, Albumin and complement proteins, Apolipoprotein E, Secretogranin-1, Serine/threonine-protein phosphatase 2A 65 kDa regulatory subunit A alpha isoform, Cytoplasmic dynein 1 heavy chain 1, RuvB-like 1, cDNA FLJ54806, Alpha-1-acid glycoprotein 2, Ras-related protein Rab-13, Serum albumin and Pigment epithelium-derived factor or fragments thereof.

In another embodiment of the invention, the biomarker panel may comprise phospholucomutase 1 having or comprising SEQ ID NOs: 1, 6-13 and thymosin beta-4 having or comprising SEQ ID NOs: 2, 14-16 and optionally Vitamin D-binding protein having or comprising SEQ ID NOs: 5 and 18 and/or Ubiquitin carboxyl-terminal hydrolase isozyme L1 having or comprising SEQ ID NOs: 4 or 17, or fragments thereof, preferably the panel further comprises at least one or more of the following biomarkers, or fragments thereof, dynactin subunit 1 having or comprising SEQ ID NO: 37 or SEQ ID NO: 57, cofilin 1 having or comprising SEQ ID NO: 38 or SEQ ID NO:58), Apolipoprotein E having or comprising SEQ ID NO:19; SEQ ID NO:39 or amino acids 19 to 317 of SEQ ID NO:39, Secretogranin-1 having or comprising SEQ ID NO:20; SEQ ID NO:40; or amino acids 21 to 677, 440 to 513 or 617 to 673 of SEQ ID NO:40, Serine/threonine-protein phosphatase 2A 65 kDa regulatory subunit A alpha isoform having or comprising SEQ ID NO: 21 or SEQ ID NO: 41, Cytoplasmic dynein 1 heavy chain 1 having or comprising SEQ ID NO: 22; SEQ ID NO: 42 or amino acids 2 to 4646 of SEQ ID NO:42, RuvB-like 1 having or comprising SEQ ID NO: 23 or SEQ ID NO:43), cDNA FLJ54806 having or comprising SEQ ID NO: 24 or SEQ ID NO:44, Alpha-1-acid glycoprotein 2 having or comprising SEQ ID NO: 25; SEQ ID NO: 45 or amino acids 19 to 201 of SEQ ID NO:45, Ras-related protein Rab-13 having or comprising SEQ ID NO: 26 or SEQ ID NO:46, Serum albumin having or comprising SEQ ID NO: 27; SEQ ID NO: 47 or amino acids 19 to 22 or 25 to 609 of SEQ ID NO: 47, Pigment epithelium-derived factor having or comprising SEQ ID NO: 28; SEQ ID NO: 48 or amino acids 20 to 418 of SEQ ID NO: 48), Serum amyloid A-4 protein having or comprising SEQ ID NO: 29; SEQ ID NO: 49 or amino acids 19 to 130 of SEQ ID NO: 49, apolipoprotein A-I and its truncated version having or comprising SEQ ID NO: 30; SEQ ID NO: 50 or amino acids 19 to 267, 1 to 242, 25 to 267 or 25 to 266 of SEQ ID NO: 50, Fibrinogen alpha chain having or comprising SEQ ID NO: 31; SEQ ID NO: 51 or amino acids 20 to 35 or 36 to 866 of SEQ ID NO: 51, Haptoglobin having or comprising SEQ ID NO: 32; SEQ ID NO: 52 or amino acids 19 to 406, 19 to 160 or 162 to 406 of SEQ ID NO: 52, Alpha-1-antitrypsin having or comprising SEQ ID NO: 33; SEQ ID NO: 53 or amino acids 25 to 418 or 375 to 418 of SEQ ID NO: 53), Ig mu chain C region (SEQ ID NO: 34 or SEQ ID NO: 54, Hemoglobin subunit delta having or comprising SEQ ID NO: 35 or SEQ ID NO: 55, IgGFc-binding protein having or comprising SEQ ID NO: 36; SEQ ID NO: 56 or amino acids 24 to 5405 of SEQ ID NO: 56, or MARCKS-related protein having or comprising SEQ ID NO: 59.

For a list of the sequences used herein, Table 5 below shows the sequence correlation list.

TABLE 5

| Biomarker name | SEQ ID NO: |
|---|---|
| Phosphoglucomutase 1 (human) (Uniprot P36871) | 1 |
| Thymosin Beta-4 (human) (Uniprot P62328) | 2 |
| Isoform 2 of Phosphoglucomutase 1 | 3 |
| Ubiquitin carboxy-terinal hydrolase L1 (D6R956) | 4 |
| Vitamin D binding protein (D6RBJ7) | 5 |
| Phosphoglucomutase 1 (human) - peptide 1 | 6 |
| Phosphoglucomutase 1 (human) - peptide 2 | 7 |
| Phosphoglucomutase 1 (human) - peptide 3 | 8 |
| Phosphoglucomutase 1 (human) - peptide 4 | 9 |
| Phosphoglucomutase 1 (human) - peptide 5 | 10 |
| Phosphoglucomutase 1 (human) - peptide 6 | 11 |
| Phosphoglucomutase 1 (human) - peptide 7 | 12 |
| Phosphoglucomutase 1 (human) - peptide 8 | 13 |
| Thymosin Beta-4 (human) - peptide 1 | 14 |
| Thymosin Beta-4 (human) - peptide 2 | 15 |
| Thymosin Beta-4 (human) - peptide 3 | 16 |
| Ubiquitin carboxy-terinal hydrolase L1 - peptide 1 | 17 |
| Vitamin D binding protein - peptide 1 | 18 |
| Apolipoprotein E - peptide 1 | 19 |
| Secretogranin 1 - peptide 1 | 20 |
| Serine/threonine protein phosphate 2A 65 KDa regulatory subunit A alpha isoform - peptide 1 | 21 |
| Cytoplasmic dynein 1 heavy chain 1 - peptide 1 | 22 |
| RuvB-like 1 - peptide 1 | 23 |
| cDNA FLJ54806 | 24 |
| Alpha-1-acid glycoprotein 2 - peptide 1 | 25 |
| Ras-related protein Rab13 - peptide 1 | 26 |
| Serum Albumin | 27 |
| Pigment epithelium-derived factor - peptide 1 | 28 |
| Serum Amyloid A-4 protein - peptide 1 | 29 |
| Truncated apolipoprotein A-I - peptide 1 | 30 |
| Fibrinogen alpha chain - peptide 1 | 31 |
| Haptoglobin - peptide 1 | 32 |
| Alpha-1-antytrypsin - peptide 1 | 33 |
| Ig mu chain C region - peptide 1 | 34 |
| Hemoglobin subunit delta - peptide 1 | 35 |
| IgGFc-binding protein - peptide 1 | 36 |
| Dynactin Subunit 1 - peptide 1 | 37 |
| Cofilin-1 - peptide 1 | 38 |
| Apolipoprotein E (P02649) | 39 |
| Secretogranin 1 (P05060) | 40 |
| Serine/threonine protein phosphate 2A 65 KDa regulatory subunit A alpha isoform (P30153) | 41 |
| Cytoplasmic dynein 1 heavy chain 1 (Q14204) | 42 |
| RuvB-like 1 (Q9Y265, H7C4G5, E7ETR0, H7C4I3, J3QLR1, B5BUB1) | 43 |
| cDNA FLJ54806 (MGEA5), mRNA (B4DYV7) | 44 |
| Alpha-1-acid glycoprotein 2 (P19652) | 45 |
| Ras-related protein Rab13 (P51153) | 46 |
| Serum Albumin (P02768, Q16167, H0YA55, B7WNR0, D6RHD5, H7C013, Q56G89, D6RCE7, Q6LEH2) | 47 |
| Pigment epithelium-derived factor (P36955) | 48 |
| Serum Amyloid A-4 protein (P35542) | 49 |

TABLE 5-continued

| Biomarker name | SEQ ID NO: |
|---|---|
| Truncated apolipoprotein A-I (P02647) | 50 |
| Fibrinogen alpha chain (P02671) | 51 |
| Haptoglobin (P00738, J3QLC9, H0Y300, H3BS21, J3QR68, J3KRH2, J3QQI8, H3BMJ7, J3KSV1, Q14552) | 52 |
| Alpha-1-antytrypsin (P01009, G3V2B9, G3V5R8, G3V544, G3V387, G3V4I7, Q13747, A7L8C5, A7L8C6) | 53 |
| Ig mu chain C region (P01871) | 54 |
| Hemoglobin subunit delta (P02042, E9PEW8, E9PFT6, C9JRG0) | 55 |
| IgGFc-binding protein (Q9Y6R7) | 56 |
| Dynactin Subunit 1 (Q14203) | 57 |
| Cofilin-1 (P23528) | 58 |
| MARCKS-related protein (P49006) | 59 |

The biomarker panels described herein are useful for diagnosing, for staging and for assessing the likelihood of developing a neurocognitive disorder, in particular Alzheimer's disease. The use of the biomarker panels according to the present invention in any of such methods has considerable advantages. Firstly, these biomarker panels translate events and changes in pathways that occur in the brain into a peripheral signal, they allow replacing tissue testing with a peripheral fluid testing. This represents a great advantage especially as the tissue primarily affected in neurocognitive disorder is the brain tissue. Brain biopsies are not carried out and the only tissue analysis carried out is post-mortem. Secondly, these biomarker panels have been developed as capable to translate early events and changes in pathways in the brain, such as neuroinflammatory events, which are believed to be the hallway of neurocognitive disorders characterized by microglia activation, such as Alzheimer's disease. Thirdly, these biomarker panels encompass biomarkers which are not those typically reported in the literature or currently used in the clinical setting, thus lending to clinician additional tools for identifying and distinguish, at an early stage, subjects who have AD and subjects who, despite presenting symptoms of neurocognitive impairment are not affect by the early signs of AD.

Hence, the present invention provides for a method for diagnosing a neurocognitive disorder in a subject, the method comprising:
  a) assaying a sample obtained from said subject for the biomarkers of a biomarker panel;
  b) measuring in said sample the concentration or the amount of each of the biomarkers of said biomarker panel;
  c) determining whether that subject has a neurocognitive disorder by comparing said concentration or amount of each of the biomarker of the biomarker panel in said sample with reference concentrations or amounts of said biomarkers; wherein the biomarker panel comprises:
    i. phosphoglucomutase 1 comprising or having the amino acid sequence of SEQ ID NO:1 or an isoform or a variant or a fragment thereof; and/or
    ii. thymosin beta-4 comprising or having the amino acid sequence of SEQ ID NO:2 or a variant or a fragment thereof.

The present invention also provides for a method for staging a neurocognitive disorder in a subject, the method comprising:
  a) assaying a sample obtained from said subject for the biomarkers of a biomarker panel;

b) measuring in said sample the concentration or the amount of each of the biomarkers of said biomarker panel;
c) determining the stage of the neurocognitive disorder in said subject by comparing said concentration or amount of each of the biomarkers of the biomarker panel in said sample with reference concentrations or amounts of said biomarkers, wherein the biomarker panel comprises:
  i. phosphoglucomutase 1 comprising or having the amino acid sequence of SEQ ID NO:1 or an isoform or a variant or a fragment thereof; and/or
  ii. thymosin beta-4 comprising or having the amino acid sequence of SEQ ID NO:2 or a variant or a fragment thereof.

The present invention also provides for a method for assessing in a subject the likelihood of developing a neurocognitive disorder, the method comprising:
a) assaying a sample obtained from said subject for the biomarkers of a biomarker panel;
b) measuring in said sample the concentration or the amount of each of the biomarkers of said biomarker panel;
c) determining whether that subject is likely to develop a neurocognitive disorder by comparing said concentration or amount of each of the biomarkers of the biomarker panel in said sample with reference concentrations or amounts of said biomarkers wherein the biomarker panel comprises:
  i. phosphoglucomutase 1 comprising or having the amino acid sequence of SEQ ID NO:1 or an isoform or a variant or a fragment thereof; and/or
  ii. thymosin beta-4 comprising or having the amino acid sequence of SEQ ID NO:2 or a variant or a fragment thereof.

In some embodiments, the biomarker panel for use in the method for diagnosing, staging or assessing in a subject the likelihood of developing a the neurocognitive disorder comprises phosphoglucomutase 1 comprising or having the amino acid sequence of SEQ ID NO:1 or an isoform or a variant or a fragment thereof; and thymosin beta-4 comprising or having the amino acid sequence of SEQ ID NO:2 or a variant or a fragment thereof.

In some other embodiments, the biomarker panel for use in the method for diagnosing, staging or assessing in a subject the likelihood of developing a the neurocognitive disorder comprises phosphoglucomutase 1 comprising or having the amino acid sequence of SEQ ID NO:1 or an isoform or a variant or a fragment thereof; and thymosin beta-4 comprising or having the amino acid sequence of SEQ ID NO:2 or a variant or a fragment thereof and, optionally ubiquitin carboxy-terminal hydrolase L1 which comprises or has an amino acid sequence of SEQ ID NO:4 or an isoform or a variant or a fragment thereof and/or vitamin D binding protein which comprises or has an amino acid sequence of SEQ ID NO: 5 or an isoform or variant or a fragment thereof.

In some embodiments of the methods described herein the neurocognitive disorder is selected from the group of mild cognitive impairment, Alzheimer's disease, vascular dementia, dementia with lewy bodies, fronto-temporal dementia or combinations thereof. Preferably, the neurocognitive disorder is Alzheimer's disease (AD).

In some of these embodiments of the method described herein, the neurocognitive disorder, preferably AD, is characterised by microglia activation.

In one embodiment of the present invention, the method for diagnosing a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining whether that subject has a neurocognitive disorder by comparing said concentration or amount of each of the biomarker of the biomarker panel in said sample with reference concentrations or amounts of said biomarkers; wherein the neurocognitive disorder is Alzheimer's disease and, optionally the biomarker panel further comprises at least one, alternatively two or more, biomarkers selected from any one of Tables 1, 2, 3, 4, 5, 6, 7, or 8 or fragments thereof.

In another embodiment of the present invention, the method for staging a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining the stage of the neurocognitive disorder in said subject by comparing said concentration or amount of each of the biomarker of the biomarker panel in said sample with reference concentrations or amounts of said biomarkers; wherein the neurocognitive disorder is Alzheimer's disease and, optionally the biomarker panel further comprises at least one, alternatively two or more, biomarkers selected from any one of Tables 1, 2, 3, 4, 5, 6, 7, or 8 or fragments thereof.

In another embodiment of the present invention, the method for assessing in a subject the likelihood of developing a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining whether that subject is likely to develop a neurocognitive disorder in said subject by comparing said concentration or amount of each of the biomarker of the biomarker panel in said sample with reference concentrations or amounts of said biomarkers; wherein the neurocognitive disorder is Alzheimer's disease and, optionally the biomarker panel further comprises at least one, alternatively two or more, biomarkers selected from any one of Tables 1, 2, 3, 4, 5, 6, 7, or 8 or fragments thereof.

The present invention also provides for a method for treating Alzheimer's disease in a subject, the method comprising:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining whether that subject has Alzheimer's disease by comparing said concentration or amount of each of the biomarkers in said sample with reference concentrations or amounts of said biomarkers;
d) administering to said subject an Alzheimer's disease treatment selected from the group of memantine (e.g. Namenda®), galantamine (e.g. Razadyne®), rivastigmine (e.g. Exelon®), donepezil (e.g. Aricept®), solanezumab, 5HT$_5$ antagonists or combinations thereof.

Optionally, the biomarker panel further comprises at least one, alternatively two or more, biomarkers selected from any one of Tables 1, 2, 3, 4, 5, 6, 7, or 8 or fragments thereof.

The present invention further provides for a method for aiding the prognosis of a treatment for Alzheimer's disease in a subject, the method comprising:
a) assaying a sample obtained from said subject for biomarkers of a biomarker panel;
b) measuring in said sample the concentration or the amount of each of the biomarkers of said biomarker panel;
c) determining whether said treatment for Alzheimer's disease is successful by comparing said concentration or amount of each of the biomarker in said sample with reference concentrations or amounts of said biomarkers. Preferably the treatment for Alzheimer's disease is selected from the group of memantine (e.g. Namenda®), galantamine (e.g. Razadyne®), rivastigmine (e.g. Exelon®), donepezil (e.g. Aricept®), solanezumab, 5HT$_5$ antagonists or combinations thereof. Optionally, the biomarker panel further comprises at least one, alternatively two or more, biomarkers selected from any one of Tables 1, 2, 3, 4, 5, 6, 7, or 8 or fragments thereof.

The sample used in the methods according to the present invention may be selected from the group of cerebrospinal fluid (CSF), blood, plasma, serum, saliva, urine, tissue (e.g. brain tissue) or combinations thereof.

In one embodiment, the sample is cerebrospinal fluid (CSF).

In one embodiment of the present invention, the method for diagnosing a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining whether that subject has a neurocognitive disorder by comparing said concentration or amount of each of the biomarker of the biomarker panel in said sample with reference concentrations or amounts of said biomarkers; wherein the neurocognitive disorder is Alzheimer's disease, wherein the sample is cerebrospinal fluid (CSF) and, optionally the biomarker panel further comprises at least one, alternatively two or more, biomarkers selected from any one of Tables 1, 2, 3, 4, 5, 6, 7, or 8 or fragments thereof.

In another embodiment of the present invention, the method for staging a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining the stage of the neurocognitive disorder in said subject by comparing said concentration or amount of each of the biomarker of the biomarker panel in said sample with reference concentrations or amounts of said biomarkers; wherein the neurocognitive disorder is Alzheimer's disease, wherein the sample is cerebrospinal fluid (CSF) and, optionally the biomarker panel further comprises at least one, alternatively two or more, biomarkers selected from any one of Tables 1, 2, 3, 4, 5, 6, 7, or 8 or fragments thereof.

In another embodiment of the present invention, the method for assessing in a subject the likelihood of developing a neurocognitive disorder in a subject comprises:
a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;
c) determining whether that subject is likely to develop a neurocognitive disorder in said subject by comparing said concentration or amount of each of the biomarker of the biomarker panel in said sample with reference concentrations or amounts of said biomarkers; wherein the neurocognitive disorder is Alzheimer's disease, wherein the sample is cerebrospinal fluid (CSF) and, optionally, the biomarker panel further comprises at least one, alternatively two or more, biomarkers selected from any one of Tables 1, 2, 3, 4, 5, 6, 7, or 8 or fragments thereof.

In another embodiment the method for treating Alzheimer's disease in a subject comprises:
a) assaying a sample obtained from said subject for the biomarkers of the biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measuring in said sample the concentration or the amount of each of the biomarkers of said biomarker panel;

c) determining whether that subject has Alzheimer's disease by comparing said concentration or amount of each of the biomarkers in said sample with reference concentrations or amounts of said biomarkers;

d) administering to said subject an Alzheimer's disease treatment selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof; wherein the sample is cerebrospinal fluid (CSF) and optionally, the biomarker panel further comprises at least one, alternatively two or more, biomarkers selected from any one of Tables 1, 2, 3, 4, 5, 6, 7, or 8 or fragments thereof.

In another embodiment the method for aiding the prognosis of a treatment for Alzheimer's disease in a subject comprises:

a) assaying a sample obtained from said subject for biomarkers of a biomarker panel;

b) measuring in said sample the concentration or the amount of each of the biomarkers of said biomarker panel;

c) determining whether said treatment for Alzheimer's disease is successful by comparing said concentration or amount of each of the biomarker in said sample with reference concentrations or amounts of said biomarkers, and wherein the sample is cerebrospinal fluid (CSF). Preferably the treatment for Alzheimer's disease is selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof. Optionally, the biomarker panel further comprises at least one, alternatively two or more, biomarkers selected from any one of Tables 1, 2, 3, 4, 5, 6, 7, or 8 or fragments thereof. In the methods described herein, the subject is preferably a human subject, who may have or may have not been previously diagnosed with mild cognitive impairment.

In some embodiments, the human subject may be undergoing further clinical assessment of dementia.

In some embodiments of the methods described herein, the assaying in step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv).

In particular, the assaying step a) and/or the measuring step b) may comprise detecting one or more fragments of said biomarker in the biomarker panel. Optionally, the sample is immobilised on a solid support.

Therefore, in one embodiment, the method for diagnosing Alzheimer's disease in a human subject comprises:

a) assaying a cerebrospinal fluid (CSF) sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;

b) measuring in said sample the concentration or the amount of each of the biomarkers of said biomarker panel;

c) determining whether that subject has Alzheimer's disease by comparing said concentration or amount of each of the biomarker of the biomarker panel in said sample with reference concentrations or amounts of said biomarkers;

wherein the assaying is step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv); and optionally, the biomarker panel further comprises at least one, alternatively two or more, biomarkers selected from any one of Tables 1, 2, 3, 4, 5, 6, 7, or 8 or fragments thereof.

In another embodiment of the present invention, the method for staging Alzheimer's disease in a human subject comprises:

a) assaying a cerebrospinal fluid (CSF) sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;

b) measuring in said sample the concentration or the amount of each of the biomarkers of said biomarker panel;

c) determining the stage of Alzheimer's disease in said subject by comparing said concentration or amount of each of the biomarker of the biomarker panel in said sample with reference concentrations or amounts of said biomarkers;

wherein the assaying is step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv); and optionally the biomarker panel further comprises at least one, alternatively two or more, biomarkers selected from any one of Tables 1, 2, 3, 4, 5, 6, 7, or 8 or fragments thereof.

In another embodiment of the present invention, the method for assessing in a subject the likelihood of developing Alzheimer's disease in a human subject comprises:

a) assaying a cerebrospinal fluid (CSF) sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;

b) measuring in said sample the concentration or the amount of each of the biomarkers of said biomarker panel;

c) determining whether that subject is likely to develop Alzheimer's disease by comparing said concentration or amount of each of the biomarker of the biomarker panel in said sample with reference concentrations or amounts of said biomarkers;

wherein the assaying is step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv); and optionally the biomarker panel further comprises at least one, alternatively two or more, biomarkers selected from any one of Tables 1, 2, 3, 4, 5, 6, 7, or 8 or fragments thereof.

In another embodiment, the method for treating Alzheimer's disease in a human subject comprises:

a) assaying a cerebrospinal fluid (CSF) sample obtained from said subject for biomarkers of the biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;

b) measuring in said sample the concentration or the amount of each of the biomarkers of said biomarker panel;

c) determining whether that subject has Alzheimer's disease by comparing said concentration or amount of each of the biomarkers in said sample with reference concentrations or amounts of said biomarkers;

d) administering to said subject an Alzheimer's disease treatment selected from the group of memantine (e.g. Namenda®), galantamine (e.g. Razadyne®), rivastigmine (e.g. Exelon®), donepezil (e.g. Aricept®), solanezumab, 5HT$_5$ antagonists or combinations thereof;

wherein the assaying is step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv); and optionally the biomarker panel further comprises at least one, alternatively two or more, biomarkers selected from any one of Tables 1, 2, 3, 4, 5, 6, 7, or 8 or fragments thereof.

In another embodiment the method for aiding the prognosis of a treatment for Alzheimer's disease in a human subject comprises:

a) assaying a sample obtained from said subject for biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;

b) measuring in said sample the concentration or the amount of each of the biomarkers of said biomarker panel;

c) determining whether said treatment for Alzheimer's disease is successful by comparing said concentration or amount of each of the biomarker in said sample with reference concentrations or amounts of said biomarkers, wherein the treatment for Alzheimer's disease is selected from the group of memantine (e.g. Namenda®), galantamine (e.g. Razadyne®), rivastigmine (e.g. Exelon®), donepezil (e.g. Aricept®), solanezumab, 5HT$_5$ antagonists or combinations thereof, and wherein the assaying is step a) and/or the measuring in step b) may further comprise:

i) contacting said sample with one or more binding agents to each of said biomarkers of the biomarker panel; or ii) detecting in said sample autoantibodies specific to each of said biomarkers; or iii) detecting in said sample by mass spectrometry each of said biomarkers of the biomarker panel, optionally by previously labelling said sample with one or more isobaric reactive mass labels; or iv) detecting in said sample by 2D gel electrophoresis each of said biomarkers of the biomarker panel; or v) any combinations of i), ii), iii) and/or iv).

Optionally, the biomarker panel further comprises at least one, alternatively two or more, biomarkers selected from any one of Tables 1, 2, 3, 4, 5, 6, 7, or 8 or fragments thereof.

In some preferred embodiments of all the methods described herein, the concentration or the amount of phosphoglucomutase 1 which comprises or has the amino acid sequence of SEQ ID NO:1 or an isoform or a variant or a fragment thereof is increased compared to its reference concentration or amount.

In some other preferred embodiments of all the methods described herein, the concentration or the amount of thymosin beta-4 which comprises or has the amino acid sequence of SEQ ID NO:2 or a variant or a fragment thereof is increased compared to its reference concentration or amount.

In some other preferred embodiments of all the methods described herein, the concentration or the amount of phosphoglucomutase 1 which comprises or has the amino acid sequence of SEQ ID NO:1 or an isoform or a variant or a fragment thereof is increased compared to its reference concentration or amount and the concentration or the amount of thymosin beta-4 which comprises or has the amino acid sequence of SEQ ID NO:2 or a variant or a fragment thereof is increased compared to its reference concentration or amount.

The present invention further provide for a method for identifying biomarkers in a sample obtained from a subject, wherein the biomarkers are suitable for diagnosing or staging Alzheimer's disease, wherein the method comprises using activate microglia cells (e.g. BV2 cells) and/or their culture media in mass spectrometry and/or wherein the biomarkers are identified in said sample by using activated microglia cells as a reference. Preferably the biomarker panel comprises the biomarkers as defined herein. The sample as described above may be selected from the group of CSF, blood, serum or plasma.

2. Kits

The present invention also provides for kits comprising reagents for assaying and/or measuring in a sample biomarkers of a biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof.

Optionally, the biomarker panel further comprises at least one, alternatively two or more, biomarkers selected from any one of Tables 1, 2, 3, or 4 or fragments thereof.

Preferably, the kit allows the diagnosing and staging of neurocognitive disorders, in particular Alzheimer's disease.

The reagents of the kits according to the invention may comprise one or more binding agents which specifically bind to the biomarkers of the biomarker panels. Preferably, the one or more binding agents are primary antibodies, wherein each primary antibody specifically binds to a different biomarker of the biomarker panel.

More preferably, the primary antibodies are antibodies against human phosphoglucomutase 1 which comprises or has the amino acid sequence of SEQ ID NO:1 or an isoform or a variant or a fragment thereof; and/or human thymosin beta-4 which comprises or has the amino acid sequence of SEQ ID NO:2 or a variant or a fragment thereof.

The primary antibodies may be immobilised on an assay plate, beads, microspheres or particles. Optionally, beads, microspheres or particles may be dyed, tagged or labelled.

When the kits comprise primary antibodies against the biomarkers of the biomarker panel, the kits may further comprise one or more secondary antibodies which specifically bind to said primary antibodies.

Optionally, the secondary antibodies may be labelled for example fluorescent labelled or tagged.

The kits according to the invention may further comprise one or more detection reagents for detecting the presence of the tagged secondary antibodies.

The sample is selected from the group of cerebrospinal fluid (CSF), blood, plasma, serum, saliva, urine, tissue (e.g. brain tissue) or combinations thereof.

The kits of the invention allows the user to:
a) assay a sample obtained from a subject for the biomarkers of the biomarker panel comprising phosphoglucomutase 1 which comprises or has the amino acid sequence of SEQ ID NO:1 or an isoform or a variant or a fragment thereof; and/or thymosin beta-4 which comprises or has the amino acid sequence of SEQ ID NO:2 or a variant or a fragment thereof;
b) measure in said sample the concentration or the amount of each of the biomarkers of said biomarker panel;
c) determine whether that subject has a neurocognitive disorder, in particular Alzheimer's disease, by comparing said concentration or amount of each of the biomarkers in said sample with reference concentrations or amounts of said biomarkers;

In particular, the kits according to the invention may instruct the user to assay (as in step a)) and/or to measure (as in step b)) the sample by:
i) contacting said sample with one or more binding agents to each of said biomarkers of the biomarker panel; or
ii) detecting in said sample autoantibodies specific to each of said biomarkers; or
iii) detecting in said sample by mass spectrometry each of said biomarkers of the biomarker panel, optionally by previously labelling said sample with one or more isobaric reactive mass labels; or
iv) detecting in said sample by 2D gel electrophoresis each of said biomarkers of the biomarker panel; or
v) any combinations of i), ii), iii) and/or iv).

In yet another embodiment, the kits may comprise reagents suitable for preparing brain tissue, optionally for preparing formalin-fixed paraffin-embedded brain tissue sections.

The kit may additionally provide a reference which provides a quantitative measure by which determination of a concentration or amount of one or more biomarkers can be compared. The reference may indicate the amount or concentration of biomarkers which indicate the presence or staging or likelihood of developing a neurocognitive disorder in particular AD.

The kit may also comprise printed instructions for performing the methods according to the present invention.

In one embodiment, the kit may be for performance of a mass spectrometry assay and may comprise a set of reference peptides (e.g. SRM peptides) in an assay compatible format wherein each peptide in the set is uniquely representative of each of the biomarkers provided in Tables 1, 2, 3, 4, 5, 6, 7, or 8. Preferably two or more of such unique peptides are used for each biomarker for which the kit is designed, and wherein each set of unique peptides are provided in known amounts which reflect the amount or concentration of such biomarker in a sample of a healthy subject.

Optionally, the kit may also provide protocols and reagents for the isolation and extraction of the biomarkers according to the invention from a sample, a purified preparation of a proteolytic enzyme such as trypsin and a detailed protocol of the method including details of the precursor mass and specific transitions to be monitored. The peptides may be synthetic peptides and may comprise one or more heavy isotopes of carbon, nitrogen, oxygen and/or hydrogen.

Optionally, the kits of the present invention may also comprise appropriate cells, vessels, growth media and buffers.

3. Detection and Measurement of Biomarkers

The biomarker panels described herein comprise both biomarkers where expression is modulated, i.e. quantitatively increased or decreased, and biomarkers which are exclusively present or absent, i.e. qualitatively expressed, in normal versus disease states. The degree to which expression differs in normal versus disease states need only be large enough to be visualised via standard characterisation techniques.

Methods for the detection and quantification of biomarkers are well known in the art and any suitable method may be employed.

In one embodiment, the biomarker(s) in the biomarker panel may be detected using a binding agent, such as an antibody, specific to that biomarker, for example in an ELISA assay or Western blotting.

Methods relating to the production of antibodies capable of specifically recognising one or more epitopes of the individual biomarkers in the biomarker panels described herein are known in the art. Such antibodies may include, but are not limited to, polyclonal antibodies, monoclonal antibodies (mAbs), humanised or chimeric antibodies, single chain antibodies, Fab fragments, F(ab')2 fragments, fragments produced by a Fab expression library, anti-idiotypic (anti-Id) antibodies, and epitope-binding fragments of any of the above.

For the production of antibodies, various host animals may be immunised by injection with a protein, or a portion thereof. Such host animals may include, but are not limited to, rabbits, mice and rats. Various adjuvants may be used to increase the immunological response, depending on the host species, including active substances such as lysolecithin, Pluronic polyols, polyanions, peptides, oil emulsions, keyhole limpet hemocyamin, dinitrophenol, and potentially useful human adjuvant such as BCG bacille Calmette-Fuerin) and *Corynebacterium parvum*.

Polyclonal antibodies are heterogeneous populations of antibody molecules derived from the sera of animals immunised with an antigen, such as target proteins, or an antigenic functional derivative thereof. For the production of polyclonal antibodies, host animals such as those described above, may be immunised by injection with differentially expressed or pathway protein supplemented with adjuvants as also described above.

Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975, Nature 256:495-7; and U.S. Pat. No. 4,376,110), the human β-cell hybridoma technique (Kosbor, et al., 1983, Immunology Today 4:72; Cole, et al., 1983, Proc. Natl. Acad. Sci. USA 80:2026-30), and the EBV-hybridoma technique (Cole, et al., 1985, Monoclonal Antibodies and Cancer Therapy, Alan R. Liss Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of 'chimeric antibodies' (Morrison, et al., 1984, Proc. Natl. Acad. Sci. 81:6851-5; Neuberger, et al., 1984, Nature 312: 604-8; Takeda, et al., 1985, Nature 314:452-4) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242: 423-6; Huston, et al., 1988, Proc. Natl. Acad. Sci. USA 85:5879-83; and Ward, et al., 1989, Nature 334: 544-6) can be adapted to produce differentially expressed or pathway protein-single chain antibodies. Single chain antibodies are formed by linking the heavy and light chain fragments of the Fv region via an amino acid bridge, resulting in a single chain polypeptide.

Antibody fragments, which recognise specific epitopes, may be generated by known techniques.

For example, such fragments include, but are not limited to, the F(ab')2 fragments which can be produced by pepsin digestion of the antibody molecule and the Fab fragments which can be generated by reducing the disulfide bridges of the F(ab')2 fragments. Alternative, Fab expression libraries may be constructed (Huse, et al., 1989, Science 246:1275-81) to allow rapid and easy identification of monoclonal Fab fragments with the desired specificity.

In some embodiments of the methods described herein, the sample may be immobilised on a solid support for analysis. An antibody sandwich technique may be employed in which binding agents, such as antibodies, specific for the individual biomarkers in the biomarker panel are immobilized on a solid support such as a planar surface or a microparticle bead and biomarkers in the panel are captured by the immobilised binding agents, such as immobilized antibodies. The captured biomarkers are then detected using a second binding agent, such as a secondary antibody, that may be directly labelled with a signal generating agent (enzyme, fluorescent tag, radiolabel etc.) or may be detected using further amplification (labelled secondary antibody, streptavidin/biotin systems with enzyme, fluorophore, radiolabel etc.). Other methods may include, but are not limited to, one-dimensional or two-dimensional (2D) gel electrophoresis of samples. Such methods are followed by transfer to a solid surface using techniques such as Western blotting and subsequent detection using antibodies specific for the AD biomarkers.

In other embodiments, autoantibodies to the biomarkers may be detected using the Western blotting approach described above using samples from a healthy subject, a patient or representative of AD, and then detecting the presence of auto-antibodies specific for the biomarker that are present in the sample, but not in healthy subjects.

An example of a non-antibody binding agent is an aptamer. Examples of aptamers include nucleic acid aptamers and peptide aptamers.

Alternatively, the biomarkers may be detected by, amongst others, silver staining of 2D gel electrophoresis or mass spectrometry techniques including LS/MS/MS, MALDI-TOF, SELDI-TOF and TMT-SRM.

Other such standard characterisation techniques by which expression differences may be visualised are well known to those skilled in the art. These include successive chromatographic separations of fractions and comparisons of the peaks, capillary electrophoresis, separations using microchannel networks, including on a micro-chip, SELDI analysis and qPST analysis.

Chromatographic separations can be carried out by high performance liquid chromatography as described in literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electro-osmotic flow (EOF) of the sample, the positive ions move fastest, followed by uncharged material and negatively charged ions. Thus, proteins are separated essentially according to charge on them.

Micro-channel networks function similarly to capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20:727-31.

Surface enhanced laser desorption ionisation time of flight mass spectrometry (SELDI-TOF-MS) combined with ProteinChip technology can also provide a rapid and sensitive means of profiling biomarkers and is used as an alternative to 2D gel electrophoresis in a complementary fashion. The ProteinChip system consists of aluminium chips to which protein samples can be selectively bound on the surface chemistry of the chip (e.g. anionic, cationic, hydrophobic, hydrophilic, etc.). Bound biomarkers are then co-crystallised with a molar excess of small energy-absorbing molecules. The chip is then analysed by short intense pulses of N2 320 nm UV laser with protein separation and detection being by time of flight mass spectrometry. Spectral profiles of each group within an experiment are compared and any peaks of interest can be further analysed using techniques as described below to establish the identity of the biomarkers.

Isotopic or isobaric Tandem Mass Tags® (TMT® Thermo Scientific, Rockford, USA) technology may also be used to detect biomarkers such as proteins of a biomarker panel described herein. Briefly, the proteins in the samples for comparison are optionally digested, labelled with a stable isotope tag and quantified by mass spectrometry. In this way, expression of equivalent proteins in the different samples can be compared directly by comparing the intensities of their respective isotopic peaks or of reporter ions released from the TMT® reagents during fragmentation in a tandem mass spectrometry experiment.

Detection of biomarkers of biomarker panels described herein may be preceded by a depletion step to remove the most abundant proteins from the sample. The large majority of the protein composition of serum/plasma consists of just a few proteins. For example, albumin, which is present at a concentration of 35-50 mg/ml, represents approximately 54% of the total protein content with IgG adding other 16%. In contrast, proteins changing in response to disease, for example as a result of tissue leakage, may circulate at 10 ng/ml. This vast dynamic range of protein concentrations represents a major analytical challenge and to overcome the problem, a multiple affinity depletion column may be used to remove the most highly abundant proteins (e.g. the 2, 3, 4, 5, 6, 7, 8, 9 or 10 or more highly abundant proteins). This enables the detection of changes in lower abundance ranges because more starting material can be used and there is less interference from the highly abundant molecules. Such a depletion strategy can be applied before any detection method.

4. Method to Screen and Select Test Agents for the Treatment of Neurocognitive Disorders The biomarker panels described herein may be used to test agents for the ability to prevent or ameliorate neurocognitive disorders, such as AD, or one or more symptoms thereof.

Such agents may be tested in human subjects in clinical trials. Any agent which restores the expression of the proteins in a biomarker panel described herein towards levels found in healthy individuals or towards its absence or presence as the case may be, is of potential use in treating a neurocognitive disorder, such as AD, i.e. reducing AD symptoms or slowing the progression of AD.

During clinical trials, for example, the amount or concentration of one or more biomarkers of a biomarker panel as described herein can be determined in the presence or absence of the agent being tested. The efficacy of the agent can be followed by comparing the expression data obtained to the corresponding known expression patterns in a normal state. Agents exhibiting efficacy are those which alter the presence, amount or concentration of the biomarkers in the biomarker panel to more closely resemble that of the normal state.

The detection of the biomarkers in the biomarker panel in the neurocognitive disorder relative to their expression or presence in a normal state can also be used for monitoring the efficacy of potential agents for the treatment of a neurocognitive disorder, such as AD, during clinical trials. During clinical trials, the level and/or presence of the biomarkers in the biomarker panel can be determined in cerebrospinal fluid (CSF) in the presence or absence of the agent being tested. The efficacy of the agent can be followed by comparing the biomarker levels and/or presence of the biomarkers in the data obtained, to the corresponding known levels/presence for the cells and/or tissues and/or body fluids in a normal state. Agents exhibiting efficacy are those which alter the presence, amount or concentration of the biomarker panel of the cell and/or tissue sample and/or body fluid from a subject to more closely resemble that of the normal state or which stabilise the pattern i.e. prevent progression of the disease. Because the present biomarker panels translate events and changes in pathways that occur in the brain into a peripheral signal, they allow replacing tissue testing with a peripheral fluid testing. This represents a great advantage especially as the tissue primarily affected in neurocognitive disorder is the brain tissue. Brain biopsies are not carried out and the only tissue analysis carried out is post-mortem.

With regard to intervention, any treatments that restore or partially restore the expression of biomarkers in a biomarker panel described herein to healthy levels should be considered as candidates for therapeutic intervention in neurocognitive disorders such as AD. Dosages of test agents may be determined by deriving dose-response curves.

Similarly, any treatments that can prevent the development of neurocognitive disorders such as AD or prevent progression to levels of more advanced AD should be considered as candidates for the AD therapeutic intervention.

An agent may be selected if it prevents or slows the change over time in presence, concentration or amount of the biomarkers of the biomarker panels relative to controls.

Preferably, the agent is selected if it converts the amount or concentration of a biomarker of the biomarker panels towards that of a normal subject.

The agent may be selected if it slows or stops the change of concentration or amount over time. For example, agents which exhibit inhibitory activity, may be used in accordance with the invention to prevent mild cognitive impairment or AD symptoms. Such molecules may include, but are not limited to, peptides (such as, for example, peptides representing soluble extracellular portions of target protein transmembrane receptors), phosphopeptides, small organic or inorganic molecules, or antibodies (including, for example, polyclonal, monoclonal, humanised, anti-idiotypic, chimeric or single chain antibodies, and Fab, F(ab')2 and Fab expression library fragments, and epitope-binding fragments thereof).

5. Examples

Certain aspects and embodiments of the invention will now be illustrated by way of example and with reference to the figures and tables described above. All documents mentioned in this specification are incorporated herein by reference in their entirety for all purposes.

All reagents for the cell culture and samples preparation were purchased from Sigma Aldrich® (Dorset, UK) unless stated. Tandem Mass Tags® (Thermo Scientific®); Acetonitrile (Fisher Scientific®, Loughborough, UK); Trypsin (Roche Diagnostics®, West Sussex, UK).

BV2 Cells Samples—

BV2 cells were seeded into 6 well plates at 80,000 cells per well and maintained at 37° C. at 5% $CO_2$. Cells were cultured for 24 hours in Dulbecco's modified eagle medium (Gibco®, Life Technologies) with 10% fetal bovine serum (Gibco®) supplemented with 2 mM L-glutamine, 100 U/mL penicillin and 100 mg/mL streptomycin, gentamycin and *mycoplasma* removal agent (AbD Serotec®). To activate the cells, a solution made of 2 µg/ml lipopolysaccharide (LPS) and 10 ng/ml interferon-gamma (IFNγ) (R&D Systems®) (Gordon S, et al., Nat Rev Immunol. 2005, 5, 12, 953-64. Dale D C, et al., Blood. 2008, 15, 112, 4, 935-45) was applied for 24 hours prior to harvesting. Cells were lysed in 8M urea, 75 mM NaCl, 50 mM Tris (pH 8.2) before sonication on ice (20×1 sec 20% amplitude) and centrifuged at 12,500 g for 10 mins at 4° C. The protein concentration of the cell lysate was estimated by Bradford assay. Samples were aliquoted to prevent freeze-thawing and stored at −80° C. The BV2 cells samples will be referred herein after as "calibrator" as they will be used to create calibration curves in the following experiments.

Cerebrospinal Fluid Samples—

CSF samples were from subjects who sought medical advice because of cognitive impairment. Subjects were designated as normal or AD according to CSF biomarker concentrations using cutoffs that are 90% sensitive and specific for AD): total tau (T-tau)>350 ng/L, phospho-tau (P-tau)>80 ng/L and Aβ42<530 ng/L (Hansson O, et al., Lancet Neurol. 2006, 5:228-34. None of the biochemically normal subjects fulfilled these criteria. CSF T-tau, P-tau and Aβ42 concentration were determined using INNOTEST enzyme-linked immunosorbent assays (Fujirebio, Ghent, Belgium) by board-certified laboratory technicians according to protocols approved by the Swedish Board for Accreditation and Conformity Assessment (SWEDAC). The study was approved by the regional ethics committee at the University of Gothenburg.

In-Solution Tryptic Digest and Tandem Mass Taq® (TMT®) Labelling—

Figure 6:
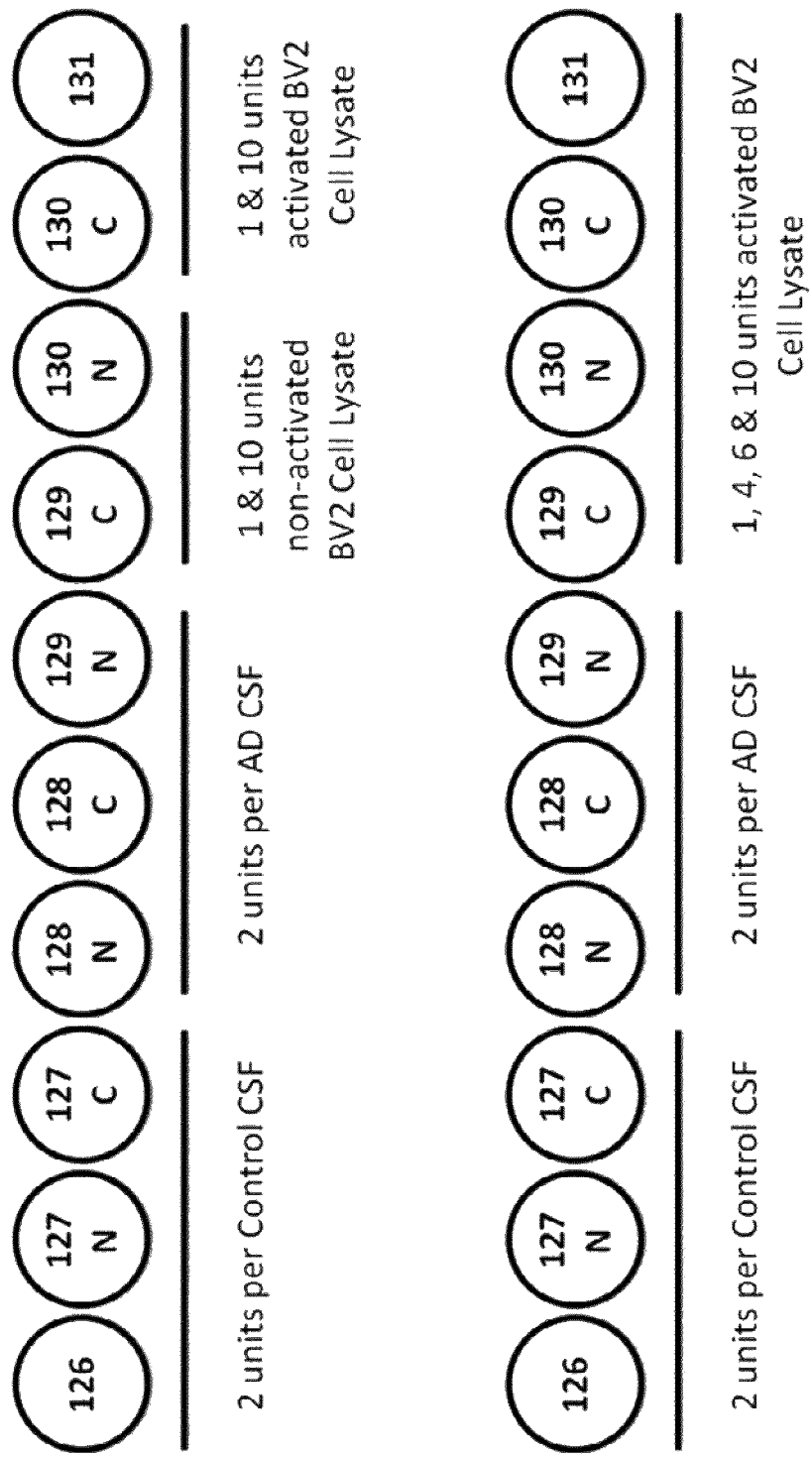
FIG. 6. Sample design showing the $TMT^{10}$-plex set up used in experiment A (left panel) and experiment B (right panel).

Following solubilization and denaturation in 100 mM TEAB buffer and 0.1% sodium dodecyl sulphate (SDS), the CSF samples and the BV2 cell-line (calibrator) were reduced with 1 mM TCEP at 55° C. for 60 min and alkylated with 7.5 mM iodoacetamide at room temperature for 60 min. Trypsin was used for digestion at an approximate 1:25 weight ratio of trypsin-to-total protein and incubated at 37° C. overnight (~18 h). Following digestion, the peptides obtained were labeled with one of the TMT® 10-plex reagents at 15 mM and incubated for 60 min at room temperature. To quench the TMT® reaction, 0.25% hydroxylamine was added to each sample and incubated for 15 min. The samples were then combined to generate an analytical sample comprising a 1:10 calibration curve of non-activated BV2 cells, a 1:10 calibration curve of activated BV2 cells and equal amount of six CSF samples and incubated for a further 15 min (FIG. 6). Each sample was desalted using RP18 columns (Waters, Manchester, UK) and excess reagents and SDS were removed by strong cation exchange (SCX) purification. Peptides were eluted in 75% acetonitrile (ACN)+400 mM NH4Oac (Ammonium Acetate) and dried to completion. For mass spectrometry (MS) analysis the sample was resuspended in 2% ACN+0.1% formic acid.

LC-MS/MS—

Quantitative analysis was performed in triplicate using an Orbitrap Fusion Tribrid® mass spectrometer (Thermo Scientific®) in the positive mode with EASYnLC1000 system and a 50 cm EASY-Spray column (Thermo Scientific®). The column temperature was maintained at 40° C., and the peptides were separated at a flow rate of 200 nL/min.

Peptides were eluted from the column over a 300 min gradient, from 3% to 30% solvent B (acetonitrile with 0.1% formic acid) in 280 min, followed by an increase to 80% solvent B in 10 mins, which was held for a further 10 mins. Solvent A was water with 0.1% formic acid. Wash and blank LC-MS/MS runs preceded the analysis.

A Top10 CID-HCD MS3 SPS method with a 2 second cycle time was utilized and the parameters were as follows: MS; Spray voltage—2000V; ion transfer tube temperature—275° C.; detector—Orbitrap; scan range (m/z)—400-1400; resolution—120000; AGC target—5×105. MS/MS (CID); Isolation mode—quadropole; collision energy—35%; detector—Ion trap; AGC target—4×103. MS3 (HCD); detector—Orbitrap; collision energy—55%; scan range—100-1000 m/z; resolution power—30000; AGC target—6×104.

Bioinformatics—

LC-MS/MS data was initially processed using SequestHT and Mascot within Proteome Discoverer 1.4, against the Uniprot human protein database (uniprot.org/pub/databases/uniprot/currentrelease/knowledgebase/proteomes/). After applying a 5% false discovery rate (FDR)) to filter the data in Proteome Discoverer, the number of peptide and protein identifications was determined.

Experiment A

This experiment was designed to incorporate two 2-point calibration curves using the control (i.e. non-activated) BV2 cells and activated (IFN-γ+LPS) BV2 cells, alongside six (6) CSF samples constituted of three (3) AD CSF samples and 3 non-AD CSF samples); 3 AD CSF samples were compared with three (3) non-AD control CSF samples using a two× 2-point calibration curve of control and activated BV2 cells to detect biomarkers of activation in a 3 vs 3 vs 2 vs 2 TMT® 10-plex MS3 method. The experiment was designed so that the protein content from the BV2 cells dominated the total protein content in the sample. The two×2-point calibration curve samples were spiked at a ratio of 1:10 and the 6 CSF samples were calculated to fall within this range. The total protein content that can be injected onto the MS column is 2 µg, therefore, the CSF samples' protein content per inject is limited to 121 ng per channel per CSF sample.

All CSF samples and the BV2 cells samples were solubilised, reduced and alkylated (as outlined above) prior to overnight tryptic digestion. Subsequently, all peptide samples were TMT® labelled as below, using the $TMT^{10}$plex reagents:

126—control CSF 1
127e—control CSF 2
127—control CSF 3

128e—AD CSF 1
128—AD CSF 2
129e—AD CSF 3
129—non-activated BV2 cell line
130e—non-activated cultured BV2 cell line
130—IFNγ+LPS activated BV2 cell line
131—IFNγ+LPS activated BV2 cell line The TMT$^{10}$plex labelled samples were mixed so as to generate a 1:10 calibration curve for the resting cells (channels 129 & 130e), a 1:10 calibration curve for the activated cells (channels 130 & 131) and equal levels of the 6 CSF samples wherein the total protein content from the cell digests is approximately double that for the CSF samples (FIG. 6). The mixed analytical sample was de-salted and cleaned (excess TMT® labels removed) and split into 2. Half of the sample was frozen and the remainder was fractionated by high pH reverse phase fractionation into 8 separate fractions. These were analysed on the new generation Orbitrap Fusion using a gradient of 3 hours.

The raw data files from all MS injections were searched using SequestHT and Mascot in Proteome Discoverer 1.4, against the Uniprot human protein database.

The reporter ion signal intensities from the 6 CSF channels were normalised by sum-scale normalization, a mathematical approach to remove experimental bias. The process involves summing the intensity values for all analytes measured in a given sample and then calculating the median value across all the summed values. The median value is divided by each summed value to create a correction factor which is multiplied to the original intensity values to give the normalized sum scaled measurement (Robinson M D, et al., Bioinformatics 2010, 26:139-40; De Livera A M, et al., Anal. Chem. 2012, 84, 24, 10768-76) and the variability across the CSF dataset was investigated using Principle Component Analysis (PCA) plots. It was found that the CSF samples separate by disease status at the peptide and protein level with the first principle component accounting for 79.9% of the total variation leading to group separation (data not shown).

In the first analysis of the MS data, the ratio of the signal intensity in the calibrator channels (129, 130e, 130 and 131) was expected to be 1:10 for the non-activated (129 and 130e) and 1:10 in the activated cells (130 and 131). The observed intensities across the two non-activated cell channels and across the two activated cell channels (calibrator) was calculated for every single peptide. Peptides with a ratio of 1:10±15% were considered to be acceptable calibrators. Only 22 peptides were found to contain an acceptable calibrator using these parameters.

In a second approach to identify which peptides show regulation with disease, the log 2 ratio of the average signal intensities in the three AD CSF samples compared to the average signal in the three control CSF samples was determined. A p-value for this ratio was established following a 2-sample t-test across the two CSF groups for every single peptide and protein (providing a signal was present in all 6 of the CSF TMT® channels). The log 2 ratio of the two calibrator channels in the non-activated cells and the activated cells was also calculated to show which peptides are regulated with BV2 cell activation. The ratio was calculated for the low spike calibrator in activated and control cells, and also for the high spike calibrator.

A total of 564 peptides were found to be up-regulated by at least 60% in the activated vs control BV2 cells (filtered for 60% increase in both the high and low calibrator ratio's). These were shown to map to 9 KEGG pathways, the most significant being the complement and coagulation cascades pathway, followed by the glycolysis/glycogenesis, the prion disease, the amino and nucleotide sugar metabolism, the antigen processing and presentation, the extracellular matrix-receptor interaction, the focal adhesion, the regulation of actin cytoskeleton and alanine/aspartate/glutamate metabolism pathways.

This first data set processing included all the peptides detected, regardless of missing TMR® reporter ion channels and allow the identification of peptides that are present in the CSF of AD patients that are absent in controls, or similarly, peptides which are present in activated BV2 cells that are not present in non-activated BV2 cells.

Of the 564 peptides up-regulated in activated BV2 cells, 75 were also found to be at least 60% elevated in AD CSF compared to control CSF. These 75 peptides map to 58 proteins as listed in Table 1. Proteins which are well known to be elevated in the brain of AD patients like Peroxiredoxin (Kim S H et al., J Neural Transm Suppl. 2001; (61):223-35)(FIG. 3A) and are considered biomarkers of oxidative stress (Poynton R A et al., Biochim Biophys Acta. 2014, 1840:906-12) are present along with proteins well known to be elevated in BV2 cells upon activation by LPS for example MARCKS-related protein (FIG. 3B), (Sunohara J R et al., J Neurochem. 2001 78:664-72) and amyloid-beta (Murphy A et al., Neurosci Lett. 2003, 347:9-12); Moesin (FIG. 3C), part of the extra-cellular matrix complex, which helps in the non-amyloidogenic processing of APP; Actin (FIG. 3D), known to be increased in AD patients' CSF, specifically in those individuals carrying the ApoE4 allele (Merched A et al., FEBS Lett. 1998, 425:225-8).

From the list of regulated peptides, 35 peptides from 29 proteins had a signal in all 10 channels, with 4 peptides having significant regulation (p≤0.05) as shown in Table 6.

TABLE 6

| SEQ ID NO: | Peptide | Protein | P value |
| --- | --- | --- | --- |
| 6 | QFSANDK | Phosphoglucomutase-1 | 0.031 |
| 14 | NPLPSKETIEQEK | Thymosin beta-4 | 0.050 |
| 17 | QIEELKGQEVSPK | Ubiquitin carboxyl-terminal hydrolase isozyme L1 | 0.047 |
| 18 | HQPQEFPTYVEPTNDEICEAFRK | Vitamin D-binding protein | 0.002 |

These peptides are found to be regulated by at least 60% with BV2 cell activation and are significantly up-regulated by at least 60% in the CSF of AD patients (FIG. 4A-D). Peptide NPLPSKETIEQEK (SEQ ID NO: 14) is found in both TMSB4XP4 protein and homologous protein Thymosin beta-4. The protein sequences of these two proteins are identical apart from the first 19 residues of TMSB4XP4 which are absent in Thymosin beta-4.

Phosphoglucomutase 1 was not detected when the CSF samples were measured in the absence of the BV2 cell sample calibrator, whilst Thymosin beta-4 was detected in both settings. Of the total eight (8) peptides detected for Phosphoglucomutase 1 (Table 7), 5 were regulated (≥60%; in bold in Table 7) but not significantly and only one was found to be significantly regulated with a P value ≤0.05 (QFSANDK; SEQ ID NO:6).

Three (3) peptides were detected for Thymosin beta-4 but only peptide NPLPSKETIEQEK (SEQ ID NO:14) was significantly regulated (Table 7) with one other also regulated ≥60% but not significantly (also in bold in Table 7).

When the data are filtered to identify peptides regulated in the CSF from AD samples compared to the non-AD samples, 1924 peptides were found to be up-regulated by at least 60% in AD CSF compared to non-AD CSF. A total of 63 peptides, mapping to 53 proteins were found to be significantly up-regulated (p≤0.05) as shown in Table 2. The list in Table 2 shows some proteins that are known to be regulated in AD CSF, like ApoE, Gelsolin, Secretogranin, Albumin and complement proteins. These examples demonstrate that the approach used herein allows the identification and quantification of peptides from well-known AD biomarkers which commonly appear in CSF in addition to peptides that represent novel CSF biomarkers of early changes in AD following microglia activation.

The top 10 most up-regulated peptides in AD CSF compared to non-AD and their corresponding proteins are shown in Table 8.

TABLE 7

| Phosphoglucomutase-1 | | | | | | | | |
|---|---|---|---|---|---|---|---|---|
| Peptide SEQ ID NO: | Control CSF | AD CSF | Calibrator | | | | Log2 AD/C | Pvalue (peptide) |
| QFSANDK 6 | 783.61 1291.05 2946.03 | 3435.34 4495.23 5220.72 | 6060 | 78200 | 17800 | 137000 | 1.799 | 0.0313 |
| IDAMHGVV GPYVK 7 | 1167.54 NA 2673.66 | 4756.93 5036.78 20413.03 | 26300 | 406000 | 84500 | 654000 | 1.390 | 0.3109 |
| VDLGVLGK 8 | 1194.79 2901.17 4574.59 | 2424.98 4295.25 15990.21 | 15600 | 205000 | 44600 | 376000 | 0.566 | 0.3430 |
| LYIDSYEK 9 | 1200.04 1406.51 3993.841 | 855.75 3055.20 6859.42 | 693 | 13700 | 3100 | 24300 | 1.119 | 0.5194 |
| SMPTSGAL DR 10 | 2822.50 1003.93 1326.44 | 2375.48 464.43 1925.31 | 1930 | 29400 | 6470 | 42800 | 0.537 | 0.8801 |
| YDYEEVEA EGANK 11 | 442.82 NA NA | NA 649.20 1973.66 | 8410 | 141000 | 14400 | 119000 | 1.566 | NA |
| IALYETPTG WK 12 | NA NA 938.10 | 623.68 789.49 6944.43 | 8250 | 115000 | 26300 | 201000 | -0.248 | NA |
| QSVEDILK 13 | NA 587.03 576.36 | NA NA 3463.72 | 2900 | 41700 | 9360 | 59200 | 2.573 | NA |

| Thymosin beta-4 | | | | | | | | |
|---|---|---|---|---|---|---|---|---|
| Peptide SEQ ID NO: | Control CSF | AD CSF | Calibrator | | | | Log2 AD/C | Pvalue (peptide) |
| NPLPSKETI EQEK 14 | 4033.76 7534.52 7128.95 | 11913.75 10537.66 18341.59 | 3810 | 56000 | 9160 | 122000 | 0.7409 | 0.0497 |
| TETQEKNPL PSK 15 | 3098.65 5362.34 5895.98 | 9727.02 6806.84 14528.34 | 8350 | 155000 | 23700 | 360000 | 0.8591 | 0.0819 |
| ETIEQEK 16 | 19629.59 33720.30 39302.79 | 35338.74 37756.83 96515.70 | 2890 | 43300 | 7980 | 44200 | 0.1631 | 0.2858 |

TABLE 8

| Peptide SEQ ID NO: | Protein names | Log2_AD/C | Pvalue |
|---|---|---|---|
| AYKSELEEQLTPVAEETR 19 | Apolipoprotein E | 4.300 | 0.0024 |
| GYPGVQAPEDLEWER 20 | Secretogranin-1 | 3.717 | 0.0411 |
| AVGPEITK 21 | Serine/threonine-protein phosphatase 2A 65 kDa reregulatory subunit A alpha isoform | 2.768 | 0.0121 |
| LRDQLGTAK 22 | Cytoplasmic dynein 1 heavy chain 1 | 2.759 | 0.0001 |
| KTEITDK 23 | RuvB-like 1 | 2.153 | 0.0445 |
| WELNTYLYAPK 24 | cDNA FLJ54806 | 2.115 | 0.0478 |
| SDVMYTDWKK 25 | Alpha-1-acid glycoprotein 2 | 2.050 | 0.0283 |
| FFETSAK 26 | Ras-related protein Rab-13 | 1.966 | 0.0467 |
| DAHKSEVAHR 27 | Serum albumin | 1.901 | 0.0093 |
| LKLSYEGEVTK 28 | Pigment epithelium-derived factor | 1.887 | 0.0085 |

Down regulation was also observed, although the peptide numbers were much lower. Eight (8) peptides were down-regulated by at least 60% in the activated BV2 cells and in AD CSF, and only 1 of these, Serum amyloid A4 protein, had a significant p value (p=0.014) based on the 3 vs 3 CSF channels.

proteins dominated the overall protein content of the TMT® 10-plex sample. These are arbitrary values allowing to determine a suitable protein load from the CSF samples for analysis. Six individual CSF samples were combined at a 2:2:2:2:2:2 ratio, falling within the 4-point calibration curve.

TABLE 9

| Peptide SEQ ID NO: | Protein names | Log2_AD/C | Pvalue |
|---|---|---|---|
| EALQGVGDMGR 29 | Serum amyloid A-4 protein | -1.067 | 0.0138 |
| LAEYHAK 30 | Truncated apolipoprotein A-I | -1.236 | 0.0194 |
| TVIGPDGHK 31 | Fibrinogen alpha chain | -1.389 | 0.1340 |
| DIAPTLTLYVGK 32 | Haptoglobin | -1.616 | 0.1480 |
| SASLHLPK 33 | Alpha-1-antitrypsin | -0.845 | 0.1816 |
| FTCTVTHTDLPSPLK 34 | Ig mu chain C region | -2.516 | 0.3394 |
| VLGAFSDGLAHLDNLK 35 | Hemoglobin subunit delta | -2.468 | 0.4325 |
| ISVAQGASK 36 | IgGFc-binding protein | -0.759 | 0.5297 |

Experiment B

In order to enhance the MS data acquisition from the BV2 cell line calibrator, experiment B was designed as a 4-point calibration curve to be spiked into the total combined CSF samples at a ratio of 1:4:6:10 in order to ensure the calibrator As the maximum load on column is 2 µg, the true protein load per channel can be determined by dividing the maximum 2 µg by the total number of arbitrary values (x) needed, which in this case is 33 (4 calibrator channels plus 6 CSF channels). If 33x equals 2 µg, 1x is therefore 0.06 µg and this can then be used to determine the total amount of protein from each of the 10 channels contributing to the calibrator analytical sample. Just 0.12 µg of each CSF sample is required (2×), along with a 4-point calibrator comprised of 0.06 µg (1×), 0.24 µg (4×), 0.36 µg (6×) and 0.6 µg (10×). This results in a total of 0.72 µg of protein from all the CSF samples and 1.26 µg of protein from the BV2 cell line calibrator—the calibrator proteins are therefore 1.75 fold more prevalent than the total CSF protein load.

The calibrator sample was analysed in triplicate on the Oribtrap Fusion Tribrid using an MS3 SPS method over a 300 minute gradient. The raw data files from all three MS injections were searched using SequestHT and Mascot in Proteome Discoverer 1.4, against the Uniprot human protein database. Results for the triplicate injections were merged resulting in one large data set for analysis. After applying a 5% false discovery rate (FDR) to filter the data in Proteome Discoverer, the number of peptide and protein IDs from calibrator-derived only, CSF sample derived only, and peptides common to both the microglia cell line calibrator and CSF samples, was determined. The design of this experiment ensured that the MS acquisition was driven by the more prevalent microglia cell line peptides, and this was evident in the peptide IDs recorded. No peptides specific to CSF samples were detected, confirming the premise that the calibrator approach circumvents the issues surrounding highly dominant CSF proteins. Instead, the peptides identified were either specific to the BV2 microglia cells (2,317), or common to CSF and BV2 microglial cells (11,150). These shared peptides were the focus for further analysis to isolate any biomarkers of microglial cells activation present in the CSF. All peptides with signal for all 10 TMT® reporter ions were taken forward for processing through a set of in-house bioinformatics scripts developed in R.

The reporter ion signal intensities from the six CSF channels were normalized by sum-scale normalization. Following normalization the variability across the CSF dataset was investigated using Principal Component Analysis (PCA). Group separation of AD and control CSF was seen at the peptide and protein level, forming the first principal component, and accounting for 44.6% of the total variation seen in the dataset. The second principal component explained 19.6% of the variability in the dataset, and this corresponded to the biological variation within the groups.

To further filter the data, we normalized the cell line calibrator data to one of the calibrator channels (channel 129 as in the previous experiment). This was carried out for the four channels dedicated to calibrator, which allowed us to filter for an expected TMT® calibrator signal signature or pattern. Following normalization, the ratio of the signal intensity in channels 129, 130e, 130 and 131 (calibrator channels) was expected to be 1:4:6:10. To measure a correspondence between expected calibrator signal intensities to observed calibrator intensities, an $R^2$ value across all four channels was calculated for every single peptide. PSM level intensities for the four TMT® calibrator channels show marginal deviation from expected linear calibrator signal intensity ratio of 1:4:6:10. A 39.3% of the peptides had a calibrator $R^2$ of ≥0.95 and were taken on for further data analysis.

The normalized dataset, filtered for the presence of an expected linear calibrator signal intensity was further filtered based on the significance following a 2-sample t-test across the two CSF groups for every single peptide and protein. Peptides with a p value ≤0.05 were considered significant. The log 2 ratio of the average AD CSF signal intensities (channels 128e, 128 and 129e) to control CSF signal intensities (channels 126, 127e and 127) was also normalized to the 129 TMT® calibrator channel. This provided a means of identifying which of the peptide sequences common to the activated microglia cell line and CSF samples were differentially regulated between control and AD CSF. We identified 84 unique peptide sequences from 77 proteins that were significantly up-regulated at least 60% (log 2 ratio ≤−0.7) in AD CSF compared to controls, and 34 unique peptides from 26 proteins that were significantly down-regulated by at least 60% (log 2 ratio ≥0.7).

Figure 5:
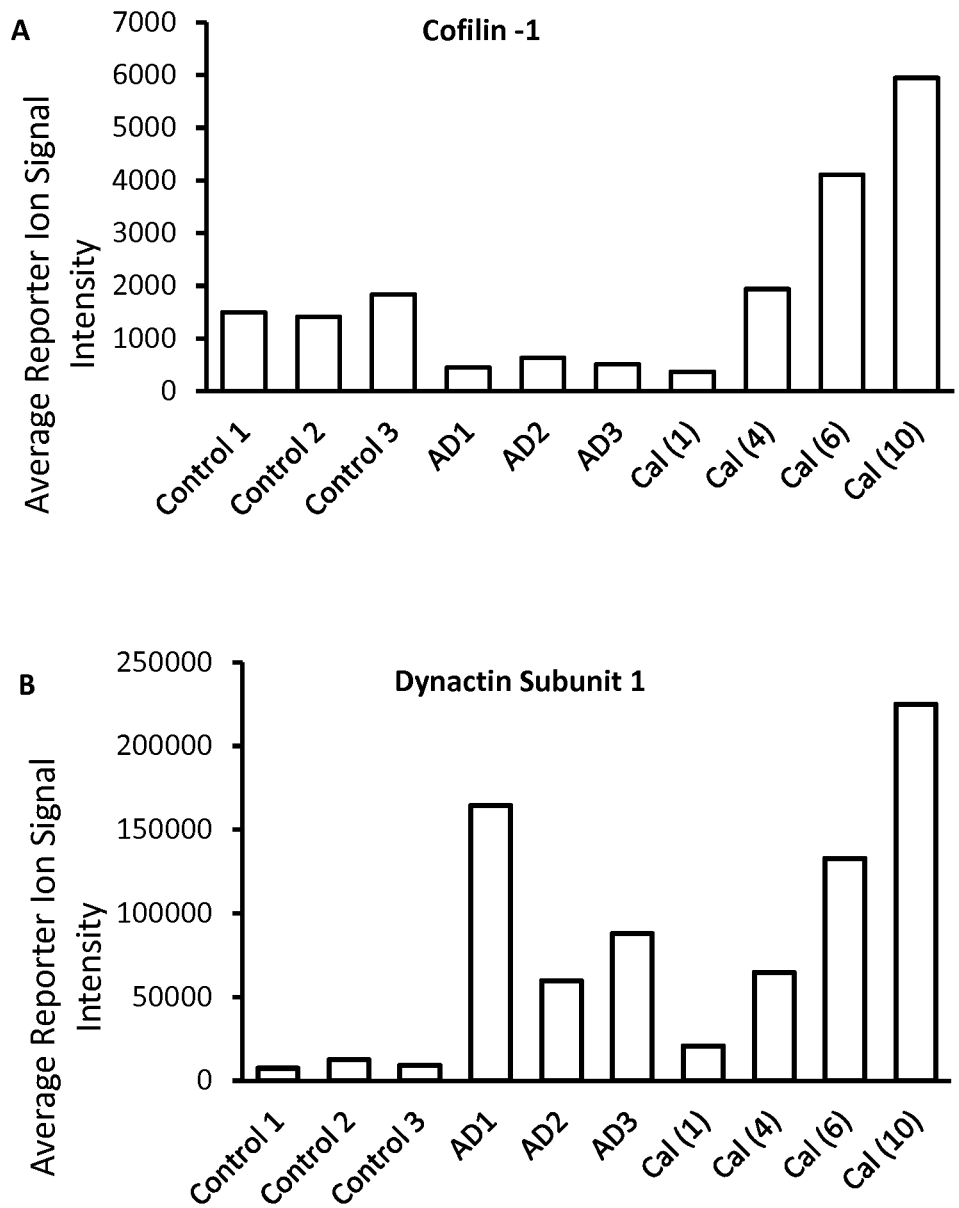
FIG. 5. Up-regulation of Dynactin Subunit 1 (A) and down-regulation of Cofilin-1 (B) in AD CSF versus control CSF shown as function of the average signal intensity.

When the list of regulated peptides in the CSF of AD patients is analysed, the benefit of TMT® calibrator over the traditional proteomics approach can be seen. As stated, the maximum protein load on the 75 µm diameter analytical LC column per injection is 2 ug. In the TMT® calibrator design the 2 µg is split unequally between the 4-point calibrator and the six CSF samples (1:4:6:10 ratio for the calibrator, 2:2:2 for AD CSF and 2:2:2 for non-AD CSF). Without the addition of the calibrator, the six CSF samples could be labelled with TMT in a multiplex experiment, with 0.33 µg combined from each sample per inject. This would not overcome the problems associated with high abundant CSF proteins which would dominate the MS acquisition, preventing lower abundant biomarkers from being detected. To highlight the different results seen after inclusion of the cell line calibrator, the same six CSF samples used in the TMT® calibrator study were equally combined and a total load of 2 µg was analysed in triplicate using the same method. Following the same bioinformatics processing, the results were filtered and analyzed to identify significantly regulated peptides in the AD CSF compared to control CSF samples. Seventy three proteins were significantly regulated by at least 60% (up or down regulation) in CSF but only 16 of these overlapped with significantly regulated peptides in the TMT® calibrator study. The majority of the proteins identified in the CSF samples are known to be secreted proteins, annotated as such under their Uniprot accession entries (such as plasminogen, mimecan and hemopexin). Intracellular biomarkers, such as proteins found commonly in the nucleus, are of particular interest. With the aid of the calibrator, it was possible to identify from the significantly regulated list total of 29 biomarkers which are localized in the nucleus. In the absence of the calibrator, only 5 proteins were found. A large proportion of the significantly regulated proteins found without TMT® calibrator are proteins that are commonly observed in CSF studies including serum albumin, complement proteins (C3, C5 and C7), fibrinogen gamma chain and Ig gamma chain (Boche D, et al., Neuropathol Appl Neurobiol. 2013, 39, 1, 3-18). These proteins are likely representative of disease related changes of low specificity rather than the cellular changes specific to AD. They are some of the most abundant proteins found in the CSF and are reported in the majority of CSF proteomic analysis studies (Hühmer A F, et al., Disease Markers. 2006, 22, 1-2, 3-26). In comparison, the majority of peptides derived when the BV2 cell line is used to drive the experiment are cellular and may represent a cellular response specific to disease. These include peptides from dynactin (FIG. 5A), cofilin (FIG. 5A), alcohol dehydrogenase, filamin-A, myosin proteins and Ras-related proteins. These are cellular proteins regulated in AD that would not have been detected if the CSF samples had been analysed in the absence of the BV2 cell samples (calibrator samples). Peptide IKDALVR (SEQ ID NO: 37), corresponding to dynactin subunit 1 (FIG. 5A), was the most upregulated peptide whist peptide MIYASSK (SEQ ID NO: 38), corresponding to Cofilin-1 (FIG. 5B), was the most down regulated peptide in the CSF of AD patients when compared to non-AD controls.

To conclude, biomarkers are indicators of pathological processes and biological events. Their levels change as a result of disease and also in response to pharmacological intervention. The challenge is how to find these molecules in biofluids such as blood or CSF which contain a high protein dynamic range and hyper-abundant proteins such as albumin.

The inventors have applied a novel Tandem Mass Tag® (TMT®) mass spectrometry (MS) approach, the TMT® calibrator analysis, to look for biomarkers of microglia activation within the CSF of AD patients. BV2 cells are a microglial cell line derived from raf/myc-immortalised murine neonatal microglia (Blasi E, et al., J neuroimmunology. 1990, 27, 2-3, 229-37) and have been used extensively to study microglial activation. Studies have shown their utility as a surrogate for primary microglial cultures which are costly in terms of animals used and time consuming to prepare (Henn A, et al., Alternatives to animal experimentation. 2009, 26, 2, 83-94; Stansley B, et al., J Neuroinflammation. 2012, 31, 9, 115).

The successful application of the TMT® calibrator analysis in this study has provided a novel list of potential biomarker candidates likely originating from activated microglia and circulating in CSF and which are differentially expressed in AD patients compared with non-AD subjects.

The invention claimed is:

1. A method for treating Alzheimer's disease in a subject, comprising:
   a) assaying a sample obtained from the subject for the biomarkers of a biomarker panel comprising:
      i) a phosphoglucomutase 1 comprising the amino acid sequence of SEQ ID NO:1 or an isoform, variant or fragment thereof;
      ii) a thymosin beta-4 comprising the amino acid sequence of SEQ ID NO:2 or a variant or fragment thereof; and
      iii) at least one biomarker selected from: 1) a ubiquitin carboxy-terminal hydrolase L1 which comprises the amino acid sequence of SEQ ID NO:4 or an isoform, variant, or fragment thereof; 2) a vitamin D binding protein which comprises the amino acid sequence of SEQ ID NO: 5 or an isoform, variant, or fragment thereof; or 3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins;
   b) measuring in the sample a concentration or an amount of each of the selected biomarkers of the biomarker panel;
   c) determining whether the subject has Alzheimer's disease by comparing the concentration or the amount of each of the selected biomarkers in the sample with reference concentrations or amounts of each of the biomarkers; and
   d) administering to the subject an Alzheimer's disease treatment selected from the group consisting of memantine, galantamine, rivastigmine, donepezil, solanezumab, an $5HT_5$ antagonist, and any combination thereof;
   wherein the sample is selected from the group consisting of cerebrospinal fluid (CSF), blood, plasma, serum, saliva, urine, tissue, and any combination thereof.

2. The method for treating Alzheimer's disease of claim 1, wherein the assaying and/or measuring steps are performed using a kit comprising reagents for assaying and/or measuring in a sample the biomarkers of the biomarker panel.

3. The method for treating Alzheimer's disease of claim 2, wherein the kit is configured for performance of a mass spectrometry assay, wherein the reagents comprise one or more reference peptides in an assay compatible format, and each peptide is uniquely representative of one of the biomarkers.

4. The method for treating Alzheimer's disease of claim 3, wherein the one or more reference peptides are selected from the peptides of SEQ ID NO: 6 or SEQ ID NO: 14.

5. The method for treating Alzheimer's disease of claim 4, wherein the reagents further comprise one or more reference peptides selected from the peptides of SEQ ID NO: 17 or SEQ ID NO: 18.

6. The method for treating Alzheimer's disease of claim 4, wherein the reagents further comprise one or more reference peptides selected from any one of the peptides of SEQ ID NOs: 19-36.

7. The method for treating Alzheimer's disease of claim 3, wherein the reference peptide is a synthetic peptide.

8. The method for treating Alzheimer's disease of claim 3, wherein the reference peptide comprises one or more heavy isotopes of carbon, nitrogen, oxygen and/or hydrogen.

9. The method for treating Alzheimer's disease of claim 2, wherein the reagents comprise one or more binding agents wherein each binding agent specifically binds to a different biomarker of the biomarker panel.

10. The method for treating Alzheimer's disease of claim 9, wherein the one or more binding agents is an antibody.

11. The method of claim 1, wherein the assaying step a) and/or the measuring step b) comprise:
    i) detecting in the sample by mass spectrometry each of the biomarkers of the biomarker panel;
    ii) contacting the sample with one or more binding agents which bind to the biomarkers of the biomarker panel;
    iii) detecting in the sample autoantibodies specific to each of the biomarkers;
    iv) detecting in the sample by 2D gel electrophoresis each of the biomarkers of the biomarker panel; or
    v) any combination of i), ii), iii) or iv).

12. The method of claim 1, wherein the assaying in is step a) and/or the measuring is step b) comprise detecting one or more fragments of at least one of the biomarkers in the biomarker panel.

13. The method of claim 1, wherein the biomarker panel comprises:
    1) a ubiquitin carboxy-terminal hydrolase L1 which comprises the amino acid sequence of SEQ ID NO:4 or an isoform, variant, or fragment thereof;
    2) a vitamin D binding protein which comprises the amino acid sequence of SEQ ID NO: 5 or an isoform, variant, or fragment thereof; and
    3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

14. The method of claim 1, wherein the biomarker panel consists of:
    i) a phosphoglucomutase 1 comprising the amino acid sequence of SEQ ID NO:1 or an isoform, variant or fragment thereof;

ii) a thymosin beta-4 comprising the amino acid sequence of SEQ ID NO:2 or a variant or fragment thereof; and iii) at least one biomarker selected from: 1) a ubiquitin carboxy-terminal hydrolase L1 which comprises the amino acid sequence of SEQ ID NO:4 or an isoform, variant, or fragment thereof; 2) a vitamin D binding protein which comprises the amino acid sequence of SEQ ID NO: 5 or an isoform, variant, or fragment thereof; or 3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

15. The method of claim 1, wherein the biomarker panel consists of:
   i) a phosphoglucomutase 1 comprising the amino acid sequence of SEQ ID NO:1 or an isoform, variant or fragment thereof;
   ii) a thymosin beta-4 comprising the amino acid sequence of SEQ ID NO:2 or a variant or fragment thereof; and
   iii) a ubiquitin carboxy-terminal hydrolase L1 which comprises the amino acid sequence of SEQ ID NO:4 or an isoform, variant, or fragment thereof.

16. The method of claim 1, wherein the biomarker panel consists of:
   i) a phosphoglucomutase 1 comprising the amino acid sequence of SEQ ID NO:1 or an isoform, variant or fragment thereof;
   ii) a thymosin beta-4 comprising the amino acid sequence of SEQ ID NO:2 or a variant or fragment thereof; and
   iii) a vitamin D binding protein which comprises the amino acid sequence of SEQ ID NO: 5 or an isoform, variant, or fragment thereof.

17. A method for treating Alzheimer's disease in a subject, comprising:
   a) assaying a sample obtained from the subject for the biomarkers of a biomarker panel comprising:
      i) a phosphoglucomutase 1 comprising the amino acid sequence of SEQ ID NO:1 or an isoform, variant or fragment thereof; or a thymosin beta-4 comprising the amino acid sequence of SEQ ID NO:2 or a variant or fragment thereof; and
      ii) at least one of the following: 1) a ubiquitin carboxy-terminal hydrolase L1 which comprises the amino acid sequence of SEQ ID NO:4 or an isoform, variant, or fragment thereof; 2) a vitamin D binding protein which comprises the amino acid sequence of SEQ ID NO: 5 or an isoform, variant, or fragment thereof; or 3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins;
   b) measuring in the sample a concentration or an amount of each of the selected biomarkers of the biomarker panel;
   c) determining whether the subject has Alzheimer's disease by comparing the concentration or the amount of each of the selected biomarkers in the sample with reference concentrations or amounts of each of the biomarkers; and
   d) administering to the subject an Alzheimer's disease treatment selected from the group consisting of memantine, galantamine, rivastigmine, donepezil, solanezumab, an $5HT_5$ antagonist, and any combination thereof;

wherein the sample is selected from the group consisting of cerebrospinal fluid (CSF), blood, plasma, serum, saliva, urine, tissue, and any combination thereof.

18. The method of claim 17, wherein the biomarker panel comprises:
   1) a ubiquitin carboxy-terminal hydrolase L1 which comprises the amino acid sequence of SEQ ID NO:4 or an isoform, variant, or fragment thereof;
   2) a vitamin D binding protein which comprises the amino acid sequence of SEQ ID NO: 5 or an isoform, variant, or fragment thereof; and
   3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

19. The method of claim 17, wherein the biomarker panel consists of:
   i) a phosphoglucomutase 1 comprising the amino acid sequence of SEQ ID NO:1 or an isoform, variant or fragment thereof;
   ii) a thymosin beta-4 comprising the amino acid sequence of SEQ ID NO:2 or a variant or fragment thereof; and
   iii) at least one biomarker selected from: 1) a ubiquitin carboxy-terminal hydrolase L1 which comprises the amino acid sequence of SEQ ID NO:4 or an isoform, variant, or fragment thereof; 2) a vitamin D binding protein which comprises the amino acid sequence of SEQ ID NO: 5 or an isoform, variant, or fragment thereof; or 3) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

20. The method of claim 17, wherein the biomarker panel consists of:
   i) a phosphoglucomutase 1 comprising the amino acid sequence of SEQ ID NO:1 or an isoform, variant or fragment thereof;
   ii) a thymosin beta-4 comprising the amino acid sequence of SEQ ID NO:2 or a variant or fragment thereof; and
   iii) a ubiquitin carboxy-terminal hydrolase L1 which comprises the amino acid sequence of SEQ ID NO:4 or an isoform, variant, or fragment thereof.

21. The method of claim 17, wherein the biomarker panel consists of:
   i) a thymosin beta-4 comprising the amino acid sequence of SEQ ID NO:2 or a variant or fragment thereof;
   ii) a ubiquitin carboxy-terminal hydrolase L1 which comprises the amino acid sequence of SEQ ID NO:4 or an isoform, variant, or fragment thereof; and
   iii) at least two or more biomarkers selected from the group consisting of: Dynactin subunit 1, Cofilin-1, Peroxiredoxin-1, MARCKS-related protein, Moesin, Actin, Protein TMSB4XP4, ApoE, Gelsolin, Secretogranin, Albumin and complement proteins.

* * * * *

SEQUENCE LISTING

```
<160> NUMBER OF SEQ ID NOS: 59

<210> SEQ ID NO 1
<211> LENGTH: 562
<212> TYPE: PRT
<213> ORGANISM: Homo sapiens

<400> SEQUENCE: 1

Met Val Lys Ile Val Thr Val Lys Thr Gln Ala Tyr Gln Asp Gln Lys
1               5                   10                  15

Pro Gly Thr Ser Gly Leu Arg Lys Arg Val Lys Val Phe Gln Ser Ser
            20                  25                  30

Ala Asn Tyr Ala Glu Asn Phe Ile Gln Ser Ile Ile Ser Thr Val Glu
        35                  40                  45

Pro Ala Gln Arg Gln Glu Ala Thr Leu Val Val Gly Gly Asp Gly Arg
    50                  55                  60

Phe Tyr Met Lys Glu Ala Ile Gln Leu Ile Ala Arg Ile Ala Ala Ala
65                  70                  75                  80

Asn Gly Ile Gly Arg Leu Val Ile Gly Gln Asn Gly Ile Leu Ser Thr
                85                  90                  95

Pro Ala Val Ser Cys Ile Ile Arg Lys Ile Lys Ala Ile Gly Gly Ile
            100                 105                 110

Ile Leu Thr Ala Ser His Asn Pro Gly Gly Pro Asn Gly Asp Phe Gly
        115                 120                 125

Ile Lys Phe Asn Ile Ser Asn Gly Gly Pro Ala Pro Glu Ala Ile Thr
    130                 135                 140

Asp Lys Ile Phe Gln Ile Ser Lys Thr Ile Glu Glu Tyr Ala Val Cys
145                 150                 155                 160

Pro Asp Leu Lys Val Asp Leu Gly Val Leu Gly Lys Gln Gln Phe Asp
                165                 170                 175

Leu Glu Asn Lys Phe Lys Pro Phe Thr Val Glu Ile Val Asp Ser Val
            180                 185                 190

Glu Ala Tyr Ala Thr Met Leu Arg Ser Ile Phe Asp Phe Ser Ala Leu
        195                 200                 205

Lys Glu Leu Leu Ser Gly Pro Asn Arg Leu Lys Ile Arg Ile Asp Ala
    210                 215                 220

Met His Gly Val Val Gly Pro Tyr Val Lys Lys Ile Leu Cys Glu Glu
225                 230                 235                 240

Leu Gly Ala Pro Ala Asn Ser Ala Val Asn Cys Val Pro Leu Glu Asp
                245                 250                 255

Phe Gly Gly His His Pro Asp Pro Asn Leu Thr Tyr Ala Ala Asp Leu
            260                 265                 270
```

```
Val Glu Thr Met Lys Ser Gly Glu His Asp Phe Gly Ala Ala Phe Asp
            275                 280                 285

Gly Asp Gly Asp Arg Asn Met Ile Leu Gly Lys His Gly Phe Phe Val
        290                 295                 300

Asn Pro Ser Asp Ser Val Ala Val Ile Ala Ala Asn Ile Phe Ser Ile
305                 310                 315                 320

Pro Tyr Phe Gln Gln Thr Gly Val Arg Gly Phe Ala Arg Ser Met Pro
                325                 330                 335

Thr Ser Gly Ala Leu Asp Arg Val Ala Ser Ala Thr Lys Ile Ala Leu
            340                 345                 350

Tyr Glu Thr Pro Thr Gly Trp Lys Phe Phe Gly Asn Leu Met Asp Ala
        355                 360                 365

Ser Lys Leu Ser Leu Cys Gly Glu Glu Ser Phe Gly Thr Gly Ser Asp
370                 375                 380

His Ile Arg Glu Lys Asp Gly Leu Trp Ala Val Leu Ala Trp Leu Ser
385                 390                 395                 400

Ile Leu Ala Thr Arg Lys Gln Ser Val Glu Asp Ile Leu Lys Asp His
                405                 410                 415

Trp Gln Lys Tyr Gly Arg Asn Phe Phe Thr Arg Tyr Asp Tyr Glu Glu
            420                 425                 430

Val Glu Ala Glu Gly Ala Asn Lys Met Met Lys Asp Leu Glu Ala Leu
        435                 440                 445

Met Phe Asp Arg Ser Phe Val Gly Lys Gln Phe Ser Ala Asn Asp Lys
    450                 455                 460

Val Tyr Thr Val Glu Lys Ala Asp Asn Phe Glu Tyr Ser Asp Pro Val
465                 470                 475                 480

Asp Gly Ser Ile Ser Arg Asn Gln Gly Leu Arg Leu Ile Phe Thr Asp
                485                 490                 495

Gly Ser Arg Ile Val Phe Arg Leu Ser Gly Thr Gly Ser Ala Gly Ala
            500                 505                 510

Thr Ile Arg Leu Tyr Ile Asp Ser Tyr Glu Lys Asp Val Ala Lys Ile
        515                 520                 525

Asn Gln Asp Pro Gln Val Met Leu Ala Pro Leu Ile Ser Ile Ala Leu
    530                 535                 540

Lys Val Ser Gln Leu Gln Glu Arg Thr Gly Arg Thr Ala Pro Thr Val
545                 550                 555                 560

Ile Thr

<210> SEQ ID NO 2
<211> LENGTH: 44
<212> TYPE: PRT
<213> ORGANISM: Homo sapiens

<400> SEQUENCE: 2

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40

<210> SEQ ID NO 3
<211> LENGTH: 580
<212> TYPE: PRT
<213> ORGANISM: Homo sapiens
```

```
<400> SEQUENCE: 3

Met Ser Asp Phe Glu Glu Trp Ile Ser Gly Thr Tyr Arg Lys Met Glu
1               5                   10                  15

Glu Gly Pro Leu Pro Leu Leu Thr Phe Ala Thr Ala Pro Tyr His Asp
            20                  25                  30

Gln Lys Pro Gly Thr Ser Gly Leu Arg Lys Lys Thr Tyr Tyr Phe Glu
        35                  40                  45

Glu Lys Pro Cys Tyr Leu Glu Asn Phe Ile Gln Ser Ile Phe Phe Ser
    50                  55                  60

Ile Asp Leu Lys Asp Arg Gln Gly Ser Ser Leu Val Gly Gly Asp
65                  70                  75                  80

Gly Arg Tyr Phe Asn Lys Ser Ala Ile Glu Thr Ile Val Gln Met Ala
                85                  90                  95

Ala Ala Asn Gly Ile Gly Arg Leu Val Ile Gly Gln Asn Gly Ile Leu
            100                 105                 110

Ser Thr Pro Ala Val Ser Cys Ile Ile Arg Lys Ile Lys Ala Ile Gly
        115                 120                 125

Gly Ile Ile Leu Thr Ala Ser His Asn Pro Gly Gly Pro Asn Gly Asp
    130                 135                 140

Phe Gly Ile Lys Phe Asn Ile Ser Asn Gly Gly Pro Ala Pro Glu Ala
145                 150                 155                 160

Ile Thr Asp Lys Ile Phe Gln Ile Ser Lys Thr Ile Glu Glu Tyr Ala
                165                 170                 175

Val Cys Pro Asp Leu Lys Val Asp Leu Gly Val Leu Gly Lys Gln Gln
            180                 185                 190

Phe Asp Leu Glu Asn Lys Phe Lys Pro Phe Thr Val Glu Ile Val Asp
        195                 200                 205

Ser Val Glu Ala Tyr Ala Thr Met Leu Arg Ser Ile Phe Asp Phe Ser
    210                 215                 220

Ala Leu Lys Glu Leu Leu Ser Gly Pro Asn Arg Leu Lys Ile Arg Ile
225                 230                 235                 240

Asp Ala Met His Gly Val Val Gly Pro Tyr Val Lys Lys Ile Leu Cys
                245                 250                 255

Glu Glu Leu Gly Ala Pro Ala Asn Ser Ala Val Asn Cys Val Pro Leu
            260                 265                 270

Glu Asp Phe Gly His His Pro Asp Pro Asn Leu Thr Tyr Ala Ala
        275                 280                 285

Asp Leu Val Glu Thr Met Lys Ser Gly Glu His Asp Phe Gly Ala Ala
    290                 295                 300

Phe Asp Gly Asp Gly Asp Arg Asn Met Ile Leu Gly Lys His Gly Phe
305                 310                 315                 320

Phe Val Asn Pro Ser Asp Ser Val Ala Val Ile Ala Ala Asn Ile Phe
                325                 330                 335

Ser Ile Pro Tyr Phe Gln Gln Thr Gly Val Arg Gly Phe Ala Arg Ser
            340                 345                 350

Met Pro Thr Ser Gly Ala Leu Asp Arg Val Ala Ser Ala Thr Lys Ile
        355                 360                 365

Ala Leu Tyr Glu Thr Pro Thr Gly Trp Lys Phe Phe Gly Asn Leu Met
    370                 375                 380

Asp Ala Ser Lys Leu Ser Leu Cys Gly Glu Glu Ser Phe Gly Thr Gly
385                 390                 395                 400

Ser Asp His Ile Arg Glu Lys Asp Gly Leu Trp Ala Val Leu Ala Trp
                405                 410                 415
```

-continued

Leu Ser Ile Leu Ala Thr Arg Lys Gln Ser Val Glu Asp Ile Leu Lys
            420                 425                 430

Asp His Trp Gln Lys Tyr Gly Arg Asn Phe Phe Thr Arg Tyr Asp Tyr
            435                 440                 445

Glu Glu Val Glu Ala Glu Gly Ala Asn Lys Met Met Lys Asp Leu Glu
        450                 455                 460

Ala Leu Met Phe Asp Arg Ser Phe Val Gly Lys Gln Phe Ser Ala Asn
465                 470                 475                 480

Asp Lys Val Tyr Thr Val Glu Lys Ala Asp Asn Phe Glu Tyr Ser Asp
                485                 490                 495

Pro Val Asp Gly Ser Ile Ser Arg Asn Gln Gly Leu Arg Leu Ile Phe
            500                 505                 510

Thr Asp Gly Ser Arg Ile Val Phe Arg Leu Ser Gly Thr Gly Ser Ala
            515                 520                 525

Gly Ala Thr Ile Arg Leu Tyr Ile Asp Ser Tyr Glu Lys Asp Val Ala
        530                 535                 540

Lys Ile Asn Gln Asp Pro Gln Val Met Leu Ala Pro Leu Ile Ser Ile
545                 550                 555                 560

Ala Leu Lys Val Ser Gln Leu Gln Glu Arg Thr Gly Arg Thr Ala Pro
                565                 570                 575

Thr Val Ile Thr
            580

<210> SEQ ID NO 4
<211> LENGTH: 241
<212> TYPE: PRT
<213> ORGANISM: Homo sapiens

<400> SEQUENCE: 4

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Val Ile Phe Gly Met His Leu Phe Leu Met Thr Leu Pro

```
                195                 200                 205
Arg Ser Ala Glu Asn Ser Pro Ser Val Ser Lys Glu Lys Ser Ala Ser
210                 215                 220

Leu Pro Trp Leu Ser Ala Arg Gln Pro Asn Ala Leu Trp Glu Gly Leu
225                 230                 235                 240

Cys

<210> SEQ ID NO 5
<211> LENGTH: 348
<212> TYPE: PRT
<213> ORGANISM: Homo sapiens

<400> SEQUENCE: 5

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
```

```
                   325                 330                 335
Pro Gly Asn Thr Lys Val Met Asp Lys Ala Leu Tyr
                340                 345

<210> SEQ ID NO 6
<211> LENGTH: 7
<212> TYPE: PRT
<213> ORGANISM: Artificial Sequence
<220> FEATURE:
<223> OTHER INFORMATION: Phosphoglucomutase 1 - peptide 1

<400> SEQUENCE: 6

Gln Phe Ser Ala Asn Asp Lys
1               5

<210> SEQ ID NO 7
<211> LENGTH: 13
<212> TYPE: PRT
<213> ORGANISM: Artificial Sequence
<220> FEATURE:
<223> OTHER INFORMATION: Phosphoglucomutase 1 - peptide 2

<400> SEQUENCE: 7

Ile Asp Ala Met His Gly Val Val Gly Pro Tyr Val Lys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Phosphoglucomutase 1 - peptide 3

<400> SEQUENCE: 8

Val Asp Leu Gly Val Leu Gly Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Phosphoglucomutase 1 - peptide 4

<400> SEQUENCE: 9

Leu Tyr Ile Asp Ser Tyr Glu Lys
1               5

<210> SEQ ID NO 10
<211> LENGTH: 10
<212> TYPE: PRT
<213> ORGANISM: Artificial Sequence
<220> FEATURE:
<223> OTHER INFORMATION: Phosphoglucomutase 1 - peptide 5

<400> SEQUENCE: 10

Ser Met Pro Thr Ser Gly Ala Leu Asp Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Phosphoglucomutase 1 - peptide 6

<400> SEQUENCE: 11
```

Tyr Asp Tyr Glu Glu Val Glu Ala Glu Gly Ala Asn Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Phosphoglucomutase 1 - peptide 7

<400> SEQUENCE: 12

Ile Ala Leu Tyr Glu Thr Pro Thr Gly Trp Lys
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Phosphoglucomutase 1 - peptide 8

<400> SEQUENCE: 13

Gln Ser Val Glu Asp Ile Leu Lys
1               5

<210> SEQ ID NO 14
<211> LENGTH: 13
<212> TYPE: PRT
<213> ORGANISM: Artificial Sequence
<220> FEATURE:
<223> OTHER INFORMATION: Thymosine beta-4 - peptide 1

<400> SEQUENCE: 14

Asn Pro Leu Pro Ser Lys Glu Thr Ile Glu Gln Glu Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Thymosine beta-4 - peptide 2

<400> SEQUENCE: 15

Thr Glu Thr Gln Glu Lys Asn Pro Leu Pro Ser Lys
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Thymosine beta-4 - peptide 3

<400> SEQUENCE: 16

Glu Thr Ile Glu Gln Glu Lys
1               5

<210> SEQ ID NO 17
<211> LENGTH: 13
<212> TYPE: PRT
<213> ORGANISM: Artificial Sequence
<220> FEATURE:
<223> OTHER INFORMATION: Ubiquitin carboxyl-terminal hydrolase isoenzyme
      L1 - peptide 1

<400> SEQUENCE: 17

```
Gln Ile Glu Glu Leu Lys Gly Gln Glu Val Ser Pro Lys
1               5                   10

<210> SEQ ID NO 18
<211> LENGTH: 23
<212> TYPE: PRT
<213> ORGANISM: Artificial Sequence
<220> FEATURE:
<223> OTHER INFORMATION: Vitamin D binding protein - peptide 1

<400> SEQUENCE: 18

His Gln Pro Gln Glu Phe Pro Thr Tyr Val Glu Pro Thr Asn Asp Glu
1               5                   10                  15

Ile Cys Glu Ala Phe Arg Lys
            20

<210> SEQ ID NO 19
<211> LENGTH: 18
<212> TYPE: PRT
<213> ORGANISM: Artificial Sequence
<220> FEATURE:
<223> OTHER INFORMATION: Apolipoprotein E - peptide 1

<400> SEQUENCE: 19

Ala Tyr Lys Ser Glu Leu Glu Glu Gln Leu Thr Pro Val Ala Glu Glu
1               5                   10                  15

Thr Arg

<210> SEQ ID NO 20
<211> LENGTH: 15
<212> TYPE: PRT
<213> ORGANISM: Artificial Sequence
<220> FEATURE:
<223> OTHER INFORMATION: Secretogranin-1 - peptide 1

<400> SEQUENCE: 20

Gly Tyr Pro Gly Val Gln Ala Pro Glu Asp Leu Glu Trp Glu Arg
1               5                   10                  15

<210> SEQ ID NO 21
<211> LENGTH: 8
<212> TYPE: PRT
<213> ORGANISM: Artificial Sequence
<220> FEATURE:
<223> OTHER INFORMATION: Serine/threonine-protein phosphatase 2A 65 kDa
      reregulatory subunit A alpha isoform - peptide 1

<400> SEQUENCE: 21

Ala Val Gly Pro Glu Ile Thr Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Cytoplasmic dynein 1 heavy chain 1- peptide 1

<400> SEQUENCE: 22

Leu Arg Asp Gln Leu Gly Thr Ala Lys
1               5

<210> SEQ ID NO 23
<211> LENGTH: 7
<212> TYPE: PRT
```

```
<213> ORGANISM: Artificial Sequence
<220> FEATURE:
<223> OTHER INFORMATION: RuvB-like 1- peptide 1

<400> SEQUENCE: 23

Lys Thr Glu Ile Thr Asp Lys
1               5

<210> SEQ ID NO 24
<211> LENGTH: 11
<212> TYPE: PRT
<213> ORGANISM: Artificial Sequence
<220> FEATURE:
<223> OTHER INFORMATION: cDNA FLJ54806- peptide 1

<400> SEQUENCE: 24

Trp Glu Leu Asn Thr Tyr Leu Tyr Ala Pro Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Alpha-1-acid glycoprotein 2- peptide 1

<400> SEQUENCE: 25

Ser Asp Val Met Tyr Thr Asp Trp Lys Lys
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Ras-related protein Rab-13- peptide 1

<400> SEQUENCE: 26

Phe Phe Glu Thr Ser Ala Lys
1               5

<210> SEQ ID NO 27
<211> LENGTH: 10
<212> TYPE: PRT
<213> ORGANISM: Artificial Sequence
<220> FEATURE:
<223> OTHER INFORMATION: Serum albumin - peptide 1

<400> SEQUENCE: 27

Asp Ala His Lys Ser Glu Val Ala His Arg
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Pigment epithelium-derived factor - peptide 1

<400> SEQUENCE: 28

Leu Lys Leu Ser Tyr Glu Gly Glu Val Thr Lys
1               5                   10

<210> SEQ ID NO 29
<211> LENGTH: 11
<212> TYPE: PRT
<213> ORGANISM: Artificial Sequence
```

```
<220> FEATURE:
<223> OTHER INFORMATION: Amyloid A-4 protein - peptide 1

<400> SEQUENCE: 29

Glu Ala Leu Gln Gly Val Gly Asp Met Gly Arg
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Truncated apolipoprotein A-I - peptide 1

<400> SEQUENCE: 30

Leu Ala Glu Tyr His Ala Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Fibrinogen alpha chain - peptide 1

<400> SEQUENCE: 31

Thr Val Ile Gly Pro Asp Gly His Lys
1               5

<210> SEQ ID NO 32
<211> LENGTH: 12
<212> TYPE: PRT
<213> ORGANISM: Artificial Sequence
<220> FEATURE:
<223> OTHER INFORMATION: Haptoglobin - peptide 1

<400> SEQUENCE: 32

Asp Ile Ala Pro Thr Leu Thr Leu Tyr Val Gly Lys
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Alpha-1-antitrypsin - peptide 1

<400> SEQUENCE: 33

Ser Ala Ser Leu His Leu Pro Lys
1               5

<210> SEQ ID NO 34
<211> LENGTH: 15
<212> TYPE: PRT
<213> ORGANISM: Artificial Sequence
<220> FEATURE:
<223> OTHER INFORMATION: Ig mu chain C region - peptide 1

<400> SEQUENCE: 34

Phe Thr Cys Thr Val Thr His Thr Asp Leu Pro Ser Pro Leu Lys
1               5                   10                  15

<210> SEQ ID NO 35
<211> LENGTH: 16
<212> TYPE: PRT
<213> ORGANISM: Artificial Sequence
<220> FEATURE:
```

<223> OTHER INFORMATION: Hemoglobin subunit delta - peptide 1

<400> SEQUENCE: 35

Val Leu Gly Ala Phe Ser Asp Gly Leu Ala His Leu Asp Asn Leu Lys
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: Hemoglobin subunit delta - peptide 1

<400> SEQUENCE: 36

Ile Ser Val Ala Gln Gly Ala Ser Lys
1               5

<210> SEQ ID NO 37
<211> LENGTH: 7
<212> TYPE: PRT
<213> ORGANISM: Artificial Sequence
<220> FEATURE:
<223> OTHER INFORMATION: Dynactin Subunit 1 - peptide 1

<400> SEQUENCE: 37

Ile Lys Asp Ala Leu Val Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Cofilin-1 - peptide 1

<400> SEQUENCE: 38

Met Ile Tyr Ala Ser Ser Lys
1               5

<210> SEQ ID NO 39
<211> LENGTH: 317
<212> TYPE: PRT
<213> ORGANISM: Homo sapiens

<400> SEQUENCE: 39

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu 130                 135                 140
Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
                195                 200                 205

Arg Ala Ala Thr Val Gly Ser Leu Ala Gly Gln Pro Leu Gln Glu Arg
                210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
                290                 295                 300

Val Gly Thr Ser Ala Ala Pro Val Pro Ser Asp Asn His
305                 310                 315

<210> SEQ ID NO 40
<211> LENGTH: 677
<212> TYPE: PRT
<213> ORGANISM: Homo sapiens

<400> SEQUENCE: 40

Met Gln Pro Thr Leu Leu Leu Ser Leu Leu Gly Ala Val Gly Leu Ala
1               5                   10                  15

Ala Val Asn Ser Met Pro Val Asp Asn Arg Asn His Asn Glu Gly Met
                20                  25                  30

Val Thr Arg Cys Ile Ile Glu Val Leu Ser Asn Ala Leu Ser Lys Ser
                35                  40                  45

Ser Ala Pro Pro Ile Thr Pro Glu Cys Arg Gln Val Leu Lys Thr Ser
                50                  55                  60

Arg Lys Asp Val Lys Asp Lys Glu Thr Thr Glu Asn Glu Asn Thr Lys
65                  70                  75                  80

Phe Glu Val Arg Leu Leu Arg Asp Pro Ala Asp Ala Ser Glu Ala His
                85                  90                  95

Glu Ser Ser Ser Arg Gly Glu Ala Gly Ala Pro Gly Glu Glu Asp Ile
                100                 105                 110

Gln Gly Pro Thr Lys Ala Asp Thr Glu Lys Trp Ala Glu Gly Gly Gly
                115                 120                 125

His Ser Arg Glu Arg Ala Asp Glu Pro Gln Trp Ser Leu Tyr Pro Ser
                130                 135                 140

Asp Ser Gln Val Ser Glu Glu Val Lys Thr Arg His Ser Glu Lys Ser
145                 150                 155                 160

Gln Arg Glu Asp Glu Glu Glu Glu Gly Glu Asn Tyr Gln Lys Gly
                165                 170                 175

Glu Arg Gly Glu Asp Ser Ser Glu Glu Lys His Leu Glu Glu Pro Gly
                180                 185                 190

```
Glu Thr Gln Asn Ala Phe Leu Asn Glu Arg Lys Gln Ala Ser Ala Ile
            195                 200                 205
Lys Lys Glu Glu Leu Val Ala Arg Ser Glu Thr His Ala Ala Gly His
    210                 215                 220
Ser Gln Glu Lys Thr His Ser Arg Glu Lys Ser Ser Gln Glu Ser Gly
225                 230                 235                 240
Glu Glu Thr Gly Ser Gln Glu Asn His Pro Gln Glu Ser Lys Gly Gln
                245                 250                 255
Pro Arg Ser Gln Glu Ser Glu Gly Glu Asp Ala Thr Ser
            260                 265                 270
Glu Val Asp Lys Arg Arg Thr Arg Pro Arg His His Gly Arg Ser
        275                 280                 285
Arg Pro Asp Arg Ser Ser Gln Gly Gly Ser Leu Pro Ser Glu Glu Lys
    290                 295                 300
Gly His Pro Gln Glu Glu Ser Glu Glu Ser Asn Val Ser Met Ala Ser
305                 310                 315                 320
Leu Gly Glu Lys Arg Asp His His Ser Thr His Tyr Arg Ala Ser Glu
                325                 330                 335
Glu Glu Pro Glu Tyr Gly Glu Glu Ile Lys Gly Tyr Pro Gly Val Gln
            340                 345                 350
Ala Pro Glu Asp Leu Glu Trp Glu Arg Tyr Arg Gly Arg Gly Ser Glu
        355                 360                 365
Glu Tyr Arg Ala Pro Arg Pro Gln Ser Glu Glu Ser Trp Asp Glu Glu
    370                 375                 380
Asp Lys Arg Asn Tyr Pro Ser Leu Glu Leu Asp Lys Met Ala His Gly
385                 390                 395                 400
Tyr Gly Glu Glu Ser Glu Glu Glu Arg Gly Leu Glu Pro Gly Lys Gly
                405                 410                 415
Arg His His Arg Gly Arg Gly Glu Pro Arg Ala Tyr Phe Met Ser
            420                 425                 430
Asp Thr Arg Glu Glu Lys Arg Phe Leu Gly Gly His His Arg Val
        435                 440                 445
Gln Glu Asn Gln Met Asp Lys Ala Arg Arg His Pro Gln Gly Ala Trp
    450                 455                 460
Lys Glu Leu Asp Arg Asn Tyr Leu Asn Tyr Gly Glu Glu Gly Ala Pro
465                 470                 475                 480
Gly Lys Trp Gln Gln Gln Gly Asp Leu Gln Asp Thr Lys Glu Asn Arg
                485                 490                 495
Glu Glu Ala Arg Phe Gln Asp Lys Gln Tyr Ser Ser His His Thr Ala
            500                 505                 510
Glu Lys Arg Lys Arg Leu Gly Glu Leu Phe Asn Pro Tyr Tyr Asp Pro
        515                 520                 525
Leu Gln Trp Lys Ser Ser His Phe Glu Arg Arg Asp Asn Met Asn Asp
    530                 535                 540
Asn Phe Leu Glu Gly Glu Glu Asn Glu Leu Thr Leu Asn Glu Lys
545                 550                 555                 560
Asn Phe Phe Pro Glu Tyr Asn Tyr Asp Trp Trp Glu Lys Lys Pro Phe
                565                 570                 575
Ser Glu Asp Val Asn Trp Gly Tyr Glu Lys Arg Asn Leu Ala Arg Val
            580                 585                 590
Pro Lys Leu Asp Leu Lys Arg Gln Tyr Asp Arg Val Ala Gln Leu Asp
        595                 600                 605
Gln Leu Leu His Tyr Arg Lys Lys Ser Ala Glu Phe Pro Asp Phe Tyr
```

```
                610                 615                 620
Asp Ser Glu Glu Pro Val Ser Thr His Gln Glu Ala Glu Asn Glu Lys
625                 630                 635                 640

Asp Arg Ala Asp Gln Thr Val Leu Thr Glu Asp Glu Lys Lys Glu Leu
                645                 650                 655

Glu Asn Leu Ala Ala Met Asp Leu Glu Leu Gln Lys Ile Ala Glu Lys
                660                 665                 670

Phe Ser Gln Arg Gly
        675

<210> SEQ ID NO 41
<211> LENGTH: 589
<212> TYPE: PRT
<213> ORGANISM: Homo sapiens

<400> SEQUENCE: 41

Met Ala Ala Ala Asp Gly Asp Ser Leu Tyr Pro Ile Ala Val Leu
1               5                   10                  15

Ile Asp Glu Leu Arg Asn Glu Asp Val Gln Leu Arg Leu Asn Ser Ile
                20                  25                  30

Lys Lys Leu Ser Thr Ile Ala Leu Ala Leu Gly Val Glu Arg Thr Arg
            35                  40                  45

Ser Glu Leu Leu Pro Phe Leu Thr Asp Thr Ile Tyr Asp Glu Asp Glu
        50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95

Ala Thr Val Glu Glu Thr Val Val Arg Asp Lys Ala Val Glu Ser Leu
            100                 105                 110

Arg Ala Ile Ser His Glu His Ser Pro Ser Asp Leu Glu Ala His Phe
        115                 120                 125

Val Pro Leu Val Lys Arg Leu Ala Gly Gly Asp Trp Phe Thr Ser Arg
130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ala Ser Lys Leu Gly Glu Phe
            180                 185                 190

Ala Lys Val Leu Glu Leu Asp Asn Val Lys Ser Glu Ile Ile Pro Met
        195                 200                 205

Phe Ser Asn Leu Ala Ser Asp Glu Gln Asp Ser Val Arg Leu Leu Ala
    210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
            260                 265                 270

Ala Val Gly Pro Glu Ile Thr Lys Thr Asp Leu Val Pro Ala Phe Gln
        275                 280                 285

Asn Leu Met Lys Asp Cys Glu Ala Glu Val Arg Ala Ala Ala Ser His
    290                 295                 300
```

Lys Val Lys Glu Phe Cys Glu Asn Leu Ser Ala Asp Cys Arg Glu Asn
305                 310                 315                 320

Val Ile Met Ser Gln Ile Leu Pro Cys Ile Lys Glu Leu Val Ser Asp
            325                 330                 335

Ala Asn Gln His Val Lys Ser Ala Leu Ala Ser Val Ile Met Gly Leu
        340                 345                 350

Ser Pro Ile Leu Gly Lys Asp Asn Thr Ile Glu His Leu Leu Pro Leu
    355                 360                 365

Phe Leu Ala Gln Leu Lys Asp Glu Cys Pro Glu Val Arg Leu Asn Ile
370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
            420                 425                 430

Gln Leu Gly Val Glu Phe Phe Asp Glu Lys Leu Asn Ser Leu Cys Met
        435                 440                 445

Ala Trp Leu Val Asp His Val Tyr Ala Ile Arg Glu Ala Ala Thr Ser
450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
            500                 505                 510

Gly Gln Asp Ile Thr Thr Lys His Met Leu Pro Thr Val Leu Arg Met
        515                 520                 525

Ala Gly Asp Pro Val Ala Asn Val Arg Phe Asn Val Ala Lys Ser Leu
530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
            580                 585

<210> SEQ ID NO 42
<211> LENGTH: 4646
<212> TYPE: PRT
<213> ORGANISM: Homo sapiens

<400> SEQUENCE: 42

Met Ser Glu Pro Gly Gly Gly Gly Glu Asp Gly Ser Ala Gly Leu
1               5                   10                  15

Glu Val Ser Ala Val Gln Asn Val Ala Asp Val Ser Val Leu Gln Lys
            20                  25                  30

His Leu Arg Lys Leu Val Pro Leu Leu Leu Glu Asp Gly Gly Glu Ala
        35                  40                  45

Pro Ala Ala Leu Glu Ala Ala Leu Glu Glu Lys Ser Ala Leu Glu Gln
    50                  55                  60

Met Arg Lys Phe Leu Ser Asp Pro Gln Val His Thr Val Leu Val Glu
65                  70                  75                  80

Arg Ser Thr Leu Lys Glu Asp Val Gly Asp Glu Gly Glu Glu Glu Lys
                85                  90                  95

-continued

```
Glu Phe Ile Ser Tyr Asn Ile Asn Ile Asp Ile His Tyr Gly Val Lys
            100                 105                 110

Ser Asn Ser Leu Ala Phe Ile Lys Arg Thr Pro Val Ile Asp Ala Asp
        115                 120                 125

Lys Pro Val Ser Ser Gln Leu Arg Val Leu Thr Leu Ser Glu Asp Ser
130                 135                 140

Pro Tyr Glu Thr Leu His Ser Phe Ile Ser Asn Ala Val Ala Pro Phe
145                 150                 155                 160

Phe Lys Ser Tyr Ile Arg Glu Ser Gly Lys Ala Asp Arg Asp Gly Asp
                165                 170                 175

Lys Met Ala Pro Ser Val Glu Lys Lys Ile Ala Glu Leu Glu Met Gly
                180                 185                 190

Leu Leu His Leu Gln Gln Asn Ile Glu Ile Pro Glu Ile Ser Leu Pro
        195                 200                 205

Ile His Pro Met Ile Thr Asn Val Ala Lys Gln Cys Tyr Glu Arg Gly
        210                 215                 220

Glu Lys Pro Lys Val Thr Asp Phe Gly Asp Lys Val Glu Asp Pro Thr
225                 230                 235                 240

Phe Leu Asn Gln Leu Gln Ser Gly Val Asn Arg Trp Ile Arg Glu Ile
                245                 250                 255

Gln Lys Val Thr Lys Leu Asp Arg Asp Pro Ala Ser Gly Thr Ala Leu
        260                 265                 270

Gln Glu Ile Ser Phe Trp Leu Asn Leu Glu Arg Ala Leu Tyr Arg Ile
        275                 280                 285

Gln Glu Lys Arg Glu Ser Pro Glu Val Leu Leu Thr Leu Asp Ile Leu
        290                 295                 300

Lys His Gly Lys Arg Phe His Ala Thr Val Ser Phe Asp Thr Asp Thr
305                 310                 315                 320

Gly Leu Lys Gln Ala Leu Glu Thr Val Asn Asp Tyr Asn Pro Leu Met
                325                 330                 335

Lys Asp Phe Pro Leu Asn Asp Leu Leu Ser Ala Thr Glu Leu Asp Lys
                340                 345                 350

Ile Arg Gln Ala Leu Val Ala Ile Phe Thr His Leu Arg Lys Ile Arg
        355                 360                 365

Asn Thr Lys Tyr Pro Ile Gln Arg Ala Leu Arg Leu Val Glu Ala Ile
370                 375                 380

Ser Arg Asp Leu Ser Ser Gln Leu Leu Lys Val Leu Gly Thr Arg Lys
385                 390                 395                 400

Leu Met His Val Ala Tyr Glu Phe Glu Lys Val Met Val Ala Cys
                405                 410                 415

Phe Glu Val Phe Gln Thr Trp Asp Asp Glu Tyr Glu Lys Leu Gln Val
                420                 425                 430

Leu Leu Arg Asp Ile Val Lys Arg Lys Arg Glu Glu Asn Leu Lys Met
        435                 440                 445

Val Trp Arg Ile Asn Pro Ala His Arg Lys Leu Gln Ala Arg Leu Asp
        450                 455                 460

Gln Met Arg Lys Phe Arg Arg Gln His Glu Gln Leu Arg Ala Val Ile
465                 470                 475                 480

Val Arg Val Leu Arg Pro Gln Val Thr Ala Val Ala Gln Asn Gln
                485                 490                 495

Gly Glu Val Pro Glu Pro Gln Asp Met Lys Val Ala Glu Val Leu Phe
                500                 505                 510
```

-continued

```
Asp Ala Ala Asp Ala Asn Ala Ile Glu Glu Val Asn Leu Ala Tyr Glu
            515                 520                 525
Asn Val Lys Glu Val Asp Gly Leu Asp Val Ser Lys Glu Gly Thr Glu
        530                 535                 540
Ala Trp Glu Ala Ala Met Lys Arg Tyr Asp Glu Arg Ile Asp Arg Val
545                 550                 555                 560
Glu Thr Arg Ile Thr Ala Arg Leu Arg Asp Gln Leu Gly Thr Ala Lys
                565                 570                 575
Asn Ala Asn Glu Met Phe Arg Ile Phe Ser Arg Phe Asn Ala Leu Phe
            580                 585                 590
Val Arg Pro His Ile Arg Gly Ala Ile Arg Glu Tyr Gln Thr Gln Leu
        595                 600                 605
Ile Gln Arg Val Lys Asp Asp Ile Glu Ser Leu His Asp Lys Phe Lys
    610                 615                 620
Val Gln Tyr Pro Gln Ser Gln Ala Cys Lys Met Ser His Val Arg Asp
625                 630                 635                 640
Leu Pro Pro Val Ser Gly Ser Ile Ile Trp Ala Lys Gln Ile Asp Arg
                645                 650                 655
Gln Leu Thr Ala Tyr Met Lys Arg Val Glu Asp Val Leu Gly Lys Gly
            660                 665                 670
Trp Glu Asn His Val Glu Gly Gln Lys Leu Lys Gln Asp Gly Asp Ser
        675                 680                 685
Phe Arg Met Lys Leu Asn Thr Gln Glu Ile Phe Asp Asp Trp Ala Arg
    690                 695                 700
Lys Val Gln Gln Arg Asn Leu Gly Val Ser Gly Arg Ile Phe Thr Ile
705                 710                 715                 720
Glu Ser Thr Arg Val Arg Gly Arg Thr Gly Asn Val Leu Lys Leu Lys
                725                 730                 735
Val Asn Phe Leu Pro Glu Ile Ile Thr Leu Ser Lys Glu Val Arg Asn
            740                 745                 750
Leu Lys Trp Leu Gly Phe Arg Val Pro Leu Ala Ile Val Asn Lys Ala
        755                 760                 765
His Gln Ala Asn Gln Leu Tyr Pro Phe Ala Ile Ser Leu Ile Glu Ser
    770                 775                 780
Val Arg Thr Tyr Glu Arg Thr Cys Glu Lys Val Glu Glu Arg Asn Thr
785                 790                 795                 800
Ile Ser Leu Leu Val Ala Gly Leu Lys Lys Glu Val Gln Ala Leu Ile
                805                 810                 815
Ala Glu Gly Ile Ala Leu Val Trp Glu Ser Tyr Lys Leu Asp Pro Tyr
            820                 825                 830
Val Gln Arg Leu Ala Glu Thr Val Phe Asn Phe Gln Glu Lys Val Asp
        835                 840                 845
Asp Leu Leu Ile Ile Glu Glu Lys Ile Asp Leu Glu Val Arg Ser Leu
    850                 855                 860
Glu Thr Cys Met Tyr Asp His Lys Thr Phe Ser Glu Ile Leu Asn Arg
865                 870                 875                 880
Val Gln Lys Ala Val Asp Asp Leu Asn Leu His Ser Tyr Ser Asn Leu
                885                 890                 895
Pro Ile Trp Val Asn Lys Leu Asp Met Glu Ile Glu Arg Ile Leu Gly
            900                 905                 910
Val Arg Leu Gln Ala Gly Leu Arg Ala Trp Thr Gln Val Leu Leu Gly
        915                 920                 925
Gln Ala Glu Asp Lys Ala Glu Val Asp Met Asp Thr Asp Ala Pro Gln
```

```
              930                 935                 940
Val Ser His Lys Pro Gly Gly Glu Pro Lys Ile Lys Asn Val Val His
        945                 950                 955                 960

Glu Leu Arg Ile Thr Asn Gln Val Ile Tyr Leu Asn Pro Pro Ile Glu
                    965                 970                 975

Glu Cys Arg Tyr Lys Leu Tyr Gln Glu Met Phe Ala Trp Lys Met Val
                980                 985                 990

Val Leu Ser Leu Pro Arg Ile Gln Ser Gln Arg Tyr Gln Val Gly Val
            995                 1000                1005

His Tyr Glu Leu Thr Glu Glu Lys Phe Tyr Arg Asn Ala Leu
        1010                1015                1020

Thr Arg Met Pro Asp Gly Pro Val Ala Leu Glu Glu Ser Tyr Ser
        1025                1030                1035

Ala Val Met Gly Ile Val Ser Glu Val Glu Gln Tyr Val Lys Val
        1040                1045                1050

Trp Leu Gln Tyr Gln Cys Leu Trp Asp Met Gln Ala Glu Asn Ile
        1055                1060                1065

Tyr Asn Arg Leu Gly Glu Asp Leu Asn Lys Trp Gln Ala Leu Leu
        1070                1075                1080

Val Gln Ile Arg Lys Ala Arg Gly Thr Phe Asp Asn Ala Glu Thr
        1085                1090                1095

Lys Lys Glu Phe Gly Pro Val Val Ile Asp Tyr Gly Lys Val Gln
        1100                1105                1110

Ser Lys Val Asn Leu Lys Tyr Asp Ser Trp His Lys Glu Val Leu
        1115                1120                1125

Ser Lys Phe Gly Gln Met Leu Gly Ser Asn Met Thr Glu Phe His
        1130                1135                1140

Ser Gln Ile Ser Lys Ser Arg Gln Glu Leu Glu Gln His Ser Val
        1145                1150                1155

Asp Thr Ala Ser Thr Ser Asp Ala Val Thr Phe Ile Thr Tyr Val
        1160                1165                1170

Gln Ser Leu Lys Arg Lys Ile Lys Gln Phe Glu Lys Gln Val Glu
        1175                1180                1185

Leu Tyr Arg Asn Gly Gln Arg Leu Leu Glu Lys Gln Arg Phe Gln
        1190                1195                1200

Phe Pro Pro Ser Trp Leu Tyr Ile Asp Asn Ile Glu Gly Glu Trp
        1205                1210                1215

Gly Ala Phe Asn Asp Ile Met Arg Arg Lys Asp Ser Ala Ile Gln
        1220                1225                1230

Gln Gln Val Ala Asn Leu Gln Met Lys Ile Val Gln Glu Asp Arg
        1235                1240                1245

Ala Val Glu Ser Arg Thr Thr Asp Leu Leu Thr Asp Trp Glu Lys
        1250                1255                1260

Thr Lys Pro Val Thr Gly Asn Leu Arg Pro Glu Glu Ala Leu Gln
        1265                1270                1275

Ala Leu Thr Ile Tyr Glu Gly Lys Phe Gly Arg Leu Lys Asp Asp
        1280                1285                1290

Arg Glu Lys Cys Ala Lys Ala Lys Glu Ala Leu Glu Leu Thr Asp
        1295                1300                1305

Thr Gly Leu Leu Ser Gly Ser Glu Glu Arg Val Gln Val Ala Leu
        1310                1315                1320

Glu Glu Leu Gln Asp Leu Lys Gly Val Trp Ser Glu Leu Ser Lys
        1325                1330                1335
```

-continued

Val Trp Glu Gln Ile Asp Gln Met Lys Glu Gln Pro Trp Val Ser
1340                1345                1350

Val Gln Pro Arg Lys Leu Arg Gln Asn Leu Asp Ala Leu Leu Asn
1355                1360                1365

Gln Leu Lys Ser Phe Pro Ala Arg Leu Arg Gln Tyr Ala Ser Tyr
1370                1375                1380

Glu Phe Val Gln Arg Leu Leu Lys Gly Tyr Met Lys Ile Asn Met
1385                1390                1395

Leu Val Ile Glu Leu Lys Ser Glu Ala Leu Lys Asp Arg His Trp
1400                1405                1410

Lys Gln Leu Met Lys Arg Leu His Val Asn Trp Val Val Ser Glu
1415                1420                1425

Leu Thr Leu Gly Gln Ile Trp Asp Val Asp Leu Gln Lys Asn Glu
1430                1435                1440

Ala Ile Val Lys Asp Val Leu Leu Val Ala Gln Gly Glu Met Ala
1445                1450                1455

Leu Glu Glu Phe Leu Lys Gln Ile Arg Glu Val Trp Asn Thr Tyr
1460                1465                1470

Glu Leu Asp Leu Val Asn Tyr Gln Asn Lys Cys Arg Leu Ile Arg
1475                1480                1485

Gly Trp Asp Asp Leu Phe Asn Lys Val Lys Glu His Ile Asn Ser
1490                1495                1500

Val Ser Ala Met Lys Leu Ser Pro Tyr Tyr Lys Val Phe Glu Glu
1505                1510                1515

Asp Ala Leu Ser Trp Glu Asp Lys Leu Asn Arg Ile Met Ala Leu
1520                1525                1530

Phe Asp Val Trp Ile Asp Val Gln Arg Arg Trp Val Tyr Leu Glu
1535                1540                1545

Gly Ile Phe Thr Gly Ser Ala Asp Ile Lys His Leu Leu Pro Val
1550                1555                1560

Glu Thr Gln Arg Phe Gln Ser Ile Ser Thr Glu Phe Leu Ala Leu
1565                1570                1575

Met Lys Lys Val Ser Lys Ser Pro Leu Val Met Asp Val Leu Asn
1580                1585                1590

Ile Gln Gly Val Gln Arg Ser Leu Glu Arg Leu Ala Asp Leu Leu
1595                1600                1605

Gly Lys Ile Gln Lys Ala Leu Gly Glu Tyr Leu Glu Arg Glu Arg
1610                1615                1620

Ser Ser Phe Pro Arg Phe Tyr Phe Val Gly Asp Glu Asp Leu Leu
1625                1630                1635

Glu Ile Ile Gly Asn Ser Lys Asn Val Ala Lys Leu Gln Lys His
1640                1645                1650

Phe Lys Lys Met Phe Ala Gly Val Ser Ser Ile Ile Leu Asn Glu
1655                1660                1665

Asp Asn Ser Val Val Leu Gly Ile Ser Ser Arg Glu Gly Glu Glu
1670                1675                1680

Val Met Phe Lys Thr Pro Val Ser Ile Thr Glu His Pro Lys Ile
1685                1690                1695

Asn Glu Trp Leu Thr Leu Val Glu Lys Glu Met Arg Val Thr Leu
1700                1705                1710

Ala Lys Leu Leu Ala Glu Ser Val Thr Glu Val Glu Ile Phe Gly
1715                1720                1725

```
Lys Ala Thr Ser Ile Asp Pro Asn Thr Tyr Ile Thr Trp Ile Asp
1730                1735                1740

Lys Tyr Gln Ala Gln Leu Val Val Leu Ser Ala Gln Ile Ala Trp
1745                1750                1755

Ser Glu Asn Val Glu Thr Ala Leu Ser Ser Met Gly Gly Gly Gly
1760                1765                1770

Asp Ala Ala Pro Leu His Ser Val Leu Ser Asn Val Glu Val Thr
1775                1780                1785

Leu Asn Val Leu Ala Asp Ser Val Leu Met Glu Gln Pro Pro Leu
1790                1795                1800

Arg Arg Arg Lys Leu Glu His Leu Ile Thr Glu Leu Val His Gln
1805                1810                1815

Arg Asp Val Thr Arg Ser Leu Ile Lys Ser Lys Ile Asp Asn Ala
1820                1825                1830

Lys Ser Phe Glu Trp Leu Ser Gln Met Arg Phe Tyr Phe Asp Pro
1835                1840                1845

Lys Gln Thr Asp Val Leu Gln Gln Leu Ser Ile Gln Met Ala Asn
1850                1855                1860

Ala Lys Phe Asn Tyr Gly Phe Glu Tyr Leu Gly Val Gln Asp Lys
1865                1870                1875

Leu Val Gln Thr Pro Leu Thr Asp Arg Cys Tyr Leu Thr Met Thr
1880                1885                1890

Gln Ala Leu Glu Ala Arg Leu Gly Gly Ser Pro Phe Gly Pro Ala
1895                1900                1905

Gly Thr Gly Lys Thr Glu Ser Val Lys Ala Leu Gly His Gln Leu
1910                1915                1920

Gly Arg Phe Val Leu Val Phe Asn Cys Asp Glu Thr Phe Asp Phe
1925                1930                1935

Gln Ala Met Gly Arg Ile Phe Val Gly Leu Cys Gln Val Gly Ala
1940                1945                1950

Trp Gly Cys Phe Asp Glu Phe Asn Arg Leu Glu Glu Arg Met Leu
1955                1960                1965

Ser Ala Val Ser Gln Gln Val Gln Cys Ile Gln Glu Ala Leu Arg
1970                1975                1980

Glu His Ser Asn Pro Asn Tyr Asp Lys Thr Ser Ala Pro Ile Thr
1985                1990                1995

Cys Glu Leu Leu Asn Lys Gln Val Lys Val Ser Pro Asp Met Ala
2000                2005                2010

Ile Phe Ile Thr Met Asn Pro Gly Tyr Ala Gly Arg Ser Asn Leu
2015                2020                2025

Pro Asp Asn Leu Lys Lys Leu Phe Arg Ser Leu Ala Met Thr Lys
2030                2035                2040

Pro Asp Arg Gln Leu Ile Ala Gln Val Met Leu Tyr Ser Gln Gly
2045                2050                2055

Phe Arg Thr Ala Glu Val Leu Ala Asn Lys Ile Val Pro Phe Phe
2060                2065                2070

Lys Leu Cys Asp Glu Gln Leu Ser Ser Gln Ser His Tyr Asp Phe
2075                2080                2085

Gly Leu Arg Ala Leu Lys Ser Val Leu Val Ser Ala Gly Asn Val
2090                2095                2100

Lys Arg Glu Arg Ile Gln Lys Ile Lys Arg Glu Lys Glu Glu Arg
2105                2110                2115

Gly Glu Ala Val Asp Glu Gly Glu Ile Ala Glu Asn Leu Pro Glu
```

```
                2120                2125                2130

Gln Glu Ile Leu Ile Gln Ser Val Cys Glu Thr Met Val Pro Lys
    2135                2140                2145

Leu Val Ala Glu Asp Ile Pro Leu Leu Phe Ser Leu Leu Ser Asp
    2150                2155                2160

Val Phe Pro Gly Val Gln Tyr His Arg Gly Glu Met Thr Ala Leu
    2165                2170                2175

Arg Glu Glu Leu Lys Lys Val Cys Gln Glu Met Tyr Leu Thr Tyr
    2180                2185                2190

Gly Asp Gly Glu Glu Val Gly Gly Met Trp Val Glu Lys Val Leu
    2195                2200                2205

Gln Leu Tyr Gln Ile Thr Gln Ile Asn His Gly Leu Met Met Val
    2210                2215                2220

Gly Pro Ser Gly Ser Gly Lys Ser Met Ala Trp Arg Val Leu Leu
    2225                2230                2235

Lys Ala Leu Glu Arg Leu Glu Gly Val Glu Gly Val Ala His Ile
    2240                2245                2250

Ile Asp Pro Lys Ala Ile Ser Lys Asp His Leu Tyr Gly Thr Leu
    2255                2260                2265

Asp Pro Asn Thr Arg Glu Trp Thr Asp Gly Leu Phe Thr His Val
    2270                2275                2280

Leu Arg Lys Ile Ile Asp Ser Val Arg Gly Glu Leu Gln Lys Arg
    2285                2290                2295

Gln Trp Ile Val Phe Asp Gly Asp Val Asp Pro Glu Trp Val Glu
    2300                2305                2310

Asn Leu Asn Ser Val Leu Asp Asp Asn Lys Leu Leu Thr Leu Pro
    2315                2320                2325

Asn Gly Glu Arg Leu Ser Leu Pro Pro Asn Val Arg Ile Met Phe
    2330                2335                2340

Glu Val Gln Asp Leu Lys Tyr Ala Thr Leu Ala Thr Val Ser Arg
    2345                2350                2355

Cys Gly Met Val Trp Phe Ser Glu Asp Val Leu Ser Thr Asp Met
    2360                2365                2370

Ile Phe Asn Asn Phe Leu Ala Arg Leu Arg Ser Ile Pro Leu Asp
    2375                2380                2385

Glu Gly Glu Asp Glu Ala Gln Arg Arg Arg Lys Gly Lys Glu Asp
    2390                2395                2400

Glu Gly Glu Glu Ala Ala Ser Pro Met Leu Gln Ile Gln Arg Asp
    2405                2410                2415

Ala Ala Thr Ile Met Gln Pro Tyr Phe Thr Ser Asn Gly Leu Val
    2420                2425                2430

Thr Lys Ala Leu Glu His Ala Phe Gln Leu Glu His Ile Met Asp
    2435                2440                2445

Leu Thr Arg Leu Arg Cys Leu Gly Ser Leu Phe Ser Met Leu His
    2450                2455                2460

Gln Ala Cys Arg Asn Val Ala Gln Tyr Asn Ala Asn His Pro Asp
    2465                2470                2475

Phe Pro Met Gln Ile Glu Gln Leu Glu Arg Tyr Ile Gln Arg Tyr
    2480                2485                2490

Leu Val Tyr Ala Ile Leu Trp Ser Leu Ser Gly Asp Ser Arg Leu
    2495                2500                2505

Lys Met Arg Ala Glu Leu Gly Glu Tyr Ile Arg Arg Ile Thr Thr
    2510                2515                2520
```

-continued

Val Pro Leu Pro Thr Ala Pro Asn Ile Pro Ile Ile Asp Tyr Glu
    2525            2530            2535

Val Ser Ile Ser Gly Glu Trp Ser Pro Trp Gln Ala Lys Val Pro
    2540            2545            2550

Gln Ile Glu Val Glu Thr His Lys Val Ala Ala Pro Asp Val Val
    2555            2560            2565

Val Pro Thr Leu Asp Thr Val Arg His Glu Ala Leu Leu Tyr Thr
    2570            2575            2580

Trp Leu Ala Glu His Lys Pro Leu Val Leu Cys Gly Pro Pro Gly
    2585            2590            2595

Ser Gly Lys Thr Met Thr Leu Phe Ser Ala Leu Arg Ala Leu Pro
    2600            2605            2610

Asp Met Glu Val Val Gly Leu Asn Phe Ser Ser Ala Thr Thr Pro
    2615            2620            2625

Glu Leu Leu Leu Lys Thr Phe Asp His Tyr Cys Glu Tyr Arg Arg
    2630            2635            2640

Thr Pro Asn Gly Val Val Leu Ala Pro Val Gln Leu Gly Lys Trp
    2645            2650            2655

Leu Val Leu Phe Cys Asp Glu Ile Asn Leu Pro Asp Met Asp Lys
    2660            2665            2670

Tyr Gly Thr Gln Arg Val Ile Ser Phe Ile Arg Gln Met Val Glu
    2675            2680            2685

His Gly Gly Phe Tyr Arg Thr Ser Asp Gln Thr Trp Val Lys Leu
    2690            2695            2700

Glu Arg Ile Gln Phe Val Gly Ala Cys Asn Pro Pro Thr Asp Pro
    2705            2710            2715

Gly Arg Lys Pro Leu Ser His Arg Phe Leu Arg His Val Pro Val
    2720            2725            2730

Val Tyr Val Asp Tyr Pro Gly Pro Ala Ser Leu Thr Gln Ile Tyr
    2735            2740            2745

Gly Thr Phe Asn Arg Ala Met Leu Arg Leu Ile Pro Ser Leu Arg
    2750            2755            2760

Thr Tyr Ala Glu Pro Leu Thr Ala Ala Met Val Glu Phe Tyr Thr
    2765            2770            2775

Met Ser Gln Glu Arg Phe Thr Gln Asp Thr Gln Pro His Tyr Ile
    2780            2785            2790

Tyr Ser Pro Arg Glu Met Thr Arg Trp Val Arg Gly Ile Phe Glu
    2795            2800            2805

Ala Leu Arg Pro Leu Glu Thr Leu Pro Val Glu Gly Leu Ile Arg
    2810            2815            2820

Ile Trp Ala His Glu Ala Leu Arg Leu Phe Gln Asp Arg Leu Val
    2825            2830            2835

Glu Asp Glu Glu Arg Arg Trp Thr Asp Glu Asn Ile Asp Thr Val
    2840            2845            2850

Ala Leu Lys His Phe Pro Asn Ile Asp Arg Glu Lys Ala Met Ser
    2855            2860            2865

Arg Pro Ile Leu Tyr Ser Asn Trp Leu Ser Lys Asp Tyr Ile Pro
    2870            2875            2880

Val Asp Gln Glu Glu Leu Arg Asp Tyr Val Lys Ala Arg Leu Lys
    2885            2890            2895

Val Phe Tyr Glu Glu Glu Leu Asp Val Pro Leu Val Leu Phe Asn
    2900            2905            2910

-continued

| | | | | | | | | | | | |
|---|---|---|---|---|---|---|---|---|---|---|---|
| Glu | Val | Leu | Asp | His | Val | Leu | Arg | Ile | Asp | Arg | Ile |
| 2915 | | | | | 2920 | | | | | 2925 | |
| Phe | Arg | Gln | | | | | | | | | |
| Pro | Gln | Gly | His | Leu | Leu | Leu | Ile | Gly | Val | Ser | Gly |
| 2930 | | | | | 2935 | | | | | 2940 | |
| Ala | Gly | Lys | | | | | | | | | |
| Thr | Thr | Leu | Ser | Arg | Phe | Val | Ala | Trp | Met | Asn | Gly |
| 2945 | | | | | 2950 | | | | | 2955 | |
| Leu | Ser | Val | | | | | | | | | |
| Tyr | Gln | Ile | Lys | Val | His | Arg | Lys | Tyr | Thr | Gly | Glu |
| 2960 | | | | | 2965 | | | | | 2970 | |
| Asp | Phe | Asp | | | | | | | | | |
| Glu | Asp | Leu | Arg | Thr | Val | Leu | Arg | Arg | Ser | Gly | Cys |
| 2975 | | | | | 2980 | | | | | 2985 | |
| Lys | Asn | Glu | | | | | | | | | |
| Lys | Ile | Ala | Phe | Ile | Met | Asp | Glu | Ser | Asn | Val | Leu |
| 2990 | | | | | 2995 | | | | | 3000 | |
| Asp | Ser | Gly | | | | | | | | | |
| Phe | Leu | Glu | Arg | Met | Asn | Thr | Leu | Leu | Ala | Asn | Gly |
| 3005 | | | | | 3010 | | | | | 3015 | |
| Glu | Val | Pro | | | | | | | | | |
| Gly | Leu | Phe | Glu | Gly | Asp | Glu | Tyr | Ala | Thr | Leu | Met |
| 3020 | | | | | 3025 | | | | | 3030 | |
| Thr | Gln | Cys | | | | | | | | | |
| Lys | Glu | Gly | Ala | Gln | Lys | Glu | Gly | Leu | Met | Leu | Asp |
| 3035 | | | | | 3040 | | | | | 3045 | |
| Ser | His | Glu | | | | | | | | | |
| Glu | Leu | Tyr | Lys | Trp | Phe | Thr | Ser | Gln | Val | Ile | Arg |
| 3050 | | | | | 3055 | | | | | 3060 | |
| Asn | Leu | His | | | | | | | | | |
| Val | Val | Phe | Thr | Met | Asn | Pro | Ser | Ser | Glu | Gly | Leu |
| 3065 | | | | | 3070 | | | | | 3075 | |
| Lys | Asp | Arg | | | | | | | | | |
| Ala | Ala | Thr | Ser | Pro | Ala | Leu | Phe | Asn | Arg | Cys | Val |
| 3080 | | | | | 3085 | | | | | 3090 | |
| Leu | Asn | Trp | | | | | | | | | |
| Phe | Gly | Asp | Trp | Ser | Thr | Glu | Ala | Leu | Tyr | Gln | Val |
| 3095 | | | | | 3100 | | | | | 3105 | |
| Gly | Lys | Glu | | | | | | | | | |
| Phe | Thr | Ser | Lys | Met | Asp | Leu | Glu | Lys | Pro | Asn | Tyr |
| 3110 | | | | | 3115 | | | | | 3120 | |
| Ile | Val | Pro | | | | | | | | | |
| Asp | Tyr | Met | Pro | Val | Val | Tyr | Asp | Lys | Leu | Pro | Gln |
| 3125 | | | | | 3130 | | | | | 3135 | |
| Pro | Pro | Ser | | | | | | | | | |
| His | Arg | Glu | Ala | Ile | Val | Asn | Ser | Cys | Val | Phe | Val |
| 3140 | | | | | 3145 | | | | | 3150 | |
| His | Gln | Thr | | | | | | | | | |
| Leu | His | Gln | Ala | Asn | Ala | Arg | Leu | Ala | Lys | Arg | Gly |
| 3155 | | | | | 3160 | | | | | 3165 | |
| Gly | Arg | Thr | | | | | | | | | |
| Met | Ala | Ile | Thr | Pro | Arg | His | Tyr | Leu | Asp | Phe | Ile |
| 3170 | | | | | 3175 | | | | | 3180 | |
| Asn | His | Tyr | | | | | | | | | |
| Ala | Asn | Leu | Phe | His | Glu | Lys | Arg | Ser | Glu | Leu | Glu |
| 3185 | | | | | 3190 | | | | | 3195 | |
| Glu | Gln | Gln | | | | | | | | | |
| Met | His | Leu | Asn | Val | Gly | Leu | Arg | Lys | Ile | Lys | Glu |
| 3200 | | | | | 3205 | | | | | 3210 | |
| Thr | Val | Asp | | | | | | | | | |
| Gln | Val | Glu | Glu | Leu | Arg | Arg | Asp | Leu | Arg | Ile | Lys |
| 3215 | | | | | 3220 | | | | | 3225 | |
| Ser | Gln | Glu | | | | | | | | | |
| Leu | Glu | Val | Lys | Asn | Ala | Ala | Ala | Asn | Asp | Lys | Leu |
| 3230 | | | | | 3235 | | | | | 3240 | |
| Lys | Lys | Met | | | | | | | | | |
| Val | Lys | Asp | Gln | Gln | Glu | Ala | Glu | Lys | Lys | Lys | Val |
| 3245 | | | | | 3250 | | | | | 3255 | |
| Met | Ser | Gln | | | | | | | | | |
| Glu | Ile | Gln | Glu | Gln | Leu | His | Lys | Gln | Gln | Glu | Val |
| 3260 | | | | | 3265 | | | | | 3270 | |
| Ile | Ala | Asp | | | | | | | | | |
| Lys | Gln | Met | Ser | Val | Lys | Glu | Asp | Leu | Asp | Lys | Val |
| 3275 | | | | | 3280 | | | | | 3285 | |
| Glu | Pro | Ala | | | | | | | | | |
| Val | Ile | Glu | Ala | Gln | Asn | Ala | Val | Lys | Ser | Ile | Lys |
| 3290 | | | | | 3295 | | | | | 3300 | |
| Lys | Gln | His | | | | | | | | | |
| Leu | Val | Glu | Val | Arg | Ser | Met | Ala | Asn | Pro | Pro | Ala |
| | | | | | | | | | | | Ala | Val | Lys |

```
            3305                3310                3315

Leu Ala Leu Glu Ser Ile Cys Leu Leu Leu Gly Glu Ser Thr Thr
    3320                3325                3330

Asp Trp Lys Gln Ile Arg Ser Ile Ile Met Arg Glu Asn Phe Ile
    3335                3340                3345

Pro Thr Ile Val Asn Phe Ser Ala Glu Ile Ser Asp Ala Ile
    3350                3355                3360

Arg Glu Lys Met Lys Lys Asn Tyr Met Ser Asn Pro Ser Tyr Asn
    3365                3370                3375

Tyr Glu Ile Val Asn Arg Ala Ser Leu Ala Cys Gly Pro Met Val
    3380                3385                3390

Lys Trp Ala Ile Ala Gln Leu Asn Tyr Ala Asp Met Leu Lys Arg
    3395                3400                3405

Val Glu Pro Leu Arg Asn Glu Leu Gln Lys Leu Glu Asp Asp Ala
    3410                3415                3420

Lys Asp Asn Gln Gln Lys Ala Asn Glu Val Glu Gln Met Ile Arg
    3425                3430                3435

Asp Leu Glu Ala Ser Ile Ala Arg Tyr Lys Glu Glu Tyr Ala Val
    3440                3445                3450

Leu Ile Ser Glu Ala Gln Ala Ile Lys Ala Asp Leu Ala Ala Val
    3455                3460                3465

Glu Ala Lys Val Asn Arg Ser Thr Ala Leu Leu Lys Ser Leu Ser
    3470                3475                3480

Ala Glu Arg Glu Arg Trp Glu Lys Thr Ser Glu Thr Phe Lys Asn
    3485                3490                3495

Gln Met Ser Thr Ile Ala Gly Asp Cys Leu Leu Ser Ala Ala Phe
    3500                3505                3510

Ile Ala Tyr Ala Gly Tyr Phe Asp Gln Gln Met Arg Gln Asn Leu
    3515                3520                3525

Phe Thr Thr Trp Ser His His Leu Gln Gln Ala Asn Ile Gln Phe
    3530                3535                3540

Arg Thr Asp Ile Ala Arg Thr Glu Tyr Leu Ser Asn Ala Asp Glu
    3545                3550                3555

Arg Leu Arg Trp Gln Ala Ser Ser Leu Pro Ala Asp Asp Leu Cys
    3560                3565                3570

Thr Glu Asn Ala Ile Met Leu Lys Arg Phe Asn Arg Tyr Pro Leu
    3575                3580                3585

Ile Ile Asp Pro Ser Gly Gln Ala Thr Glu Phe Ile Met Asn Glu
    3590                3595                3600

Tyr Lys Asp Arg Lys Ile Thr Arg Thr Ser Phe Leu Asp Asp Ala
    3605                3610                3615

Phe Arg Lys Asn Leu Glu Ser Ala Leu Arg Phe Gly Asn Pro Leu
    3620                3625                3630

Leu Val Gln Asp Val Glu Ser Tyr Asp Pro Val Leu Asn Pro Val
    3635                3640                3645

Leu Asn Arg Glu Val Arg Arg Thr Gly Gly Arg Val Leu Ile Thr
    3650                3655                3660

Leu Gly Asp Gln Asp Ile Asp Leu Ser Pro Ser Phe Val Ile Phe
    3665                3670                3675

Leu Ser Thr Arg Asp Pro Thr Val Glu Phe Pro Pro Asp Leu Cys
    3680                3685                3690

Ser Arg Val Thr Phe Val Asn Phe Thr Val Thr Arg Ser Ser Leu
    3695                3700                3705
```

Gln Ser Gln Cys Leu Asn Glu Val Leu Lys Ala Glu Arg Pro Asp
    3710            3715                3720

Val Asp Glu Lys Arg Ser Asp Leu Leu Lys Leu Gln Gly Glu Phe
    3725            3730                3735

Gln Leu Arg Leu Arg Gln Leu Glu Lys Ser Leu Leu Gln Ala Leu
    3740            3745                3750

Asn Glu Val Lys Gly Arg Ile Leu Asp Asp Thr Ile Ile Thr
    3755            3760                3765

Thr Leu Glu Asn Leu Lys Arg Glu Ala Ala Glu Val Thr Arg Lys
    3770            3775                3780

Val Glu Glu Thr Asp Ile Val Met Gln Glu Val Glu Thr Val Ser
    3785            3790                3795

Gln Gln Tyr Leu Pro Leu Ser Thr Ala Cys Ser Ser Ile Tyr Phe
    3800            3805                3810

Thr Met Glu Ser Leu Lys Gln Ile His Phe Leu Tyr Gln Tyr Ser
    3815            3820                3825

Leu Gln Phe Phe Leu Asp Ile Tyr His Asn Val Leu Tyr Glu Asn
    3830            3835                3840

Pro Asn Leu Lys Gly Val Thr Asp His Thr Gln Arg Leu Ser Ile
    3845            3850                3855

Ile Thr Lys Asp Leu Phe Gln Val Ala Phe Asn Arg Val Ala Arg
    3860            3865                3870

Gly Met Leu His Gln Asp His Ile Thr Phe Ala Met Leu Leu Ala
    3875            3880                3885

Arg Ile Lys Leu Lys Gly Thr Val Gly Glu Pro Thr Tyr Asp Ala
    3890            3895                3900

Glu Phe Gln His Phe Leu Arg Gly Asn Glu Ile Val Leu Ser Ala
    3905            3910                3915

Gly Ser Thr Pro Arg Ile Gln Gly Leu Thr Val Glu Gln Ala Glu
    3920            3925                3930

Ala Val Val Arg Leu Ser Cys Leu Pro Ala Phe Lys Asp Leu Ile
    3935            3940                3945

Ala Lys Val Gln Ala Asp Glu Gln Phe Gly Ile Trp Leu Asp Ser
    3950            3955                3960

Ser Ser Pro Glu Gln Thr Val Pro Tyr Leu Trp Ser Glu Glu Thr
    3965            3970                3975

Pro Ala Thr Pro Ile Gly Gln Ala Ile His Arg Leu Leu Leu Ile
    3980            3985                3990

Gln Ala Phe Arg Pro Asp Arg Leu Leu Ala Met Ala His Met Phe
    3995            4000                4005

Val Ser Thr Asn Leu Gly Glu Ser Phe Met Ser Ile Met Glu Gln
    4010            4015                4020

Pro Leu Asp Leu Thr His Ile Val Gly Thr Glu Val Lys Pro Asn
    4025            4030                4035

Thr Pro Val Leu Met Cys Ser Val Pro Gly Tyr Asp Ala Ser Gly
    4040            4045                4050

His Val Glu Asp Leu Ala Ala Glu Gln Asn Thr Gln Ile Thr Ser
    4055            4060                4065

Ile Ala Ile Gly Ser Ala Glu Gly Phe Asn Gln Ala Asp Lys Ala
    4070            4075                4080

Ile Asn Thr Ala Val Lys Ser Gly Arg Trp Val Met Leu Lys Asn
    4085            4090                4095

-continued

Val His Leu Ala Pro Gly Trp Leu Met Gln Leu Glu Lys Lys Leu
4100                4105                4110

His Ser Leu Gln Pro His Ala Cys Phe Arg Leu Phe Leu Thr Met
4115                4120                4125

Glu Ile Asn Pro Lys Val Pro Val Asn Leu Leu Arg Ala Gly Arg
4130                4135                4140

Ile Phe Val Phe Glu Pro Pro Gly Val Lys Ala Asn Met Leu
4145                4150                4155

Arg Thr Phe Ser Ser Ile Pro Val Ser Arg Ile Cys Lys Ser Pro
4160                4165                4170

Asn Glu Arg Ala Arg Leu Tyr Phe Leu Leu Ala Trp Phe His Ala
4175                4180                4185

Ile Ile Gln Glu Arg Leu Arg Tyr Ala Pro Leu Gly Trp Ser Lys
4190                4195                4200

Lys Tyr Glu Phe Gly Glu Ser Asp Leu Arg Ser Ala Cys Asp Thr
4205                4210                4215

Val Asp Thr Trp Leu Asp Asp Thr Ala Lys Gly Arg Gln Asn Ile
4220                4225                4230

Ser Pro Asp Lys Ile Pro Trp Ser Ala Leu Lys Thr Leu Met Ala
4235                4240                4245

Gln Ser Ile Tyr Gly Gly Arg Val Asp Asn Glu Phe Asp Gln Arg
4250                4255                4260

Leu Leu Asn Thr Phe Leu Glu Arg Leu Phe Thr Thr Arg Ser Phe
4265                4270                4275

Asp Ser Glu Phe Lys Leu Ala Cys Lys Val Asp Gly His Lys Asp
4280                4285                4290

Ile Gln Met Pro Asp Gly Ile Arg Arg Glu Glu Phe Val Gln Trp
4295                4300                4305

Val Glu Leu Leu Pro Asp Thr Gln Thr Pro Ser Trp Leu Gly Leu
4310                4315                4320

Pro Asn Asn Ala Glu Arg Val Leu Leu Thr Thr Gln Gly Val Asp
4325                4330                4335

Met Ile Ser Lys Met Leu Lys Met Gln Met Leu Glu Asp Glu Asp
4340                4345                4350

Asp Leu Ala Tyr Ala Glu Thr Glu Lys Lys Thr Arg Thr Asp Ser
4355                4360                4365

Thr Ser Asp Gly Arg Pro Ala Trp Met Arg Thr Leu His Thr Thr
4370                4375                4380

Ala Ser Asn Trp Leu His Leu Ile Pro Gln Thr Leu Ser His Leu
4385                4390                4395

Lys Arg Thr Val Glu Asn Ile Lys Asp Pro Leu Phe Arg Phe Phe
4400                4405                4410

Glu Arg Glu Val Lys Met Gly Ala Lys Leu Leu Gln Asp Val Arg
4415                4420                4425

Gln Asp Leu Ala Asp Val Val Gln Val Cys Glu Gly Lys Lys Lys
4430                4435                4440

Gln Thr Asn Tyr Leu Arg Thr Leu Ile Asn Glu Leu Val Lys Gly
4445                4450                4455

Ile Leu Pro Arg Ser Trp Ser His Tyr Thr Val Pro Ala Gly Met
4460                4465                4470

Thr Val Ile Gln Trp Val Ser Asp Phe Ser Glu Arg Ile Lys Gln
4475                4480                4485

Leu Gln Asn Ile Ser Leu Ala Ala Ala Ser Gly Gly Ala Lys Glu

```
              4490           4495             4500

Leu Lys Asn Ile His Val Cys Leu Gly Gly Leu Phe Val Pro Glu
    4505                4510                4515

Ala Tyr Ile Thr Ala Thr Arg Gln Tyr Val Ala Gln Ala Asn Ser
    4520                4525                4530

Trp Ser Leu Glu Glu Leu Cys Leu Glu Val Asn Val Thr Thr Ser
    4535                4540                4545

Gln Gly Ala Thr Leu Asp Ala Cys Ser Phe Gly Val Thr Gly Leu
    4550                4555                4560

Lys Leu Gln Gly Ala Thr Cys Asn Asn Asn Lys Leu Ser Leu Ser
    4565                4570                4575

Asn Ala Ile Ser Thr Ala Leu Pro Leu Thr Gln Leu Arg Trp Val
    4580                4585                4590

Lys Gln Thr Asn Thr Glu Lys Lys Ala Ser Val Val Thr Leu Pro
    4595                4600                4605

Val Tyr Leu Asn Phe Thr Arg Ala Asp Leu Ile Phe Thr Val Asp
    4610                4615                4620

Phe Glu Ile Ala Thr Lys Glu Asp Pro Arg Ser Phe Tyr Glu Arg
    4625                4630                4635

Gly Val Ala Val Leu Cys Thr Glu
    4640                4645

<210> SEQ ID NO 43
<211> LENGTH: 456
<212> TYPE: PRT
<213> ORGANISM: Homo sapiens

<400> SEQUENCE: 43

Met Lys Ile Glu Glu Val Lys Ser Thr Thr Lys Thr Gln Arg Ile Ala
1               5                   10                  15

Ser His Ser His Val Lys Gly Leu Gly Leu Asp Glu Ser Gly Leu Ala
                20                  25                  30

Lys Gln Ala Ala Ser Gly Leu Val Gly Gln Glu Asn Ala Arg Glu Ala
            35                  40                  45

Cys Gly Val Ile Val Glu Leu Ile Lys Ser Lys Met Ala Gly Arg
        50                  55                  60

Ala Val Leu Leu Ala Gly Pro Pro Gly Thr Gly Lys Thr Ala Leu Ala
65                  70                  75                  80

Leu Ala Ile Ala Gln Glu Leu Gly Ser Lys Val Pro Phe Cys Pro Met
                85                  90                  95

Val Gly Ser Glu Val Tyr Ser Thr Glu Ile Lys Lys Thr Glu Val Leu
                100                 105                 110

Met Glu Asn Phe Arg Arg Ala Ile Gly Leu Arg Ile Lys Glu Thr Lys
            115                 120                 125

Glu Val Tyr Glu Gly Glu Val Thr Glu Leu Thr Pro Cys Glu Thr Glu
        130                 135                 140

Asn Pro Met Gly Gly Tyr Gly Lys Thr Ile Ser His Val Ile Ile Gly
145                 150                 155                 160

Leu Lys Thr Ala Lys Gly Thr Lys Gln Leu Lys Leu Asp Pro Ser Ile
                165                 170                 175

Phe Glu Ser Leu Gln Lys Glu Arg Val Glu Ala Gly Asp Val Ile Tyr
            180                 185                 190

Ile Glu Ala Asn Ser Gly Ala Val Lys Arg Gln Gly Arg Cys Asp Thr
        195                 200                 205
```

```
Tyr Ala Thr Glu Phe Asp Leu Glu Ala Glu Glu Tyr Val Pro Leu Pro
    210                 215                 220

Lys Gly Asp Val His Lys Lys Glu Ile Ile Gln Asp Val Thr Leu
225                 230                 235                 240

His Asp Leu Asp Val Ala Asn Ala Arg Pro Gln Gly Gly Gln Asp Ile
                245                 250                 255

Leu Ser Met Met Gly Gln Leu Met Lys Pro Lys Lys Thr Glu Ile Thr
            260                 265                 270

Asp Lys Leu Arg Gly Glu Ile Asn Lys Val Val Asn Lys Tyr Ile Asp
                275                 280                 285

Gln Gly Ile Ala Glu Leu Val Pro Gly Val Leu Phe Val Asp Glu Val
    290                 295                 300

His Met Leu Asp Ile Glu Cys Phe Thr Tyr Leu His Arg Ala Leu Glu
305                 310                 315                 320

Ser Ser Ile Ala Pro Ile Val Ile Phe Ala Ser Asn Arg Gly Asn Cys
                325                 330                 335

Val Ile Arg Gly Thr Glu Asp Ile Thr Ser Pro His Gly Ile Pro Leu
                340                 345                 350

Asp Leu Leu Asp Arg Val Met Ile Ile Arg Thr Met Leu Tyr Thr Pro
                355                 360                 365

Gln Glu Met Lys Gln Ile Ile Lys Ile Arg Ala Gln Thr Glu Gly Ile
    370                 375                 380

Asn Ile Ser Glu Glu Ala Leu Asn His Leu Gly Glu Ile Gly Thr Lys
385                 390                 395                 400

Thr Thr Leu Arg Tyr Ser Val Gln Leu Leu Thr Pro Ala Asn Leu Leu
                405                 410                 415

Ala Lys Ile Asn Gly Lys Asp Ser Ile Glu Lys Glu His Val Glu Glu
                420                 425                 430

Ile Ser Glu Leu Phe Tyr Asp Ala Lys Ser Ser Ala Lys Ile Leu Ala
    435                 440                 445

Asp Gln Gln Asp Lys Tyr Met Lys
    450                 455

<210> SEQ ID NO 44
<211> LENGTH: 151
<212> TYPE: PRT
<213> ORGANISM: Homo sapiens

<400> SEQUENCE: 44

Met Val Gln Lys Glu Ser Gln Ala Thr Leu Glu Glu Arg Glu Ser Glu
1               5                   10                  15

Leu Ser Ser Asn Pro Ala Ala Ser Ala Gly Ala Ser Leu Glu Pro Pro
                20                  25                  30

Ala Ala Pro Ala Pro Gly Glu Asp Asn Pro Ala Gly Ala Gly Gly Ala
            35                  40                  45

Ala Val Ala Gly Ala Ala Gly Gly Ala Arg Arg Phe Leu Cys Gly Val
        50                  55                  60

Val Glu Gly Phe Tyr Gly Arg Pro Trp Val Met Glu Gln Arg Lys Glu
65              70                  75                  80

Leu Phe Arg Arg Leu Gln Lys Trp Glu Leu Asn Thr Tyr Leu Tyr Ala
                85                  90                  95

Pro Lys Asp Asp Tyr Lys His Arg Met Phe Trp Arg Glu Met Tyr Ser
                100                 105                 110

Val Glu Glu Ala Gly Ser Phe Leu Phe Phe Tyr Leu Val Thr Ile Gln
            115                 120                 125
```

```
Leu Ala Glu Ile Glu Arg Val Leu Cys Ala Ser Lys Val Met Thr Ile
            130                 135                 140

Cys Val Ile Ser Trp Ala Cys
145                 150

<210> SEQ ID NO 45
<211> LENGTH: 201
<212> TYPE: PRT
<213> ORGANISM: Homo sapiens

<400> SEQUENCE: 45

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Arg Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asn Gln Cys Phe Tyr Asn Ser Ser Tyr
                85                  90                  95

Leu Asn Val Gln Arg Glu Asn Gly Thr Val Ser Arg Tyr Glu Gly Gly
            100                 105                 110

Arg Glu His Val Ala His Leu Leu Phe Leu Arg Asp Thr Lys Thr Leu
        115                 120                 125

Met Phe Gly Ser Tyr Leu Asp Asp Glu Lys Asn Trp Gly Leu Ser Phe
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Cys Ile Pro Arg Ser Asp Val Met Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 46
<211> LENGTH: 203
<212> TYPE: PRT
<213> ORGANISM: Homo sapiens

<400> SEQUENCE: 46

Met Ala Lys Ala Tyr Asp His Leu Phe Lys Leu Leu Ile Gly Asp
1               5                   10                  15

Ser Gly Val Gly Lys Thr Cys Leu Ile Ile Arg Phe Ala Glu Asp Asn
            20                  25                  30

Phe Asn Asn Thr Tyr Ile Ser Thr Ile Gly Ile Asp Phe Lys Ile Arg
        35                  40                  45

Thr Val Asp Ile Glu Gly Lys Lys Ile Lys Leu Gln Val Trp Asp Thr
    50                  55                  60

Ala Gly Gln Glu Arg Phe Lys Thr Ile Thr Thr Ala Tyr Tyr Arg Gly
65                  70                  75                  80

Ala Met Gly Ile Ile Leu Val Tyr Asp Ile Thr Asp Glu Lys Ser Phe
                85                  90                  95
```

Glu Asn Ile Gln Asn Trp Met Lys Ser Ile Lys Glu Asn Ala Ser Ala
            100                 105                 110

Gly Val Glu Arg Leu Leu Leu Gly Asn Lys Cys Asp Met Glu Ala Lys
            115                 120                 125

Arg Lys Val Gln Lys Glu Gln Ala Asp Lys Leu Ala Arg Glu His Gly
130                 135                 140

Ile Arg Phe Phe Glu Thr Ser Ala Lys Ser Ser Met Asn Val Asp Glu
145                 150                 155                 160

Ala Phe Ser Ser Leu Ala Arg Asp Ile Leu Leu Lys Ser Gly Gly Arg
                165                 170                 175

Arg Ser Gly Asn Gly Asn Lys Pro Pro Ser Thr Asp Leu Lys Thr Cys
            180                 185                 190

Asp Lys Lys Asn Thr Asn Lys Cys Ser Leu Gly
            195                 200

<210> SEQ ID NO 47
<211> LENGTH: 609
<212> TYPE: PRT
<213> ORGANISM: Homo sapiens

<400> SEQUENCE: 47

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly

```
            260                 265                 270
Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu

<210> SEQ ID NO 48
<211> LENGTH: 418
<212> TYPE: PRT
<213> ORGANISM: Homo sapiens

<400> SEQUENCE: 48

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
```

```
            20                  25                  30
Pro Asp Ser Thr Gly Ala Leu Val Glu Glu Asp Pro Phe Phe Lys
            35                  40                  45
Val Pro Val Asn Lys Leu Ala Ala Val Ser Asn Phe Gly Tyr Asp
            50                  55                  60
Leu Tyr Arg Val Arg Ser Ser Thr Ser Pro Thr Thr Asn Val Leu Leu
65                  70                  75                  80
Ser Pro Leu Ser Val Ala Thr Ala Leu Ser Ala Leu Ser Leu Gly Ala
                85                  90                  95
Glu Gln Arg Thr Glu Ser Ile Ile His Arg Ala Leu Tyr Tyr Asp Leu
                100                 105                 110
Ile Ser Ser Pro Asp Ile His Gly Thr Tyr Lys Glu Leu Leu Asp Thr
                115                 120                 125
Val Thr Ala Pro Gln Lys Asn Leu Lys Ser Ala Ser Arg Ile Val Phe
                130                 135                 140
Glu Lys Lys Leu Arg Ile Lys Ser Ser Phe Val Ala Pro Leu Glu Lys
145                 150                 155                 160
Ser Tyr Gly Thr Arg Pro Arg Val Leu Thr Gly Asn Pro Arg Leu Asp
                165                 170                 175
Leu Gln Glu Ile Asn Asn Trp Val Gln Ala Gln Met Lys Gly Lys Leu
                180                 185                 190
Ala Arg Ser Thr Lys Glu Ile Pro Asp Glu Ile Ser Ile Leu Leu Leu
                195                 200                 205
Gly Val Ala His Phe Lys Gly Gln Trp Val Thr Lys Phe Asp Ser Arg
                210                 215                 220
Lys Thr Ser Leu Glu Asp Phe Tyr Leu Asp Glu Glu Arg Thr Val Arg
225                 230                 235                 240
Val Pro Met Met Ser Asp Pro Lys Ala Val Leu Arg Tyr Gly Leu Asp
                245                 250                 255
Ser Asp Leu Ser Cys Lys Ile Ala Gln Leu Pro Leu Thr Gly Ser Met
                260                 265                 270
Ser Ile Ile Phe Phe Leu Pro Leu Lys Val Thr Gln Asn Leu Thr Leu
                275                 280                 285
Ile Glu Glu Ser Leu Thr Ser Glu Phe Ile His Asp Ile Asp Arg Glu
                290                 295                 300
Leu Lys Thr Val Gln Ala Val Leu Thr Val Pro Lys Leu Lys Leu Ser
305                 310                 315                 320
Tyr Glu Gly Glu Val Thr Lys Ser Leu Gln Glu Met Lys Leu Gln Ser
                325                 330                 335
Leu Phe Asp Ser Pro Asp Phe Ser Lys Ile Thr Gly Lys Pro Ile Lys
                340                 345                 350
Leu Thr Gln Val Glu His Arg Ala Gly Phe Glu Trp Asn Glu Asp Gly
                355                 360                 365
Ala Gly Thr Thr Pro Ser Pro Gly Leu Gln Pro Ala His Leu Thr Phe
                370                 375                 380
Pro Leu Asp Tyr His Leu Asn Gln Pro Phe Ile Phe Val Leu Arg Asp
385                 390                 395                 400
Thr Asp Thr Gly Ala Leu Leu Phe Ile Gly Lys Ile Leu Asp Pro Arg
                405                 410                 415
Gly Pro

<210> SEQ ID NO 49
<211> LENGTH: 130
```

```
<212> TYPE: PRT
<213> ORGANISM: Homo sapiens

<400> SEQUENCE: 49

Met Arg Leu Phe Thr Gly Ile Val Phe Cys Ser Leu Val Met Gly Val
1               5                   10                  15

Thr Ser Glu Ser Trp Arg Ser Phe Phe Lys Glu Ala Leu Gln Gly Val
            20                  25                  30

Gly Asp Met Gly Arg Ala Tyr Trp Asp Ile Met Ile Ser Asn His Gln
        35                  40                  45

Asn Ser Asn Arg Tyr Leu Tyr Ala Arg Gly Asn Tyr Asp Ala Ala Gln
    50                  55                  60

Arg Gly Pro Gly Gly Val Trp Ala Ala Lys Leu Ile Ser Arg Ser Arg
65                  70                  75                  80

Val Tyr Leu Gln Gly Leu Ile Asp Cys Tyr Leu Phe Gly Asn Ser Ser
                85                  90                  95

Thr Val Leu Glu Asp Ser Lys Ser Asn Glu Lys Ala Glu Glu Trp Gly
            100                 105                 110

Arg Ser Gly Lys Asp Pro Asp Arg Phe Arg Pro Asp Gly Leu Pro Lys
        115                 120                 125

Lys Tyr
    130

<210> SEQ ID NO 50
<211> LENGTH: 267
<212> TYPE: PRT
<213> ORGANISM: Homo sapiens

<400> SEQUENCE: 50

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205
```

```
Gly Gly Ala Arg Leu Ala Glu Tyr His Ala Lys Ala Thr Glu His Leu
210                 215                 220
Ser Thr Leu Ser Glu Lys Ala Lys Pro Ala Leu Glu Asp Leu Arg Gln
225                 230                 235                 240
Gly Leu Leu Pro Val Leu Glu Ser Phe Lys Val Ser Phe Leu Ser Ala
                245                 250                 255
Leu Glu Glu Tyr Thr Lys Lys Leu Asn Thr Gln
            260                 265

<210> SEQ ID NO 51
<211> LENGTH: 866
<212> TYPE: PRT
<213> ORGANISM: Homo sapiens

<400> SEQUENCE: 51

Met Phe Ser Met Arg Ile Val Cys Leu Val Leu Ser Val Val Gly Thr
1               5                   10                  15
Ala Trp Thr Ala Asp Ser Gly Glu Gly Asp Phe Leu Ala Glu Gly Gly
                20                  25                  30
Gly Val Arg Gly Pro Arg Val Val Glu Arg His Gln Ser Ala Cys Lys
            35                  40                  45
Asp Ser Asp Trp Pro Phe Cys Ser Asp Glu Asp Trp Asn Tyr Lys Cys
    50                  55                  60
Pro Ser Gly Cys Arg Met Lys Gly Leu Ile Asp Glu Val Asn Gln Asp
65                  70                  75                  80
Phe Thr Asn Arg Ile Asn Lys Leu Lys Asn Ser Leu Phe Glu Tyr Gln
                85                  90                  95
Lys Asn Asn Lys Asp Ser His Ser Leu Thr Thr Asn Ile Met Glu Ile
            100                 105                 110
Leu Arg Gly Asp Phe Ser Ser Ala Asn Asn Arg Asp Asn Thr Tyr Asn
        115                 120                 125
Arg Val Ser Glu Asp Leu Arg Ser Arg Ile Glu Val Leu Lys Arg Lys
130                 135                 140
Val Ile Glu Lys Val Gln His Ile Gln Leu Leu Gln Lys Asn Val Arg
145                 150                 155                 160
Ala Gln Leu Val Asp Met Lys Arg Leu Glu Val Asp Ile Asp Ile Lys
                165                 170                 175
Ile Arg Ser Cys Arg Gly Ser Cys Ser Arg Ala Leu Ala Arg Glu Val
            180                 185                 190
Asp Leu Lys Asp Tyr Glu Asp Gln Gln Lys Gln Leu Glu Gln Val Ile
        195                 200                 205
Ala Lys Asp Leu Leu Pro Ser Arg Asp Arg Gln His Leu Pro Leu Ile
210                 215                 220
Lys Met Lys Pro Val Pro Asp Leu Val Pro Gly Asn Phe Lys Ser Gln
225                 230                 235                 240
Leu Gln Lys Val Pro Pro Glu Trp Lys Ala Leu Thr Asp Met Pro Gln
                245                 250                 255
Met Arg Met Glu Leu Glu Arg Pro Gly Gly Asn Glu Ile Thr Arg Gly
            260                 265                 270
Gly Ser Thr Ser Tyr Gly Thr Gly Ser Glu Thr Glu Ser Pro Arg Asn
        275                 280                 285
Pro Ser Ser Ala Gly Ser Trp Asn Ser Gly Ser Ser Gly Pro Gly Ser
    290                 295                 300
Thr Gly Asn Arg Asn Pro Gly Ser Ser Gly Thr Gly Gly Thr Ala Thr
305                 310                 315                 320
```

```
Trp Lys Pro Gly Ser Ser Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
        370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
            435                 440                 445

Val Thr Ser Gly Ser Thr Thr Thr Arg Arg Ser Cys Ser Lys Thr
        450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
            530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
        610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
            675                 680                 685

Trp Gln Asp Tyr Lys Arg Gly Phe Gly Ser Leu Asn Asp Glu Gly Glu
        690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
                725                 730                 735
```

```
Tyr Ala Glu Tyr His Phe Arg Val Gly Ser Glu Ala Glu Gly Tyr Ala
                740                 745                 750

Leu Gln Val Ser Ser Tyr Glu Gly Thr Ala Gly Asp Ala Leu Ile Glu
            755                 760                 765

Gly Ser Val Glu Glu Gly Ala Glu Tyr Thr Ser His Asn Asn Met Gln
        770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
        835                 840                 845

Ala Asp Tyr Ser Leu Arg Ala Val Arg Met Lys Ile Arg Pro Leu Val
850                 855                 860

Thr Gln
865

<210> SEQ ID NO 52
<211> LENGTH: 406
<212> TYPE: PRT
<213> ORGANISM: Homo sapiens

<400> SEQUENCE: 52

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
            35                  40                  45

Arg Tyr Gln Cys Lys Asn Tyr Tyr Lys Leu Arg Thr Glu Gly Asp Gly
        50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
210                 215                 220

Val Gly Lys Lys Gln Leu Val Glu Ile Glu Lys Val Val Leu His Pro
225                 230                 235                 240
```

```
Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
    370                 375                 380

Glu Tyr Gly Val Tyr Val Lys Val Thr Ser Ile Gln Asp Trp Val Gln
385                 390                 395                 400

Lys Thr Ile Ala Glu Asn
                405

<210> SEQ ID NO 53
<211> LENGTH: 418
<212> TYPE: PRT
<213> ORGANISM: Homo sapiens

<400> SEQUENCE: 53

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
```

```
                195                 200                 205
Val Asn Tyr Ile Phe Lys Gly Lys Trp Glu Arg Pro Phe Glu Val
210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
                290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 54
<211> LENGTH: 452
<212> TYPE: PRT
<213> ORGANISM: Homo sapiens

<400> SEQUENCE: 54

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
                35                  40                  45

Asp Ile Ser Ser Thr Arg Gly Phe Pro Ser Val Leu Arg Gly Gly Lys
                50                  55                  60

Tyr Ala Ala Thr Ser Gln Val Leu Leu Pro Ser Lys Asp Val Met Gln
65              70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Gly Asn Pro Arg
                115                 120                 125

Lys Ser Lys Leu Ile Cys Gln Ala Thr Gly Phe Ser Pro Arg Gln Ile
                130                 135                 140

Gln Val Ser Trp Leu Arg Glu Gly Lys Gln Val Gly Ser Gly Val Thr
```

145                 150                 155                 160
    Thr Asp Gln Val Gln Ala Glu Ala Lys Glu Ser Gly Pro Thr Thr Tyr
                        165                 170                 175
    Lys Val Thr Ser Thr Leu Thr Ile Lys Glu Ser Asp Trp Leu Gly Gln
                        180                 185                 190
    Ser Met Phe Thr Cys Arg Val Asp His Arg Gly Leu Thr Phe Gln Gln
                        195                 200                 205
    Asn Ala Ser Ser Met Cys Val Pro Asp Gln Asp Thr Ala Ile Arg Val
                        210                 215                 220
    Phe Ala Ile Pro Pro Ser Phe Ala Ser Ile Phe Leu Thr Lys Ser Thr
    225                 230                 235                 240
    Lys Leu Thr Cys Leu Val Thr Asp Leu Thr Thr Tyr Asp Ser Val Thr
                        245                 250                 255
    Ile Ser Trp Thr Arg Gln Asn Gly Glu Ala Val Lys Thr His Thr Asn
                        260                 265                 270
    Ile Ser Glu Ser His Pro Asn Ala Thr Phe Ser Ala Val Gly Glu Ala
                        275                 280                 285
    Ser Ile Cys Glu Asp Asp Trp Asn Ser Gly Glu Arg Phe Thr Cys Thr
                        290                 295                 300
    Val Thr His Thr Asp Leu Pro Ser Pro Leu Lys Gln Thr Ile Ser Arg
    305                 310                 315                 320
    Pro Lys Gly Val Ala Leu His Arg Pro Asp Val Tyr Leu Leu Pro Pro
                        325                 330                 335
    Ala Arg Glu Gln Leu Asn Leu Arg Glu Ser Ala Thr Ile Thr Cys Leu
                        340                 345                 350
    Val Thr Gly Phe Ser Pro Ala Asp Val Phe Val Gln Trp Met Gln Arg
                        355                 360                 365
    Gly Gln Pro Leu Ser Pro Glu Lys Tyr Val Thr Ser Ala Pro Met Pro
                        370                 375                 380
    Glu Pro Gln Ala Pro Gly Arg Tyr Phe Ala His Ser Ile Leu Thr Val
    385                 390                 395                 400
    Ser Glu Glu Glu Trp Asn Thr Gly Glu Thr Tyr Thr Cys Val Ala His
                        405                 410                 415
    Glu Ala Leu Pro Asn Arg Val Thr Glu Arg Thr Val Asp Lys Ser Thr
                        420                 425                 430
    Gly Lys Pro Thr Leu Tyr Asn Val Ser Leu Val Met Ser Asp Thr Ala
                        435                 440                 445
    Gly Thr Cys Tyr
        450

<210> SEQ ID NO 55
<211> LENGTH: 147
<212> TYPE: PRT
<213> ORGANISM: Homo sapiens

<400> SEQUENCE: 55

Met Val His Leu Thr Pro Glu Glu Lys Thr Ala Val Asn Ala Leu Trp
    1               5                   10                  15
    Gly Lys Val Asn Val Asp Ala Val Gly Gly Glu Ala Leu Gly Arg Leu
                        20                  25                  30
    Leu Val Val Tyr Pro Trp Thr Gln Arg Phe Phe Glu Ser Phe Gly Asp
                        35                  40                  45
    Leu Ser Ser Pro Asp Ala Val Met Gly Asn Pro Lys Val Lys Ala His
                        50                  55                  60

Gly Lys Lys Val Leu Gly Ala Phe Ser Asp Gly Leu Ala His Leu Asp
65                  70                  75                  80

Asn Leu Lys Gly Thr Phe Ser Gln Leu Ser Glu Leu His Cys Asp Lys
                85                  90                  95

Leu His Val Asp Pro Glu Asn Phe Arg Leu Leu Gly Asn Val Leu Val
                100                 105                 110

Cys Val Leu Ala Arg Asn Phe Gly Lys Glu Phe Thr Pro Gln Met Gln
            115                 120                 125

Ala Ala Tyr Gln Lys Val Val Ala Gly Val Ala Asn Ala Leu Ala His
            130                 135                 140

Lys Tyr His
145

<210> SEQ ID NO 56
<211> LENGTH: 5405
<212> TYPE: PRT
<213> ORGANISM: Homo sapiens

<400> SEQUENCE: 56

Met Gly Ala Leu Trp Ser Trp Trp Ile Leu Trp Ala Gly Ala Thr Leu
1               5                   10                  15

Leu Trp Gly Leu Thr Gln Glu Ala Ser Val Asp Leu Lys Asn Thr Gly
                20                  25                  30

Arg Glu Glu Phe Leu Thr Ala Phe Leu Gln Asn Tyr Gln Leu Ala Tyr
            35                  40                  45

Ser Lys Ala Tyr Pro Arg Leu Leu Ile Ser Ser Leu Ser Glu Ser Pro
        50                  55                  60

Ala Ser Val Ser Ile Leu Ser Gln Ala Asp Asn Thr Ser Lys Lys Val
65                  70                  75                  80

Thr Val Arg Pro Gly Glu Ser Val Met Val Asn Ile Ser Ala Lys Ala
                85                  90                  95

Glu Met Ile Gly Ser Lys Ile Phe Gln His Ala Val Val Ile His Ser
                100                 105                 110

Asp Tyr Ala Ile Ser Val Gln Ala Leu Asn Ala Lys Pro Asp Thr Ala
            115                 120                 125

Glu Leu Thr Leu Leu Arg Pro Ile Gln Ala Leu Gly Thr Glu Tyr Phe
        130                 135                 140

Val Leu Thr Pro Pro Gly Thr Ser Ala Arg Asn Val Lys Glu Phe Ala
145                 150                 155                 160

Val Val Ala Gly Ala Ala Gly Ala Ser Val Ser Val Thr Leu Lys Gly
                165                 170                 175

Ser Val Thr Phe Asn Gly Lys Phe Tyr Pro Ala Gly Asp Val Leu Arg
                180                 185                 190

Val Thr Leu Gln Pro Tyr Asn Val Ala Gln Leu Gln Ser Ser Val Asp
            195                 200                 205

Leu Ser Gly Ser Lys Val Thr Ala Ser Ser Pro Val Ala Val Leu Ser
        210                 215                 220

Gly His Ser Cys Ala Gln Lys His Thr Thr Cys Asn His Val Val Glu
225                 230                 235                 240

Gln Leu Leu Pro Thr Ser Ala Trp Gly Thr His Tyr Val Pro Thr
                245                 250                 255

Leu Ala Ser Gln Ser Arg Tyr Asp Leu Ala Phe Val Val Ala Ser Gln
            260                 265                 270

Ala Thr Lys Leu Thr Tyr Asn His Gly Gly Ile Thr Gly Ser Arg Gly
        275                 280                 285

```
Leu Gln Ala Gly Asp Val Val Glu Phe Glu Val Arg Pro Ser Trp Pro
        290                 295                 300

Leu Tyr Leu Ser Ala Asn Val Gly Ile Gln Val Leu Leu Phe Gly Thr
305                 310                 315                 320

Gly Ala Ile Arg Asn Glu Val Thr Tyr Asp Pro Tyr Leu Val Leu Ile
                325                 330                 335

Pro Asp Val Ala Ala Tyr Cys Pro Ala Tyr Val Val Lys Ser Val Pro
                340                 345                 350

Gly Cys Glu Gly Val Ala Leu Val Ala Gln Thr Lys Ala Ile Ser
            355                 360                 365

Gly Leu Thr Ile Asp Gly His Ala Val Gly Ala Lys Leu Thr Trp Glu
        370                 375                 380

Ala Val Pro Gly Ser Glu Phe Ser Tyr Ala Glu Val Glu Leu Gly Thr
385                 390                 395                 400

Ala Asp Met Ile His Thr Ala Glu Ala Thr Thr Asn Leu Gly Leu Leu
                405                 410                 415

Thr Phe Gly Leu Ala Lys Ala Ile Gly Tyr Ala Thr Ala Ala Asp Cys
                420                 425                 430

Gly Arg Thr Val Leu Ser Pro Val Glu Pro Ser Cys Glu Gly Met Gln
        435                 440                 445

Cys Ala Ala Gly Gln Arg Cys Gln Val Val Gly Gly Lys Ala Gly Cys
450                 455                 460

Val Ala Glu Ser Thr Ala Val Cys Arg Ala Gln Gly Asp Pro His Tyr
465                 470                 475                 480

Thr Thr Phe Asp Gly Arg Arg Tyr Asp Met Met Gly Thr Cys Ser Tyr
                485                 490                 495

Thr Met Val Glu Leu Cys Ser Glu Asp Asp Thr Leu Pro Ala Phe Ser
                500                 505                 510

Val Glu Ala Lys Asn Glu His Arg Gly Ser Arg Val Ser Tyr Val
                515                 520                 525

Gly Leu Val Thr Val Arg Ala Tyr Ser His Ser Val Ser Leu Thr Arg
        530                 535                 540

Gly Glu Val Gly Phe Val Leu Val Asp Asn Gln Arg Ser Arg Leu Pro
545                 550                 555                 560

Val Ser Leu Ser Glu Gly Arg Leu Arg Val Tyr Gln Ser Gly Pro Arg
                565                 570                 575

Ala Val Val Glu Leu Val Phe Gly Leu Val Val Thr Tyr Asp Trp Asp
                580                 585                 590

Cys Gln Leu Ala Leu Ser Leu Pro Ala Arg Phe Gln Asp Gln Val Cys
        595                 600                 605

Gly Leu Cys Gly Asn Tyr Asn Gly Asp Pro Ala Asp Asp Phe Leu Thr
        610                 615                 620

Pro Asp Gly Ala Leu Ala Pro Asp Ala Val Glu Phe Ala Ser Ser Trp
625                 630                 635                 640

Lys Leu Asp Asp Gly Asp Tyr Leu Cys Glu Asp Gly Cys Gln Asn Asn
                645                 650                 655

Cys Pro Ala Cys Thr Pro Gly Gln Ala Gln His Tyr Glu Gly Asp Arg
                660                 665                 670

Leu Cys Gly Met Leu Thr Lys Leu Asp Gly Pro Phe Ala Val Cys His
        675                 680                 685

Asp Thr Leu Asp Pro Arg Pro Phe Leu Glu Gln Cys Val Tyr Asp Leu
        690                 695                 700
```

Cys Val Gly Gly Glu Arg Leu Ser Leu Cys Arg Gly Leu Ser Ala
705             710                 715                 720

Tyr Ala Gln Ala Cys Leu Glu Leu Gly Ile Ser Val Gly Asp Trp Arg
        725                 730                 735

Ser Pro Ala Asn Cys Pro Leu Ser Cys Pro Ala Asn Ser Arg Tyr Glu
            740                 745                 750

Leu Cys Gly Pro Ala Cys Pro Thr Ser Cys Asn Gly Ala Ala Ala Pro
                755                 760                 765

Ser Asn Cys Ser Gly Arg Pro Cys Val Glu Gly Cys Val Cys Leu Pro
770                 775                 780

Gly Phe Val Ala Ser Gly Ala Cys Val Pro Ala Ser Ser Cys Gly
785                 790                 795                 800

Cys Thr Phe Gln Gly Leu Gln Leu Ala Pro Gly Gln Glu Val Trp Ala
            805                 810                 815

Asp Glu Leu Cys Gln Arg Arg Cys Thr Cys Asn Gly Ala Thr His Gln
            820                 825                 830

Val Thr Cys Arg Asp Lys Gln Ser Cys Pro Ala Gly Glu Arg Cys Ser
        835                 840                 845

Val Gln Asn Gly Leu Leu Gly Cys Tyr Pro Asp Arg Phe Gly Thr Cys
850                 855                 860

Gln Gly Ser Gly Asp Pro His Tyr Val Ser Phe Asp Gly Arg Arg Phe
865                 870                 875                 880

Asp Phe Met Gly Thr Cys Thr Tyr Leu Leu Val Gly Ser Cys Gly Gln
                885                 890                 895

Asn Ala Ala Leu Pro Ala Phe Arg Val Leu Val Glu Asn Glu His Arg
                900                 905                 910

Gly Ser Gln Thr Val Ser Tyr Thr Arg Ala Val Arg Val Glu Ala Arg
            915                 920                 925

Gly Val Lys Val Ala Val Arg Arg Glu Tyr Pro Gly Gln Val Leu Val
        930                 935                 940

Asp Asp Val Leu Gln Tyr Leu Pro Phe Gln Ala Ala Asp Gly Gln Val
945                 950                 955                 960

Gln Val Phe Arg Gln Gly Arg Asp Ala Val Val Arg Thr Asp Phe Gly
            965                 970                 975

Leu Thr Val Thr Tyr Asp Trp Asn Ala Arg Val Thr Ala Lys Val Pro
            980                 985                 990

Ser Ser Tyr Ala Glu Ala Leu Cys Gly Leu Cys Gly Asn Phe Asn Gly
        995                 1000                1005

Asp Pro Ala Asp Asp Leu Ala Leu Arg Gly Gly Gln Ala Ala
    1010                1015                1020

Asn Ala Leu Ala Phe Gly Asn Ser Trp Gln Glu Glu Thr Arg Pro
    1025                1030                1035

Gly Cys Gly Ala Thr Glu Pro Gly Asp Cys Pro Lys Leu Asp Ser
    1040                1045                1050

Leu Val Ala Gln Gln Leu Gln Ser Lys Asn Glu Cys Gly Ile Leu
    1055                1060                1065

Ala Asp Pro Lys Gly Pro Phe Arg Glu Cys His Ser Lys Leu Asp
    1070                1075                1080

Pro Gln Gly Ala Val Arg Asp Cys Val Tyr Asp Arg Cys Leu Leu
    1085                1090                1095

Pro Gly Gln Ser Gly Pro Leu Cys Asp Ala Leu Ala Thr Tyr Ala
    1100                1105                1110

Ala Ala Cys Gln Ala Ala Gly Ala Thr Val His Pro Trp Arg Ser

```
        1115                1120                1125

Glu  Glu  Leu  Cys  Pro  Leu  Ser  Cys  Pro  His  Ser  His  Tyr  Glu
        1130                1135                1140

Ala  Cys  Ser  Tyr  Gly  Cys  Pro  Leu  Ser  Cys  Gly  Asp  Leu  Pro  Val
        1145                1150                1155

Pro  Gly  Gly  Cys  Gly  Ser  Glu  Cys  His  Glu  Gly  Cys  Val  Cys  Asp
        1160                1165                1170

Glu  Gly  Phe  Ala  Leu  Ser  Gly  Glu  Ser  Cys  Leu  Pro  Leu  Ala  Ser
        1175                1180                1185

Cys  Gly  Cys  Val  His  Gln  Gly  Thr  Tyr  His  Pro  Pro  Gly  Gln  Thr
        1190                1195                1200

Phe  Tyr  Pro  Gly  Pro  Gly  Cys  Asp  Ser  Leu  Cys  His  Cys  Gln  Glu
        1205                1210                1215

Gly  Gly  Leu  Val  Ser  Cys  Glu  Ser  Ser  Ser  Cys  Gly  Pro  His  Glu
        1220                1225                1230

Ala  Cys  Gln  Pro  Ser  Gly  Gly  Ser  Leu  Gly  Cys  Val  Ala  Val  Gly
        1235                1240                1245

Ser  Ser  Thr  Cys  Gln  Ala  Ser  Gly  Asp  Pro  His  Tyr  Thr  Thr  Phe
        1250                1255                1260

Asp  Gly  Arg  Arg  Phe  Asp  Phe  Met  Gly  Thr  Cys  Val  Tyr  Val  Leu
        1265                1270                1275

Ala  Gln  Thr  Cys  Gly  Thr  Arg  Pro  Gly  Leu  His  Arg  Phe  Ala  Val
        1280                1285                1290

Leu  Gln  Glu  Asn  Val  Ala  Trp  Gly  Asn  Gly  Arg  Val  Ser  Val  Thr
        1295                1300                1305

Arg  Val  Ile  Thr  Val  Gln  Val  Ala  Asn  Phe  Thr  Leu  Arg  Leu  Glu
        1310                1315                1320

Gln  Arg  Gln  Trp  Lys  Val  Thr  Val  Asn  Gly  Val  Asp  Met  Lys  Leu
        1325                1330                1335

Pro  Val  Val  Leu  Ala  Asn  Gly  Gln  Ile  Arg  Ala  Ser  Gln  His  Gly
        1340                1345                1350

Ser  Asp  Val  Val  Ile  Glu  Thr  Asp  Phe  Gly  Leu  Arg  Val  Ala  Tyr
        1355                1360                1365

Asp  Leu  Val  Tyr  Tyr  Val  Arg  Val  Thr  Val  Pro  Gly  Asn  Tyr  Tyr
        1370                1375                1380

Gln  Gln  Met  Cys  Gly  Leu  Cys  Gly  Asn  Tyr  Asn  Gly  Asp  Pro  Lys
        1385                1390                1395

Asp  Asp  Phe  Gln  Lys  Pro  Asn  Gly  Ser  Gln  Ala  Gly  Asn  Ala  Asn
        1400                1405                1410

Glu  Phe  Gly  Asn  Ser  Trp  Glu  Glu  Val  Val  Pro  Asp  Ser  Pro  Cys
        1415                1420                1425

Leu  Pro  Pro  Thr  Pro  Cys  Pro  Pro  Gly  Ser  Glu  Asp  Cys  Ile  Pro
        1430                1435                1440

Ser  His  Lys  Cys  Pro  Pro  Glu  Leu  Glu  Lys  Lys  Tyr  Gln  Lys  Glu
        1445                1450                1455

Glu  Phe  Cys  Gly  Leu  Leu  Ser  Ser  Pro  Thr  Gly  Pro  Leu  Ser  Ser
        1460                1465                1470

Cys  His  Lys  Leu  Val  Asp  Pro  Gln  Gly  Pro  Leu  Lys  Asp  Cys  Ile
        1475                1480                1485

Phe  Asp  Leu  Cys  Leu  Gly  Gly  Gly  Asn  Leu  Ser  Ile  Leu  Cys  Ser
        1490                1495                1500

Asn  Ile  His  Ala  Tyr  Val  Ser  Ala  Cys  Gln  Ala  Ala  Gly  Gly  His
        1505                1510                1515
```

-continued

```
Val Glu Pro Trp Arg Thr Glu Thr Phe Cys Pro Met Glu Cys Pro
    1520                1525                1530

Pro Asn Ser His Tyr Glu Leu Cys Ala Asp Thr Cys Ser Leu Gly
    1535                1540                1545

Cys Ser Ala Leu Ser Ala Pro Pro Gln Cys Gln Asp Gly Cys Ala
    1550                1555                1560

Glu Gly Cys Gln Cys Asp Ser Gly Phe Leu Tyr Asn Gly Gln Ala
    1565                1570                1575

Cys Val Pro Ile Gln Gln Cys Gly Cys Tyr His Asn Gly Val Tyr
    1580                1585                1590

Tyr Glu Pro Glu Gln Thr Val Leu Ile Asp Asn Cys Arg Gln Gln
    1595                1600                1605

Cys Thr Cys His Ala Gly Lys Gly Met Val Cys Gln Glu His Ser
    1610                1615                1620

Cys Lys Pro Gly Gln Val Cys Gln Pro Ser Gly Gly Ile Leu Ser
    1625                1630                1635

Cys Val Thr Lys Asp Pro Cys His Gly Val Thr Cys Arg Pro Gln
    1640                1645                1650

Glu Thr Cys Lys Glu Gln Gly Gly Gln Gly Val Cys Leu Pro Asn
    1655                1660                1665

Tyr Glu Ala Thr Cys Trp Leu Trp Gly Asp Pro His Tyr His Ser
    1670                1675                1680

Phe Asp Gly Arg Lys Phe Asp Phe Gln Gly Thr Cys Asn Tyr Val
    1685                1690                1695

Leu Ala Thr Thr Gly Cys Pro Gly Val Ser Thr Gln Gly Leu Thr
    1700                1705                1710

Pro Phe Thr Val Thr Thr Lys Asn Gln Asn Arg Gly Asn Pro Ala
    1715                1720                1725

Val Ser Tyr Val Arg Val Val Thr Val Ala Ala Leu Gly Thr Asn
    1730                1735                1740

Ile Ser Ile His Lys Asp Glu Ile Gly Lys Val Arg Val Asn Gly
    1745                1750                1755

Val Leu Thr Ala Leu Pro Val Ser Val Ala Asp Gly Arg Ile Ser
    1760                1765                1770

Val Thr Gln Gly Ala Ser Lys Ala Leu Leu Val Ala Asp Phe Gly
    1775                1780                1785

Leu Gln Val Ser Tyr Asp Trp Asn Trp Arg Val Asp Val Thr Leu
    1790                1795                1800

Pro Ser Ser Tyr His Gly Ala Val Cys Gly Leu Cys Gly Asn Met
    1805                1810                1815

Asp Arg Asn Pro Asn Asn Asp Gln Val Phe Pro Asn Gly Thr Leu
    1820                1825                1830

Ala Pro Ser Ile Pro Ile Trp Gly Gly Ser Trp Arg Ala Pro Gly
    1835                1840                1845

Trp Asp Pro Leu Cys Trp Asp Glu Cys Arg Gly Ser Cys Pro Thr
    1850                1855                1860

Cys Pro Glu Asp Arg Leu Glu Gln Tyr Glu Gly Pro Gly Phe Cys
    1865                1870                1875

Gly Pro Leu Ala Pro Gly Thr Gly Gly Pro Phe Thr Thr Cys His
    1880                1885                1890

Ala His Val Pro Pro Glu Ser Phe Phe Lys Gly Cys Val Leu Asp
    1895                1900                1905
```

```
Val Cys Met Gly Gly Gly Asp Arg Asp Ile Leu Cys Lys Ala Leu
1910                1915                1920

Ala Ser Tyr Val Ala Ala Cys Gln Ala Gly Val Val Ile Glu
1925                1930                1935

Asp Trp Arg Ala Gln Val Gly Cys Glu Ile Thr Cys Pro Glu Asn
1940                1945                1950

Ser His Tyr Glu Val Cys Gly Ser Pro Cys Pro Ala Ser Cys Pro
1955                1960                1965

Ser Pro Ala Pro Leu Thr Thr Pro Ala Val Cys Glu Gly Pro Cys
1970                1975                1980

Val Glu Gly Cys Gln Cys Asp Ala Gly Phe Val Leu Ser Ala Asp
1985                1990                1995

Arg Cys Val Pro Leu Asn Asn Gly Cys Gly Cys Trp Ala Asn Gly
2000                2005                2010

Thr Tyr His Glu Ala Gly Ser Glu Phe Trp Ala Asp Gly Thr Cys
2015                2020                2025

Ser Gln Trp Cys Arg Cys Gly Pro Gly Gly Ser Leu Val Cys
2030                2035                2040

Thr Pro Ala Ser Cys Gly Leu Gly Glu Val Cys Gly Leu Leu Pro
2045                2050                2055

Ser Gly Gln His Gly Cys Gln Pro Val Ser Thr Ala Glu Cys Gln
2060                2065                2070

Ala Trp Gly Asp Pro His Tyr Val Thr Leu Asp Gly His Arg Phe
2075                2080                2085

Asn Phe Gln Gly Thr Cys Glu Tyr Leu Leu Ser Ala Pro Cys His
2090                2095                2100

Gly Pro Pro Leu Gly Ala Glu Asn Phe Thr Val Thr Val Ala Asn
2105                2110                2115

Glu His Arg Gly Ser Gln Ala Val Ser Tyr Thr Arg Ser Val Thr
2120                2125                2130

Leu Gln Ile Tyr Asn His Ser Leu Thr Leu Ser Ala Arg Trp Pro
2135                2140                2145

Arg Lys Leu Gln Val Asp Gly Val Phe Val Thr Leu Pro Phe Gln
2150                2155                2160

Leu Asp Ser Leu Leu His Ala His Leu Ser Gly Ala Asp Val Val
2165                2170                2175

Val Thr Thr Thr Ser Gly Leu Ser Leu Ala Phe Asp Gly Asp Ser
2180                2185                2190

Phe Val Arg Leu Arg Val Pro Ala Ala Tyr Ala Gly Ser Leu Cys
2195                2200                2205

Gly Leu Cys Gly Asn Tyr Asn Gln Asp Pro Ala Asp Asp Leu Lys
2210                2215                2220

Ala Val Gly Gly Lys Pro Ala Gly Trp Gln Val Gly Gly Ala Gln
2225                2230                2235

Gly Cys Gly Glu Cys Val Ser Lys Pro Cys Pro Ser Pro Cys Thr
2240                2245                2250

Pro Glu Gln Gln Glu Ser Phe Gly Gly Pro Asp Ala Cys Gly Val
2255                2260                2265

Ile Ser Ala Thr Asp Gly Pro Leu Ala Pro Cys His Gly Leu Val
2270                2275                2280

Pro Pro Ala Gln Tyr Phe Gln Gly Cys Leu Leu Asp Ala Cys Gln
2285                2290                2295

Val Gln Gly His Pro Gly Gly Leu Cys Pro Ala Val Ala Thr Tyr
```

```
                      2300                2305                2310
Val Ala  Ala Cys Gln Ala Ala  Gly Ala Gln Leu Arg  Glu Trp Arg
        2315                2320                2325

Arg Pro  Asp Phe Cys Pro Phe  Gln Cys Pro Ala His  Ser His Tyr
        2330                2335                2340

Glu Leu  Cys Gly Asp Ser Cys  Pro Gly Ser Cys Pro  Ser Leu Ser
        2345                2350                2355

Ala Pro  Glu Gly Cys Glu Ser  Ala Cys Arg Glu Gly  Cys Val Cys
        2360                2365                2370

Asp Ala  Gly Phe Val Leu Ser  Gly Asp Thr Cys Val  Pro Val Gly
        2375                2380                2385

Gln Cys  Gly Cys Leu His Asp  Asp Arg Tyr Tyr Pro  Leu Gly Gln
        2390                2395                2400

Thr Phe  Tyr Pro Gly Pro Gly  Cys Asp Ser Leu Cys  Arg Cys Arg
        2405                2410                2415

Glu Gly  Gly Glu Val Ser Cys  Glu Pro Ser Ser Cys  Gly Pro His
        2420                2425                2430

Glu Thr  Cys Arg Pro Ser Gly  Ser Leu Gly Cys Val  Ala Val
        2435                2440                2445

Gly Ser  Thr Thr Cys Gln Ala  Ser Gly Asp Pro His  Tyr Thr Thr
        2450                2455                2460

Phe Asp  Gly Arg Arg Phe Asp  Phe Met Gly Thr Cys  Val Tyr Val
        2465                2470                2475

Leu Ala  Gln Thr Cys Gly Thr  Arg Pro Gly Leu His  Arg Phe Ala
        2480                2485                2490

Val Leu  Gln Glu Asn Val Ala  Trp Gly Asn Gly Arg  Val Ser Val
        2495                2500                2505

Thr Arg  Val Ile Thr Val Gln  Val Ala Asn Phe Thr  Leu Arg Leu
        2510                2515                2520

Glu Gln  Arg Gln Trp Lys Val  Thr Val Asn Gly Val  Asp Met Lys
        2525                2530                2535

Leu Pro  Val Val Leu Ala Asn  Gly Gln Ile Arg Ala  Ser Gln His
        2540                2545                2550

Gly Ser  Asp Val Val Ile Glu  Thr Asp Phe Gly Leu  Arg Val Ala
        2555                2560                2565

Tyr Asp  Leu Val Tyr Tyr Val  Arg Val Thr Val Pro  Gly Asn Tyr
        2570                2575                2580

Tyr Gln  Leu Met Cys Gly Leu  Cys Gly Asn Tyr Asn  Gly Asp Pro
        2585                2590                2595

Lys Asp  Asp Phe Gln Lys Pro  Asn Gly Ser Gln Ala  Gly Asn Ala
        2600                2605                2610

Asn Glu  Phe Gly Asn Ser Trp  Glu Glu Val Val Pro  Asp Ser Pro
        2615                2620                2625

Cys Leu  Pro Pro Pro Thr Cys  Pro Pro Gly Ser Glu  Gly Cys Ile
        2630                2635                2640

Pro Ser  Glu Glu Cys Pro Pro  Glu Leu Glu Lys Lys  Tyr Gln Lys
        2645                2650                2655

Glu Glu  Phe Cys Gly Leu Leu  Ser Ser Pro Thr Gly  Pro Leu Ser
        2660                2665                2670

Ser Cys  His Lys Leu Val Asp  Pro Gln Gly Pro Leu  Lys Asp Cys
        2675                2680                2685

Ile Phe  Asp Leu Cys Leu Gly  Gly Gly Asn Leu Ser  Ile Leu Cys
        2690                2695                2700
```

```
Ser Asn Ile His Ala Tyr Val Ser Ala Cys Gln Ala Ala Gly Gly
    2705            2710                2715

Gln Val Glu Pro Trp Arg Asn Glu Thr Phe Cys Pro Met Glu Cys
    2720            2725                2730

Pro Gln Asn Ser His Tyr Glu Leu Cys Ala Asp Thr Cys Ser Leu
    2735            2740                2745

Gly Cys Ser Ala Leu Ser Ala Pro Leu Gln Cys Pro Asp Gly Cys
    2750            2755                2760

Ala Glu Gly Cys Gln Cys Asp Ser Gly Phe Leu Tyr Asn Gly Gln
    2765            2770                2775

Ala Cys Val Pro Ile Gln Gln Cys Gly Cys Tyr His Asn Gly Ala
    2780            2785                2790

Tyr Tyr Glu Pro Glu Gln Thr Val Leu Ile Asp Asn Cys Arg Gln
    2795            2800                2805

Gln Cys Thr Cys His Val Gly Lys Val Val Cys Gln Glu His
    2810            2815                2820

Ser Cys Lys Pro Gly Gln Val Cys Gln Pro Ser Gly Gly Ile Leu
    2825            2830                2835

Ser Cys Val Asn Lys Asp Pro Cys His Gly Val Thr Cys Arg Pro
    2840            2845                2850

Gln Glu Thr Cys Lys Glu Gln Gly Gly Gln Gly Val Cys Leu Pro
    2855            2860                2865

Asn Tyr Glu Ala Thr Cys Trp Leu Trp Gly Asp Pro His Tyr His
    2870            2875                2880

Ser Phe Asp Gly Arg Lys Phe Asp Phe Gln Gly Thr Cys Asn Tyr
    2885            2890                2895

Val Leu Ala Thr Thr Gly Cys Pro Gly Val Ser Thr Gln Gly Leu
    2900            2905                2910

Thr Pro Phe Thr Val Thr Thr Lys Asn Gln Asn Arg Gly Asn Pro
    2915            2920                2925

Ala Val Ser Tyr Val Arg Val Val Thr Val Ala Ala Leu Gly Thr
    2930            2935                2940

Asn Ile Ser Ile His Lys Asp Glu Ile Gly Lys Val Arg Val Asn
    2945            2950                2955

Gly Val Leu Thr Ala Leu Pro Val Ser Val Ala Asp Gly Arg Ile
    2960            2965                2970

Ser Val Thr Gln Gly Ala Ser Lys Ala Leu Leu Val Ala Asp Phe
    2975            2980                2985

Gly Leu Gln Val Ser Tyr Asp Trp Asn Trp Arg Val Asp Val Thr
    2990            2995                3000

Leu Pro Ser Ser Tyr His Gly Ala Val Cys Gly Leu Cys Gly Asn
    3005            3010                3015

Met Asp Arg Asn Pro Asn Asn Asp Gln Val Phe Pro Asn Gly Thr
    3020            3025                3030

Leu Ala Pro Ser Ile Pro Ile Trp Gly Gly Ser Trp Arg Ala Pro
    3035            3040                3045

Gly Trp Asp Pro Leu Cys Trp Asp Glu Cys Arg Gly Ser Cys Pro
    3050            3055                3060

Thr Cys Pro Glu Asp Arg Leu Glu Gln Tyr Glu Gly Pro Gly Phe
    3065            3070                3075

Cys Gly Pro Leu Ala Pro Gly Thr Gly Gly Pro Phe Thr Thr Cys
    3080            3085                3090
```

```
His Ala His Val Pro Pro Glu Ser Phe Phe Lys Gly Cys Val Leu
3095                3100                3105

Asp Val Cys Met Gly Gly Gly Asp Arg Asp Ile Leu Cys Lys Ala
3110                3115                3120

Leu Ala Ser Tyr Val Ala Ala Cys Gln Ala Ala Gly Val Val Ile
3125                3130                3135

Glu Asp Trp Arg Ala Gln Val Gly Cys Glu Ile Thr Cys Pro Glu
3140                3145                3150

Asn Ser His Tyr Glu Val Cys Gly Pro Pro Cys Pro Ala Ser Cys
3155                3160                3165

Pro Ser Pro Ala Pro Leu Thr Thr Pro Ala Val Cys Glu Gly Pro
3170                3175                3180

Cys Val Glu Gly Cys Gln Cys Asp Ala Gly Phe Val Leu Ser Ala
3185                3190                3195

Asp Arg Cys Val Pro Leu Asn Asn Gly Cys Gly Cys Trp Ala Asn
3200                3205                3210

Gly Thr Tyr His Glu Ala Gly Ser Glu Phe Trp Ala Asp Gly Thr
3215                3220                3225

Cys Ser Gln Trp Cys Arg Cys Gly Pro Gly Gly Ser Leu Val
3230                3235                3240

Cys Thr Pro Ala Ser Cys Gly Leu Gly Glu Val Cys Gly Leu Leu
3245                3250                3255

Pro Ser Gly Gln His Gly Cys Gln Pro Val Ser Thr Ala Glu Cys
3260                3265                3270

Gln Ala Trp Gly Asp Pro His Tyr Val Thr Leu Asp Gly His Arg
3275                3280                3285

Phe Asp Phe Gln Gly Thr Cys Glu Tyr Leu Leu Ser Ala Pro Cys
3290                3295                3300

His Gly Pro Pro Leu Gly Ala Glu Asn Phe Thr Val Thr Val Ala
3305                3310                3315

Asn Glu His Arg Gly Ser Gln Ala Val Ser Tyr Thr Arg Ser Val
3320                3325                3330

Thr Leu Gln Ile Tyr Asn His Ser Leu Thr Leu Ser Ala Arg Trp
3335                3340                3345

Pro Arg Lys Leu Gln Val Asp Gly Val Phe Val Thr Leu Pro Phe
3350                3355                3360

Gln Leu Asp Ser Leu Leu His Ala His Leu Ser Gly Ala Asp Val
3365                3370                3375

Val Val Thr Thr Thr Ser Gly Leu Ser Leu Ala Phe Asp Gly Asp
3380                3385                3390

Ser Phe Val Arg Leu Arg Val Pro Ala Ala Tyr Ala Gly Ser Leu
3395                3400                3405

Cys Gly Leu Cys Gly Asn Tyr Asn Gln Asp Pro Ala Asp Asp Leu
3410                3415                3420

Lys Ala Val Gly Gly Lys Pro Ala Gly Trp Gln Val Gly Gly Ala
3425                3430                3435

Gln Gly Cys Gly Glu Cys Val Ser Lys Pro Cys Pro Ser Pro Cys
3440                3445                3450

Thr Pro Glu Gln Gln Glu Ser Phe Gly Gly Pro Asp Ala Cys Gly
3455                3460                3465

Val Ile Ser Ala Thr Asp Gly Pro Leu Ala Pro Cys His Gly Leu
3470                3475                3480

Val Pro Pro Ala Gln Tyr Phe Gln Gly Cys Leu Leu Asp Ala Cys
```

```
              3485                3490                3495
Gln Val Gln Gly His Pro Gly Gly Leu Cys Pro Ala Val Ala Thr
    3500                3505                3510

Tyr Val Ala Ala Cys Gln Ala Ala Gly Ala Gln Leu Arg Glu Trp
    3515                3520                3525

Arg Arg Pro Asp Phe Cys Pro Phe Gln Cys Pro Ala His Ser His
    3530                3535                3540

Tyr Glu Leu Cys Gly Asp Ser Cys Pro Gly Ser Cys Pro Ser Leu
    3545                3550                3555

Ser Ala Pro Glu Gly Cys Glu Ser Ala Cys Arg Glu Gly Cys Val
    3560                3565                3570

Cys Asp Ala Gly Phe Val Leu Ser Gly Asp Thr Cys Val Pro Val
    3575                3580                3585

Gly Gln Cys Gly Cys Leu His Asp Asp Arg Tyr Tyr Pro Leu Gly
    3590                3595                3600

Gln Thr Phe Tyr Pro Gly Pro Gly Cys Asp Ser Leu Cys Arg Cys
    3605                3610                3615

Arg Glu Gly Gly Glu Val Ser Cys Glu Pro Ser Ser Cys Gly Pro
    3620                3625                3630

His Glu Thr Cys Arg Pro Ser Gly Gly Ser Leu Gly Cys Val Ala
    3635                3640                3645

Val Gly Ser Thr Thr Cys Gln Ala Ser Gly Asp Pro His Tyr Thr
    3650                3655                3660

Thr Phe Asp Gly His Arg Phe Asp Phe Met Gly Thr Cys Val Tyr
    3665                3670                3675

Val Leu Ala Gln Thr Cys Gly Thr Arg Pro Gly Leu His Arg Phe
    3680                3685                3690

Ala Val Leu Gln Glu Asn Val Ala Trp Gly Asn Gly Arg Val Ser
    3695                3700                3705

Val Thr Arg Val Ile Thr Val Gln Val Ala Asn Phe Thr Leu Arg
    3710                3715                3720

Leu Glu Gln Arg Gln Trp Lys Val Thr Val Asn Gly Val Asp Met
    3725                3730                3735

Lys Leu Pro Val Val Leu Ala Asn Gly Gln Ile Arg Ala Ser Gln
    3740                3745                3750

His Gly Ser Asp Val Val Ile Glu Thr Asp Phe Gly Leu Arg Val
    3755                3760                3765

Ala Tyr Asp Leu Val Tyr Tyr Val Arg Val Thr Val Pro Gly Asn
    3770                3775                3780

Tyr Tyr Gln Leu Met Cys Gly Leu Cys Gly Asn Tyr Asn Gly Asp
    3785                3790                3795

Pro Lys Asp Asp Phe Gln Lys Pro Asn Gly Ser Gln Ala Gly Asn
    3800                3805                3810

Ala Asn Glu Phe Gly Asn Ser Trp Glu Glu Val Val Pro Asp Ser
    3815                3820                3825

Pro Cys Leu Pro Pro Thr Cys Pro Gly Ser Ala Gly Cys
    3830                3835                3840

Ile Pro Ser Asp Lys Cys Pro Glu Leu Glu Lys Lys Tyr Gln
    3845                3850                3855

Lys Glu Glu Phe Cys Gly Leu Leu Ser Ser Pro Thr Gly Pro Leu
    3860                3865                3870

Ser Ser Cys His Lys Leu Val Asp Pro Gln Gly Pro Leu Lys Asp
    3875                3880                3885
```

```
Cys Ile Phe Asp Leu Cys Leu Gly Gly Gly Asn Leu Ser Ile Leu
3890            3895            3900

Cys Ser Asn Ile His Ala Tyr Val Ser Ala Cys Gln Ala Ala Gly
3905            3910            3915

Gly His Val Glu Pro Trp Arg Asn Glu Thr Phe Cys Pro Met Glu
3920            3925            3930

Cys Pro Gln Asn Ser His Tyr Glu Leu Cys Ala Asp Thr Cys Ser
3935            3940            3945

Leu Gly Cys Ser Ala Leu Ser Ala Pro Leu Gln Cys Pro Asp Gly
3950            3955            3960

Cys Ala Glu Gly Cys Gln Cys Asp Ser Gly Phe Leu Tyr Asn Gly
3965            3970            3975

Gln Ala Cys Val Pro Ile Gln Gln Cys Gly Cys Tyr His Asn Gly
3980            3985            3990

Val Tyr Tyr Glu Pro Glu Gln Thr Val Leu Ile Asp Asn Cys Arg
3995            4000            4005

Gln Gln Cys Thr Cys His Val Gly Lys Val Val Cys Gln Glu
4010            4015            4020

His Ser Cys Lys Pro Gly Gln Val Cys Gln Pro Ser Gly Gly Ile
4025            4030            4035

Leu Ser Cys Val Thr Lys Asp Pro Cys His Gly Val Thr Cys Arg
4040            4045            4050

Pro Gln Glu Thr Cys Lys Glu Gln Gly Gly Gln Gly Val Cys Leu
4055            4060            4065

Pro Asn Tyr Glu Ala Thr Cys Trp Leu Trp Gly Asp Pro His Tyr
4070            4075            4080

His Ser Phe Asp Gly Arg Lys Phe Asp Phe Gln Gly Thr Cys Asn
4085            4090            4095

Tyr Val Leu Ala Thr Thr Gly Cys Pro Gly Val Ser Thr Gln Gly
4100            4105            4110

Leu Thr Pro Phe Thr Val Thr Thr Lys Asn Gln Asn Arg Gly Asn
4115            4120            4125

Pro Ala Val Ser Tyr Val Arg Val Val Thr Val Ala Ala Leu Gly
4130            4135            4140

Thr Asn Ile Ser Ile His Lys Asp Glu Ile Gly Lys Val Arg Val
4145            4150            4155

Asn Gly Val Leu Thr Ala Leu Pro Val Ser Val Ala Asp Gly Arg
4160            4165            4170

Ile Ser Val Ala Gln Gly Ala Ser Lys Ala Leu Leu Val Ala Asp
4175            4180            4185

Phe Gly Leu Gln Val Ser Tyr Asp Trp Asn Trp Arg Val Asp Val
4190            4195            4200

Thr Leu Pro Ser Ser Tyr His Gly Ala Val Cys Gly Leu Cys Gly
4205            4210            4215

Asn Met Asp Arg Asn Pro Asn Asn Asp Gln Val Phe Pro Asn Gly
4220            4225            4230

Thr Leu Ala Pro Ser Ile Pro Ile Trp Gly Gly Ser Trp Arg Ala
4235            4240            4245

Pro Gly Trp Asp Pro Leu Cys Trp Asp Glu Cys Arg Gly Ser Cys
4250            4255            4260

Pro Thr Cys Pro Glu Asp Arg Leu Glu Gln Tyr Glu Gly Pro Gly
4265            4270            4275
```

```
Phe Cys Gly Pro Leu Ser Ser Gly Thr Gly Gly Pro Phe Thr Thr
    4280                4285                4290

Cys His Ala His Val Pro Pro Glu Ser Phe Phe Lys Gly Cys Val
    4295                4300                4305

Leu Asp Val Cys Met Gly Gly Gly Asp Arg Asp Ile Leu Cys Lys
    4310                4315                4320

Ala Leu Ala Ser Tyr Val Ala Ala Cys Gln Ala Ala Gly Val Val
    4325                4330                4335

Ile Glu Asp Trp Arg Ala Gln Val Gly Cys Glu Ile Thr Cys Pro
    4340                4345                4350

Glu Asn Ser His Tyr Glu Val Cys Gly Pro Pro Cys Pro Ala Ser
    4355                4360                4365

Cys Pro Ser Pro Ala Pro Leu Thr Thr Pro Ala Val Cys Glu Gly
    4370                4375                4380

Pro Cys Val Glu Gly Cys Gln Cys Asp Ala Gly Phe Val Leu Ser
    4385                4390                4395

Ala Asp Arg Cys Val Pro Leu Asn Asn Gly Cys Gly Cys Trp Ala
    4400                4405                4410

Asn Gly Thr Tyr His Glu Ala Gly Ser Glu Phe Trp Ala Asp Gly
    4415                4420                4425

Thr Cys Ser Gln Trp Cys Arg Cys Gly Pro Gly Gly Gly Ser Leu
    4430                4435                4440

Val Cys Thr Pro Ala Ser Cys Gly Leu Gly Glu Val Cys Gly Leu
    4445                4450                4455

Leu Pro Ser Gly Gln His Gly Cys Gln Pro Val Ser Thr Ala Glu
    4460                4465                4470

Cys Gln Ala Trp Gly Asp Pro His Tyr Val Thr Leu Asp Gly His
    4475                4480                4485

Arg Phe Asp Phe Gln Gly Thr Cys Glu Tyr Leu Leu Ser Ala Pro
    4490                4495                4500

Cys His Gly Pro Pro Leu Gly Ala Glu Asn Phe Thr Val Thr Val
    4505                4510                4515

Ala Asn Glu His Arg Gly Ser Gln Ala Val Ser Tyr Thr Arg Ser
    4520                4525                4530

Val Thr Leu Gln Ile Tyr Asn His Ser Leu Thr Leu Ser Ala Arg
    4535                4540                4545

Trp Pro Arg Lys Leu Gln Val Asp Gly Val Phe Val Ala Leu Pro
    4550                4555                4560

Phe Gln Leu Asp Ser Leu Leu His Ala His Leu Ser Gly Ala Asp
    4565                4570                4575

Val Val Val Thr Thr Thr Ser Gly Leu Ser Leu Ala Phe Asp Gly
    4580                4585                4590

Asp Ser Phe Val Arg Leu Arg Val Pro Ala Ala Tyr Ala Ala Ser
    4595                4600                4605

Leu Cys Gly Leu Cys Gly Asn Tyr Asn Gln Asp Pro Ala Asp Asp
    4610                4615                4620

Leu Lys Ala Val Gly Gly Lys Pro Ala Gly Trp Gln Val Gly Gly
    4625                4630                4635

Ala Gln Gly Cys Gly Glu Cys Val Ser Lys Pro Cys Pro Ser Pro
    4640                4645                4650

Cys Thr Pro Glu Gln Gln Glu Ser Phe Gly Gly Pro Asp Ala Cys
    4655                4660                4665

Gly Val Ile Ser Ala Thr Asp Gly Pro Leu Ala Pro Cys His Gly
```

```
            4670            4675            4680
Leu Val Pro Pro Ala Gln Tyr Phe Gln Gly Cys Leu Leu Asp Ala
        4685            4690            4695
Cys Gln Val Gln Gly His Pro Gly Gly Leu Cys Pro Ala Val Ala
        4700            4705            4710
Thr Tyr Val Ala Ala Cys Gln Ala Ala Gly Ala Gln Leu Gly Glu
        4715            4720            4725
Trp Arg Arg Pro Asp Phe Cys Pro Leu Gln Cys Pro Ala His Ser
        4730            4735            4740
His Tyr Glu Leu Cys Gly Asp Ser Cys Pro Val Ser Cys Pro Ser
        4745            4750            4755
Leu Ser Ala Pro Glu Gly Cys Glu Ser Ala Cys Arg Glu Gly Cys
        4760            4765            4770
Val Cys Asp Ala Gly Phe Val Leu Ser Gly Asp Thr Cys Val Pro
        4775            4780            4785
Val Gly Gln Cys Gly Cys Leu His Asp Gly Arg Tyr Tyr Pro Leu
        4790            4795            4800
Gly Glu Val Phe Tyr Pro Gly Pro Glu Cys Glu Arg Arg Cys Glu
        4805            4810            4815
Cys Gly Pro Gly Gly His Val Thr Cys Gln Glu Gly Ala Ala Cys
        4820            4825            4830
Gly Pro His Glu Glu Cys Arg Leu Glu Asp Gly Val Gln Ala Cys
        4835            4840            4845
His Ala Thr Gly Cys Gly Arg Cys Leu Ala Asn Gly Gly Ile His
        4850            4855            4860
Tyr Ile Thr Leu Asp Gly Arg Val Tyr Asp Leu His Gly Ser Cys
        4865            4870            4875
Ser Tyr Val Leu Ala Gln Val Cys His Pro Lys Pro Gly Asp Glu
        4880            4885            4890
Asp Phe Ser Ile Val Leu Glu Lys Asn Ala Ala Gly Asp Leu Gln
        4895            4900            4905
Arg Leu Leu Val Thr Val Ala Gly Gln Val Val Ser Leu Ala Gln
        4910            4915            4920
Gly Gln Gln Val Thr Val Asp Gly Glu Ala Val Ala Leu Pro Val
        4925            4930            4935
Ala Val Gly Arg Val Arg Val Thr Ala Glu Gly Arg Asn Met Val
        4940            4945            4950
Leu Gln Thr Thr Lys Gly Leu Arg Leu Leu Phe Asp Gly Asp Ala
        4955            4960            4965
His Leu Leu Met Ser Ile Pro Ser Pro Phe Arg Gly Arg Leu Cys
        4970            4975            4980
Gly Leu Cys Gly Asn Phe Asn Gly Asn Trp Ser Asp Asp Phe Val
        4985            4990            4995
Leu Pro Asn Gly Ser Ala Ala Ser Ser Val Glu Thr Phe Gly Ala
        5000            5005            5010
Ala Trp Arg Ala Pro Gly Ser Ser Lys Gly Cys Gly Glu Gly Cys
        5015            5020            5025
Gly Pro Gln Gly Cys Pro Val Cys Leu Ala Glu Glu Thr Ala Pro
        5030            5035            5040
Tyr Glu Ser Asn Glu Ala Cys Gly Gln Leu Arg Asn Pro Gln Gly
        5045            5050            5055
Pro Phe Ala Thr Cys Gln Ala Val Leu Ser Pro Ser Glu Tyr Phe
        5060            5065            5070
```

```
Arg Gln Cys Val Tyr Asp Leu Cys Ala Gln Lys Gly Asp Lys Ala
    5075                5080                5085

Phe Leu Cys Arg Ser Leu Ala Ala Tyr Thr Ala Ala Cys Gln Ala
    5090                5095                5100

Ala Gly Val Ala Val Lys Pro Trp Arg Thr Asp Ser Phe Cys Pro
    5105                5110                5115

Leu His Cys Pro Ala His Ser His Tyr Ser Ile Cys Thr Arg Thr
    5120                5125                5130

Cys Gln Gly Ser Cys Ala Ala Leu Ser Gly Leu Thr Gly Cys Thr
    5135                5140                5145

Thr Arg Cys Phe Glu Gly Cys Glu Cys Asp Asp Arg Phe Leu Leu
    5150                5155                5160

Ser Gln Gly Val Cys Ile Pro Val Gln Asp Cys Gly Cys Thr His
    5165                5170                5175

Asn Gly Arg Tyr Leu Pro Val Asn Ser Ser Leu Leu Thr Ser Asp
    5180                5185                5190

Cys Ser Glu Arg Cys Ser Cys Ser Ser Ser Ser Gly Leu Thr Cys
    5195                5200                5205

Gln Ala Ala Gly Cys Pro Pro Gly Arg Val Cys Glu Val Lys Ala
    5210                5215                5220

Glu Ala Arg Asn Cys Trp Ala Thr Arg Gly Leu Cys Val Leu Ser
    5225                5230                5235

Val Gly Ala Asn Leu Thr Thr Phe Asp Gly Ala Arg Gly Ala Thr
    5240                5245                5250

Thr Ser Pro Gly Val Tyr Glu Leu Ser Ser Arg Cys Pro Gly Leu
    5255                5260                5265

Gln Asn Thr Ile Pro Trp Tyr Arg Val Val Ala Glu Val Gln Ile
    5270                5275                5280

Cys His Gly Lys Thr Glu Ala Val Gly Gln Val His Ile Phe Phe
    5285                5290                5295

Gln Asp Gly Met Val Thr Leu Thr Pro Asn Lys Gly Val Trp Val
    5300                5305                5310

Asn Gly Leu Arg Val Asp Leu Pro Ala Glu Lys Leu Ala Ser Val
    5315                5320                5325

Ser Val Ser Arg Thr Pro Asp Gly Ser Leu Leu Val Arg Gln Lys
    5330                5335                5340

Ala Gly Val Gln Val Trp Leu Gly Ala Asn Gly Lys Val Ala Val
    5345                5350                5355

Ile Val Ser Asn Asp His Ala Gly Lys Leu Cys Gly Ala Cys Gly
    5360                5365                5370

Asn Phe Asp Gly Asp Gln Thr Asn Asp Trp His Asp Ser Gln Glu
    5375                5380                5385

Lys Pro Ala Met Glu Lys Trp Arg Ala Gln Asp Phe Ser Pro Cys
    5390                5395                5400

Tyr Gly
    5405

<210> SEQ ID NO 57
<211> LENGTH: 1278
<212> TYPE: PRT
<213> ORGANISM: Homo sapiens

<400> SEQUENCE: 57

Met Ala Gln Ser Lys Arg His Val Tyr Ser Arg Thr Pro Ser Gly Ser
```

-continued

```
1               5                   10                  15
Arg Met Ser Ala Glu Ala Ser Ala Arg Pro Leu Arg Val Gly Ser Arg
                20                  25                  30

Val Glu Val Ile Gly Lys Gly His Arg Gly Thr Val Ala Tyr Val Gly
                35                  40                  45

Ala Thr Leu Phe Ala Thr Gly Lys Trp Val Gly Val Ile Leu Asp Glu
 50                      55                  60

Ala Lys Gly Lys Asn Asp Gly Thr Val Gln Gly Arg Lys Tyr Phe Thr
 65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
                100                 105                 110

Ala Ser Lys Val Leu Lys Arg Glu Gly Thr Asp Thr Thr Ala Lys Thr
                115                 120                 125

Ser Lys Leu Arg Gly Leu Lys Pro Lys Ala Pro Thr Ala Arg Lys
 130                 135                 140

Thr Thr Thr Arg Arg Pro Lys Pro Thr Arg Pro Ala Ser Thr Gly Val
 145                 150                 155                 160

Ala Gly Ala Ser Ser Ser Leu Gly Pro Ser Gly Ser Ala Ser Ala Gly
                165                 170                 175

Glu Leu Ser Ser Ser Glu Pro Ser Thr Pro Ala Gln Thr Pro Leu Ala
                180                 185                 190

Ala Pro Ile Ile Pro Thr Pro Val Leu Thr Ser Pro Gly Ala Val Pro
                195                 200                 205

Pro Leu Pro Ser Pro Ser Lys Glu Glu Glu Gly Leu Arg Ala Gln Val
 210                 215                 220

Arg Asp Leu Glu Glu Lys Leu Glu Thr Leu Arg Leu Lys Arg Ala Glu
 225                 230                 235                 240

Asp Lys Ala Lys Leu Lys Glu Leu Glu Lys His Lys Ile Gln Leu Glu
                245                 250                 255

Gln Val Gln Glu Trp Lys Ser Lys Met Gln Glu Gln Gln Ala Asp Leu
                260                 265                 270

Gln Arg Arg Leu Lys Glu Ala Arg Lys Glu Ala Lys Glu Ala Leu Glu
                275                 280                 285

Ala Lys Glu Arg Tyr Met Glu Glu Met Ala Asp Thr Ala Asp Ala Ile
                290                 295                 300

Glu Met Ala Thr Leu Asp Lys Glu Met Ala Glu Glu Arg Ala Glu Ser
 305                 310                 315                 320

Leu Gln Gln Glu Val Glu Ala Leu Lys Glu Arg Val Asp Glu Leu Thr
                325                 330                 335

Thr Asp Leu Glu Ile Leu Lys Ala Glu Ile Glu Glu Lys Gly Ser Asp
                340                 345                 350

Gly Ala Ala Ser Ser Tyr Gln Leu Lys Gln Leu Glu Glu Gln Asn Ala
                355                 360                 365

Arg Leu Lys Asp Ala Leu Val Arg Met Arg Asp Leu Ser Ser Ser Glu
                370                 375                 380

Lys Gln Glu His Val Lys Leu Gln Lys Leu Met Glu Lys Lys Asn Gln
 385                 390                 395                 400

Glu Leu Glu Val Val Arg Gln Arg Glu Arg Leu Gln Glu Glu Leu
                405                 410                 415

Ser Gln Ala Glu Ser Thr Ile Asp Glu Leu Lys Glu Gln Val Asp Ala
                420                 425                 430
```

```
Ala Leu Gly Ala Glu Glu Met Val Glu Met Leu Thr Asp Arg Asn Leu
            435                 440                 445
Asn Leu Glu Glu Lys Val Arg Glu Leu Arg Glu Thr Val Gly Asp Leu
        450                 455                 460
Glu Ala Met Asn Glu Met Asn Asp Glu Leu Gln Glu Asn Ala Arg Glu
465                 470                 475                 480
Thr Glu Leu Glu Leu Arg Glu Gln Leu Asp Met Ala Gly Ala Arg Val
                485                 490                 495
Arg Glu Ala Gln Lys Arg Val Glu Ala Ala Gln Glu Thr Val Ala Asp
                500                 505                 510
Tyr Gln Gln Thr Ile Lys Lys Tyr Arg Gln Leu Thr Ala His Leu Gln
                515                 520                 525
Asp Val Asn Arg Glu Leu Thr Asn Gln Gln Glu Ala Ser Val Glu Arg
        530                 535                 540
Gln Gln Gln Pro Pro Glu Thr Phe Asp Phe Lys Ile Lys Phe Ala
545                 550                 555                 560
Glu Thr Lys Ala His Ala Lys Ala Ile Glu Met Glu Leu Arg Gln Met
                565                 570                 575
Glu Val Ala Gln Ala Asn Arg His Met Ser Leu Leu Thr Ala Phe Met
                580                 585                 590
Pro Asp Ser Phe Leu Arg Pro Gly Gly Asp His Asp Cys Val Leu Val
            595                 600                 605
Leu Leu Leu Met Pro Arg Leu Ile Cys Lys Ala Glu Leu Ile Arg Lys
        610                 615                 620
Gln Ala Gln Glu Lys Phe Glu Leu Ser Glu Asn Cys Ser Glu Arg Pro
625                 630                 635                 640
Gly Leu Arg Gly Ala Ala Gly Glu Gln Leu Ser Phe Ala Ala Gly Leu
                645                 650                 655
Val Tyr Ser Leu Ser Leu Leu Gln Ala Thr Leu His Arg Tyr Glu His
                660                 665                 670
Ala Leu Ser Gln Cys Ser Val Asp Val Tyr Lys Lys Val Gly Ser Leu
        675                 680                 685
Tyr Pro Glu Met Ser Ala His Glu Arg Ser Leu Asp Phe Leu Ile Glu
        690                 695                 700
Leu Leu His Lys Asp Gln Leu Asp Glu Thr Val Asn Val Glu Pro Leu
705                 710                 715                 720
Thr Lys Ala Ile Lys Tyr Tyr Gln His Leu Tyr Ser Ile His Leu Ala
                725                 730                 735
Glu Gln Pro Glu Asp Cys Thr Met Gln Leu Ala Asp His Ile Lys Phe
            740                 745                 750
Thr Gln Ser Ala Leu Asp Cys Met Ser Val Glu Val Gly Arg Leu Arg
        755                 760                 765
Ala Phe Leu Gln Gly Gly Gln Glu Ala Thr Asp Ile Ala Leu Leu Leu
        770                 775                 780
Arg Asp Leu Glu Thr Ser Cys Ser Asp Ile Arg Gln Phe Cys Lys Lys
785                 790                 795                 800
Ile Arg Arg Arg Met Pro Gly Thr Asp Ala Pro Gly Ile Pro Ala Ala
                805                 810                 815
Leu Ala Phe Gly Pro Gln Val Ser Asp Thr Leu Leu Asp Cys Arg Lys
            820                 825                 830
His Leu Thr Trp Val Val Ala Val Leu Gln Glu Val Ala Ala Ala Ala
        835                 840                 845
```

-continued

```
Ala Gln Leu Ile Ala Pro Leu Ala Glu Asn Glu Gly Leu Leu Val Ala
            850             855             860
Ala Leu Glu Glu Leu Ala Phe Lys Ala Ser Glu Gln Ile Tyr Gly Thr
865             870             875             880
Pro Ser Ser Ser Pro Tyr Glu Cys Leu Arg Gln Ser Cys Asn Ile Leu
                885             890             895
Ile Ser Thr Met Asn Lys Leu Ala Thr Ala Met Gln Glu Gly Glu Tyr
            900             905             910
Asp Ala Glu Arg Pro Pro Ser Lys Pro Pro Val Glu Leu Arg Ala
            915             920             925
Ala Ala Leu Arg Ala Glu Ile Thr Asp Ala Gly Leu Gly Leu Lys
930             935             940
Leu Glu Asp Arg Glu Thr Val Ile Lys Glu Leu Lys Lys Ser Leu Lys
945             950             955             960
Ile Lys Gly Glu Glu Leu Ser Glu Ala Asn Val Arg Leu Ser Leu Leu
            965             970             975
Glu Lys Lys Leu Asp Ser Ala Ala Lys Asp Ala Asp Glu Arg Ile Glu
            980             985             990
Lys Val Gln Thr Arg Leu Glu Glu  Thr Gln Ala Leu Leu  Arg Lys Lys
            995             1000            1005
Glu Lys  Glu Phe Glu Glu Thr  Met Asp Ala Leu Gln  Ala Asp Ile
    1010            1015            1020
Asp Gln  Leu Glu Ala Glu Lys  Ala Glu Leu Lys Gln  Arg Leu Asn
    1025            1030            1035
Ser Gln  Ser Lys Arg Thr Ile  Glu Gly Leu Arg Gly  Pro Pro Pro
    1040            1045            1050
Ser Gly  Ile Ala Thr Leu Val  Ser Gly Ile Ala Gly  Glu Glu Gln
    1055            1060            1065
Gln Arg  Gly Ala Ile Pro Gly  Gln Ala Pro Gly Ser  Val Pro Gly
    1070            1075            1080
Pro Gly  Leu Val Lys Asp Ser  Pro Leu Leu Leu Gln  Gln Ile Ser
    1085            1090            1095
Ala Met  Arg Leu His Ile Ser  Gln Leu Gln His Glu  Asn Ser Ile
    1100            1105            1110
Leu Lys  Gly Ala Gln Met Lys  Ala Ser Leu Ala Ser  Leu Pro Pro
    1115            1120            1125
Leu His  Val Ala Lys Leu Ser  His Glu Gly Pro Gly  Ser Glu Leu
    1130            1135            1140
Pro Ala  Gly Ala Leu Tyr Arg  Lys Thr Ser Gln Leu  Leu Glu Thr
    1145            1150            1155
Leu Asn  Gln Leu Ser Thr His  Thr His Val Val Asp  Ile Thr Arg
    1160            1165            1170
Thr Ser  Pro Ala Ala Lys Ser  Pro Ser Ala Gln Leu  Met Glu Gln
    1175            1180            1185
Val Ala  Gln Leu Lys Ser Leu  Ser Asp Thr Val Glu  Lys Leu Lys
    1190            1195            1200
Asp Glu  Val Leu Lys Glu Thr  Val Ser Gln Arg Pro  Gly Ala Thr
    1205            1210            1215
Val Pro  Thr Asp Phe Ala Thr  Phe Pro Ser Ser Ala  Phe Leu Arg
    1220            1225            1230
Ala Lys  Glu Glu Gln Gln Asp  Asp Thr Val Tyr Met  Gly Lys Val
    1235            1240            1245
Thr Phe  Ser Cys Ala Ala Gly  Phe Gly Gln Arg His  Arg Leu Val
```

```
                  1250                1255                1260
Leu Thr Gln Glu Gln Leu His Gln Leu His Ser Arg Leu Ile Ser
        1265                1270                1275
```

<210> SEQ ID NO 58
<211> LENGTH: 166
<212> TYPE: PRT
<213> ORGANISM: Homo sapiens

<400> SEQUENCE: 58

```
Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165
```

<210> SEQ ID NO 59
<211> LENGTH: 195
<212> TYPE: PRT
<213> ORGANISM: Homo sapiens

<400> SEQUENCE: 59

```
Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
            20                  25                  30

His Val Lys Ser Asn Gly Asp Leu Ser Pro Lys Gly Glu Gly Glu Ser
        35                  40                  45

Pro Pro Val Asn Gly Thr Asp Glu Ala Ala Gly Ala Thr Gly Asp Ala
    50                  55                  60

Ile Glu Pro Ala Pro Pro Ser Gln Gly Ala Glu Ala Lys Gly Glu Val
65                  70                  75                  80

Pro Pro Lys Glu Thr Pro Lys Lys Lys Lys Phe Ser Phe Lys Lys
                85                  90                  95

Pro Phe Lys Leu Ser Gly Leu Ser Phe Lys Arg Asn Arg Lys Glu Gly
            100                 105                 110

Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
```

-continued

```
            130                 135                 140
Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195
```